(12) United States Patent
Kashfi et al.

(10) Patent No.: US 9,688,607 B2
(45) Date of Patent: Jun. 27, 2017

(54) NO- AND H$_2$S-RELEASING COMPOUNDS

(75) Inventors: Khosrow Kashfi, Dix Hills, NY (US);
Ravinder Kodela, New York, NY (US)

(73) Assignee: Research Foundation of The City University of New York, New York, NY (US)

( * ) Notice: Subject to any disclaimer, the term of this patent is extended or adjusted under 35 U.S.C. 154(b) by 279 days.

(21) Appl. No.: 13/981,378

(22) PCT Filed: Aug. 15, 2012

(86) PCT No.: PCT/US2012/050922
§ 371 (c)(1),
(2), (4) Date: Apr. 17, 2014

(87) PCT Pub. No.: WO2013/025790
PCT Pub. Date: Feb. 21, 2013

(65) Prior Publication Data
US 2014/0221316 A1     Aug. 7, 2014

Related U.S. Application Data

(60) Provisional application No. 61/523,513, filed on Aug. 15, 2011, provisional application No. 61/615,700, filed on Mar. 26, 2012, provisional application No. 61/635,624, filed on Apr. 19, 2012.

(51) Int. Cl.
| | |
|---|---|
| C07D 413/12 | (2006.01) |
| C07F 9/6561 | (2006.01) |
| C07F 9/6558 | (2006.01) |
| C07C 203/04 | (2006.01) |
| A61K 31/655 | (2006.01) |
| C07C 327/48 | (2006.01) |
| C07C 331/28 | (2006.01) |
| C07D 271/08 | (2006.01) |
| C07D 339/04 | (2006.01) |
| C07F 9/6578 | (2006.01) |

(52) U.S. Cl.
CPC .......... *C07C 203/04* (2013.01); *A61K 31/655* (2013.01); *C07C 327/48* (2013.01); *C07C 331/28* (2013.01); *C07D 271/08* (2013.01); *C07D 339/04* (2013.01); *C07D 413/12* (2013.01); *C07F 9/6578* (2013.01); *C07F 9/65583* (2013.01)

(58) Field of Classification Search
None
See application file for complete search history.

(56) References Cited

U.S. PATENT DOCUMENTS

| | | | |
|---|---|---|---|
| 2007/0275905 A1 | 11/2007 | Wallace et al. | |
| 2008/0293781 A1 | 11/2008 | Gasco et al. | |
| 2009/0203759 A1* | 8/2009 | Gasslander .......... | A61K 9/4866 514/413 |
| 2010/0210607 A1 | 8/2010 | Wallace et al. | |

FOREIGN PATENT DOCUMENTS

| | | |
|---|---|---|
| CN | 101238137 A | 8/2008 |
| CN | 102716486 B | 11/2013 |
| WO | WO 03070234 A1 * | 8/2003 |
| WO | 2006111791 A1 | 10/2006 |

OTHER PUBLICATIONS

Sparatore et al. ("Sparatore", 2009, Free Radical Bio. & Med, 46, 586-592).*
Berenbaum (Clin. exp. Immunol. (1977) 28, 1-18.).*
Weisenthanl (http://weisenthal.org/feedback. html, Feb. 4, 2002).*
Chou, T-C (Cancer Res. Jan. 15, 2010 70(2): 440-446).*
Chinese Office Action for corresponding Chinese Patent Application No. 201280021562.3, pp. 1-5 (Sep. 14, 2015).
Kodela et al., "NOSH-Aspirin: A Novel Nitric Oxide-Hydrogen Sulfide-Releasing Hybrid: A New Class of Anti-Inflammatory Pharmaceuticals", ACS Med. Chem. Lett. 3, 257-262 (2012).
Chattopadhyay et al., "Hydrogen Sulfide-Releasing Aspirin Suppresses NF-κB Signaling in Estrogen Receptor Negative Breast Cancer Cells in Vitro and in Vivo", Biochemical Pharmacology 83, 723-732 (2012).
Chattopadhyay et al., "Hydrogen Sulfide-Releasing Aspirin Modulates Xenobiotic Metabolizing Enzymes in Vitro and in Vivo", Biochemical Pharmacology 83, 733-740 (2012).
Chattopadhyay et al., "Hydrogen Sulfide-Releasing NSAIDs Inhibit the Growth of Human Cancer Cells: A General Property and Evidence of a Tissue Type-Independent Effect", Biochemical Pharmacology 83, 715-722 (2012).
Chattopadhyay et al., "NOSH-Aspirin, a Novel Nitric Oxide and Hydrogen Sulfide-Releasing Hybrid is a Potent Inhibitor of Colon Cancer Cell Growth in Vitro and in a Xenograft Mouse Model", Biochemical and Biophysical Research Communications, vol. 419, pp. 523-528, (2012).
Lazzarato et al. "New Nitric Oxide or Hydrogen Sulfide Releasing Aspirins", J. Med. Chem, vol. 54, pp. 5478-5484 (2011).

* cited by examiner

*Primary Examiner* — Misook Yu
*Assistant Examiner* — Kauser Akhoon
(74) *Attorney, Agent, or Firm* — Hoffmann & Baron, LLP

(57) ABSTRACT

This disclosure relates to novel compounds containing an H$_2$S releasing moiety and a nitric oxide (NO) releasing moiety covalently linked with a core (e.g., a salicylic acid moiety) and the use of such compounds in treating inflammatory diseases, including cancers. Therapeutic potency of these compounds is significantly higher than NSAIDs containing a H$_2$S-releasing moiety alone (HS-NSAIDs) and NSAID containing a NO-releasing moiety alone (NO-NSAIDs). The compounds, in addition, exhibit reduced side effect, e.g., reduced stomach ulcers, upon administration.

5 Claims, 18 Drawing Sheets

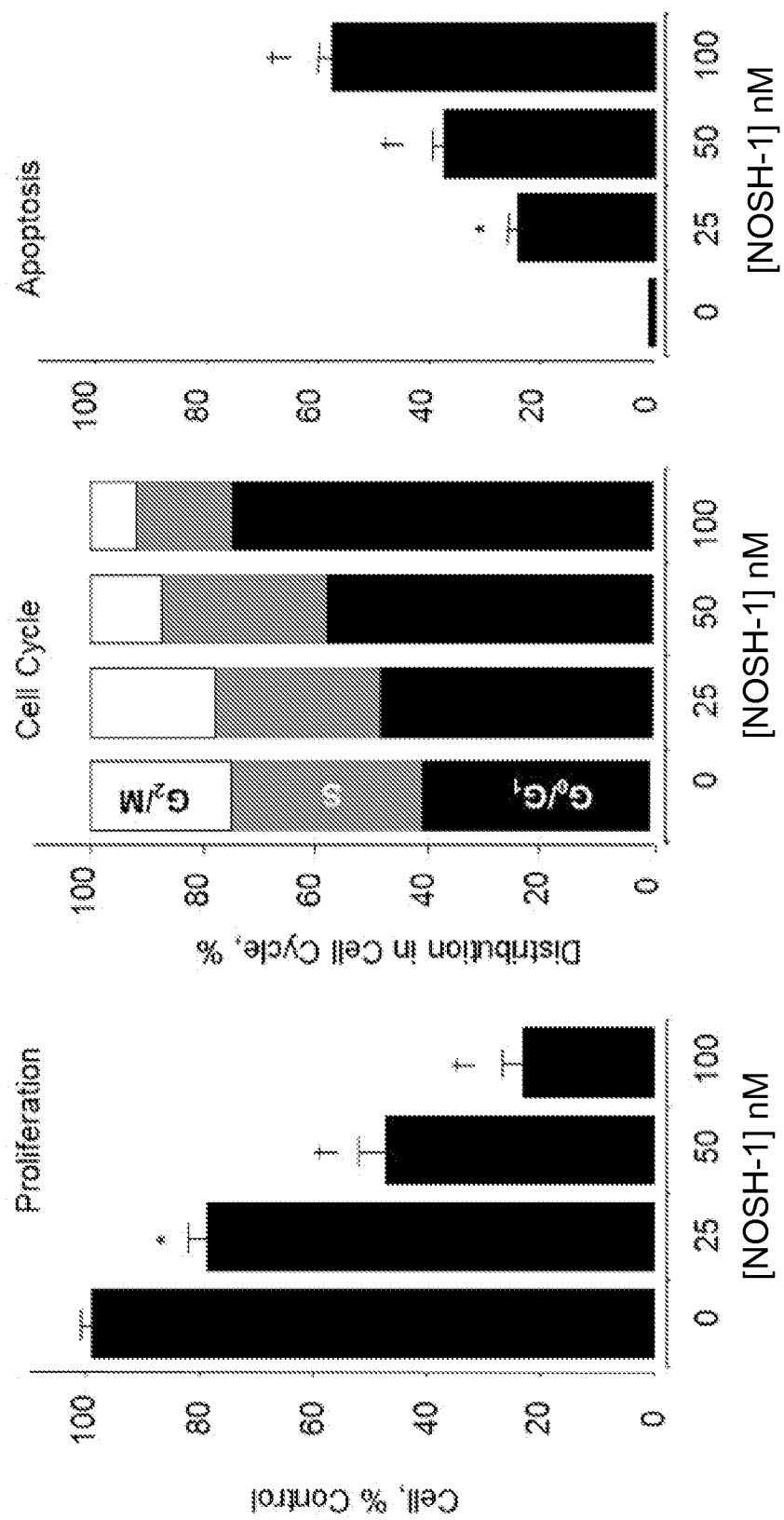

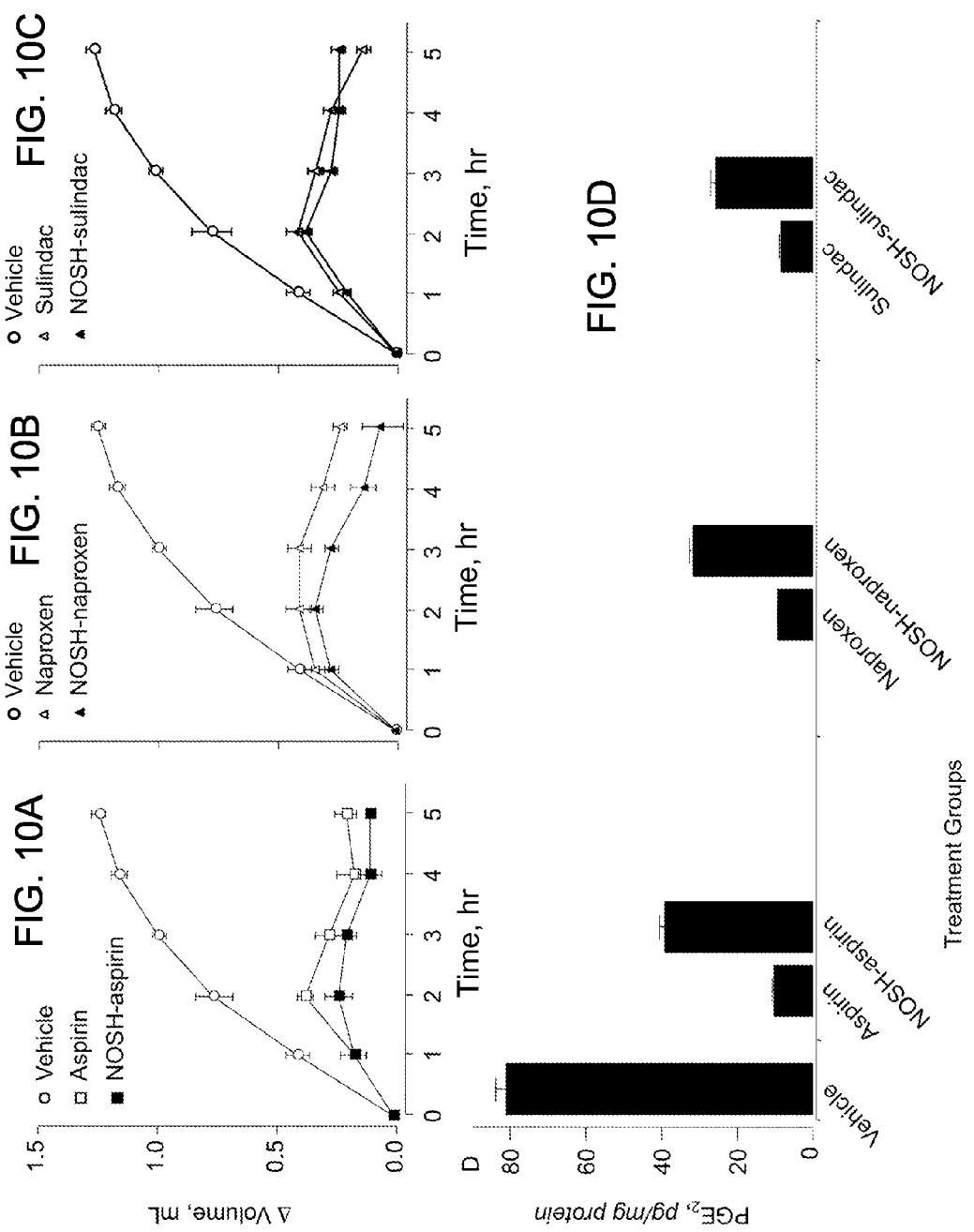

NO- AND H$_2$S-RELEASING COMPOUNDS

CROSS-REFERENCE TO RELATED APPLICATIONS

The present application asserts priority to an International Application filed under the Patent Cooperation Treaty, PCT/US2012/050922, filed Aug. 15, 2012, which claims the benefit of U.S. Provisional Patent Application Nos. 61/523,513, filed Aug. 15, 2011; 61/615,700, filed Mar. 26, 2012; and 61/635,624, filed Apr. 19, 2012. Each of the foregoing applications is herein incorporated by reference in its entirety.

TECHNICAL FIELD

This invention relates to anti-inflammatory compounds capable of releasing NO and H$_2$S, and compositions and methods of using such compounds.

BACKGROUND OF THE INVENTION

Non-steroidal anti-inflammatory drugs (NSAIDs) are prototypical agents for treatment of inflammatory conditions. NSAIDs may also have utility as therapeutic agents against many forms of cancers. Reviewed in K. Kashfi, Anti-Inflammatory Agents as Cancer Therapeutics, pp. 31-89 in Contemporary Aspects of Biomedical Research: Drug Discovery, Advances in Pharmacol., S. Enna and M. Williams (ed.), 2009, vol. 57, Elsevier, Inc. Long-term use of NSAIDs, however, may lead to serious side effects including gastrointestinal and renal side effects.

Recognition that endogenous gaseous mediators, nitric oxide (NO) and hydrogen sulfide (H$_2$S) can increase mucosal defense mechanisms has led to the development of NO- and H$_2$S-releasing NSAIDs with increased safety profiles. NO-NSAIDs and HS-NSAIDs, however, have several drawbacks. HS-NSAIDs, for example, have relatively high IC$_{50}$s for cell growth inhibition. Some NO-NSAIDs can form quinone methide intermediates, raising doubts about the role of NO in their biological activity. Other NO-NSAIDs have high IC$_{50}$s for cell growth inhibition.

We have discovered that hybrid dual action compounds that incorporate both NO and H$_2$S donor components are more potent therapeutic agents than compounds that donate only one of these groups. Such dual action compounds provide improved safety and methods of treatment of inflammatory conditions, such as cancers.

SUMMARY

In one aspect, the disclosure features a compound containing a NO-releasing moiety and a H$_2$S-releasing moiety.

In another aspect, the disclosure features a method of treating an inflammatory disease. The method includes administering to a subject in need thereof an effective amount of a compound disclosed herein.

Other features, objects, and advantages of the subject matter in this disclosure will be apparent from the description, drawings, and claims.

DESCRIPTION OF DRAWINGS

In FIG. 2A, aspirin (ASA) and NOSH-1 caused a significant reduction in paw volume at all time points. Results are mean±S.E.M. of four rats in each group, *P<0.05 versus vehicle treated rats at all time points. In FIG. 2B, ASA and NOSH-1 caused a significant reduction in PGE2 levels in the paw exudate. Results are mean±S.E.M. for four rats in each group, *P<0.01 versus vehicle. In FIG. 2C, NOSH-1 inhibited induction of COX-1 and COX-2 by carrageenan. The figures show results from 1 animal from the control group, 4 animals in the carrageenan injected group, and 2 animals that were pre-medicated with NOSH-1 one hour before carrageenan challenge. NOSH-1 was administered at 2 different doses.

FIGS. 5A, 5B, and 5C are graphs showing the effect of NOSH-1 on HT-29 colon cancer cell kinetics. NOSH-1 inhibited proliferation by altering cell cycle progression and inducing apoptosis. Cells were treated with vehicle, 0.5× IC$_{50}$ (25 nM), 1×IC$_{50}$ (50 nM) or 2×IC$_{50}$ (100 nM) NOSH-1 for 24 hours and analyzed for A) proliferation by PCNA antigen expression; B) cell cycle phases by PI staining and flow cytometry; C) apoptosis by Annexin V staining and flow cytometry. In FIGS. 5A and 5C, results are mean±SEM for 3 different experiments performed in duplicate, *P<0.05, †P<0.01 compared to control. In FIG. 5B, results are representative of two different experiments. This study was repeated twice generating results within 10% of those presented here.

In FIG. 6A, cells were treated with NOSH-1 at its IC$_{50}$ for cell growth inhibition (i.e., 50 nM) and at indicated times NO release was measured in the culture medium. Total sulfide release was measured by using the methylene blue method. Results are mean±SEM for 3 different determinations. *P<0.05 at all time points past start. In FIG. 6B, typical trace showing H$_2$S gas released from NOSH-1 by homogenized mouse liver measured in real time with a polarographic sensor.

FIG. 7A shows that athymic nude mice were injected subcutaneously with HT-29 cells for the development of subcutaneous tumors as described in Example 10. FIG. 7B shows that NOSH-1 significantly reduced tumor volume 6 days after treatment to sacrifice, *P<0.05 at day 6, †P<0.01 days 9-18.

†P<0.01 compared to vehicle, §P<0.05, compared to vehicle, *P<0.01 compared to corresponding NSAID.

FIGS. 10A, 10B, and 10C are line graphs plotting the change (Δ) in paw volume (in mL) at the indicated time points (in hours (hr)), following treatment of the animals with vehicle, aspirin or NOSH-aspirin.

FIG. 10D is a bar graph quantifying the levels of $PGE_2$ (pg/mg protein) content in paw exudates in the indicated treatment groups.

Figure 11:
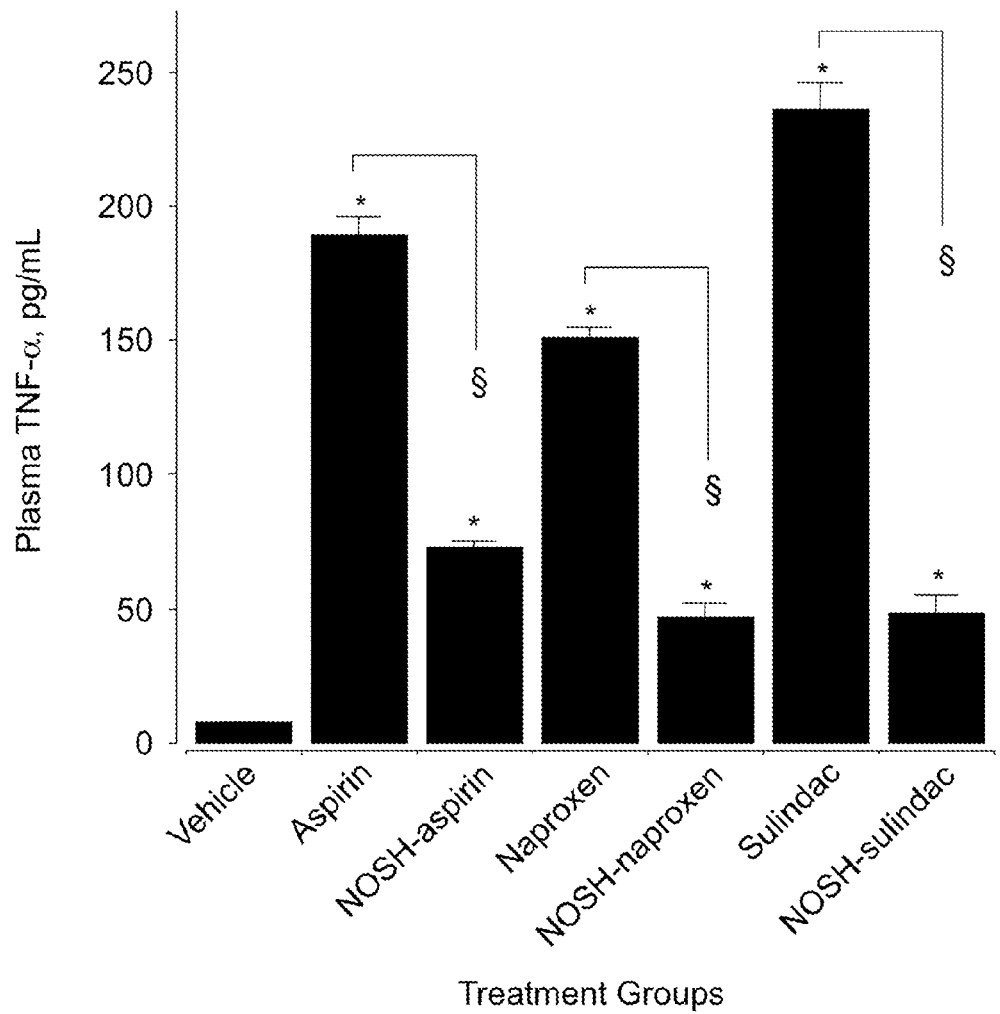

FIG. 11 is a bar graph quantifying the level (pg/ml) of plasma TNFα in plasma obtained from control and animals treated with the indicated drugs; *P<0.01 compared to vehicle, §P<0.01 compared to parent NSAID.

Figures 12A, 12B, 12C:
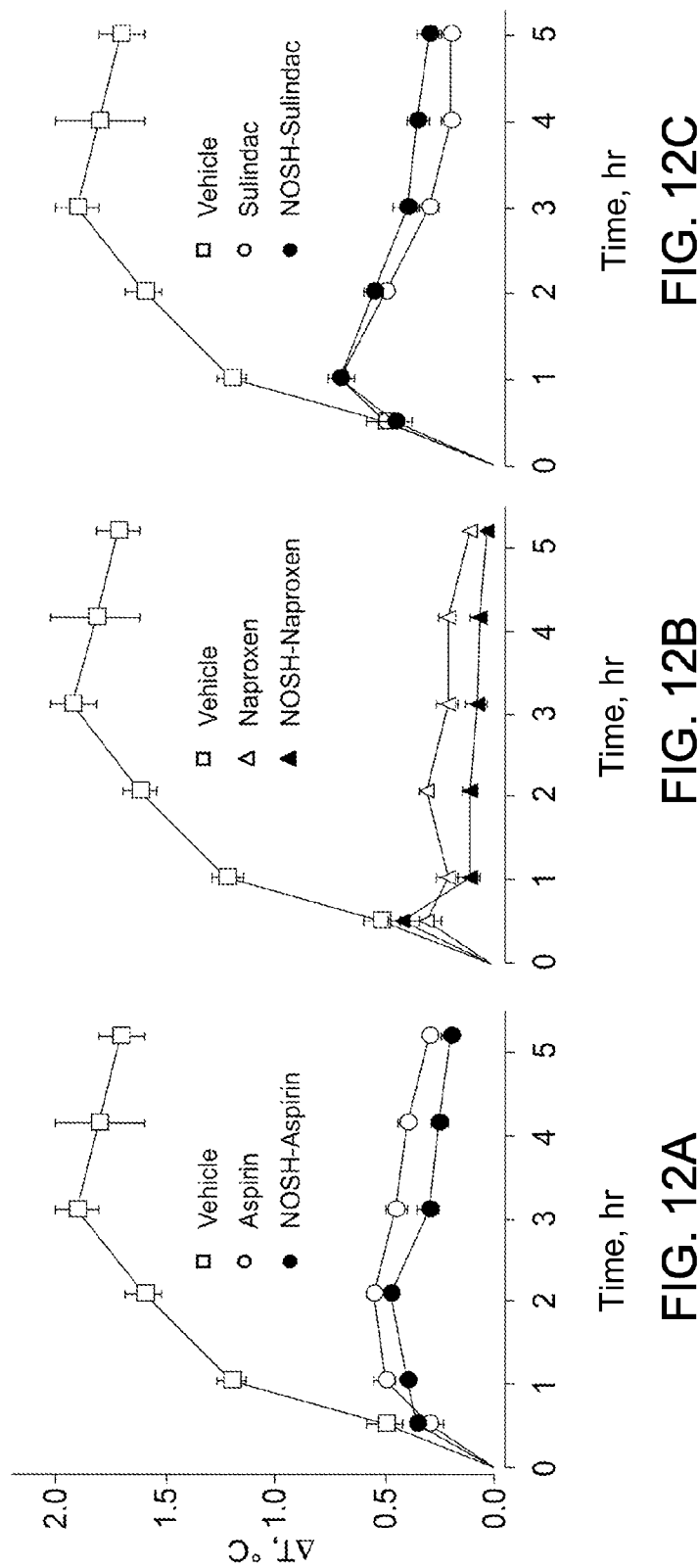

FIGS. 12A, 12B and 12C are line graphs plotting the change in body temperature (ΔT, ° C.) of experimental animals treated with vehicle, aspirin, or NOSH-aspirin and injected with LPS at the indicated time points (hours (hr)) after injection with LPS.

Figures 13A, 13B, 13C:
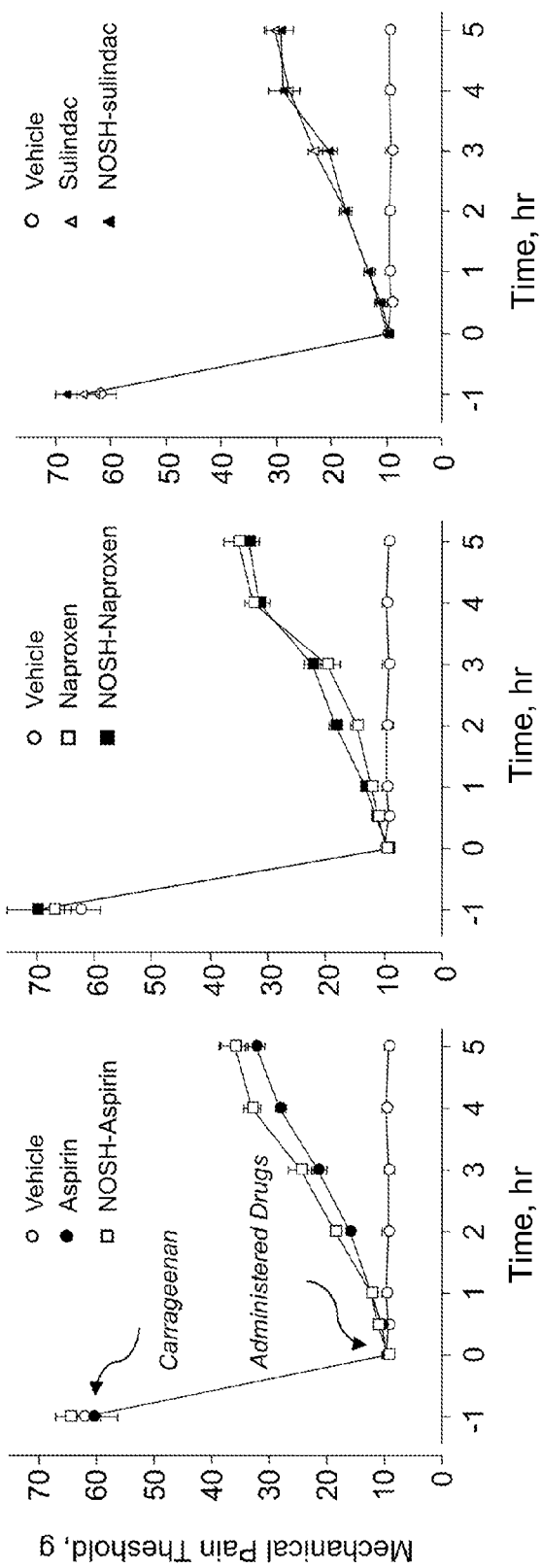

FIGS. 13A, 13B and 13C are line graphs plotting the mechanical pain threshold (g) over time (hours (hr)) of animals injected with carrageenan reagent and treated with vehicle or the indicated drug. Carrageenan was administered 1 hour before (−1 hr) treatment with vehicle or the indicated drug at 0 hr.

Figure 14:
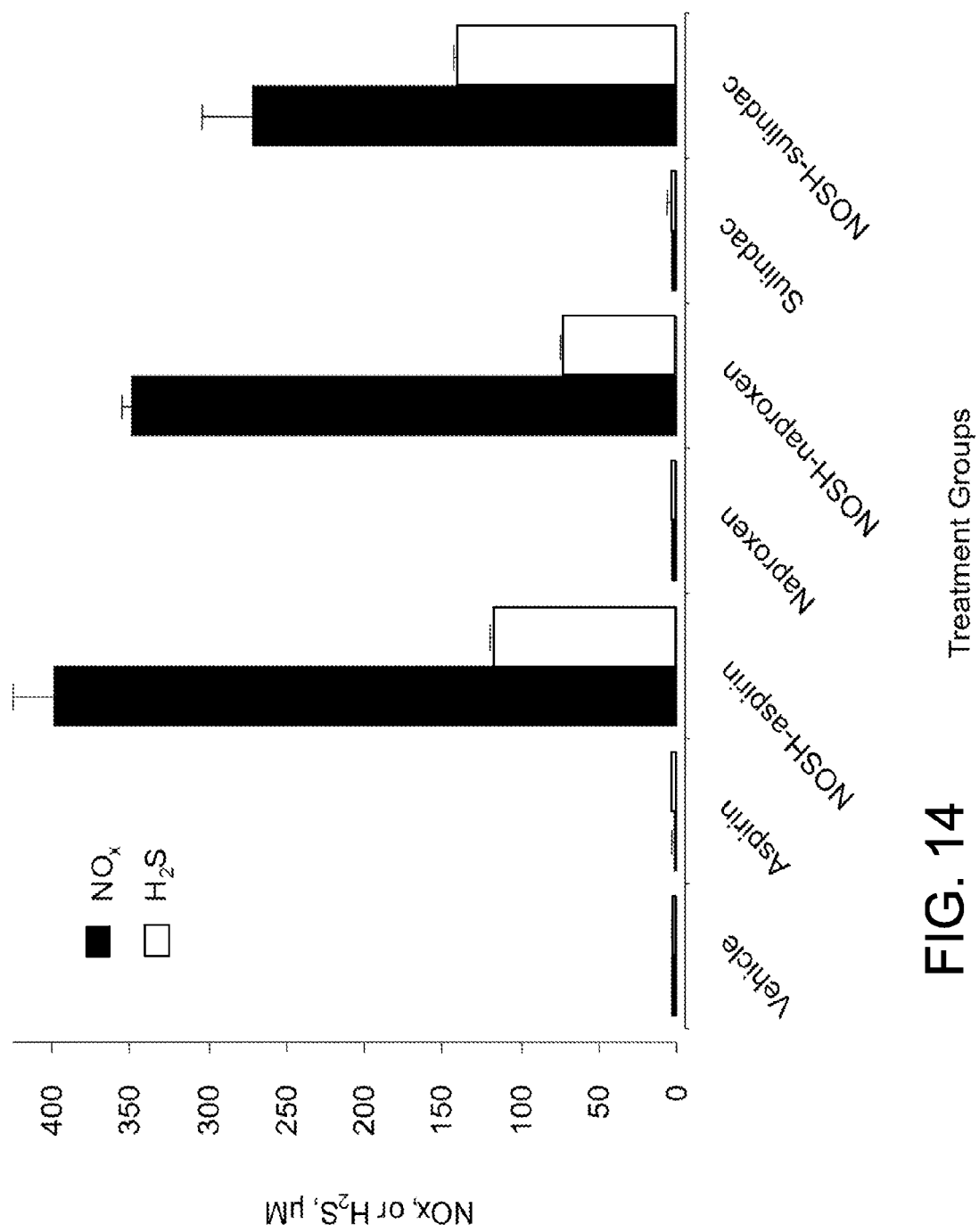

FIG. 14 is a bar graph quantifying the release of nitric oxide (NOx) and hydrogen sulfide ($H_2S$) (μM) in blood collected from vehicle, NSAID (aspirin, naproxen, or sulindac) and NOSH-NSAID-treated animals at the end of carrageenan-induced edema studies.

Figure 15:
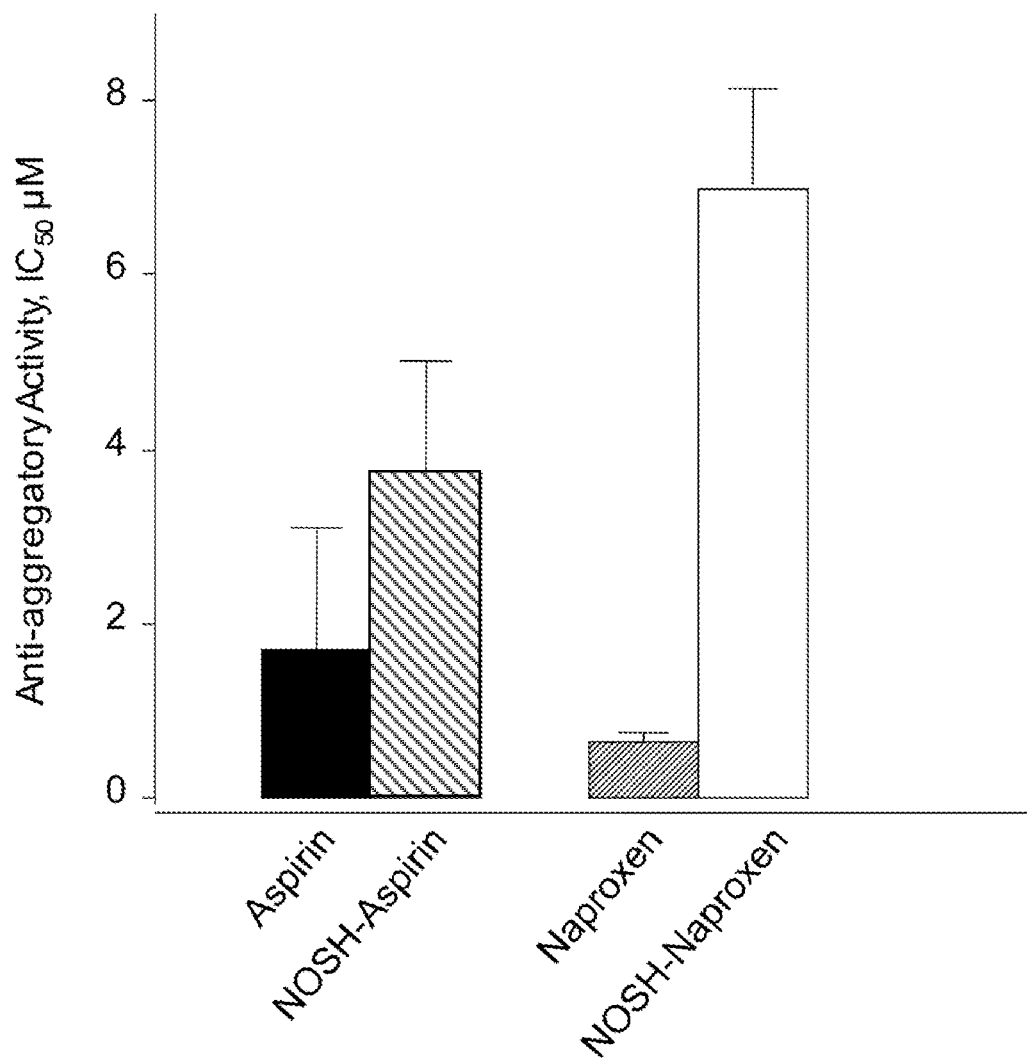

FIG. 15 is a bar graph quantifying the anti-aggregatory activity ($IC_{50}$, μM) of the indicated NSAID (aspirin or naproxen) or NOSH-NSAID, as a measure of anti-platelet activity, in human platelet-rich plasma (PRP) treated with collagen to induced platelet aggregation. Results are the mean±range for two different individuals with assays done in duplicate.

Figures 16A, 16B:
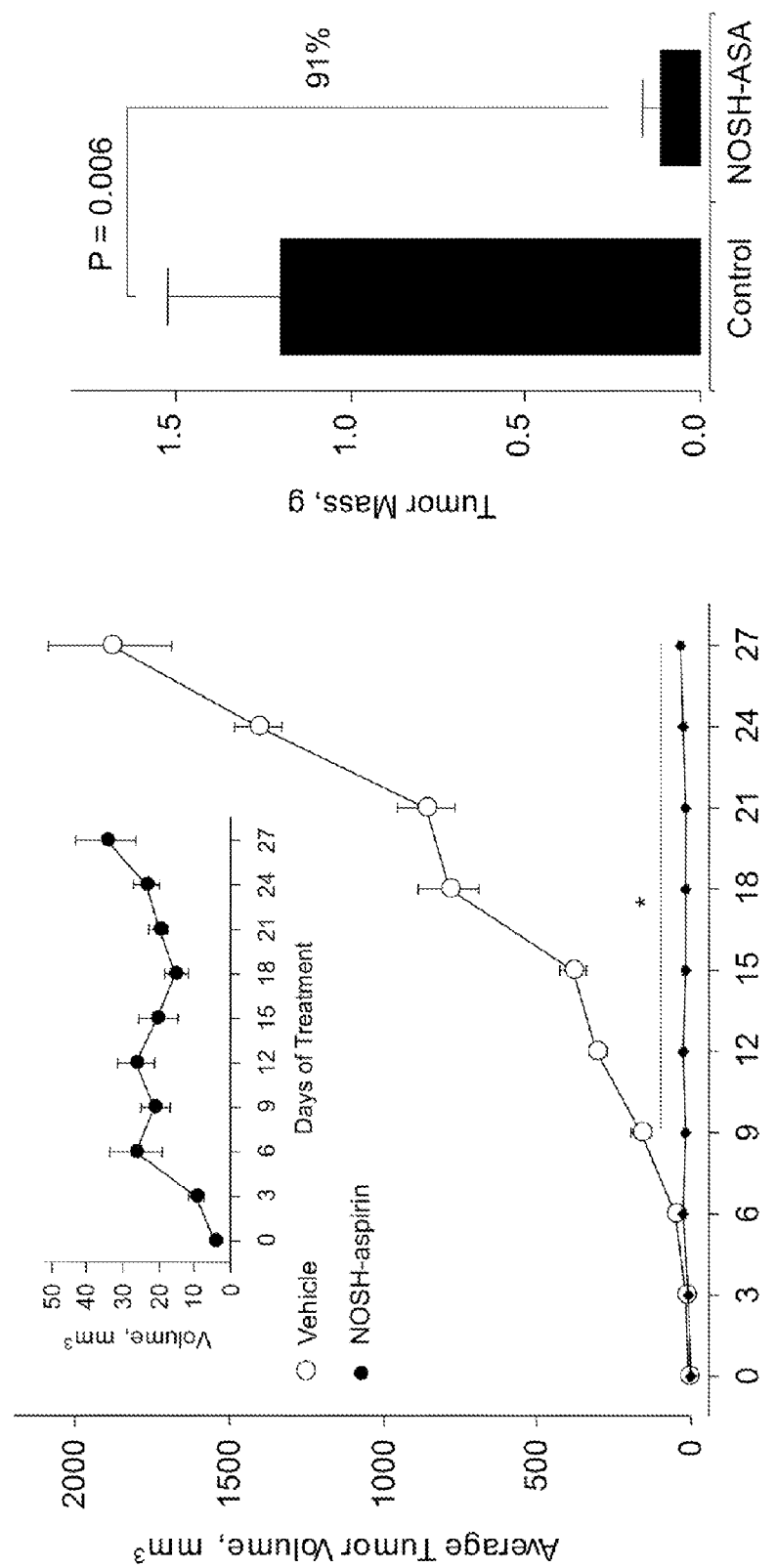
Figures 17A, 17B:
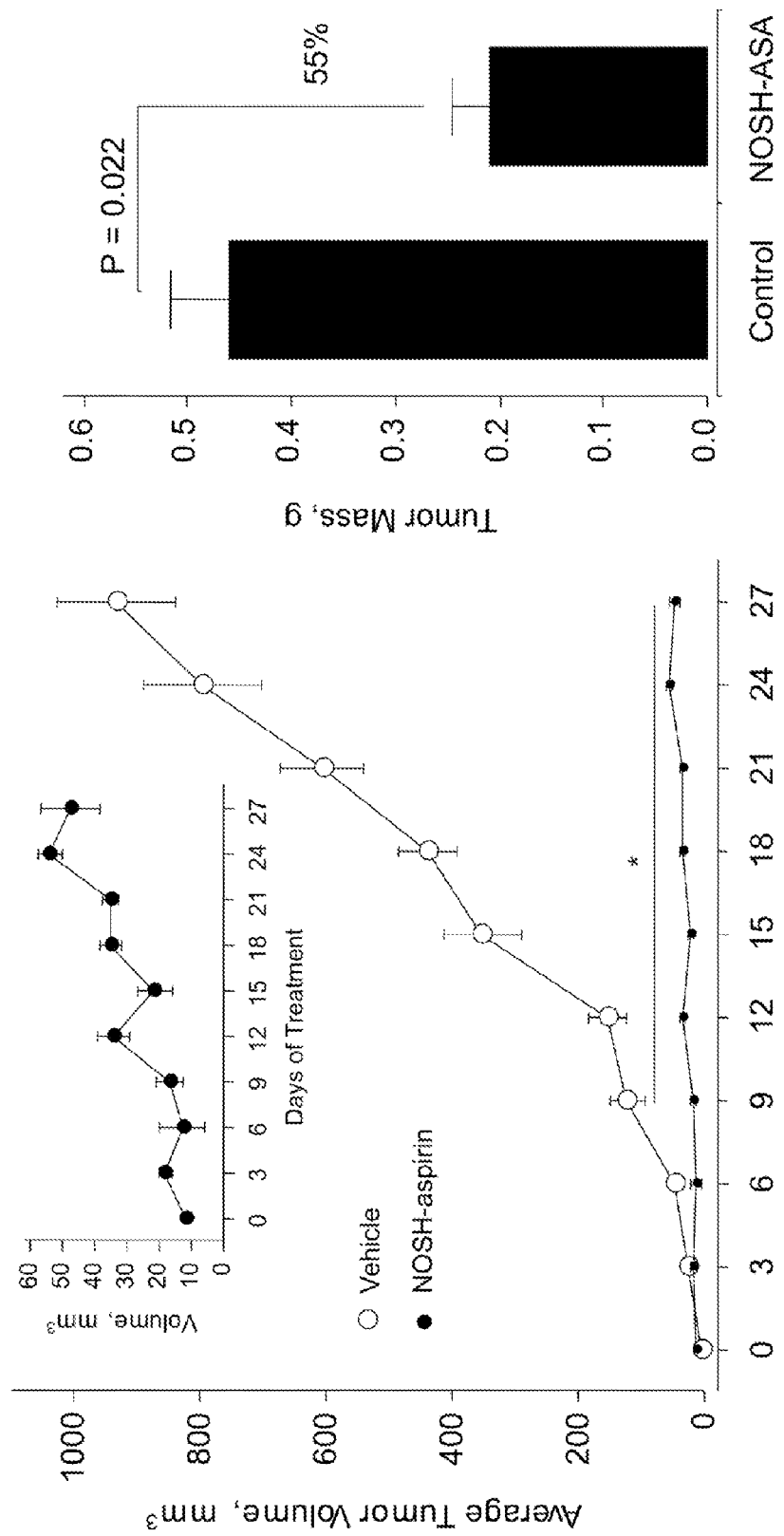
Figures 18A, 18B:
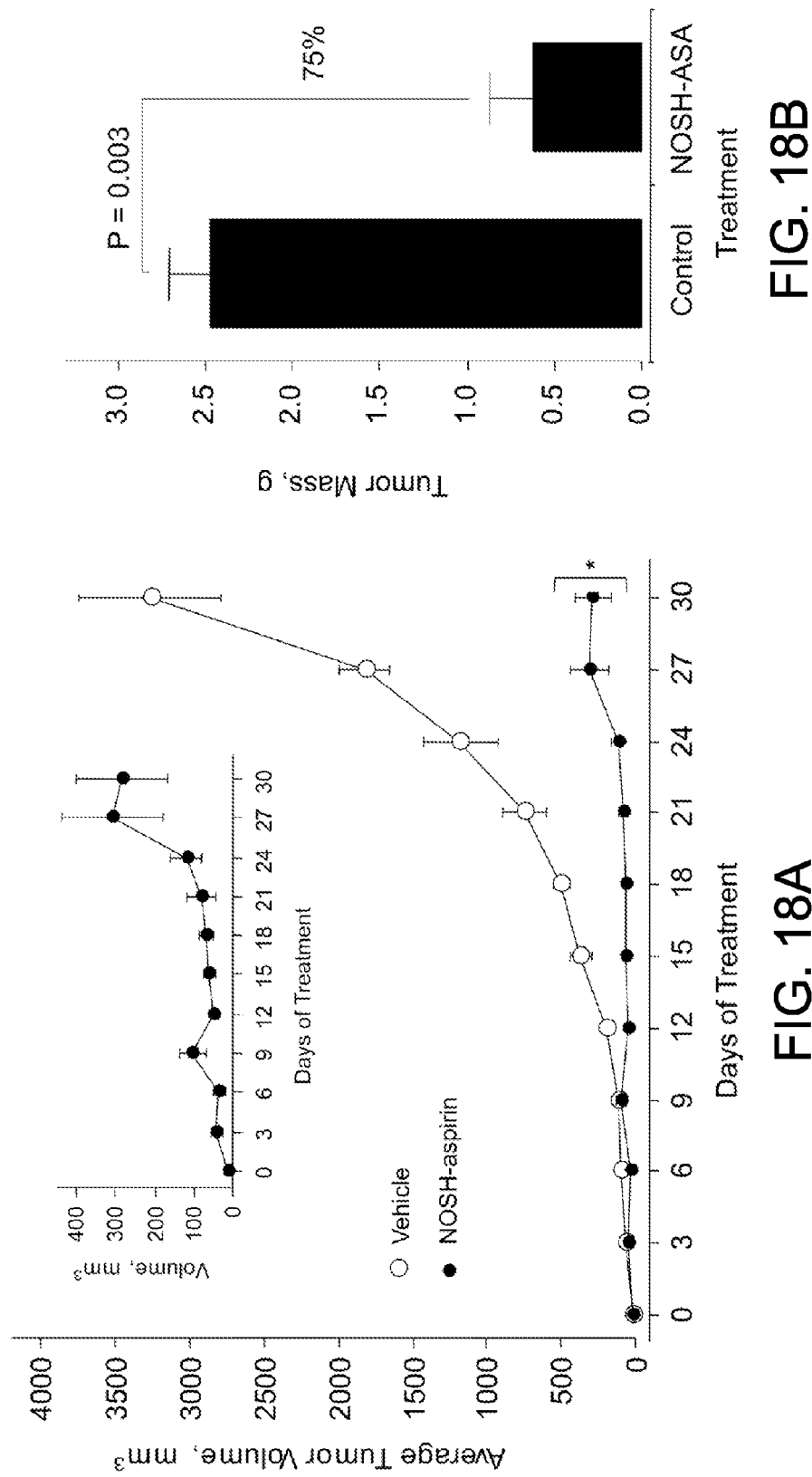
Figures 19A, 19B:
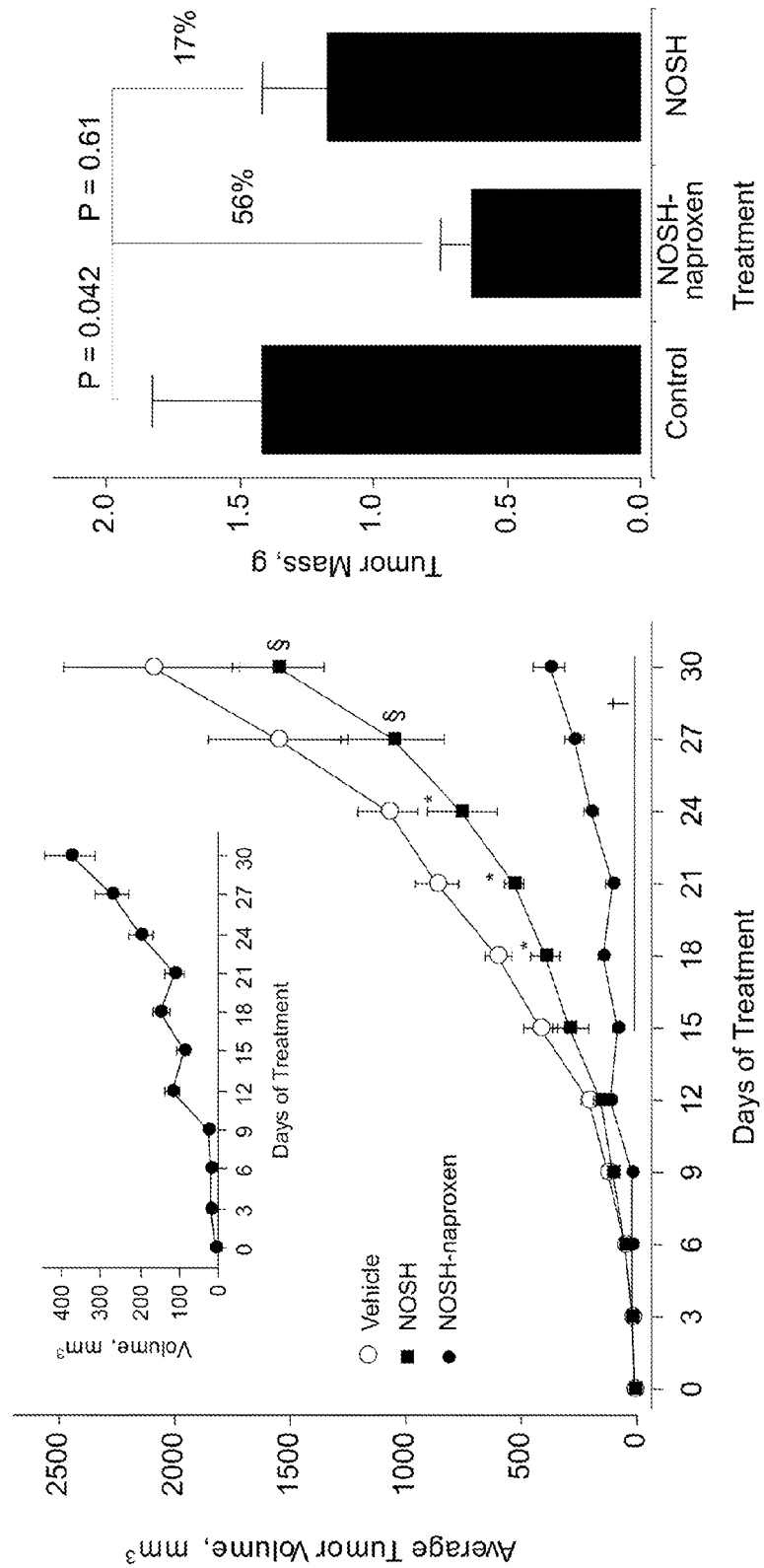

FIGS. 16A, 17A, 18A and 19A contain line graphs plotting the average tumor volume ($mm^3$) over the indicated number of days of treatment in mice with an MDA-MB-231 human estrogen receptor negative (ER−) breast cancer cell xenograft (FIG. 16A), an MCF-7 ER+ breast cancer cell xenograft (FIG. 17A), an MIA PaCa2 human pancreatic cancer cell xenograft (FIG. 18A), or an SW480 human colon cancer cell xenograft (FIG. 19A), following treatment with vehicle or the indicated NOSH-NSAID. The inset line graphs show the change in tumor volume as a function of treatment time for each NOSH-NSAID on a magnified volume scale. In FIGS. 16A, 17A, and 18A, "*" indicates P<0.01 compared to vehicle-treated animals from day 15 to the termination of the study. In FIG. 19A, "*" indicates P<0.05 compared to vehicle for days 18-24, "†" indicates P<0.01 compared to vehicle-treated animals from day 15 to the termination of the study, and "§" indicates no significant difference to vehicle treated animals on days 27-30.

FIGS. 16B, 17B, 18B and 19B are bar graphs quantifying the tumor mass (g) at end of each respective study, in control or NOSH-NSAID (NOSH-aspirin (ASA) or NOSH-naproxen) or NOSH treated mice with an MDA-MB-231 human estrogen receptor negative (ER−) breast cancer cell xenograft (FIG. 16B), an MCF-7 ER+ breast cancer cell xenograft (FIG. 17B), an MIA PaCa2 human pancreatic cancer cell xenograft (FIG. 18B), or an SW480 human colon cancer cell xenograft (FIG. 19B); P values are shown, and percentages indicate percent (%) of control.

DETAILED DESCRIPTION

The present disclosure provides novel compounds containing an $H_2S$ releasing moiety and a nitric oxide (NO) releasing moiety covalently linked with a core (e.g., a salicylic acid moiety or moieties derived from other NSAIDs such as naproxen, ibuprofen, sulindac). The compounds disclosed herein exhibited enhanced antiproliferative activity in in vitro condition against human cancer cell lines. The potency of these compounds is significantly higher than NSAIDs containing a $H_2S$-releasing moiety alone (HS-NSAIDs) and NSAID containing a NO-releasing moiety alone (NO-NSAIDs). The compounds disclosed herein also exhibited reduced side effect, e.g., reduced stomach ulcers, upon administration.

The compounds disclosed herein include at least one $H_2S$-releasing moiety and at least one NO-releasing moiety. In certain embodiments, compounds include more than one, e.g., two, or three or more, of an $H_2S$-releasing moiety and/or NO-releasing moiety.

As used herein, "a NO-releasing moiety" refers to a moiety that can be cleaved from a parent compound to generate NO under physiological conditions after the parent compound is administered to a patient. Examples of suitable NO-releasing moieties include —NO, —C(O)—$(CH_2)_n$—$ONO_2$, —O—$(CH_2)_n$—$ONO_2$, —$(CH_2)_n$—$ONO_2$, —C(O)—$CH_2$—$C(CH_3)_2$—SNO, —NH—$CH_2$—$C(CH_3)_2$—SNO, —$CH_2$—$C(CH_3)_2$—SNO,

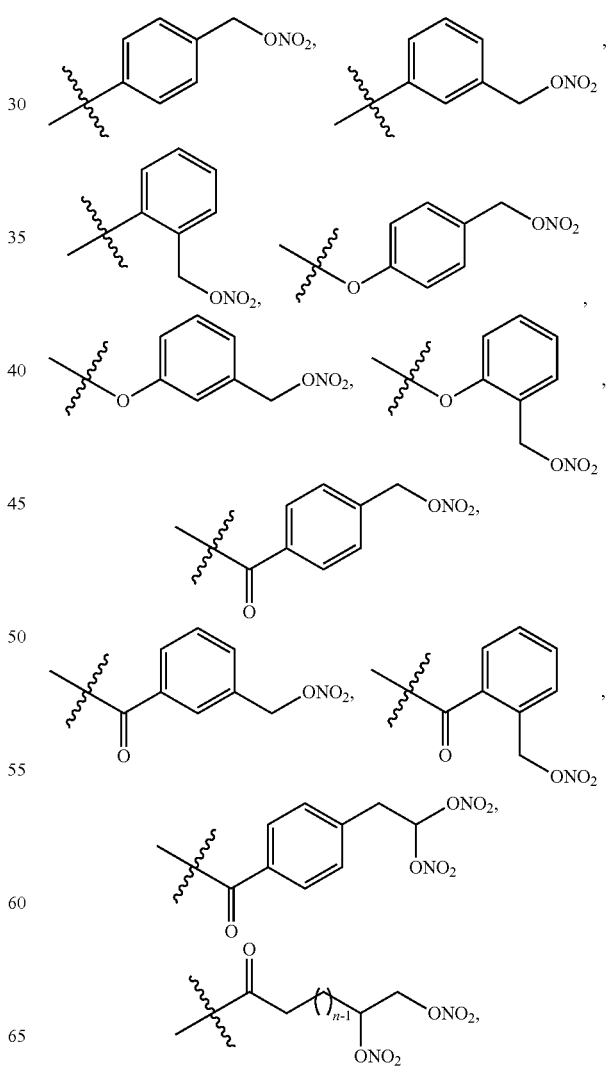

-continued

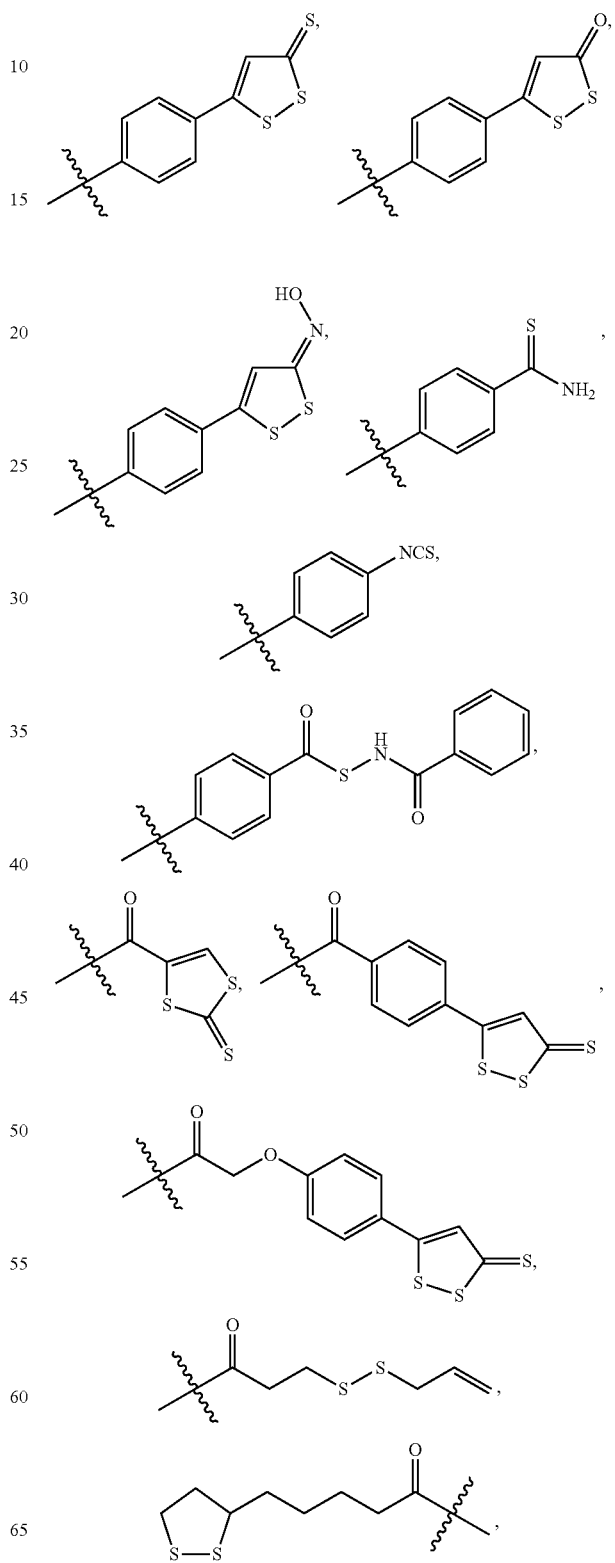

in which n is 1, 2, 3, 4, 5, 6, or 7; $R_a$ is H, $C_1$-$C_{10}$ alkyl, aryl, $S(O)_2$-aryl, CN, or $CON(R_b)_2$; and each $R_b$, independently, is H or $C_1$-$C_{10}$ alkyl.

The term "alkyl" refers to a saturated, linear or branched hydrocarbon moiety, such as —$CH_3$ or —$CH(CH_3)_2$. The term "aryl" refers to a hydrocarbon moiety having one or more aromatic rings. Examples of aryl moieties include phenyl (Ph), naphthyl, pyrenyl, anthryl, and phenanthryl. Alkyl and aryl mentioned herein include both substituted and unsubstituted moieties, unless specified otherwise. Possible substituents on aryl include, but are not limited to, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, $C_1$-$C_{10}$ alkoxy, aryl, aryloxy, heteroaryl, heteroaryloxy, amino, $C_1$-$C_{10}$ alkylamino, $C_1$-$C_{20}$ dialkylamino, arylamino, diarylamino, $C_1$-$C_{10}$ alkylsulfonamino, arylsulfonamino, $C_1$-$C_{10}$ alkylimino, arylimino, $C_1$-$C_{10}$ alkylsulfonimino, arylsulfonimino, hydroxyl, halo, thio, $C_1$-$C_{10}$ alkylthio, arylthio, $C_1$-$C_{10}$ alkylsulfonyl, arylsulfonyl, arylsulfonamide, heteroarylsulfonamide, acylamino, aminoacyl, aminothioacyl, amidino, guanidine, ureido, cyano, nitro, nitroso, azido, acyl, thioacyl, acyloxy, carboxyl, and carboxylic ester. On the other hand, possible substituents on alkyl include all of the above-recited substituents except $C_1$-$C_{10}$ alkyl.

As used herein, "a $H_2S$-releasing moiety" refers to a moiety that can be cleaved from a parent compound to generate $H_2S$ under physiological conditions after the parent compound is administered to a patient. Examples of suitable $H_2S$-releasing moieties include:

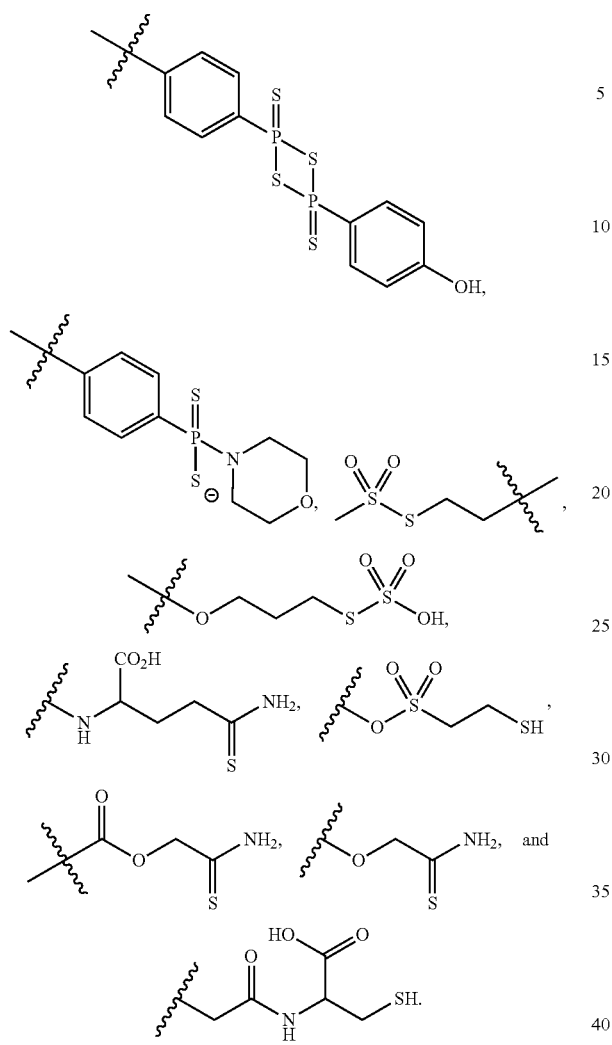
In some embodiments, the compounds disclosed herein further include a core, each of the NO-releasing moiety and the H₂S-releasing moiety being covalently bonded to the core. In some embodiments, the core includes both a —O— or —N(H)— group and a —C(O)O— or —C(O)NH— group. Examples of suitable cores include:
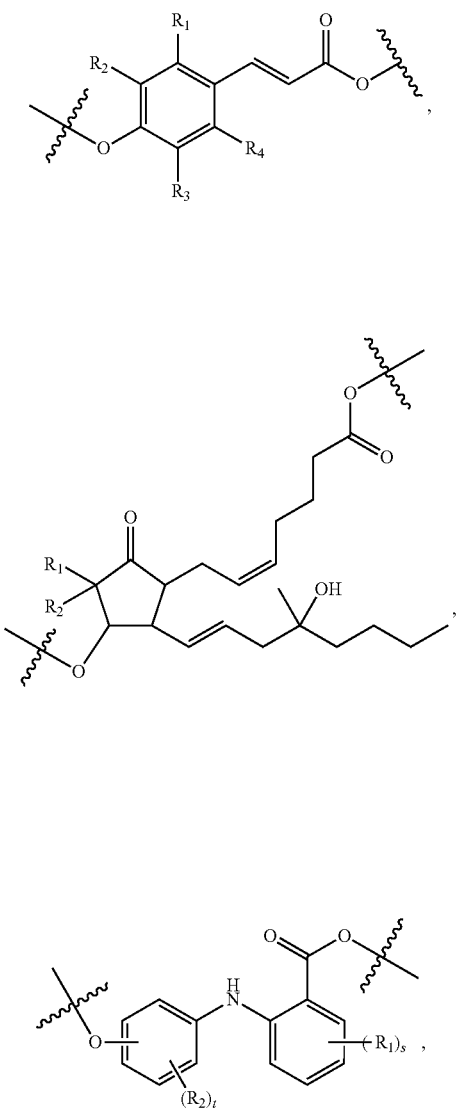
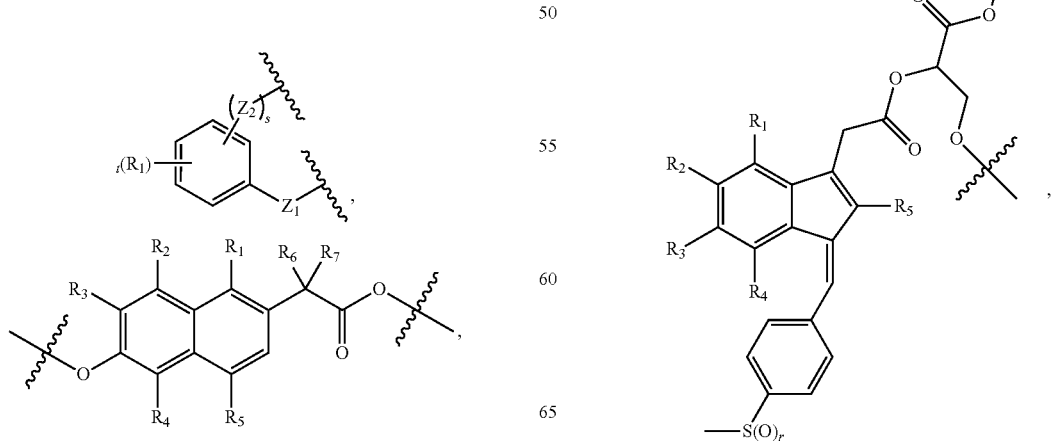

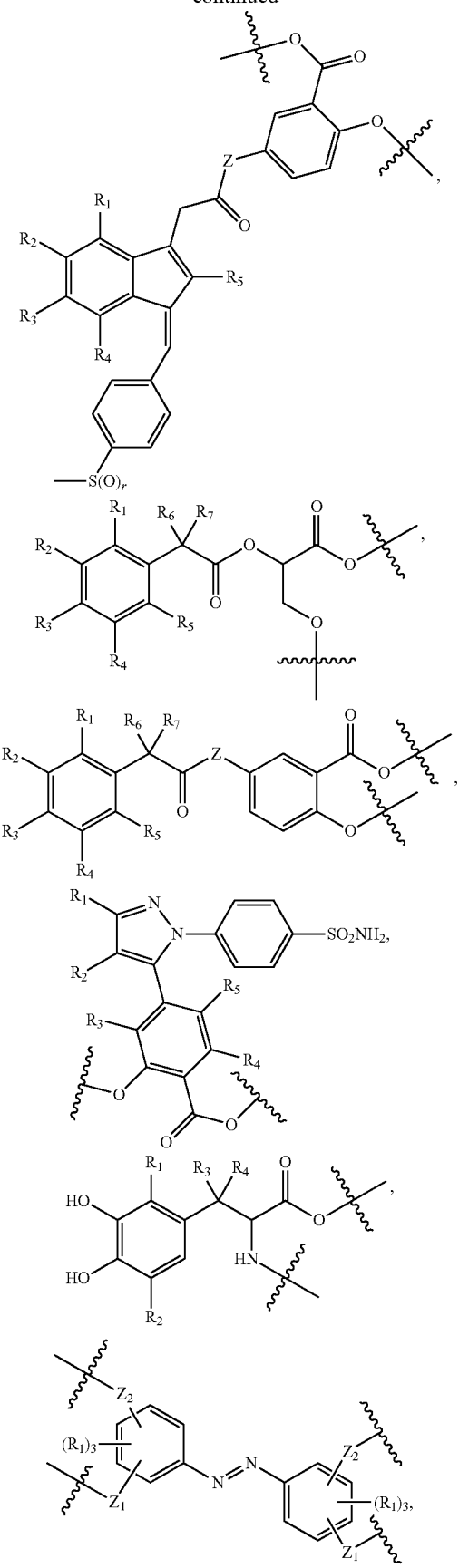
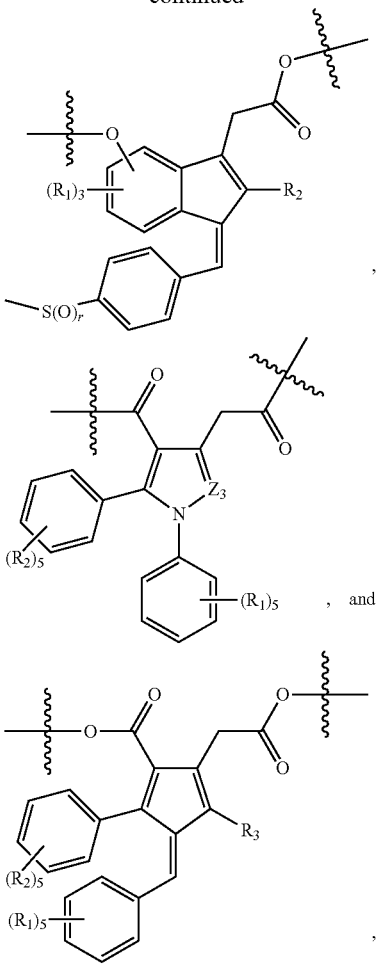

in which each of s and t, independently, is 1, 2, 3, or 4; r is 1 or 2; Z is O or NH; $Z_1$ is —O—, —NH—, —N=N—, C(O)O—, —C(O)—NH—, —NH—C(O)—, —NH—C(O)O—, or —OC(O)—NH—; each $Z_2$, independently, is —O—, —NH—, —N=N—, —C(O)O—, —C(O)—NH—, —NH—C(O)—, —NH—C(O)O—, or —OC(O)—NH—; $Z_3$ is N or C(R); each of $R_1$, $R_2$, $R_3$, $R_4$, $R_5$, $R_6$, and $R_7$, independently, is H, halo, $NO_2$, $N_3$, $C_1$-$C_{10}$ alkyl, OR, OC(O)R, N(R)$_2$, NH—C(O)R, S(O)R, or N=N—R, in which each R, independently, is H, $C_1$-$C_{10}$ alkyl, or aryl.

In some embodiments, the core is a moiety derived from a therapeutically effective compound (e.g., an anti-inflammatory drug). For example, the core can be derived from aspirin, mesalamine, cinnamic acid, caffeic acid, naproxen, celecoxib, fenmate, sulindac, ibuprofen, valproic acid, misoprostol, or their derivatives. Without wishing to be bound by theory, it is believed that incorporating both at least one NO-releasing moiety and at least one $H_2S$-releasing moiety onto a core derived from a therapeutically effective compound (e.g., anti-inflammatory compound) can result in a compound with significantly improved potency (e.g., anti-inflammatory activities when the compound is an anti-inflammatory compound).

In some embodiments, the NO-releasing moiety or the $H_2S$-releasing moiety is covalently bonded to the core through an optional linker. Examples of suitable linkers include —C(O)—, —(CH$_2$)$_m$—, —(CH$_2$)$_m$—O—, —(CH$_2$)$_m$—C(O)—, —(CH$_2$)$_m$—C(O)O—, —(CH$_2$)$_m$—

OC(O)O—, —C(O)—(CH$_2$)$_m$—O—, —C(O)—(CH$_2$)$_m$—C(O)—, —OC(O)—(CH$_2$)$_m$—O—, —OC(O)—(CH$_2$)$_m$—C(O)—, or —OC(O)—(CH$_2$)$_m$—C(O)O—, in which m is 1, 2, 3, 4, 5, 6, or 7.

In some embodiments, the anti-inflammatory compounds disclosed herein can be of formula (I):

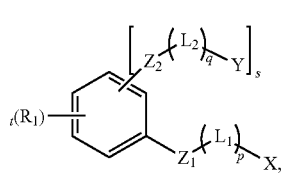

(I)

in which each of p and q, independently, is 0 or 1; s is 1 or 2; t is 3 or 4; Z$_1$ is —O—, —NH—, —N=N—, —C(O)O—, —C(O)—NH—, —NH—C(O)—, —NH—C(O)O—, or —OC(O)—NH—;
each Z$_2$, independently, is —O—, —NH—, —N=N—, —C(O)O—, —C(O)—NH—, —NH—C(O)—, —NH—C(O)O—, or —OC(O)—NH—; L$_1$ is a linker, the linker being —C(O)—, —(CH$_2$)$_m$—, —(CH$_2$)$_m$—O—, —(CH$_2$)$_m$—C(O)—, —(CH$_2$)$_m$—C(O)O—, —(CH$_2$)$_m$—OC(O)O—, —C(O)—(CH$_2$)$_m$—O—, —C(O)—(CH$_2$)$_m$—C(O)—, —OC(O)—(CH$_2$)$_m$—O—, —OC(O)—(CH$_2$)$_m$—C(O)—, or —OC(O)—(CH$_2$)$_m$—C(O)O—, in which m is 1, 2, 3, 4, 5, 6, or 7; each L$_2$, independently, is a linker, the linker being —C(O)—, —(CH$_2$)$_m$—, —(CH$_2$)$_m$—O—, —(CH$_2$)$_m$—C(O)—, —(CH$_2$)$_m$—C(O)O—, —(CH$_2$)$_m$—OC(O)O—, —C(O)—(CH$_2$)$_m$—O—, —C(O)—(CH$_2$)$_m$—C(O)—, —OC(O)—(CH$_2$)$_m$—O—, —OC(O)—(CH$_2$)$_m$—C(O)—, or —OC(O)—(CH$_2$)$_m$—C(O)O—, in which m is 1, 2, 3, 4, 5, 6, or 7; X is a H$_2$S-releasing moiety or a NO-releasing moiety; each Y, independently, is a NO-releasing moiety or a H$_2$S-releasing moiety, provided that not all of X and Y are simultaneously H$_2$S-releasing moieties or NO-releasing moieties; and each R$_1$, independently, is H, halo, NO$_2$, N$_3$, C$_1$-C$_{10}$ alkyl, OR, OC(O)R, N(R)$_2$, NH—C(O)R, S(O)R, or N=N—R, in which each R, independently, is H, C$_1$-C$_{10}$ alkyl, or aryl. The H$_2$S-releasing moiety and NO-releasing moiety assigned to X and Y in formula (I) can be those listed above.

In some embodiments, the compounds of formula (I) can be the compounds of formula (Ia):

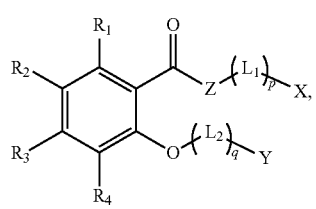

(Ia)

in which each of p and q, independently, is 0 or 1; each of L$_1$ and L$_2$, independently, is a linker, the linker being —C(O)—, —(CH$_2$)$_m$—, —(CH$_2$)$_m$—O—, —(CH$_2$)$_m$—C(O)—, —(CH$_2$)$_m$—C(O)O—, —(CH$_2$)$_m$—OC(O)O—, —C(O)—(CH$_2$)$_m$—O—, —C(O)—(CH$_2$)$_m$—C(O)—, —OC(O)—(CH$_2$)$_m$—O—, —OC(O)—(CH$_2$)$_m$—C(O)—, or —OC(O)—(CH$_2$)$_m$—C(O)O—, in which m is 1, 2, 3, 4, 5, 6, or 7; X is a H$_2$S-releasing moiety or a NO-releasing moiety; Y is a NO-releasing moiety or a H$_2$S-releasing moiety, provided that X and Y are not simultaneously H$_2$S-releasing moieties or NO-releasing moieties; Z is O or NH; and
each of R$_1$, R$_2$, R$_3$, and R$_4$, independently, is H, halo, C$_1$-C$_{10}$ alkyl, or N(R)$_2$, in which R is H or C$_1$-C$_{10}$ alkyl.

In a subset of the compounds of formula (I), X can be

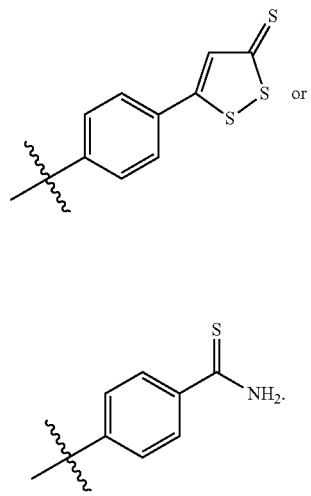

In some embodiments of such compounds, Y can be —C(O)—(CH$_2$)$_m$—ONO$_2$, p and q can be 0, s can be 1, and t can be 4. Examples of such compounds are

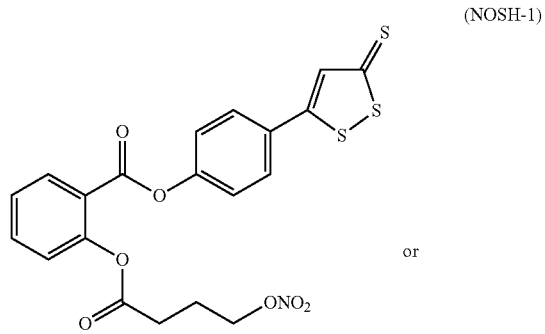

(NOSH-1)

or

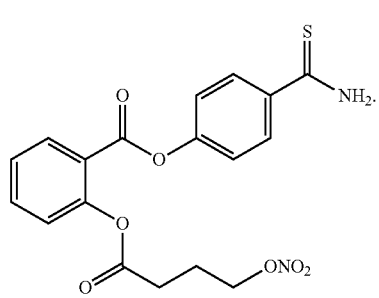

(NOSH-3)

In some embodiments of such compounds, Y can be —(CH$_2$)$_n$—ONO$_2$, p can be 0, q can be 1, s can be 1, t can be 4, and L$_2$ can be —OC(O)—(CH$_2$)$_m$—C(O)—. An example of such compounds is (NOSH-2)
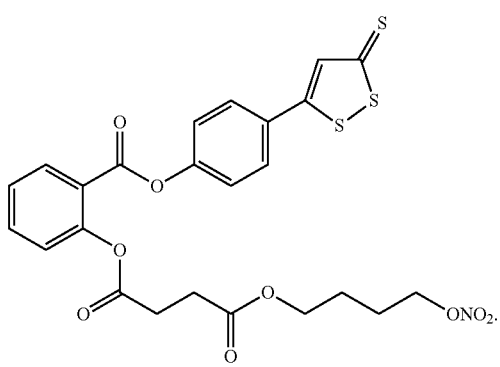
In another subset of the compounds of formula (I), X can be —C(O)—(CH$_2$)n-ONO$_2$. In such compounds, Y can be
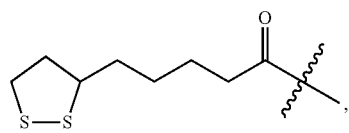 [SMILES: *C(=O)CCCCC1CCSS1]
p and q can be 0, s can be 1, and t can be 4. An example of such compounds is
(NOSH-4)
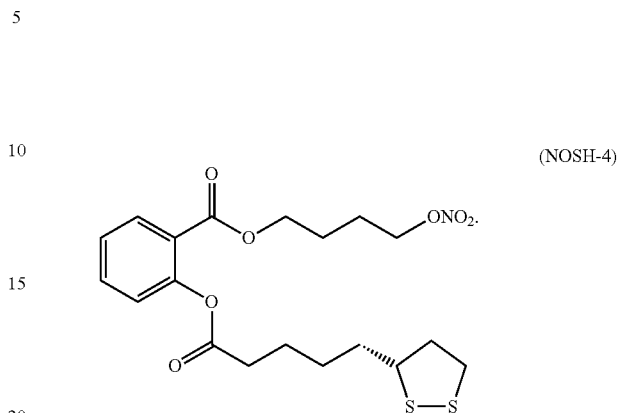
Other examples of the compounds of formula (I) include:
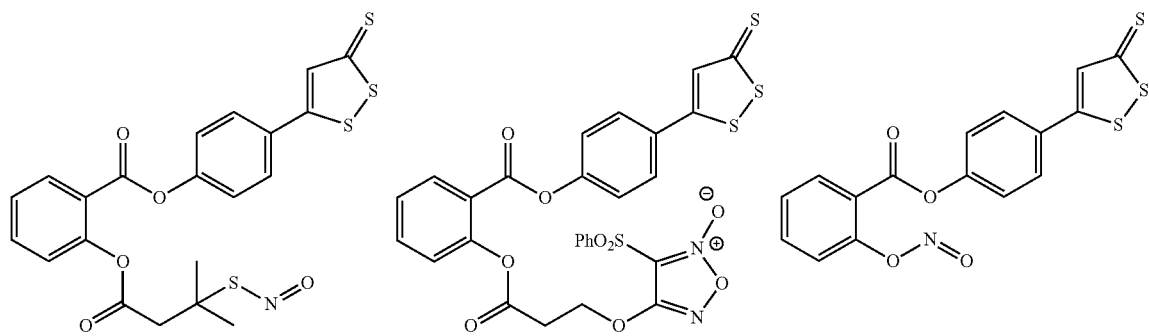
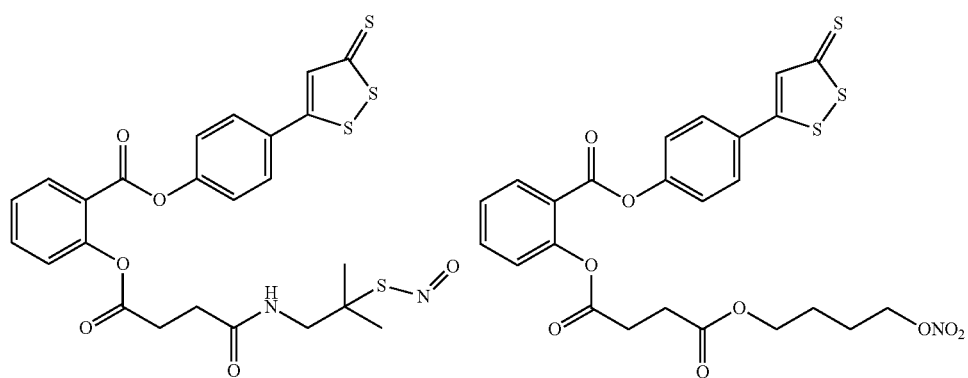

-continued
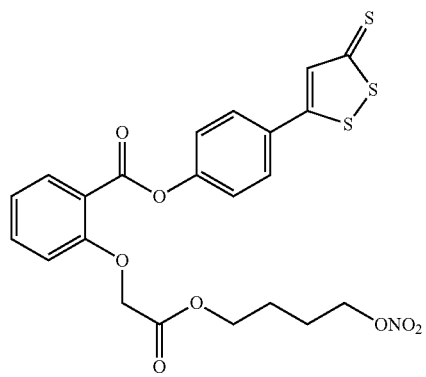
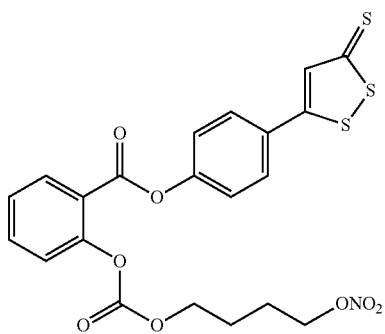
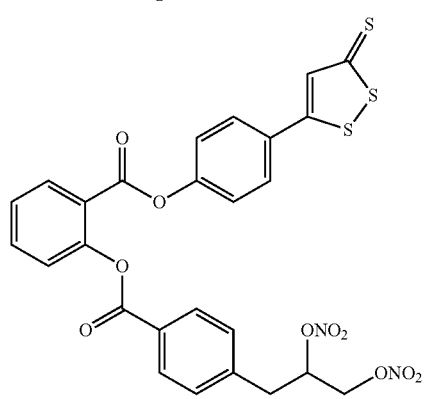
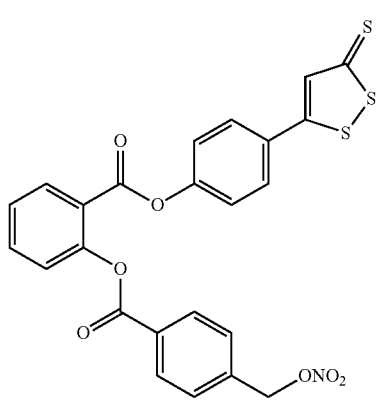
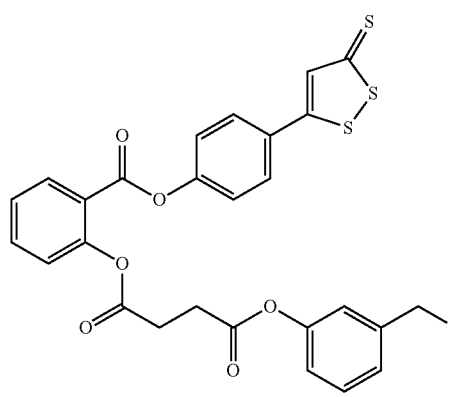
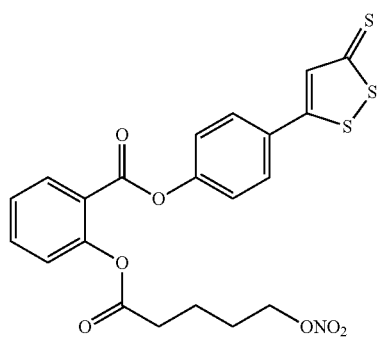
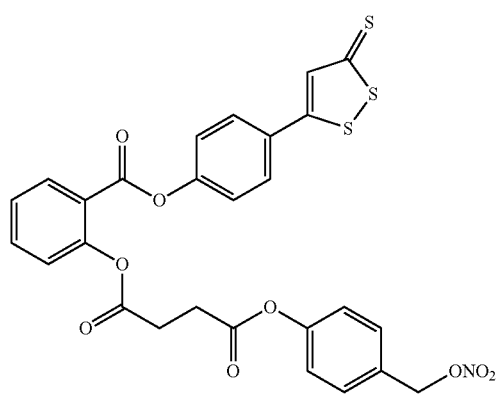
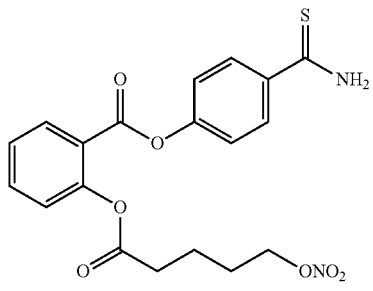

-continued
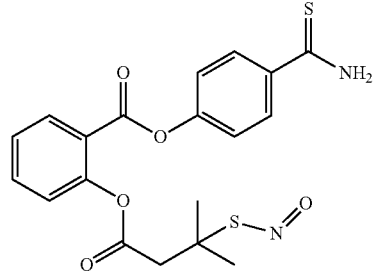
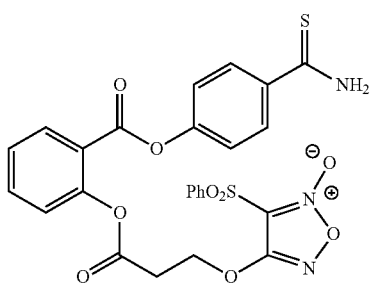
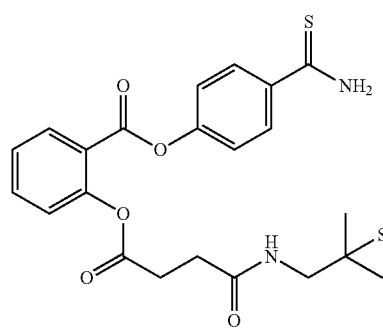
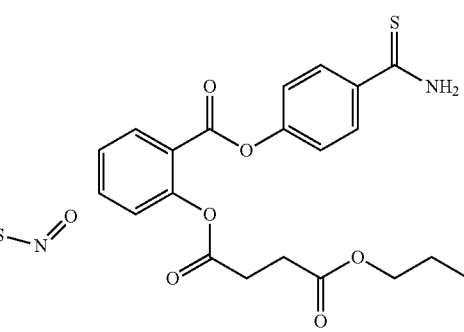
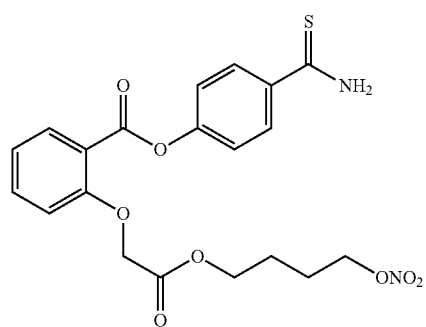
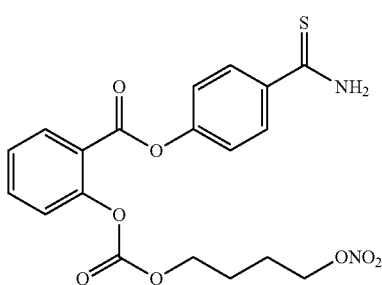
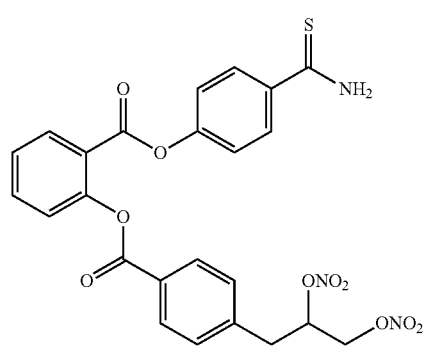
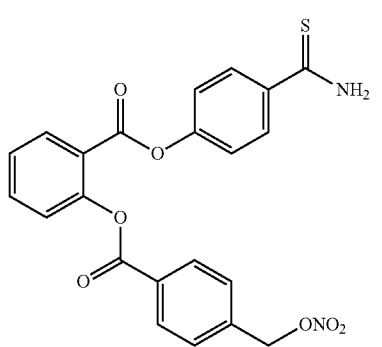
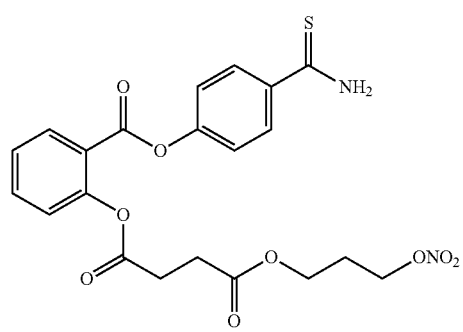
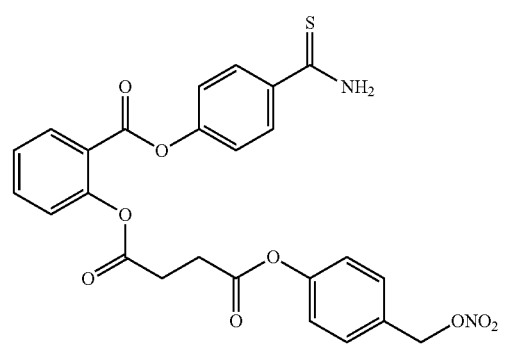

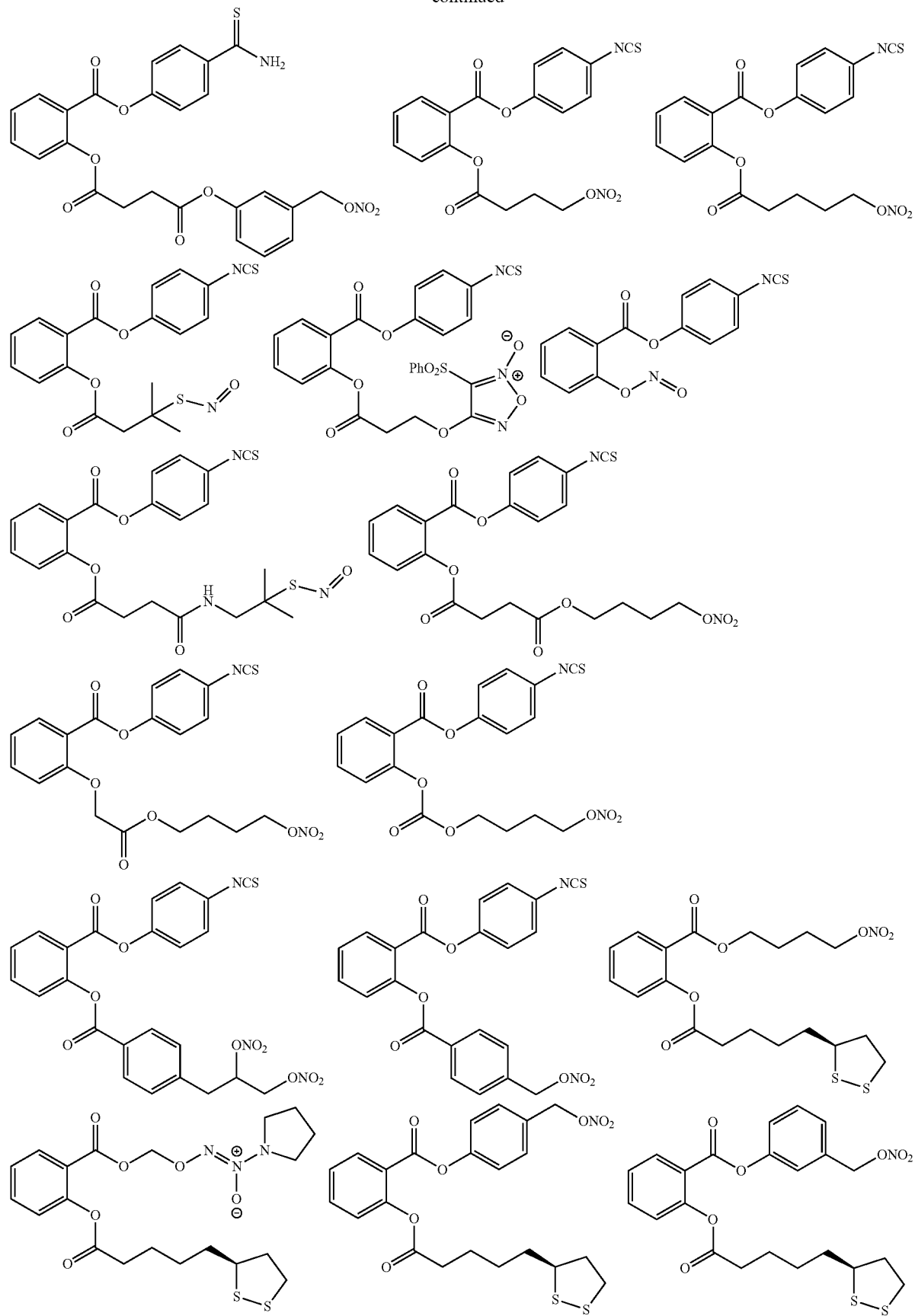
-continued

21
-continued
22
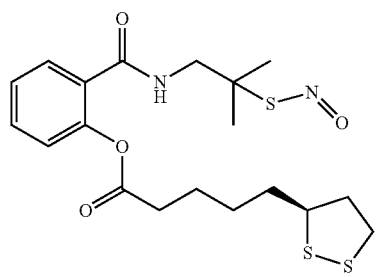 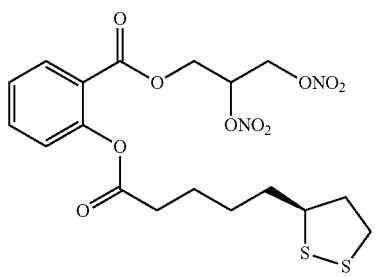 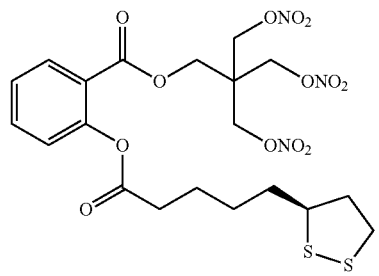
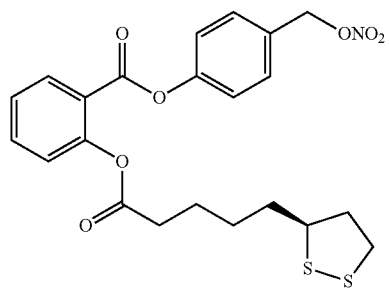 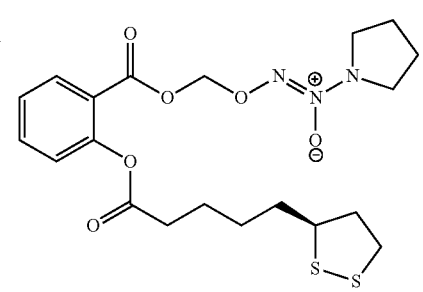 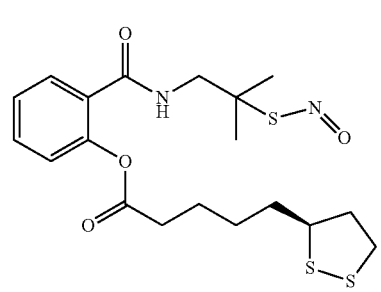
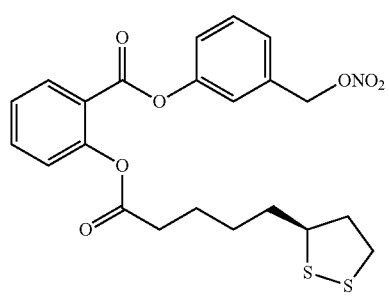 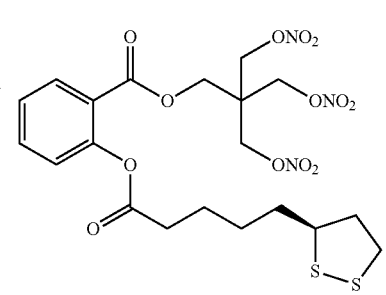 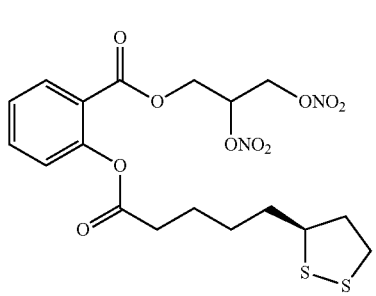
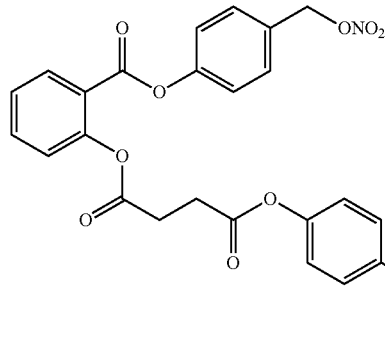 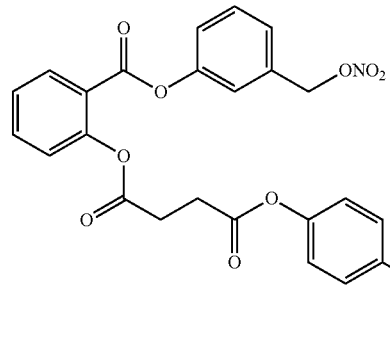
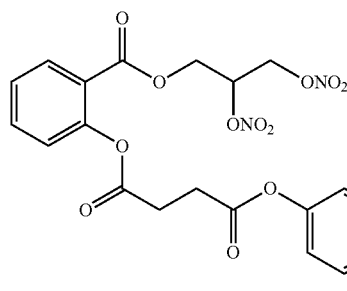 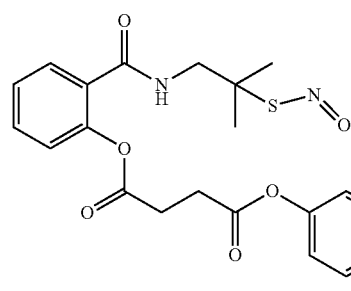

23
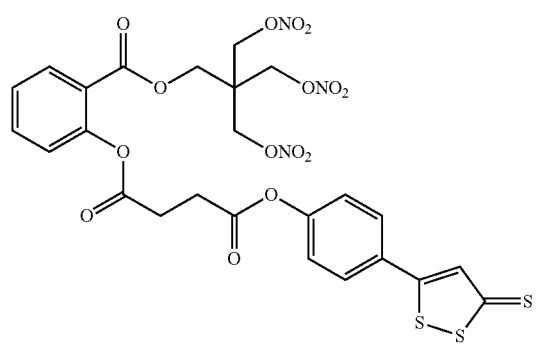
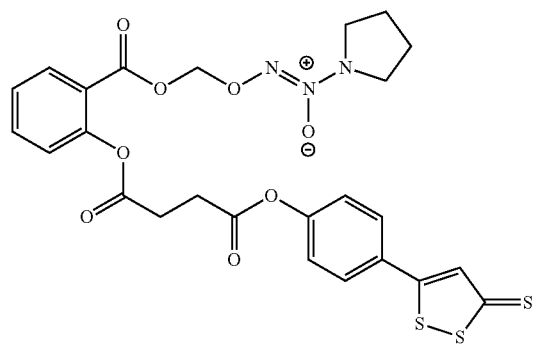
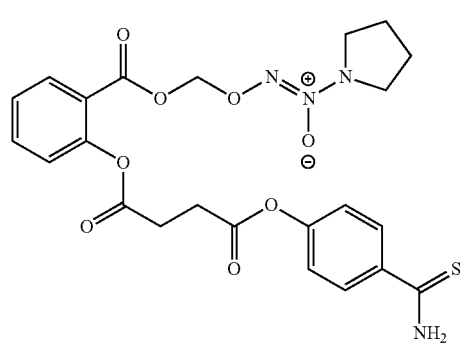
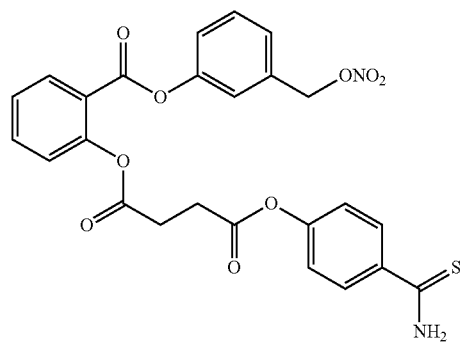
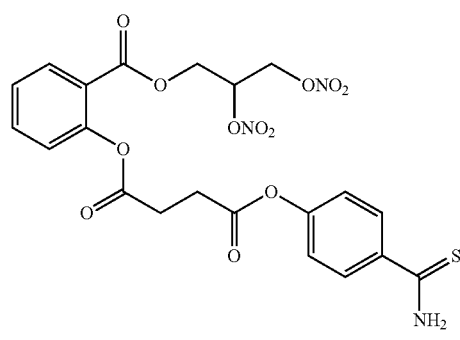
24
-continued
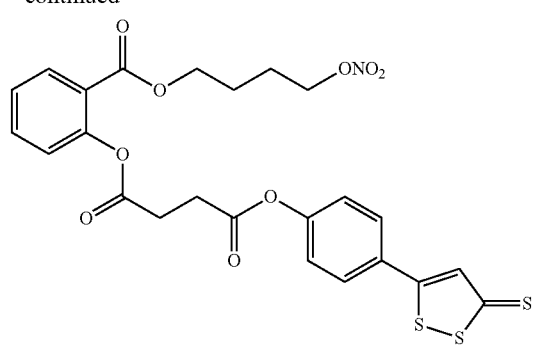
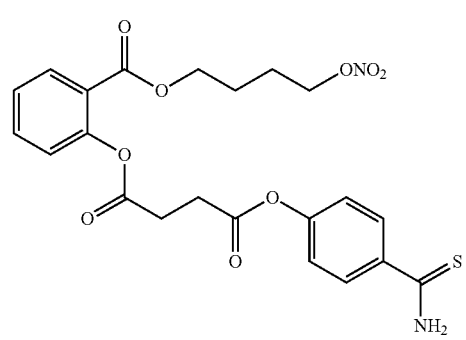
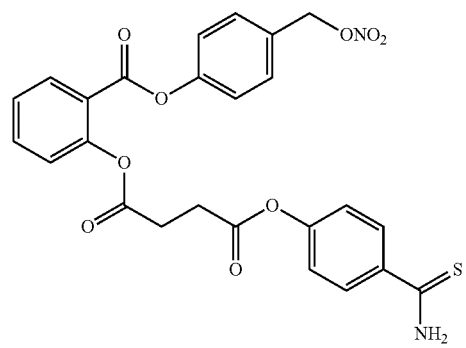
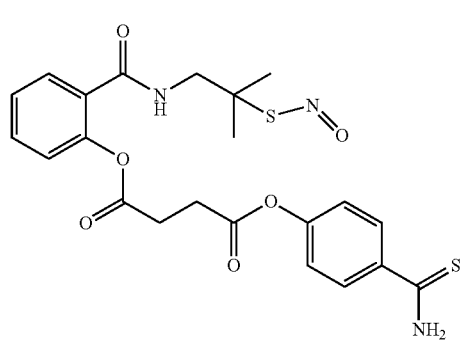
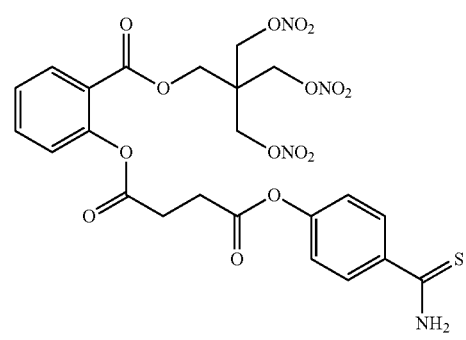

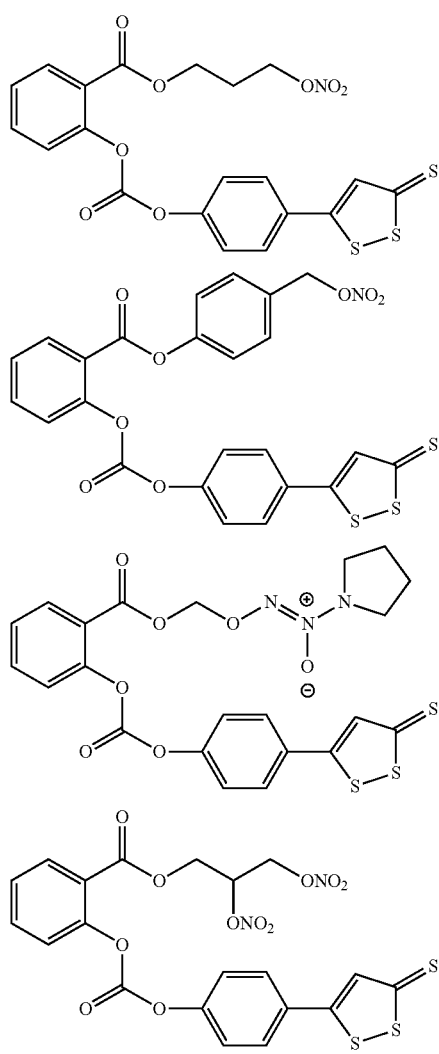
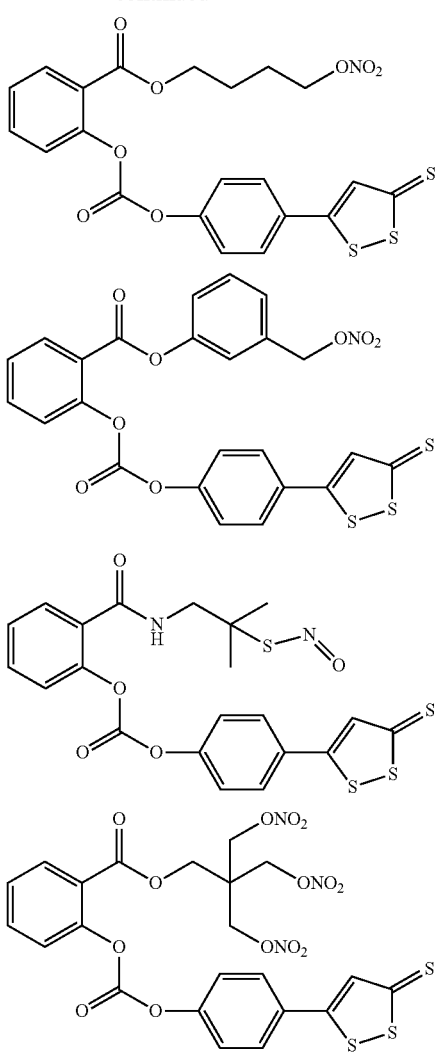
-continued
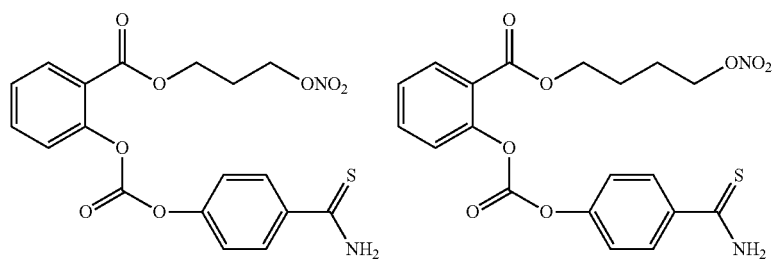
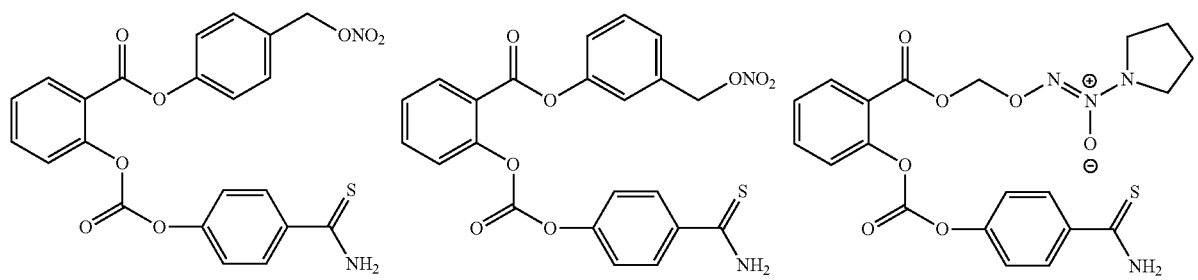

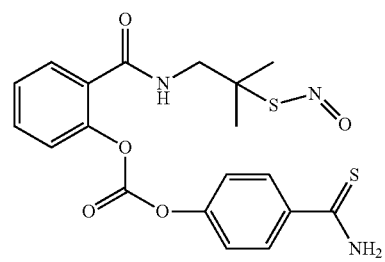
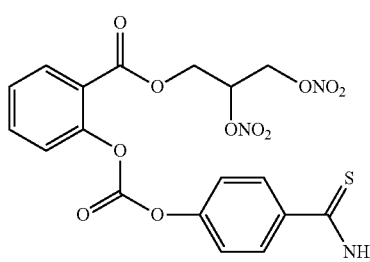
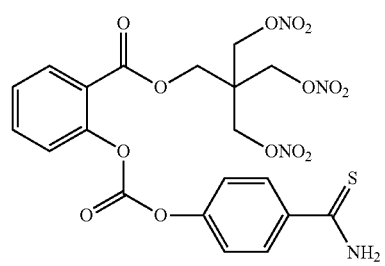
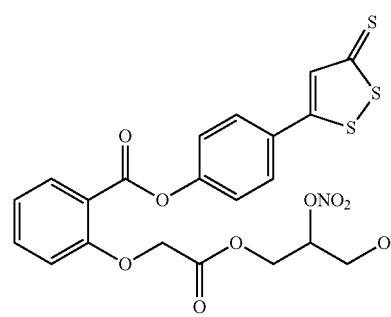
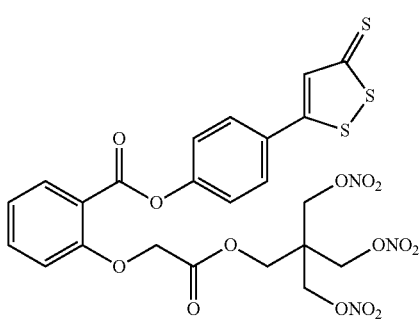
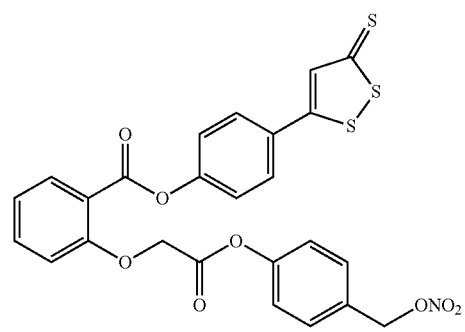
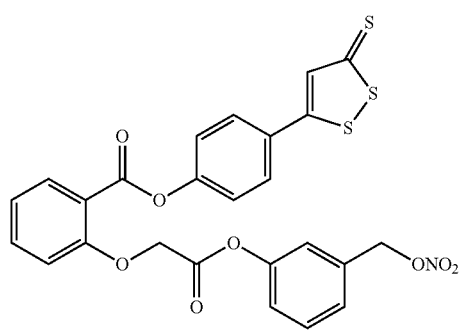
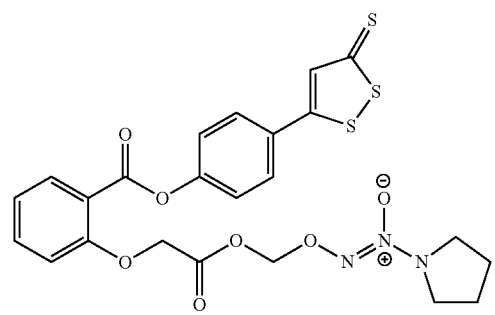
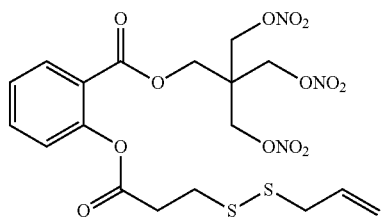
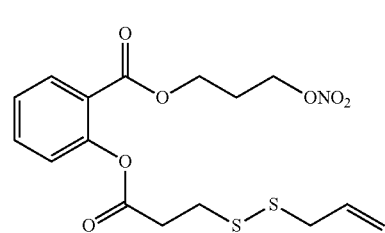
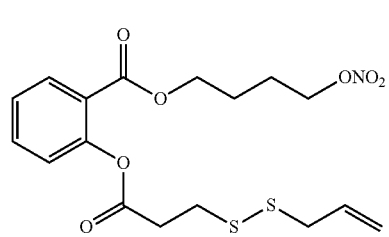
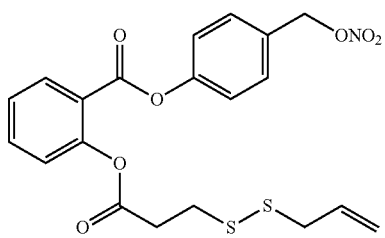
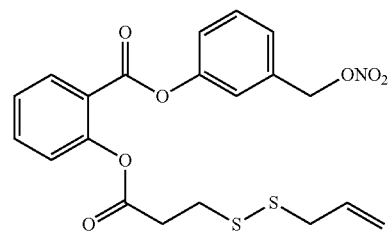
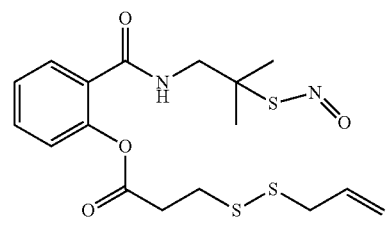
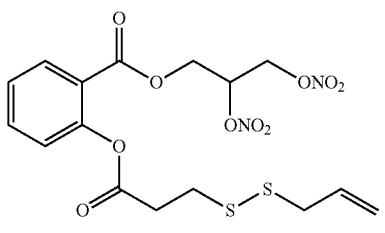

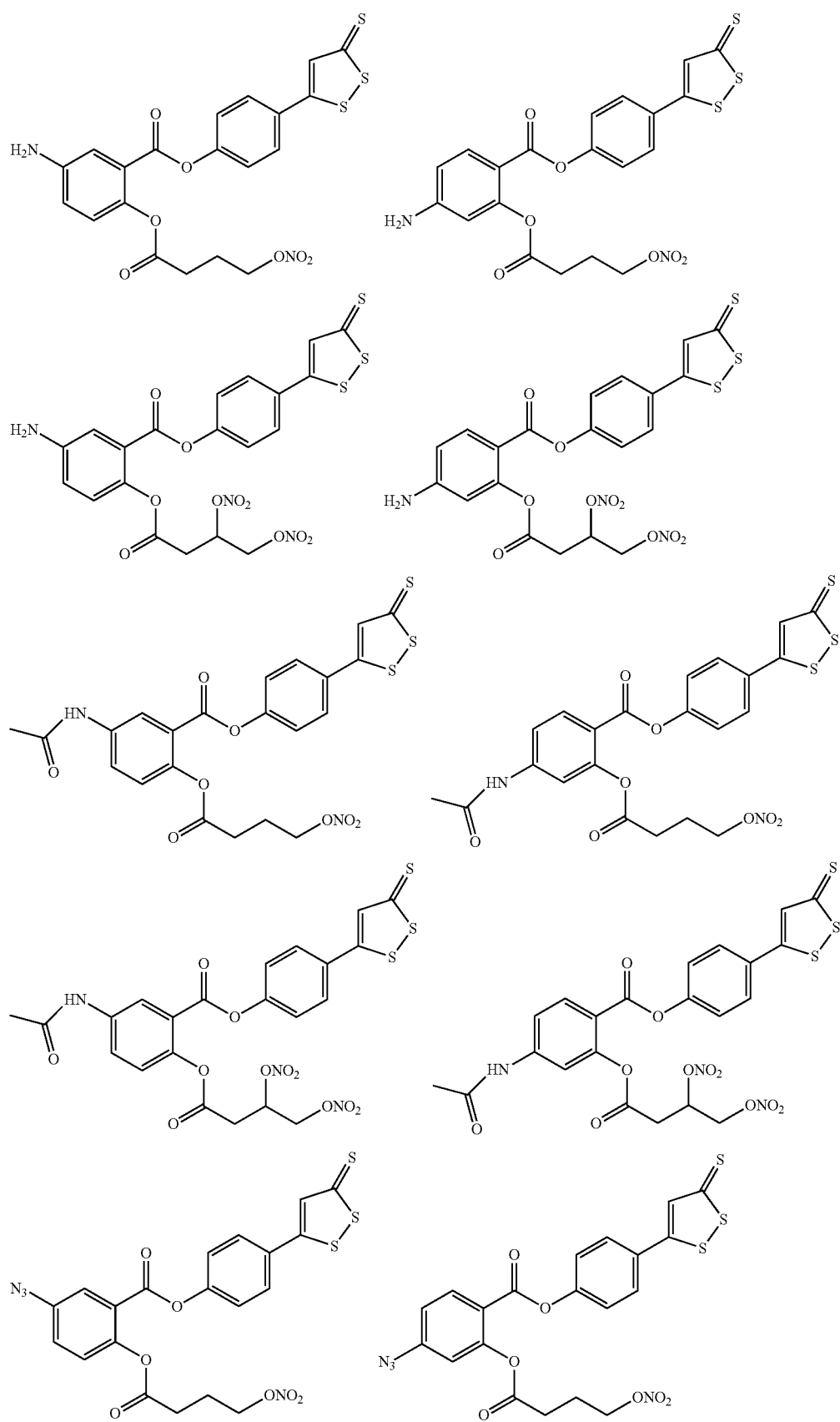

-continued
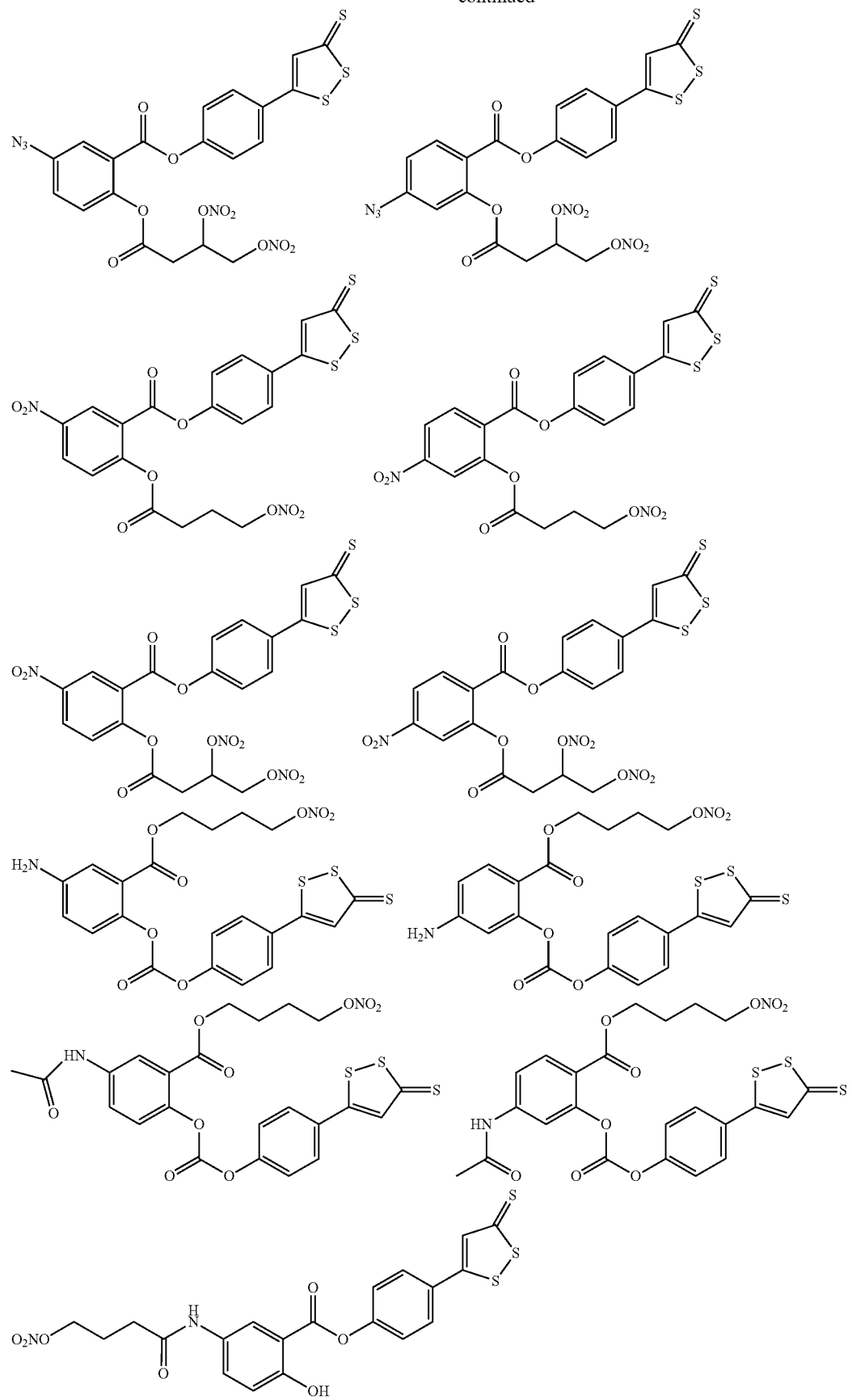

-continued
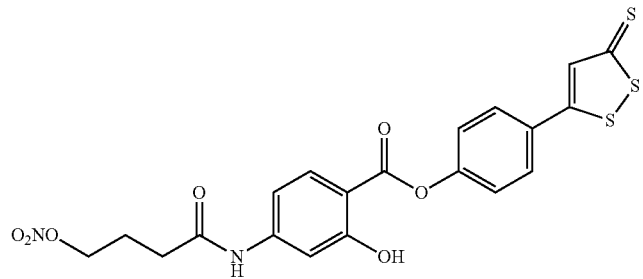
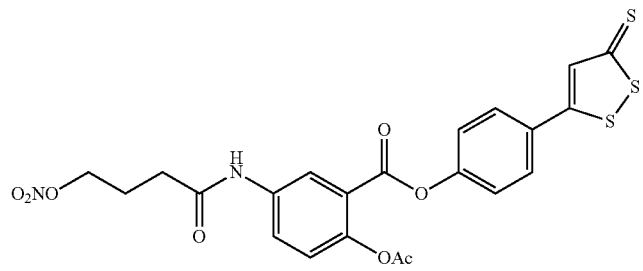
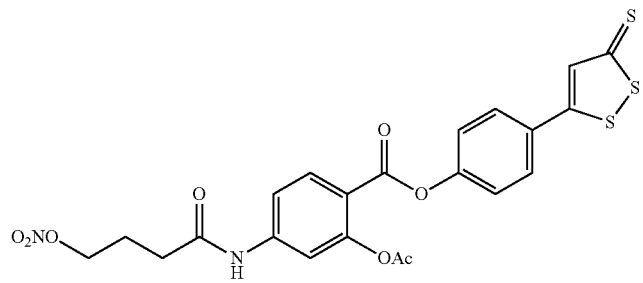
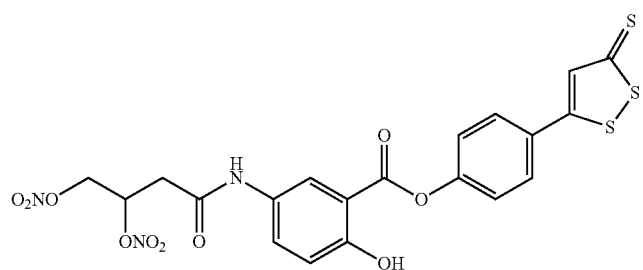
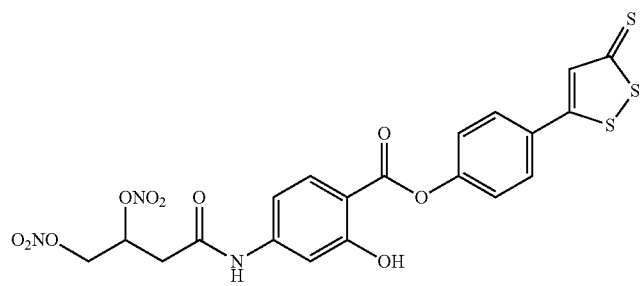
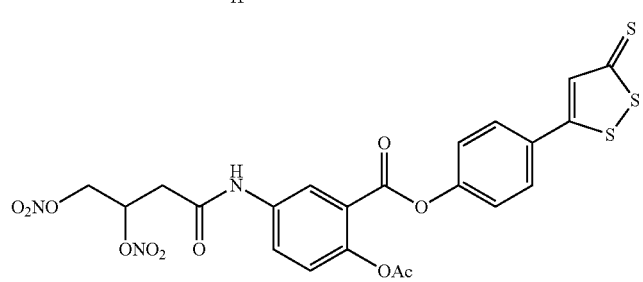

-continued
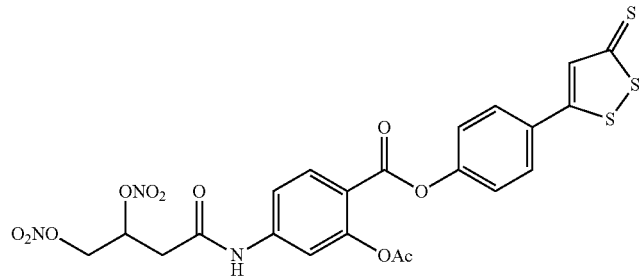
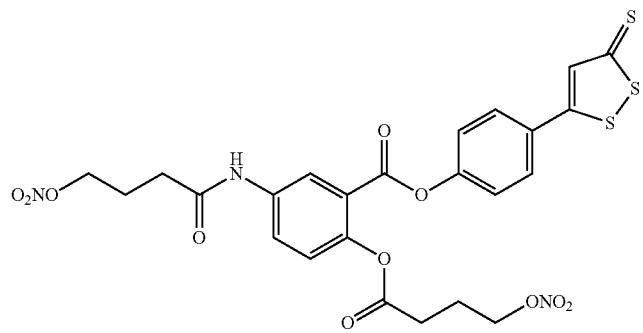
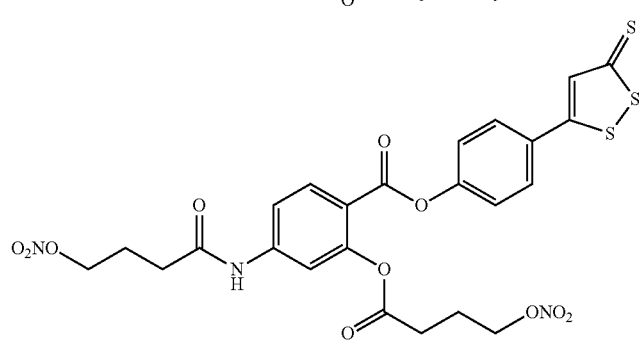
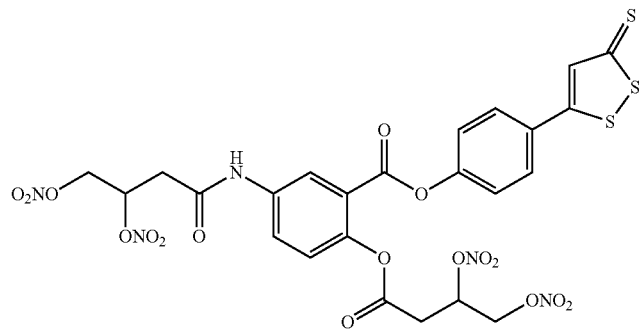
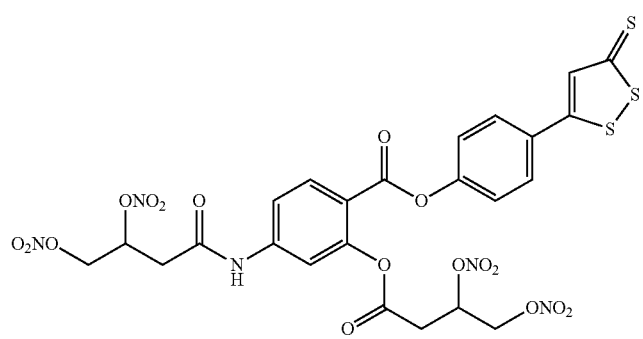
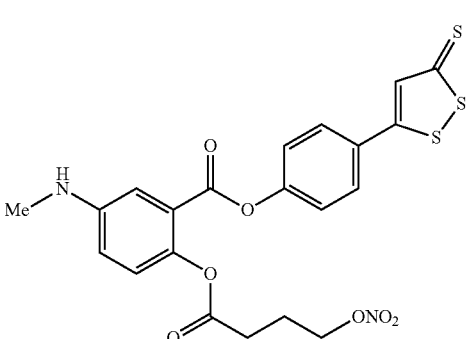

-continued
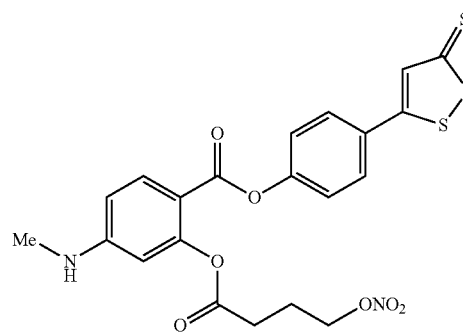
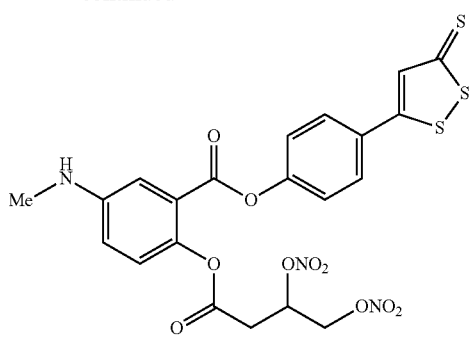
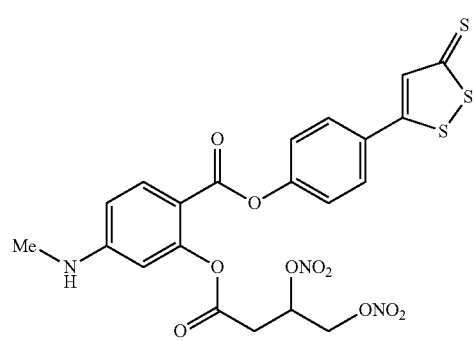
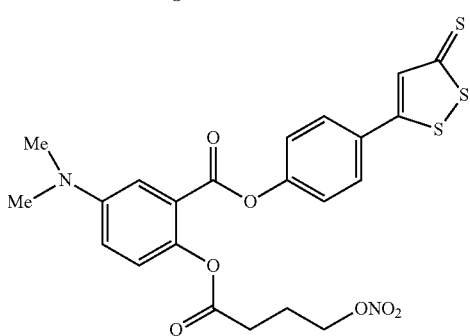
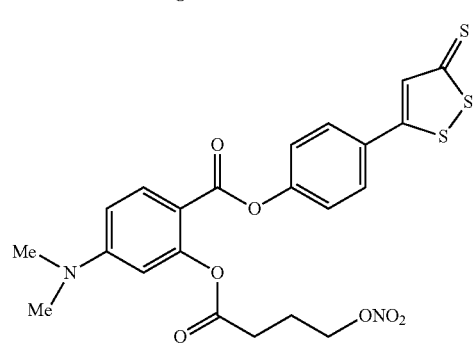
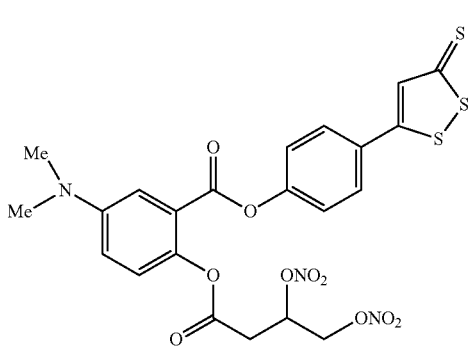
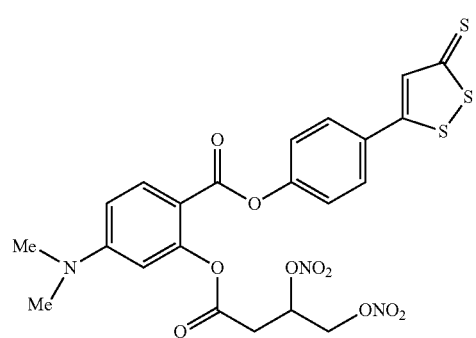
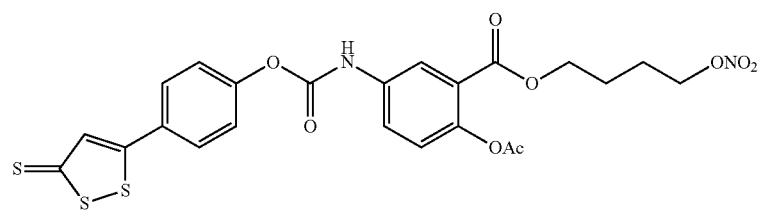

-continued
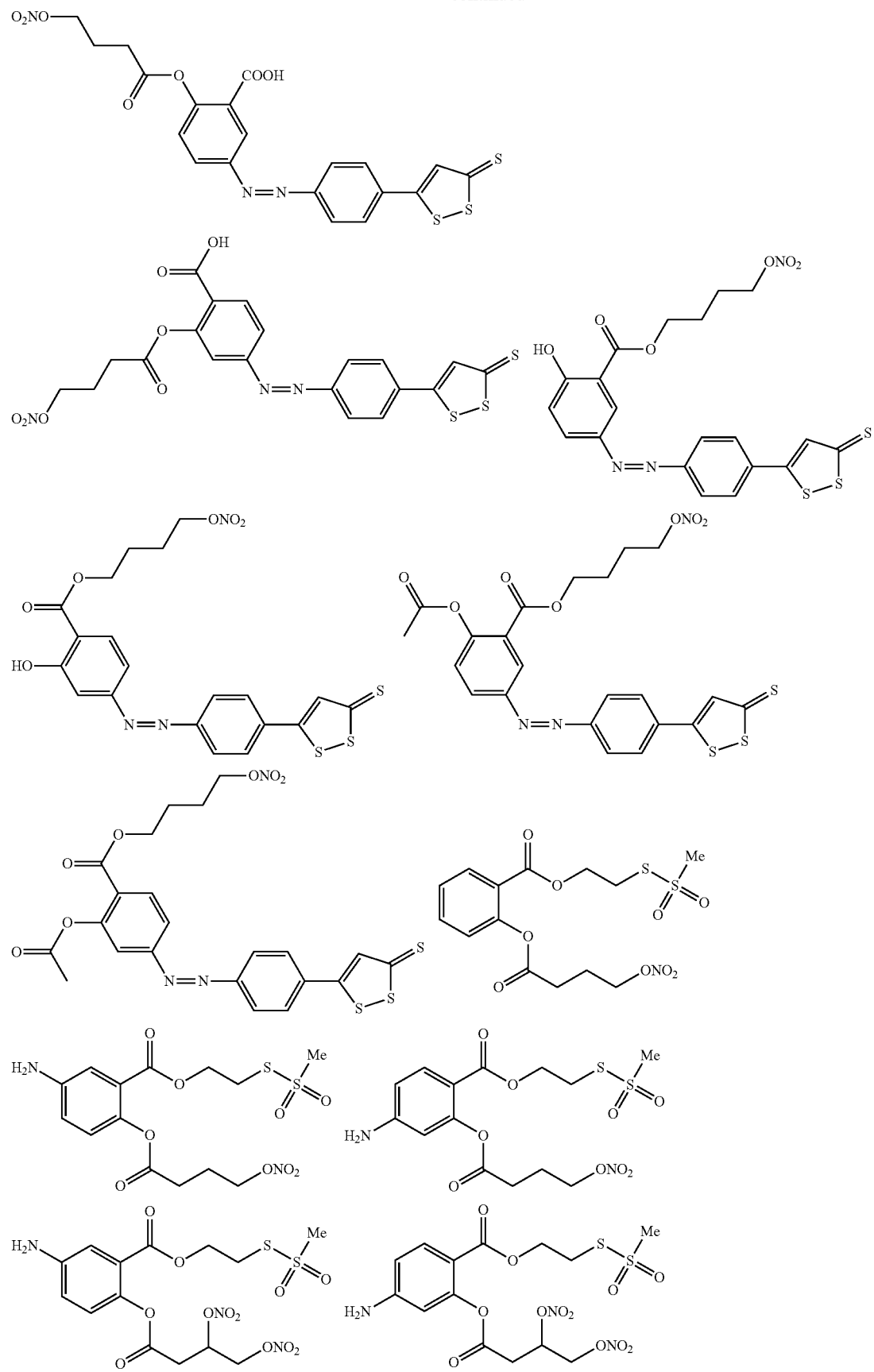

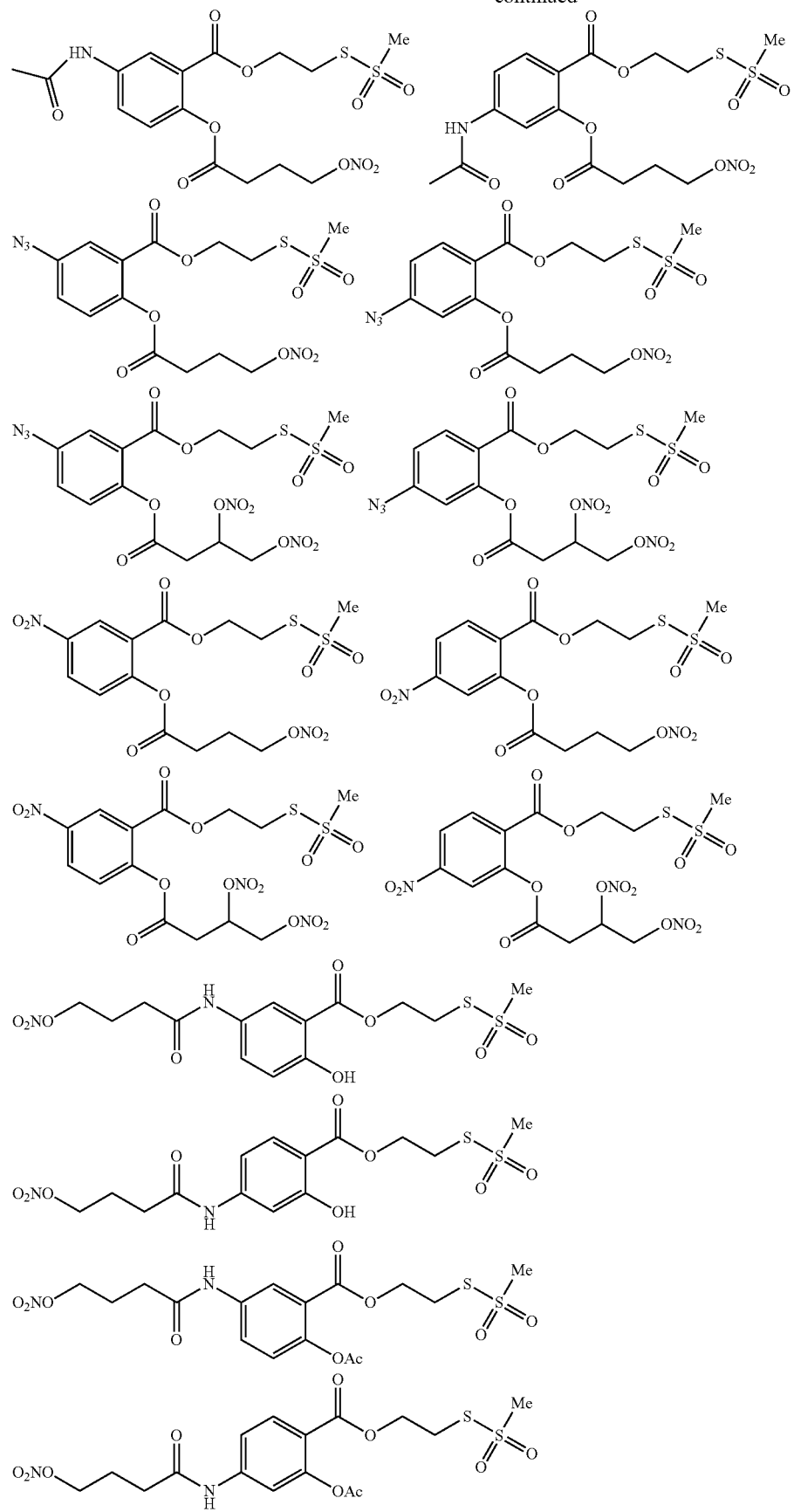

-continued
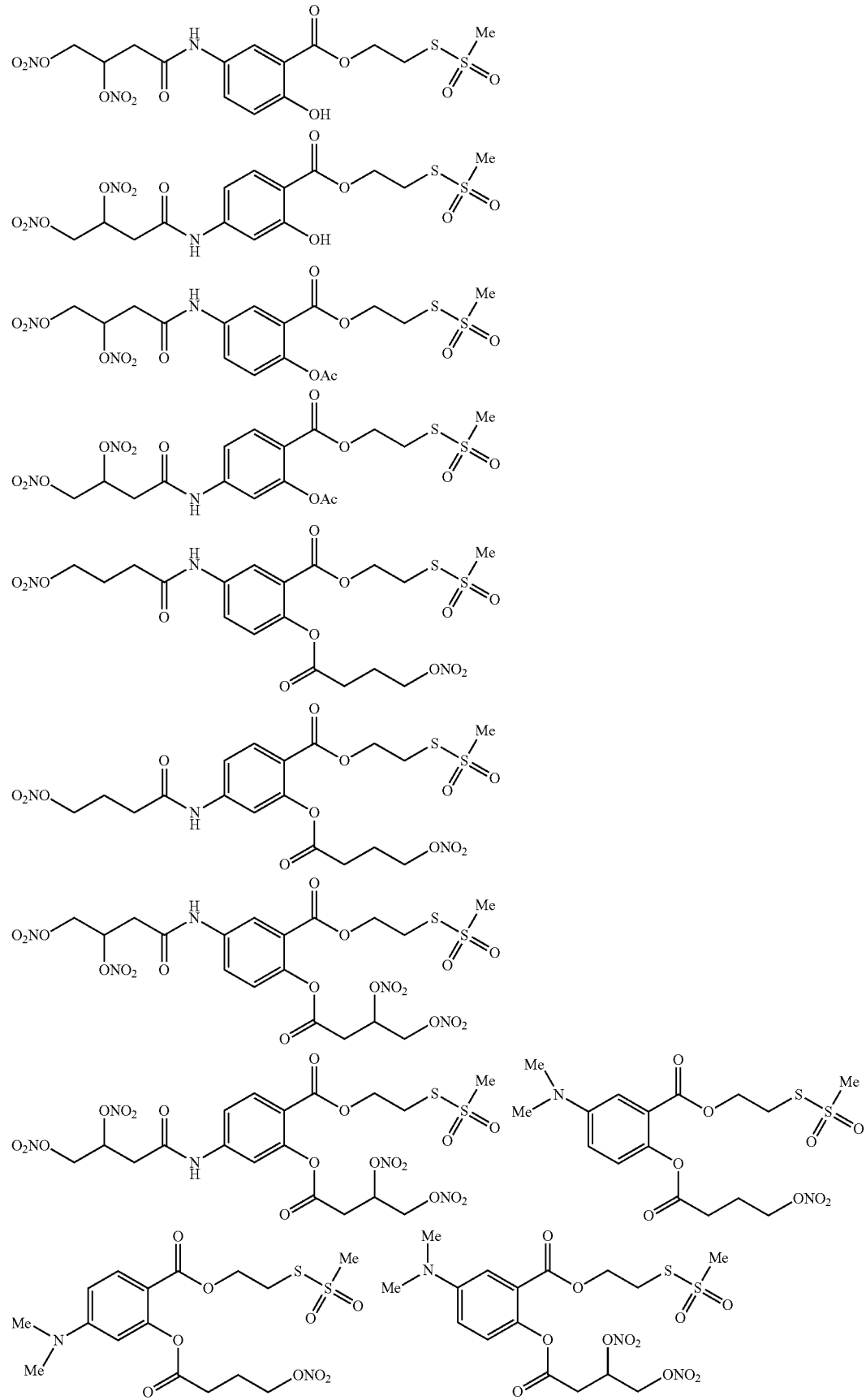

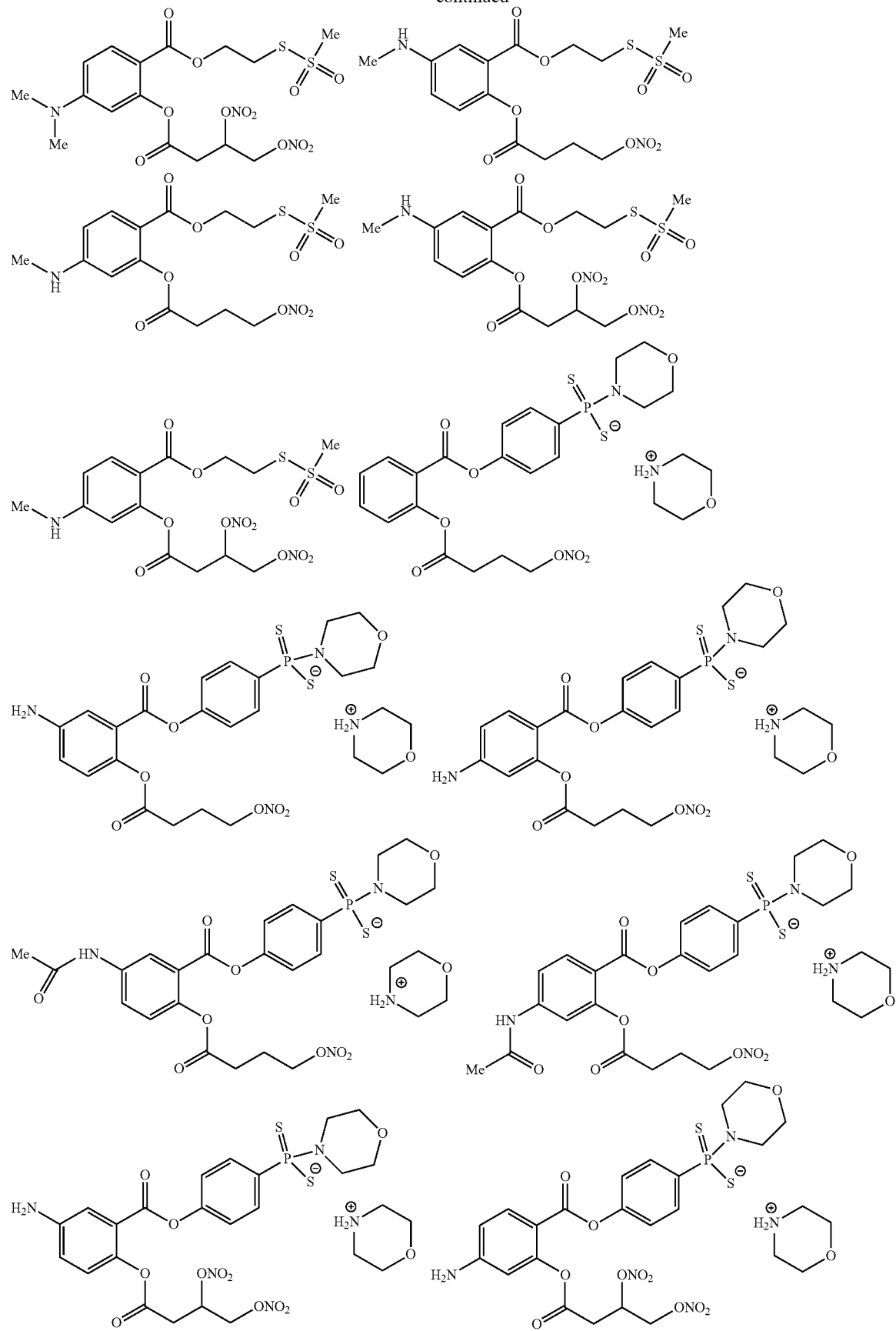

-continued
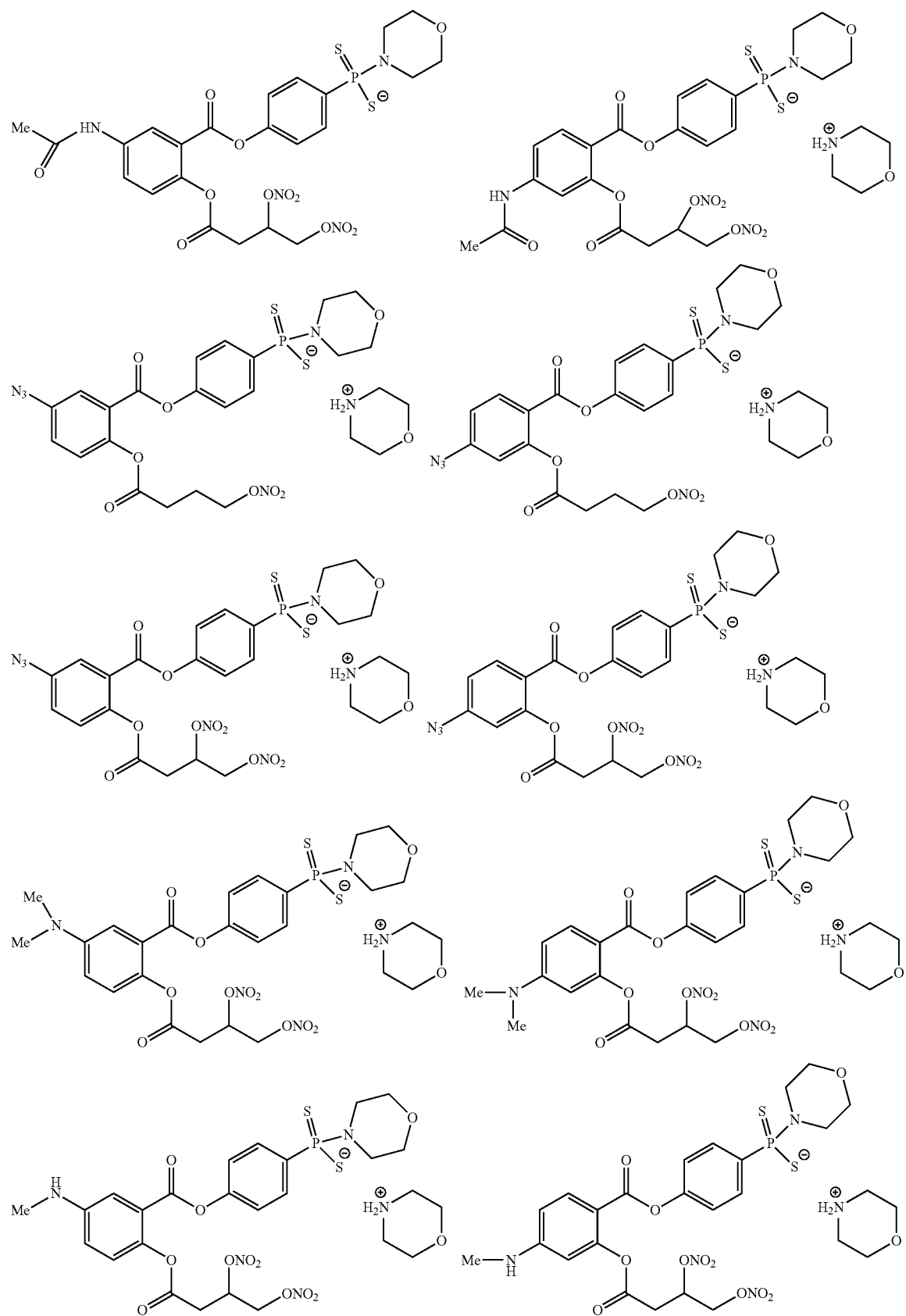

-continued
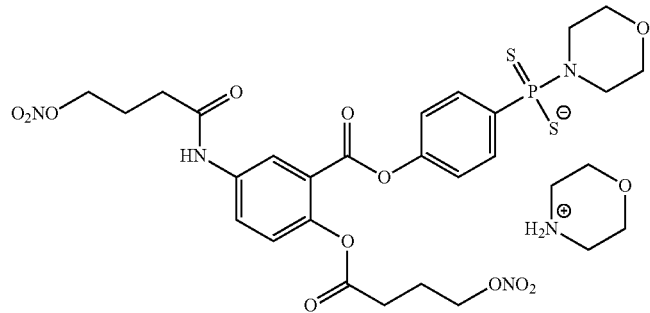
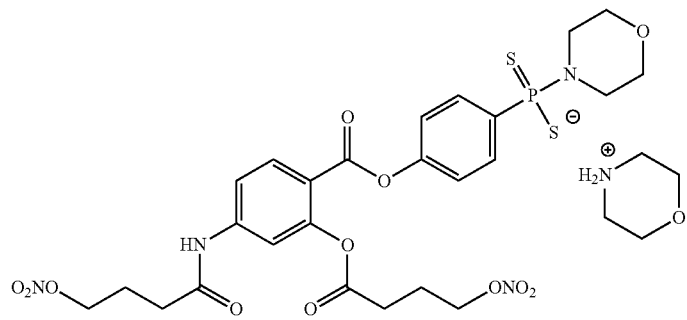
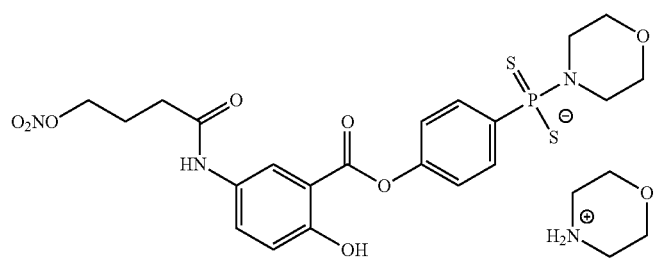
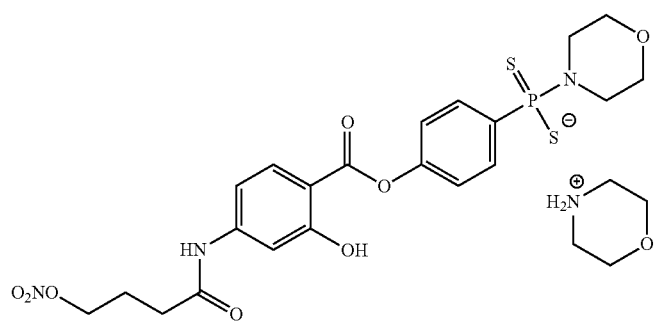
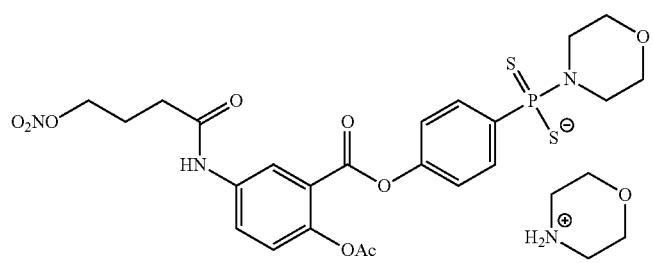

51
52
-continued
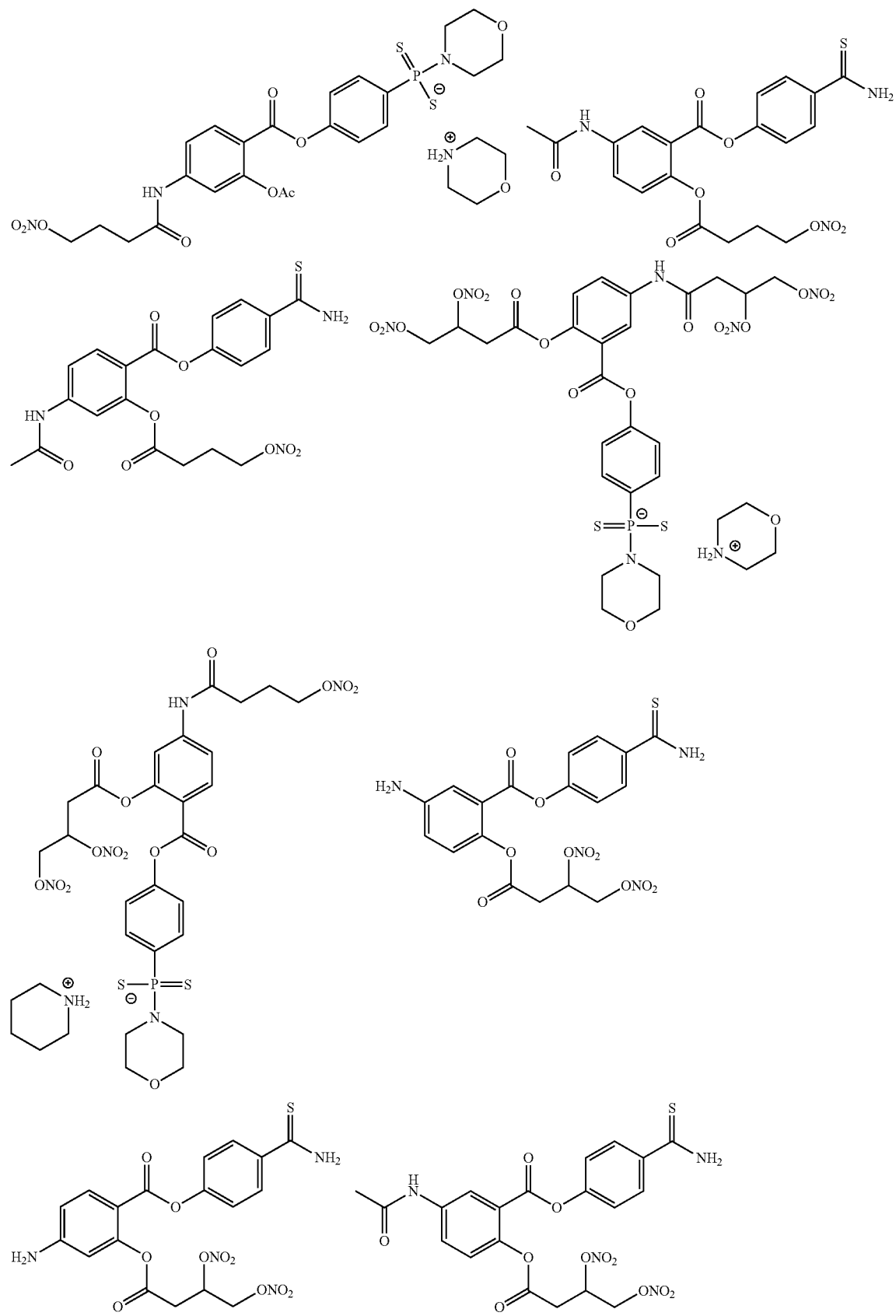

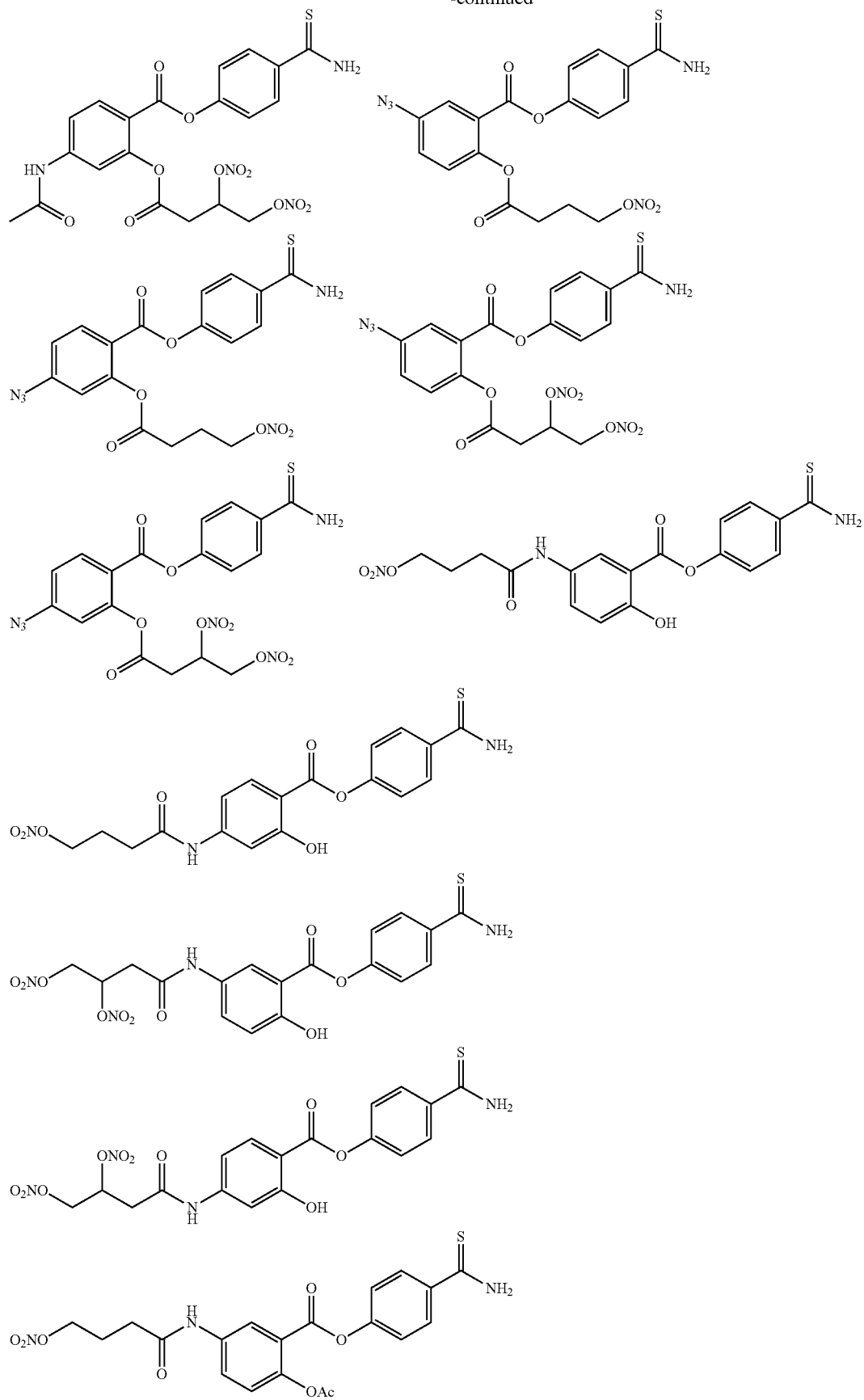

-continued
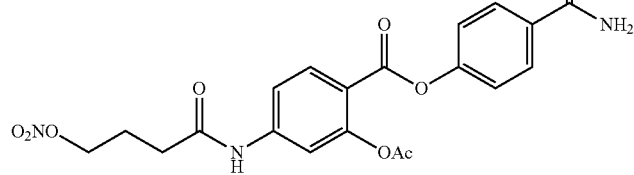
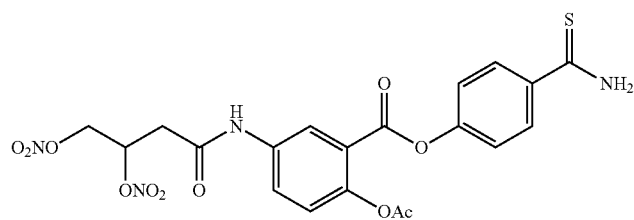
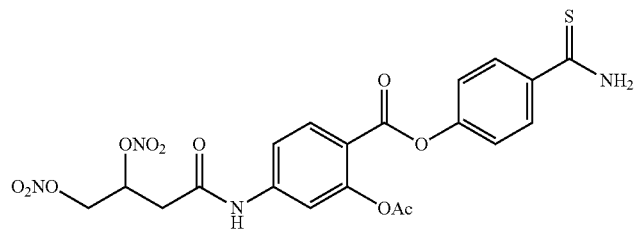
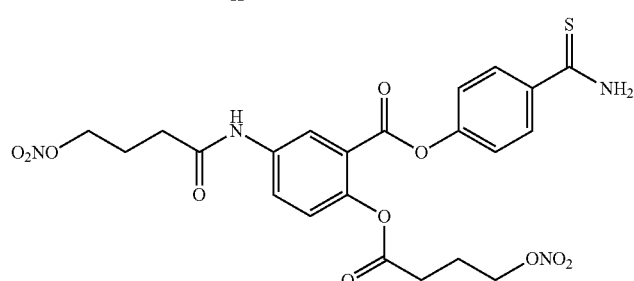
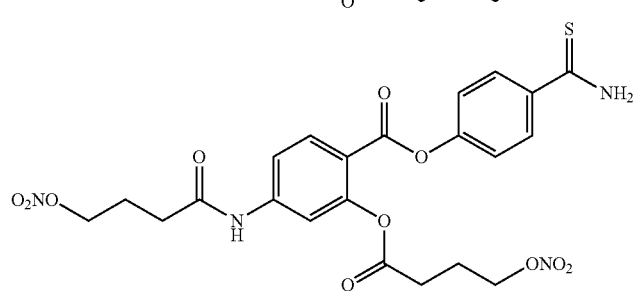
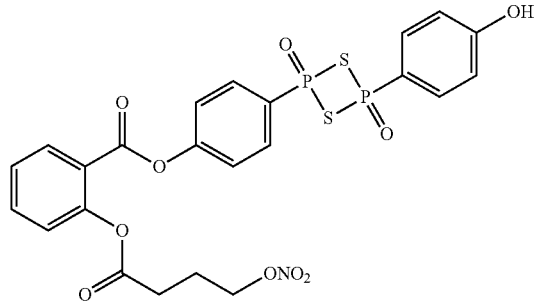
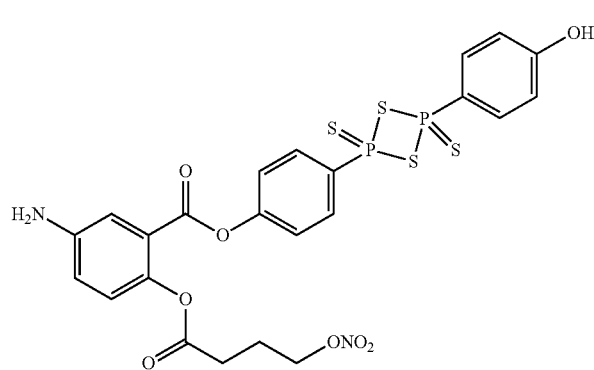
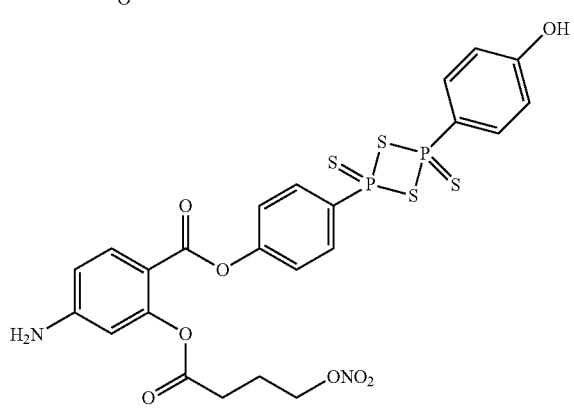

-continued
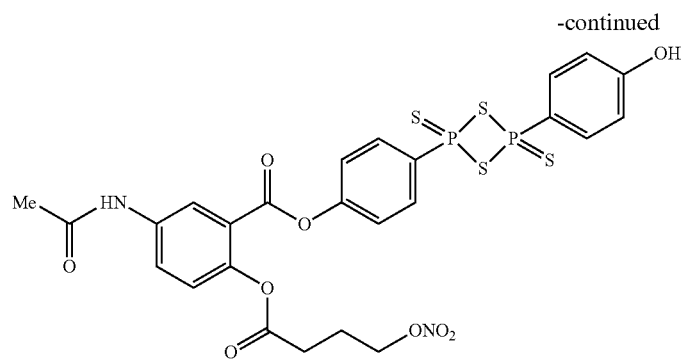
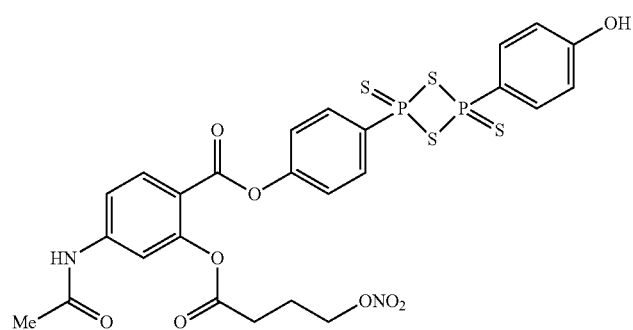
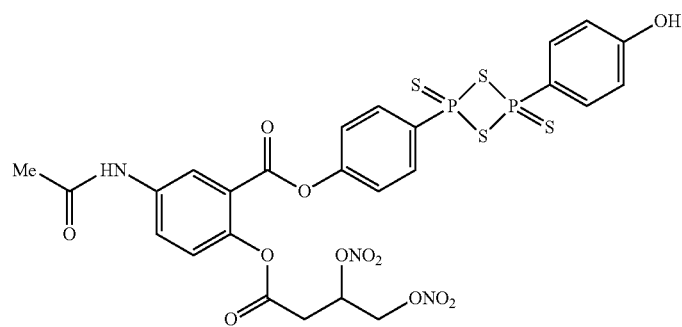
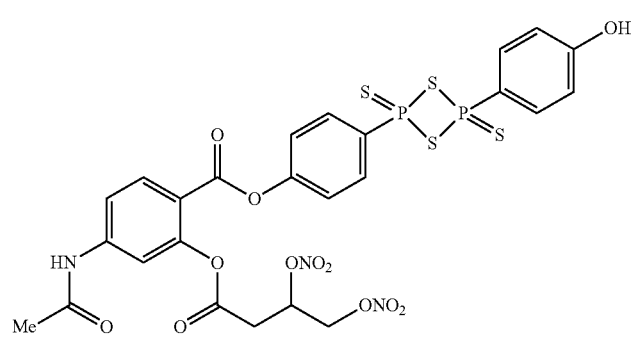
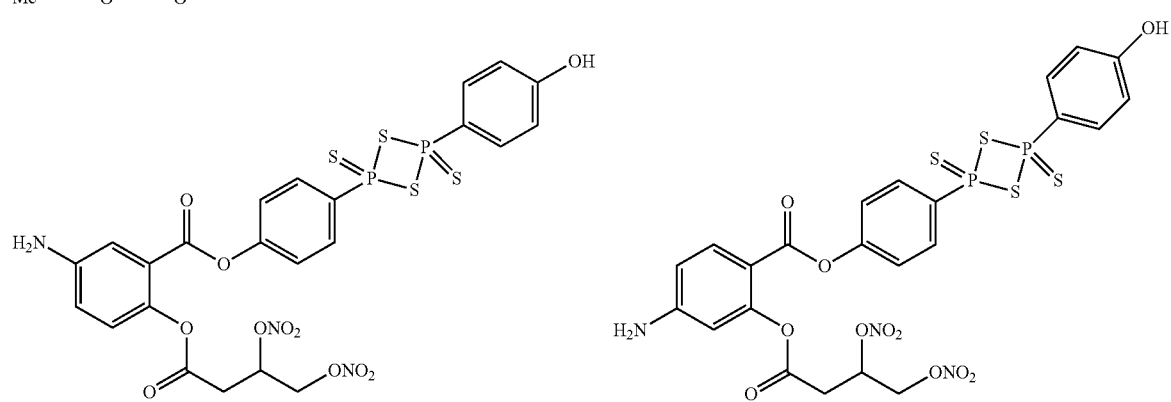

-continued
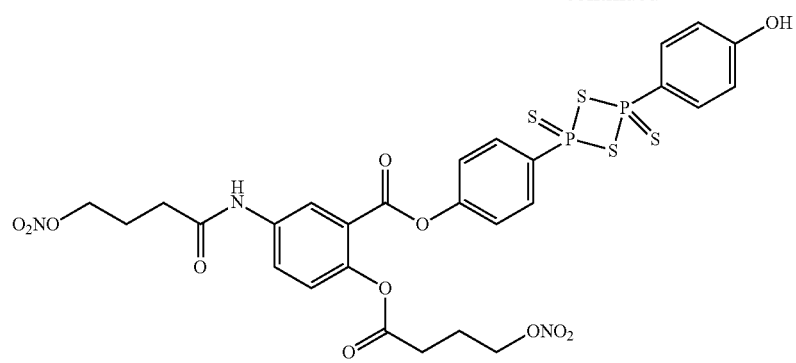
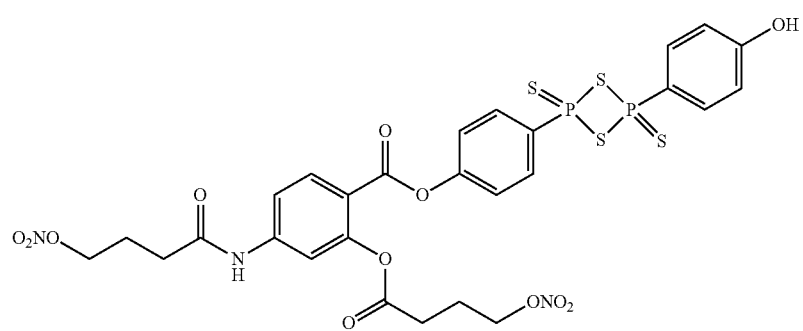
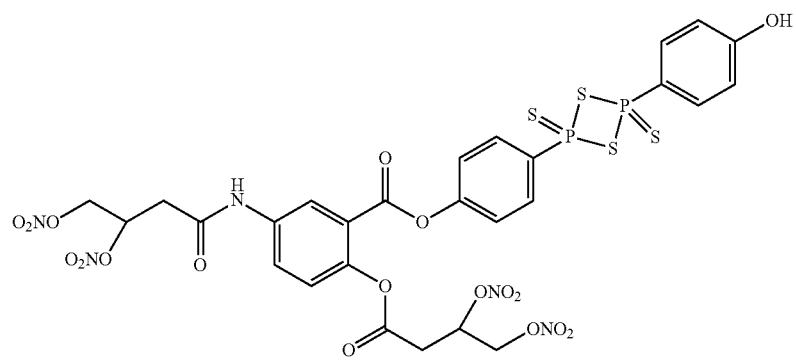
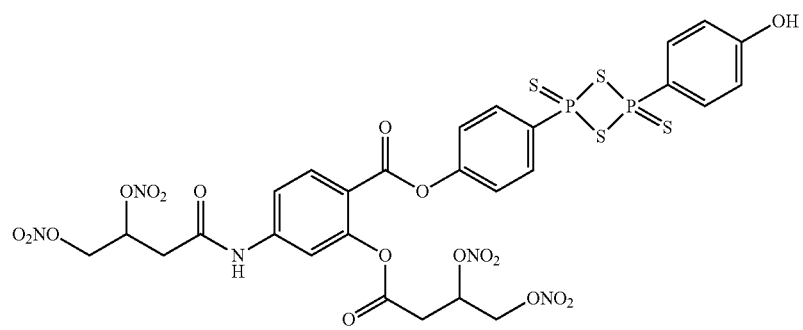
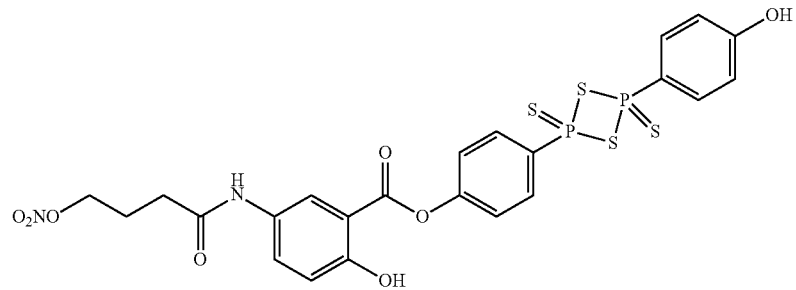

-continued
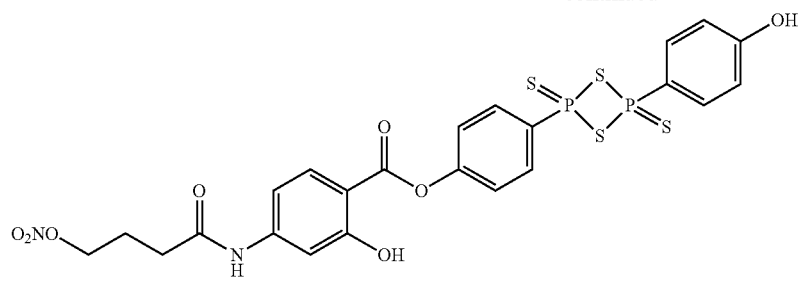
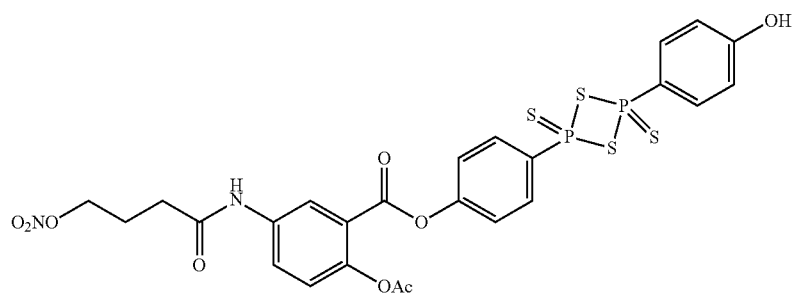
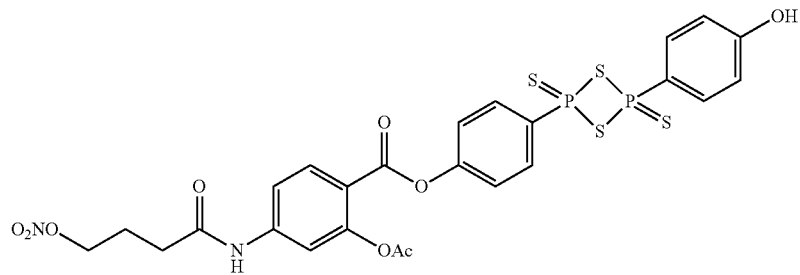
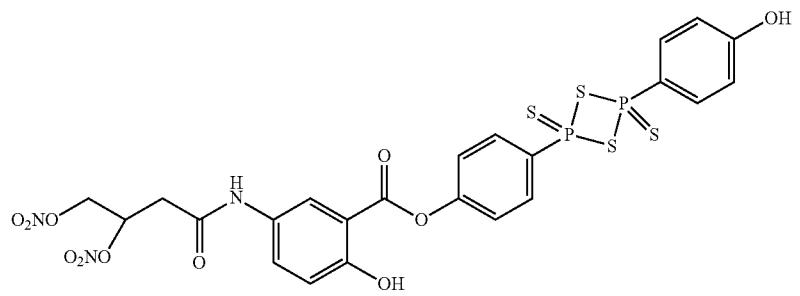
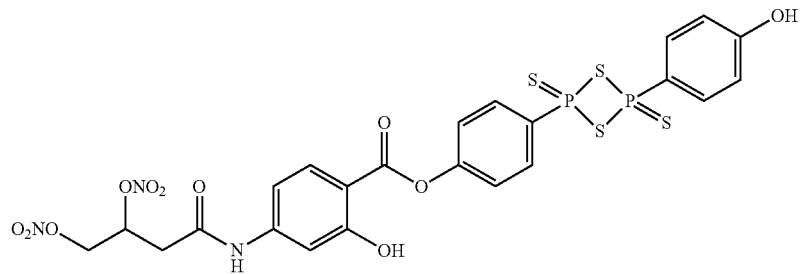
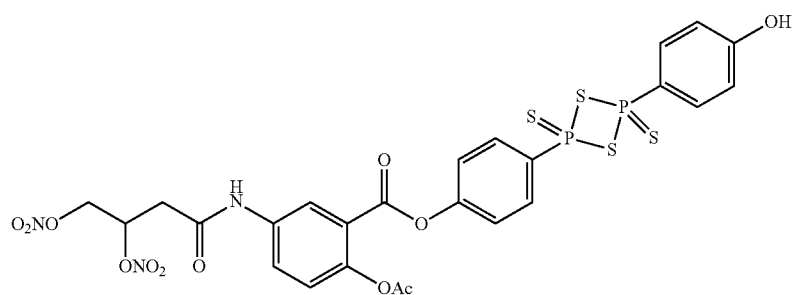

-continued
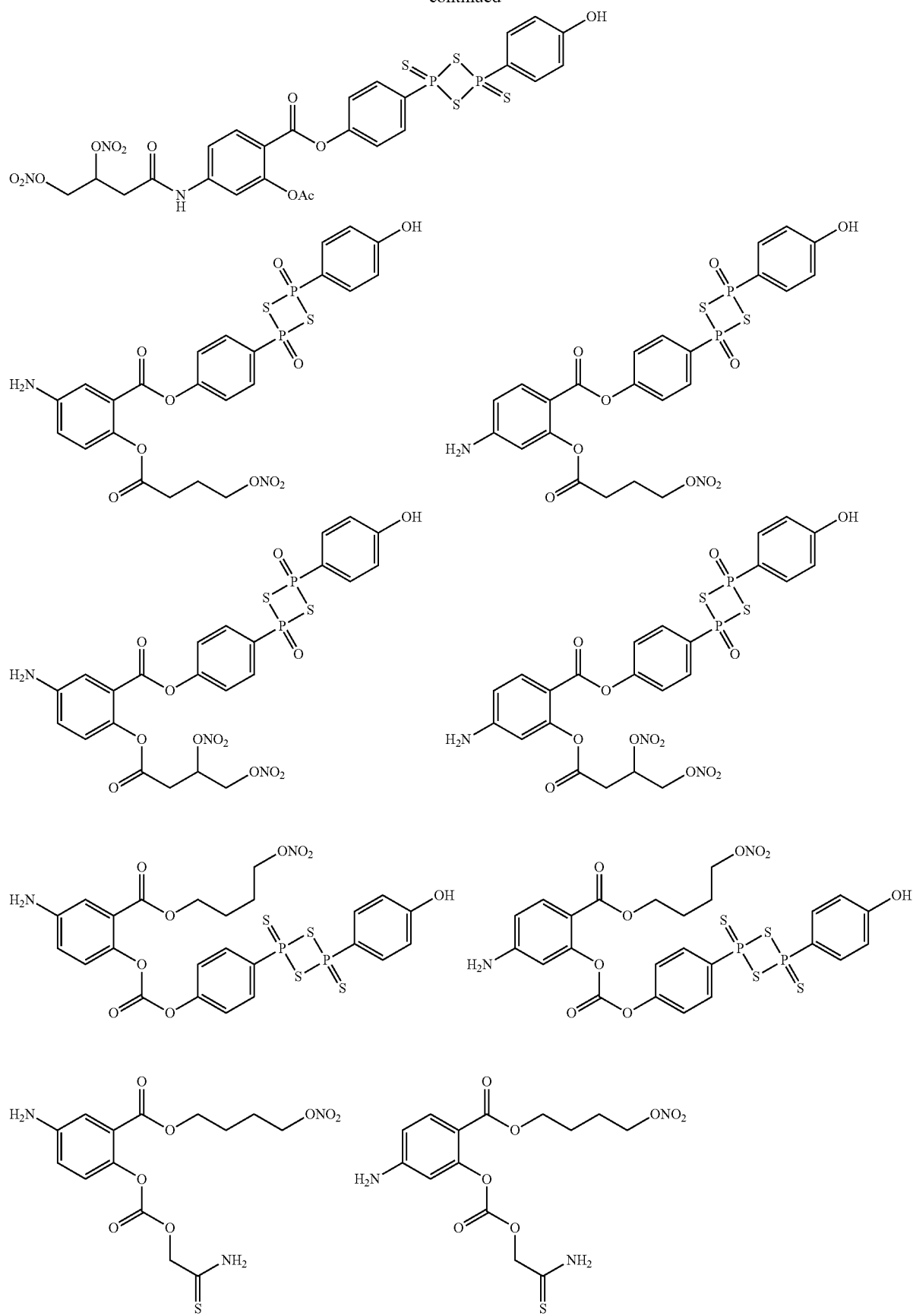

65
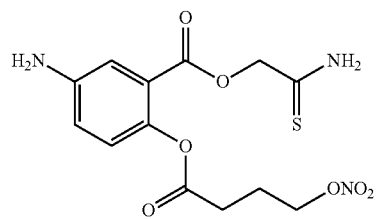
-continued
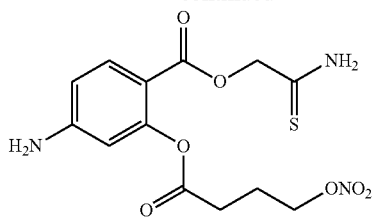
66
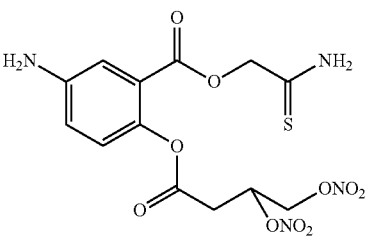
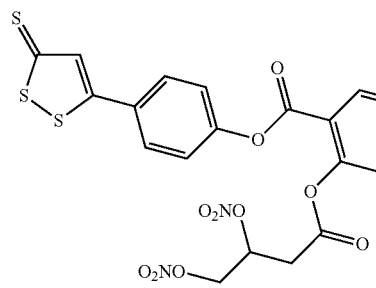
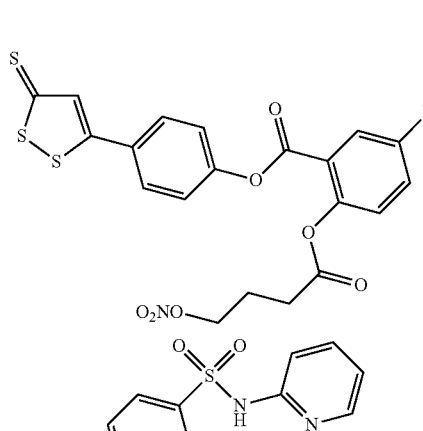
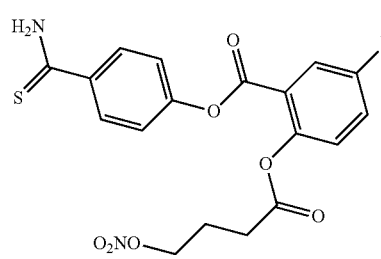
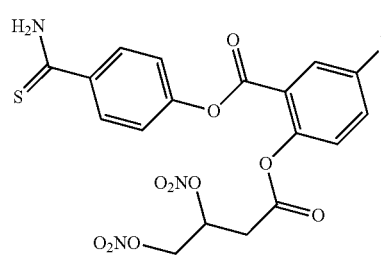

-continued
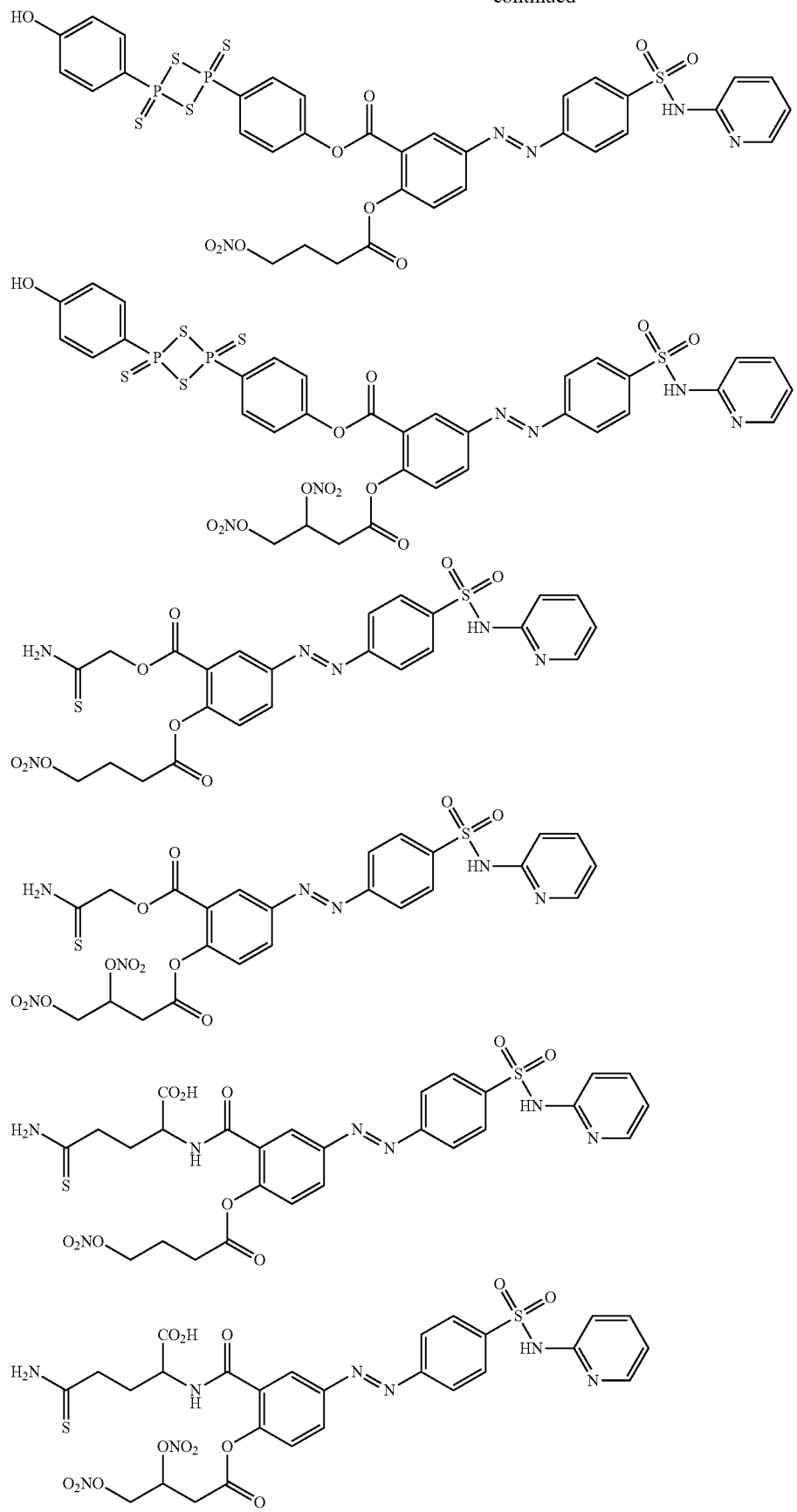

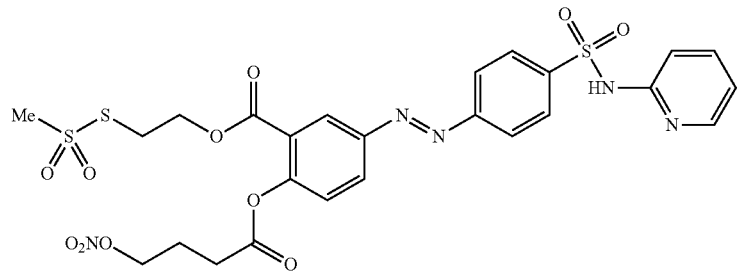
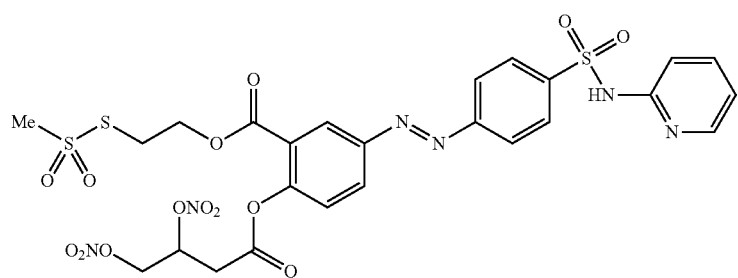
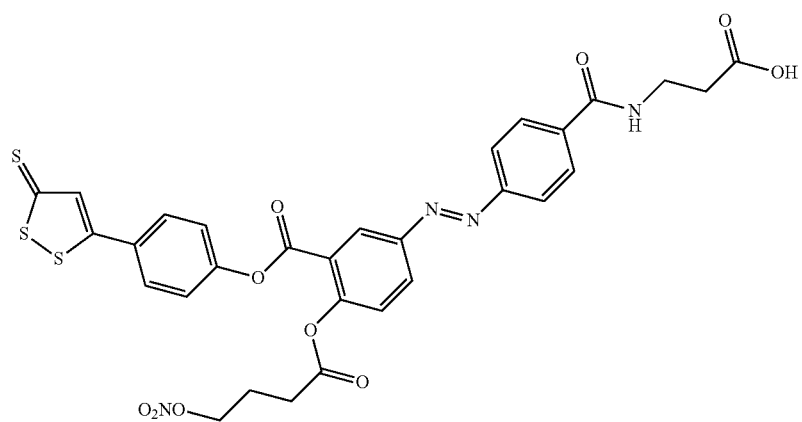
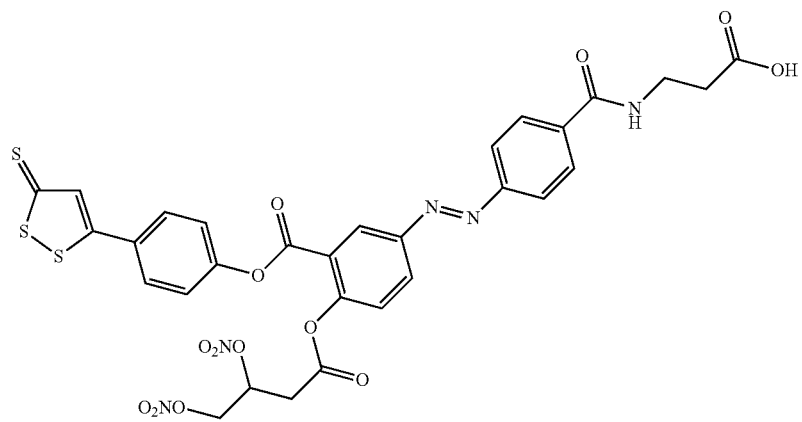

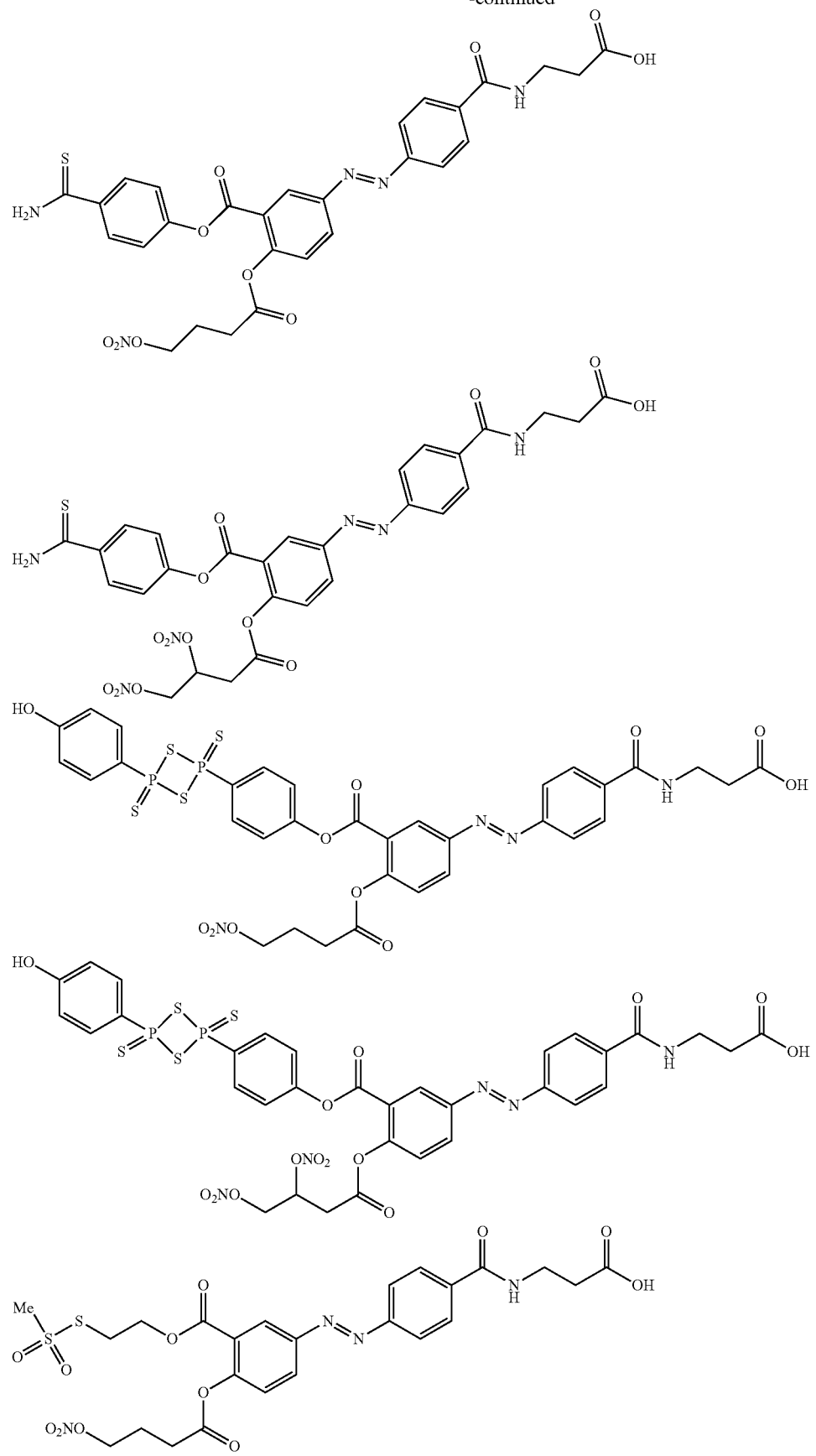

-continued

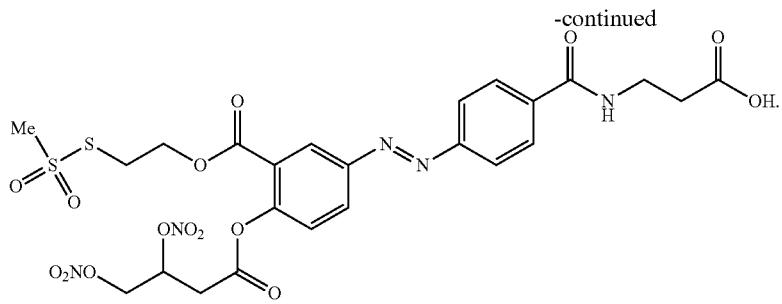

In some embodiments, the anti-inflammatory compounds disclosed herein can be of formula (II):

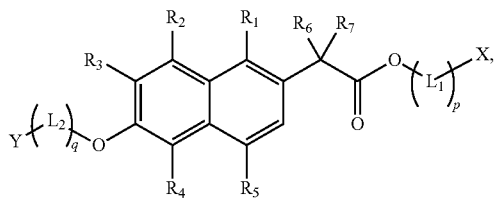

in which each of p and q, independently, is 0 or 1; each of $L_1$ and $L_2$, independently, is a linker, the linker being —C(O)—, —(CH$_2$)$_m$—, —(CH$_2$)$_m$—O—, —(CH$_2$)$_m$—C(O)—, —(CH$_2$)$_m$—C(O)O—, —(CH$_2$)$_m$—OC(O)O—, —C(O)—(CH$_2$)$_m$—O—, —C(O)—(CH$_2$)$_m$—C(O)—, —OC(O)—(CH$_2$)$_m$—O—, —OC(O)—(CH$_2$)$_m$—C(O)—, or —OC(O)—(CH$_2$)$_m$—C(O)O—, in which m is 1, 2, 3, 4, 5, 6, or 7; X is a H$_2$S-releasing moiety or a NO-releasing moiety; Y is a NO-releasing moiety or a H$_2$S-releasing moiety, provided that X and Y are not simultaneously H$_2$S-releasing moieties or NO-releasing moieties; and each of $R_1$, $R_2$, $R_3$, $R_4$, $R_5$, $R_6$, and $R_7$, independently, is H, halo, NO$_2$, N$_3$, C$_1$-C$_{10}$ alkyl, OR, OC(O)R, N(R)$_2$, NH—C(O)R, S(O)R, or N=N—R, in which each R, independently, is H, C$_1$-C$_{10}$ alkyl, or aryl. The H$_2$S-releasing moiety and NO-releasing moiety assigned to X and Y in formula (II) can be those listed above.

Examples of the compounds of formula (II) include:

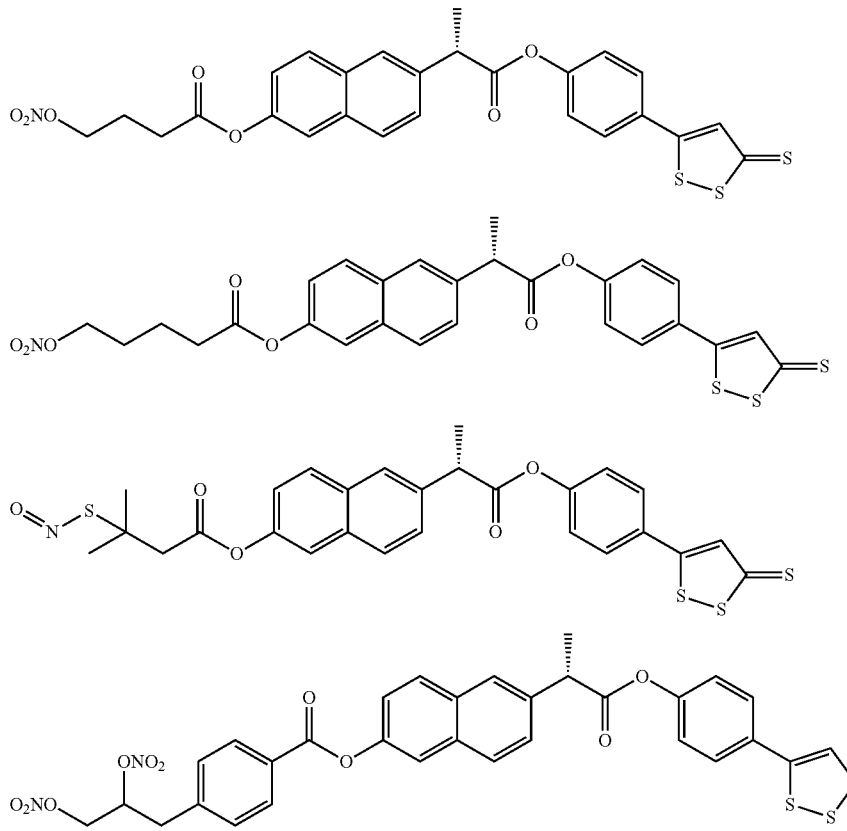

-continued
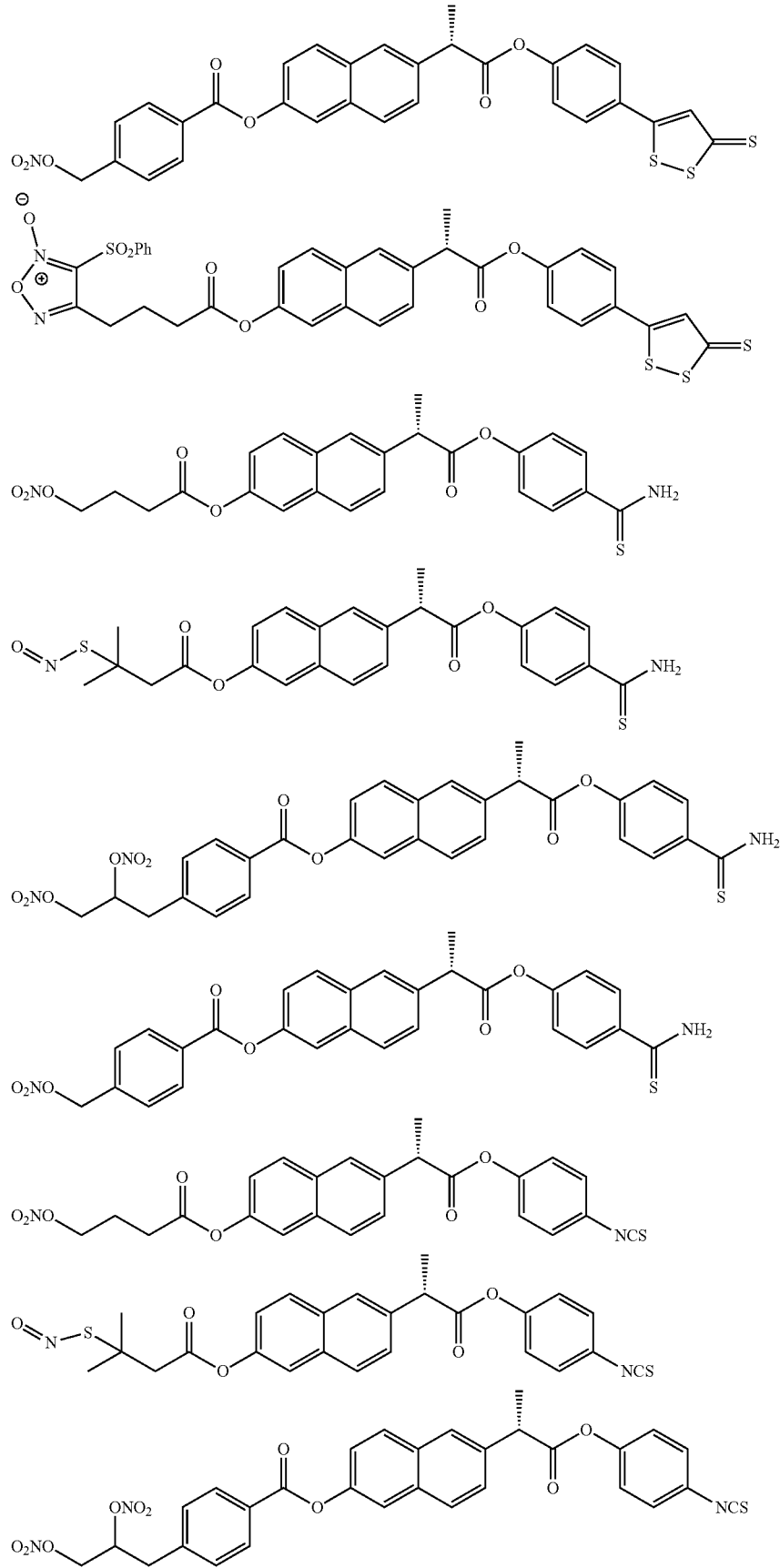

-continued
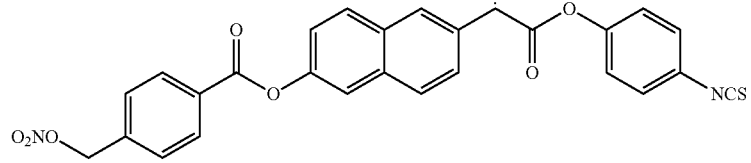
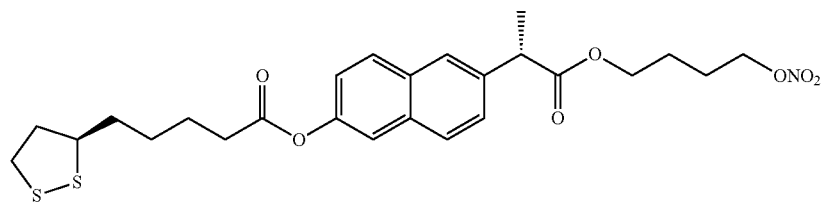
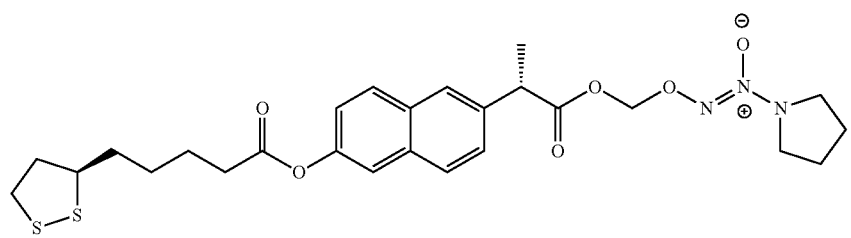
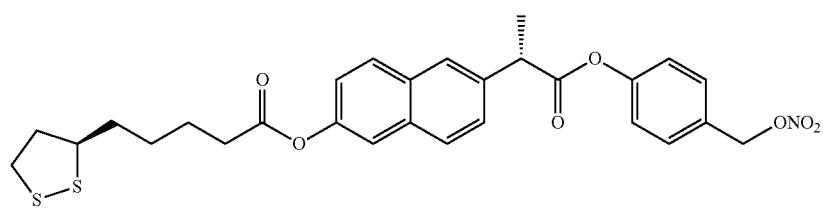
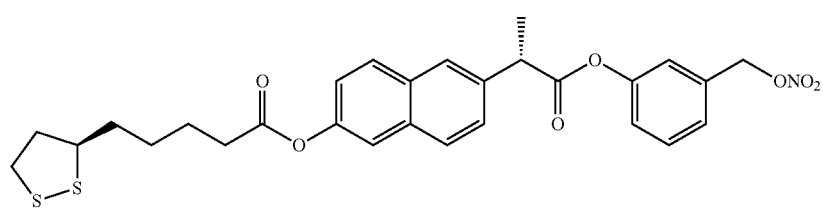
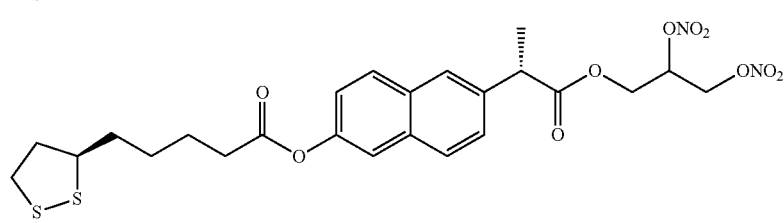
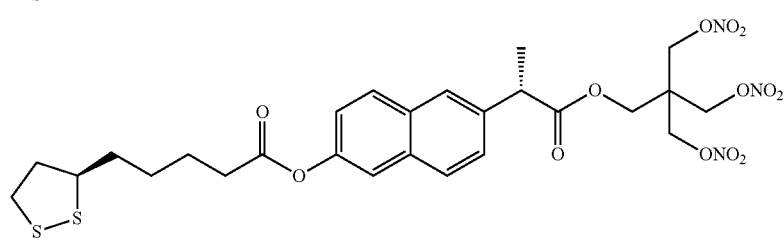
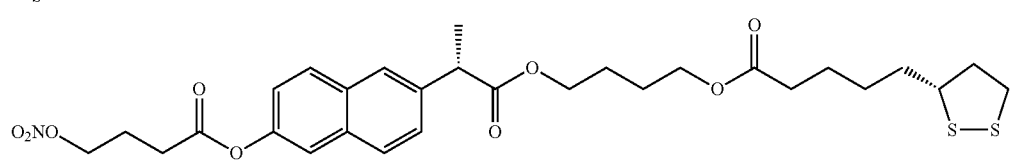

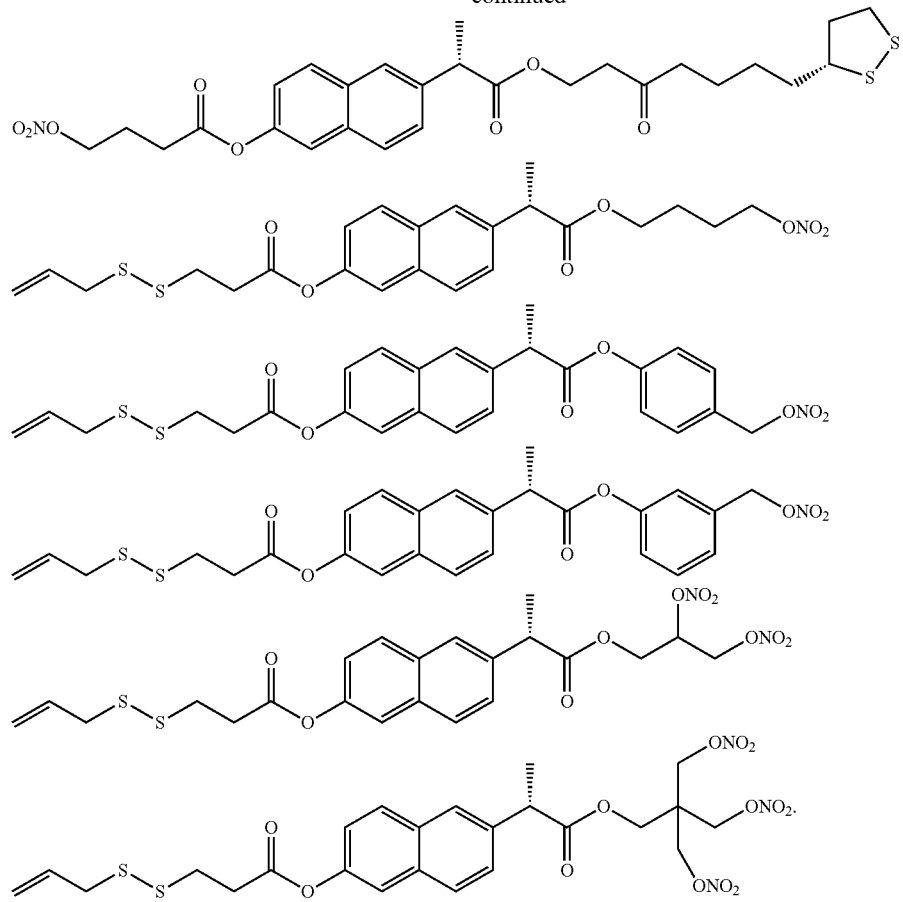

In some embodiments, the anti-inflammatory compounds disclosed herein can be of formula (III):

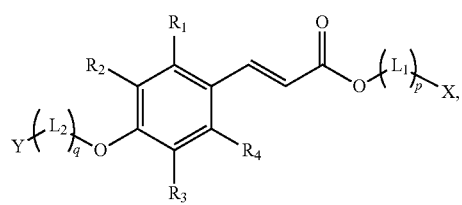

in which each of p and q, independently, is 0 or 1; each of $L_1$ and $L_2$, independently, is a linker, the linker being —C(O)—, —(CH$_2$)$_m$—, —(CH$_2$)$_m$—O—, —(CH$_2$)$_m$—C(O)—, —(CH$_2$)$_m$—C(O)O—, —(CH$_2$)$_m$—OC(O)O—, —C(O)—(CH$_2$)$_m$—O—, —C(O)—(CH$_2$)$_m$—C(O)—, —OC(O)—(CH$_2$)$_m$—O—, —OC(O)—(CH$_2$)$_m$—C(O)—, or —OC(O)—(CH$_2$)$_m$—C(O)O—, in which m is 1, 2, 3, 4, 5, 6, or 7; X is a H$_2$S-releasing moiety or a NO-releasing moiety; Y is a NO-releasing moiety or a H$_2$S-releasing moiety, provided that X and Y are not simultaneously H$_2$S-releasing moieties or NO-releasing moieties; and each of $R_1$, $R_2$, $R_3$, and $R_4$, independently, is H, halo, NO$_2$, N$_3$, C$_1$-C$_{10}$ alkyl, OR, OC(O)R, N(R)$_2$, NH—C(O)R, S(O)R, or N=N—R, in which each R, independently, is H, C$_1$-C$_{10}$ alkyl, or aryl. The H$_2$S-releasing moiety and NO-releasing moiety assigned to X and Y in formula (III) can be those listed above.

Examples of the compounds of formula (III) include:

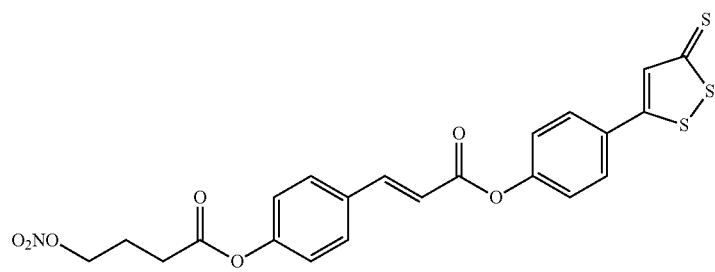

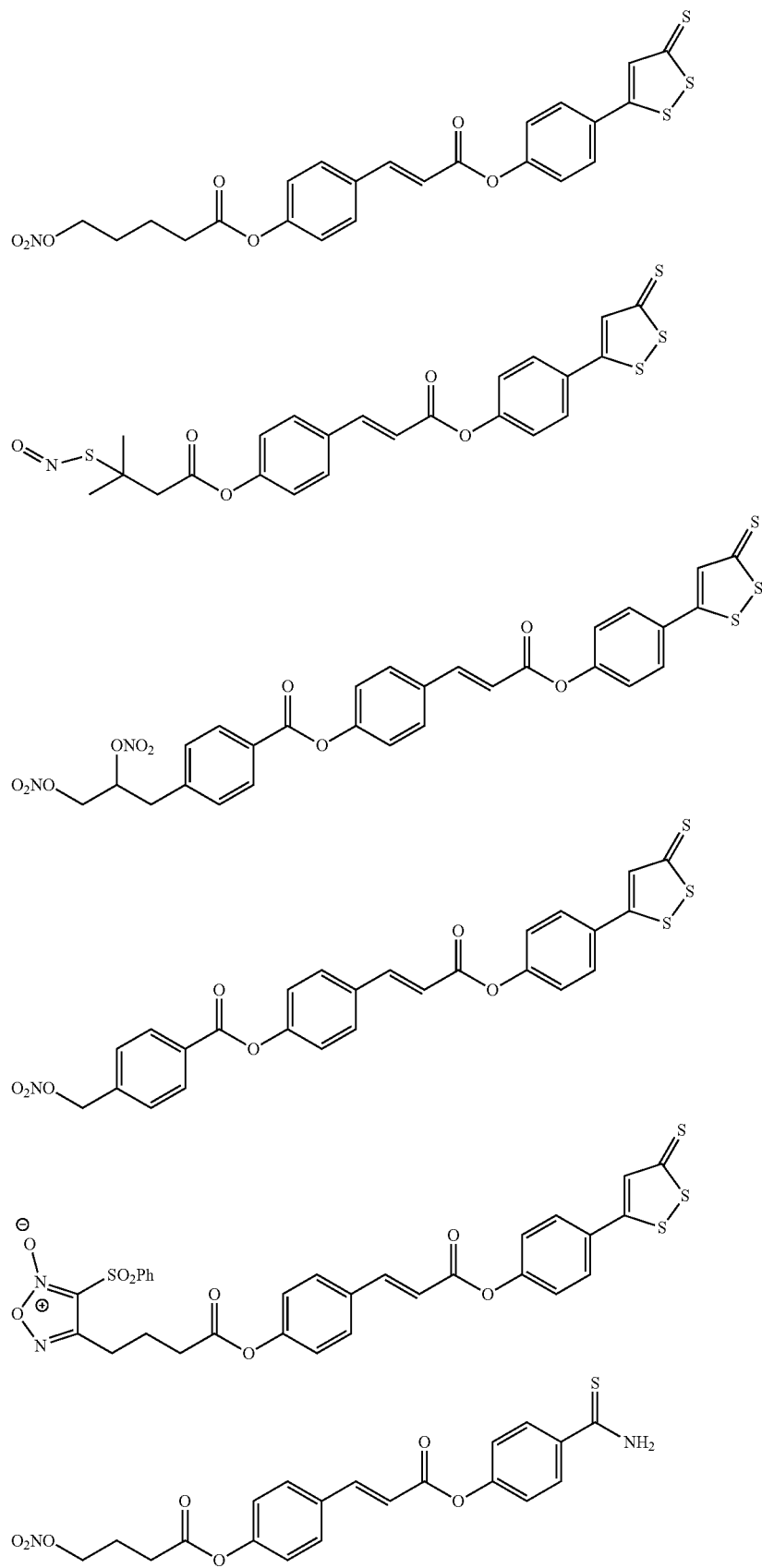

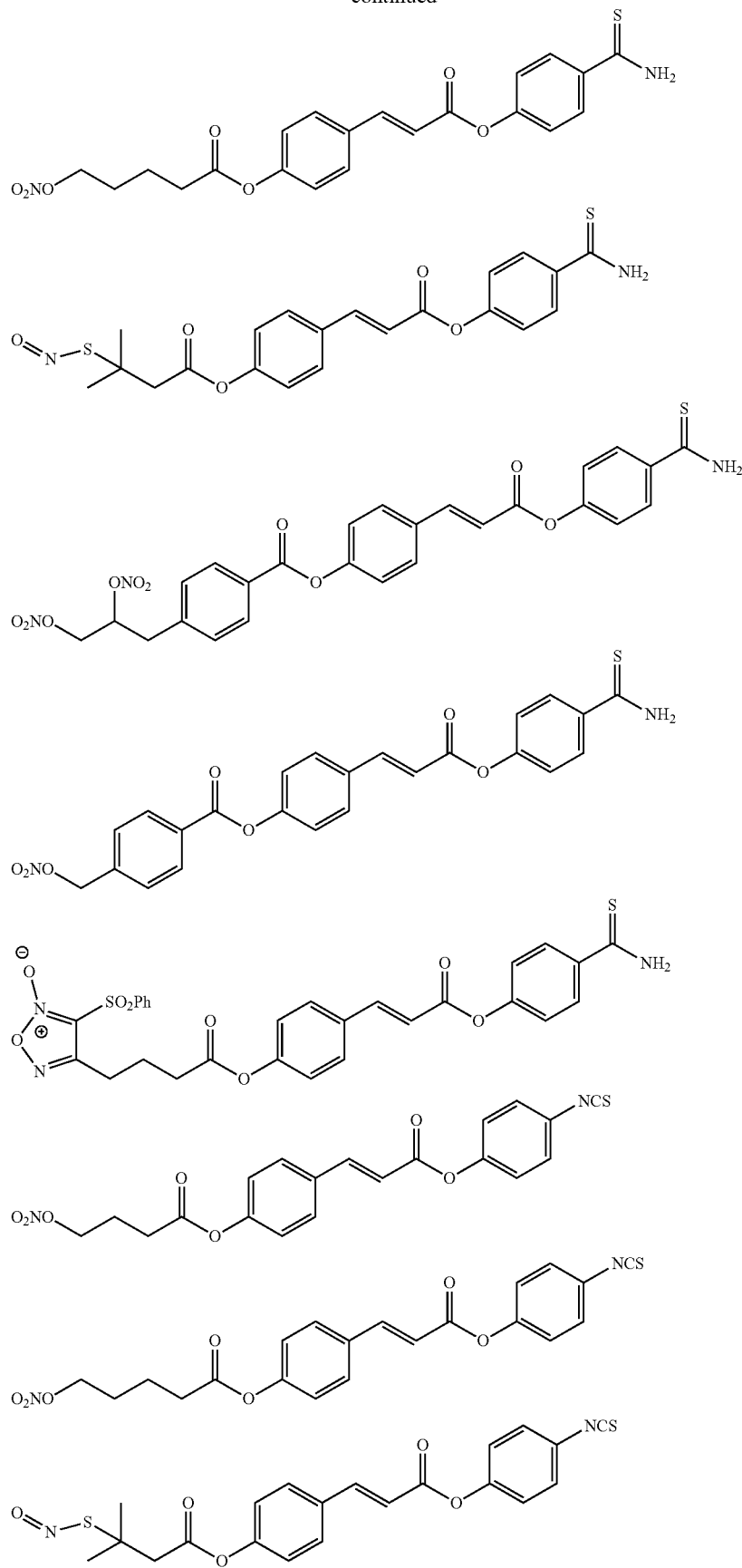

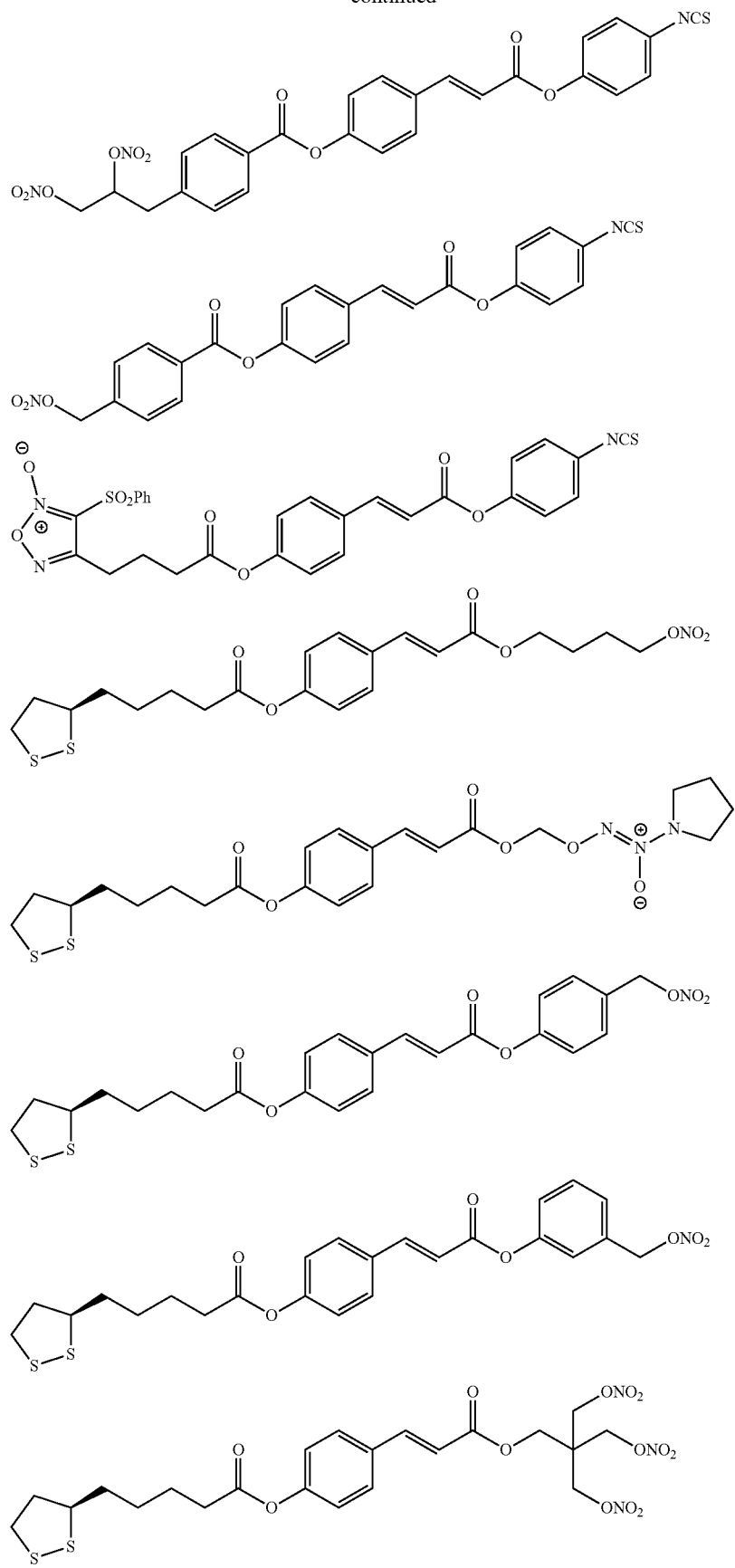

-continued

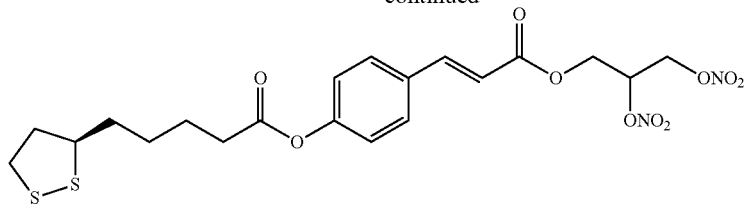

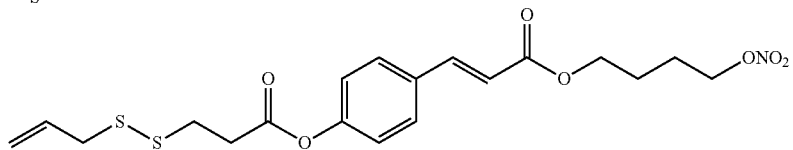

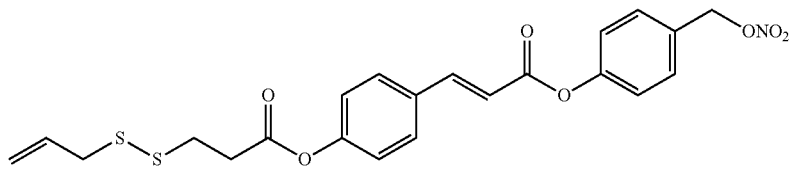

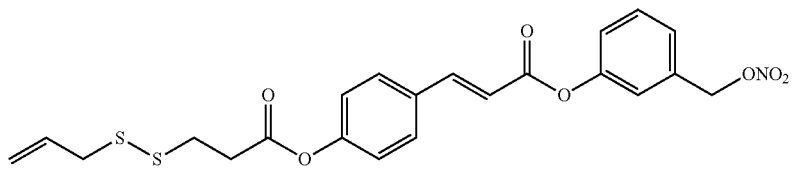

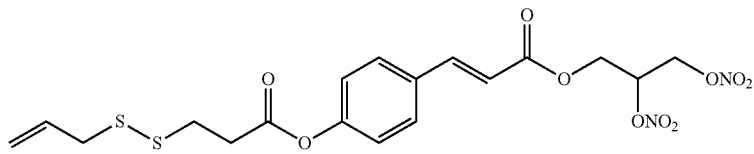

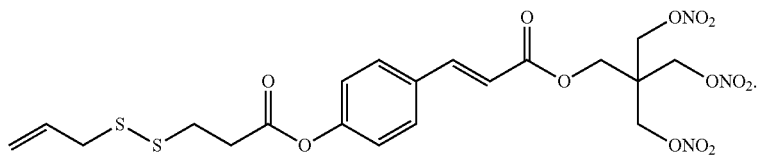

In some embodiments, the anti-inflammatory compounds disclosed herein can be of formula (IV):

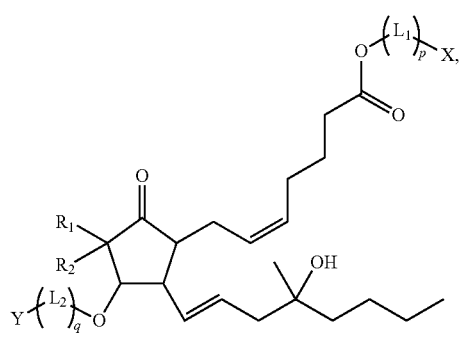

in which each of p and q, independently, is 0 or 1; each of $L_1$ and $L_2$, independently, is a linker, the linker being —C(O)—, —(CH$_2$)$_m$—, —(CH$_2$)$_m$—O—, —(CH$_2$)$_m$—C(O)—, —(CH$_2$)$_m$—C(O)O—, —(CH$_2$)$_m$—OC(O)O—, —C(O)—(CH$_2$)$_m$—O—, —C(O)—(CH$_2$)$_m$—C(O)—, —OC(O)—(CH$_2$)$_m$—O—, —OC(O)—(CH$_2$)$_m$—C(O)—, or —OC(O)—(CH$_2$)$_m$—C(O)O—, in which m is 1, 2, 3, 4, 5, 6, or 7; X is a H$_2$S-releasing moiety or a NO-releasing moiety; Y is a NO-releasing moiety or a H$_2$S-releasing moiety, provided that X and Y are not simultaneously H$_2$S-releasing moieties or NO-releasing moieties; and each of $R_1$ and $R_2$, independently, is H, halo, NO$_2$, N$_3$, C$_1$-C$_{10}$ alkyl, OR, OC(O)R, N(R)$_2$, NH—C(O)R, S(O)R, or N=N—R, in which each R, independently, is H, C$_1$-C$_{10}$ alkyl, or aryl. The H$_2$S-releasing moiety and NO-releasing moiety assigned to X and Y in formula (IV) can be those listed above.

Examples of the compounds of formula (IV) include:
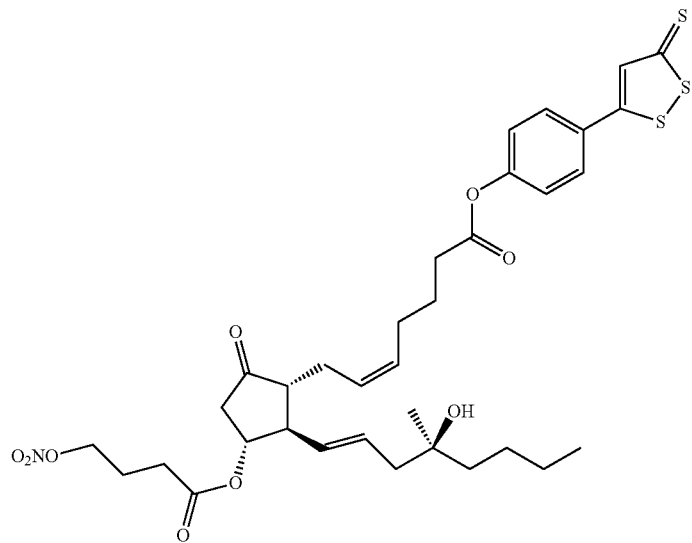
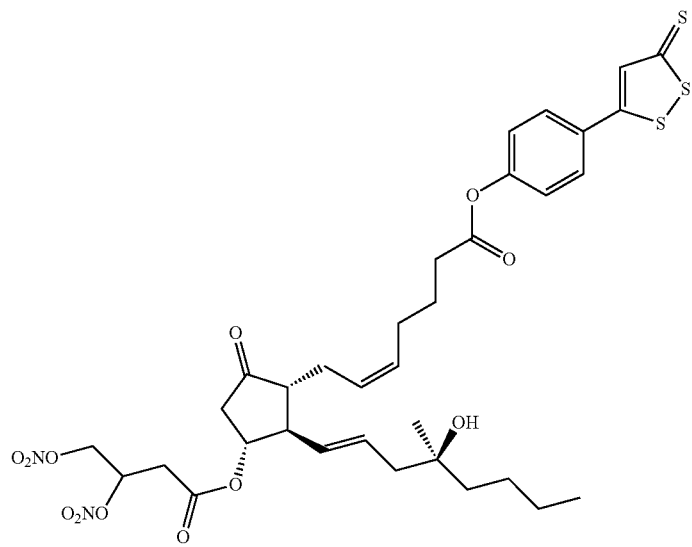
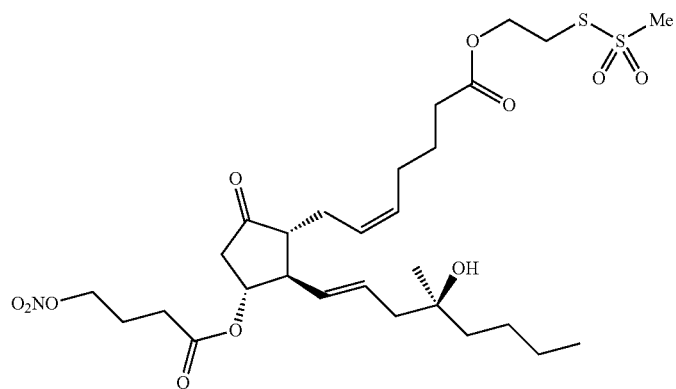

-continued
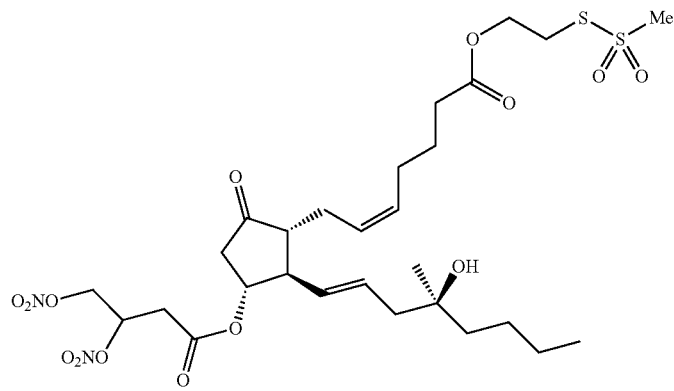
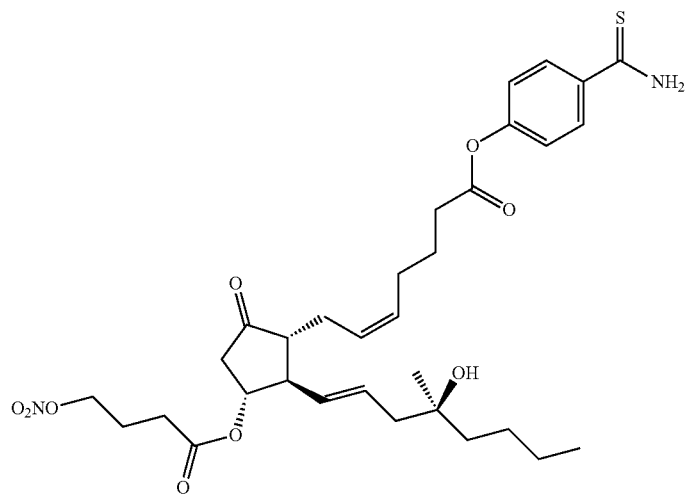
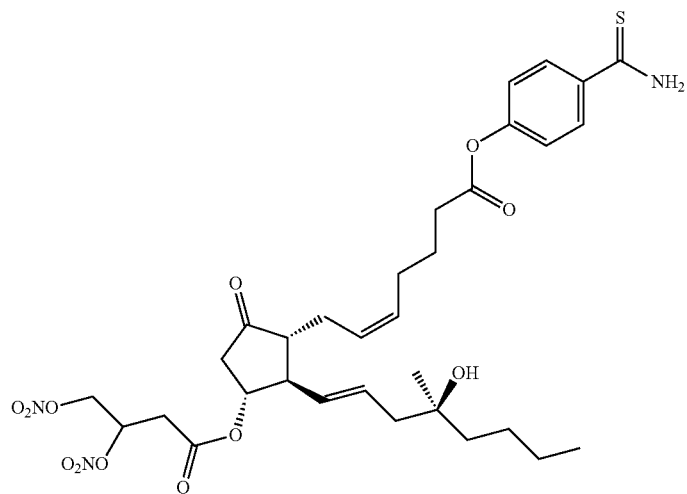

-continued
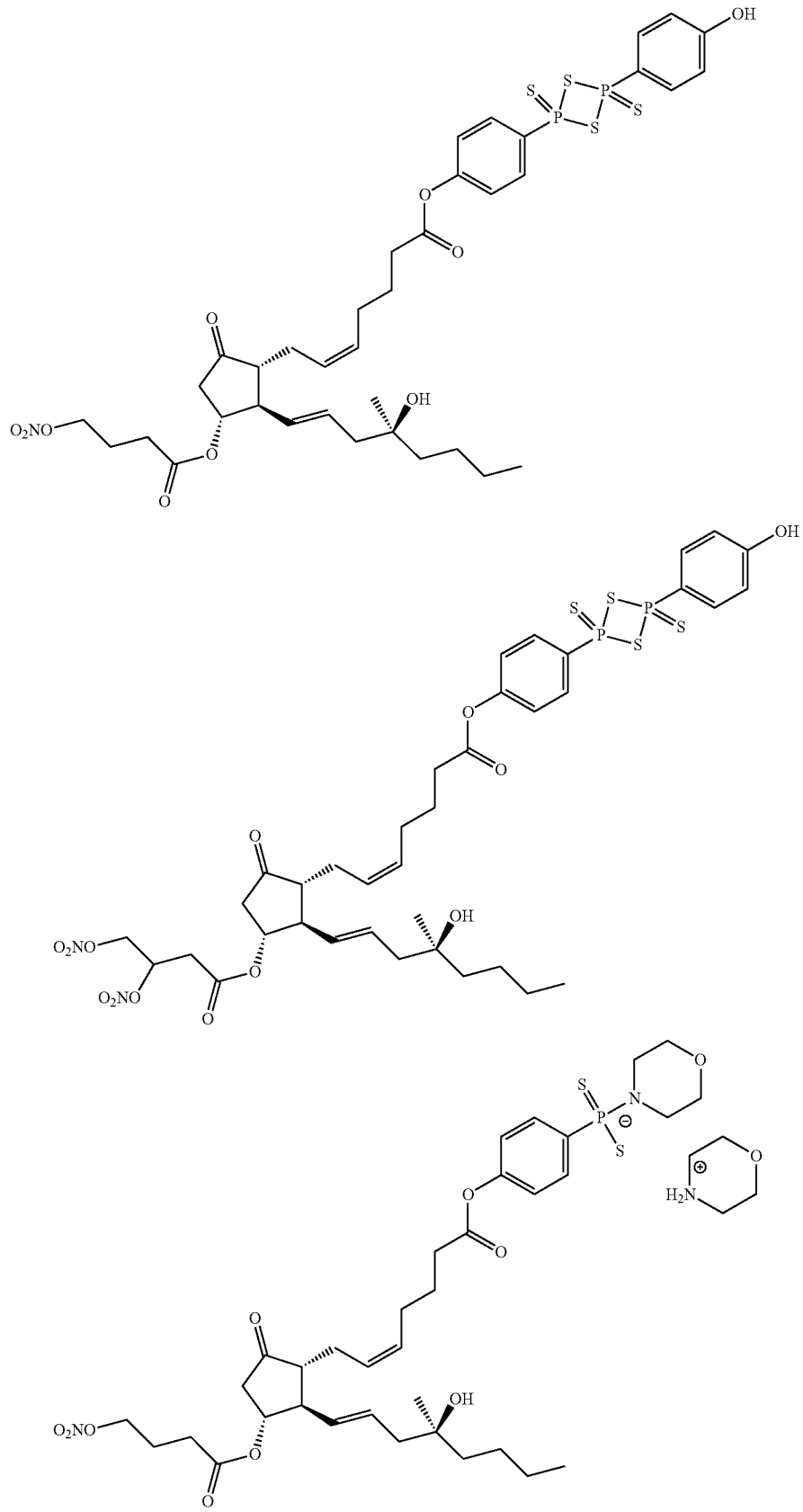

-continued

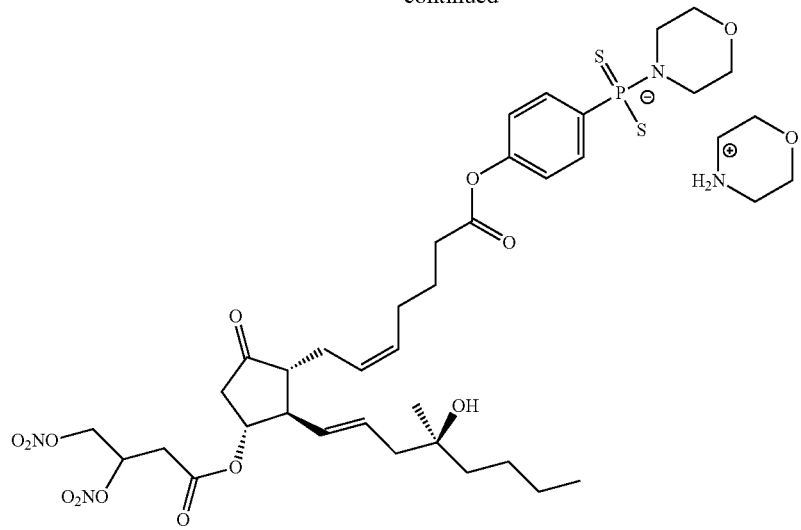

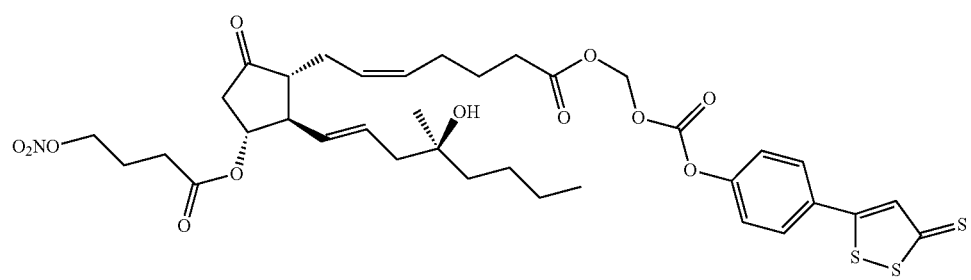

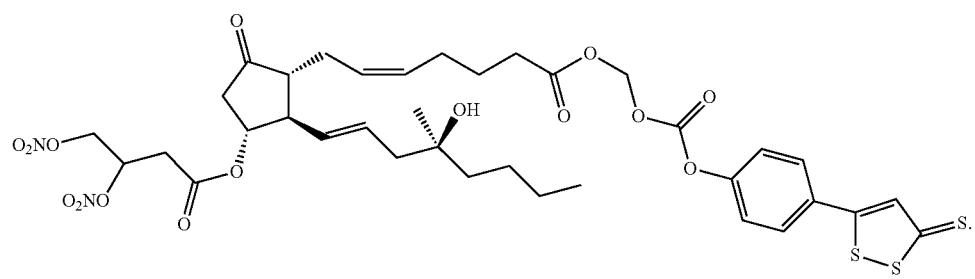

In some embodiments, the anti-inflammatory compounds disclosed herein can be of formula (V):

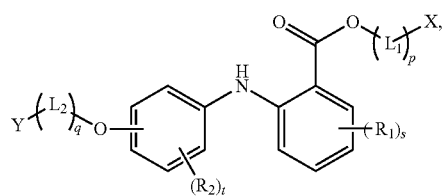

in which each of p and q, independently, is 0 or 1; each of s and t, independently, is 1, 2, 3, or 4; each of $L_1$ and $L_2$, independently, is a linker, the linker being —C(O)—, —$(CH_2)_m$—, —$(CH_2)_m$—O—, —$(CH_2)_m$—C(O)—, —$(CH_2)_m$—C(O)O—, —$(CH_2)_m$—OC(O)O—, —C(O)—$(CH_2)_m$—O—, —C(O)—$(CH_2)_m$—C(O)—, —OC(O)—$(CH_2)_m$—O—, —OC(O)—$(CH_2)_m$—C(O)—, or —OC(O)—$(CH_2)_m$C(O)O—, in which m is 1, 2, 3, 4, 5, 6, or 7; X is a $H_2$S-releasing moiety or a NO-releasing moiety; Y is a NO-releasing moiety or a $H_2$S-releasing moiety, provided that X and Y are not simultaneously $H_2$S-releasing moieties or NO-releasing moieties; and each of $R_1$ and $R_2$, independently, is H, halo, $NO_2$, $N_3$, $C_1$-$C_{10}$ alkyl, OR, OC(O)R, $N(R)_2$, NH—C(O)R, S(O)R, or N=N—R, in which each R, independently, is H, $C_1$-$C_{10}$ alkyl, or aryl. The $H_2$S-releasing moiety and NO-releasing moiety assigned to X and Y in formula (V) can be those listed above.

Examples of the compounds of formula (V) include:
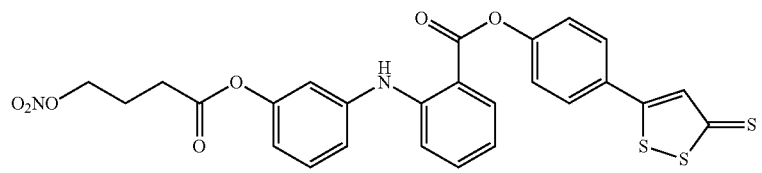
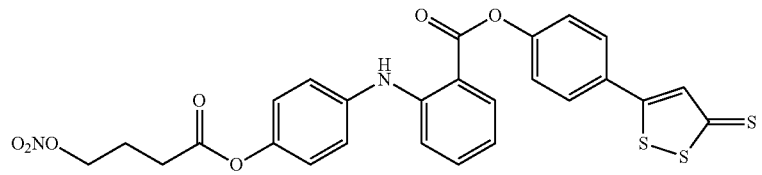
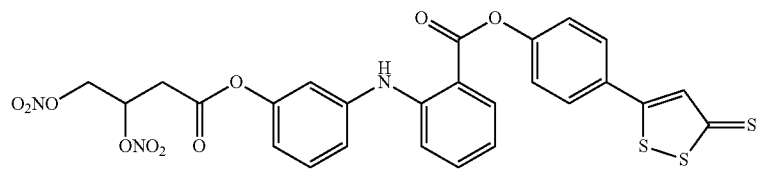
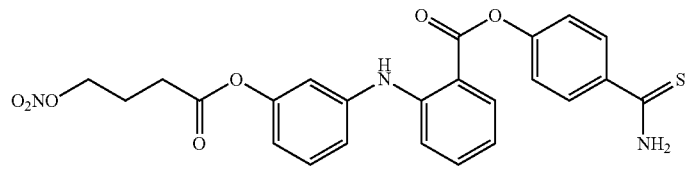
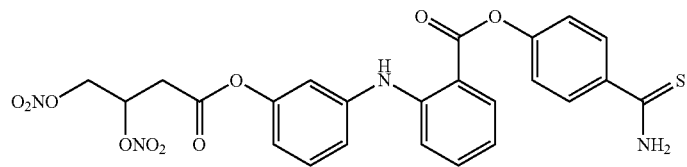
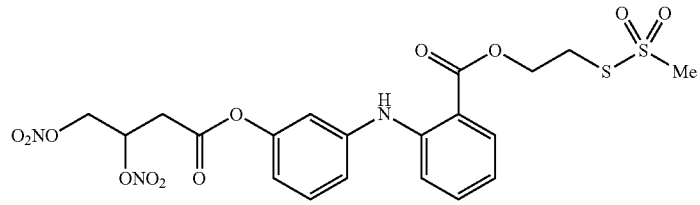
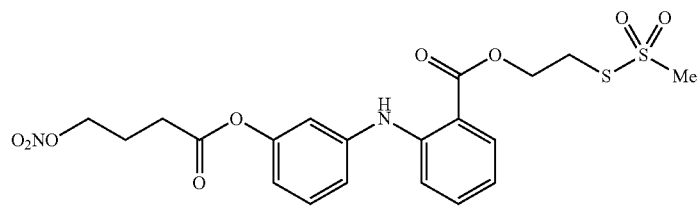
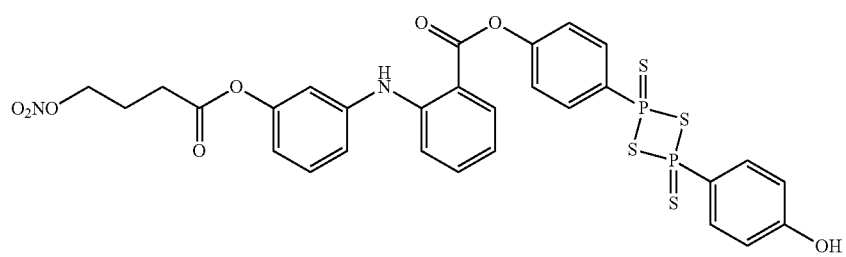

-continued

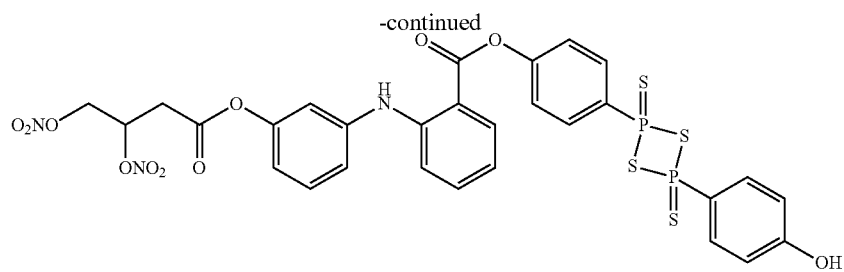

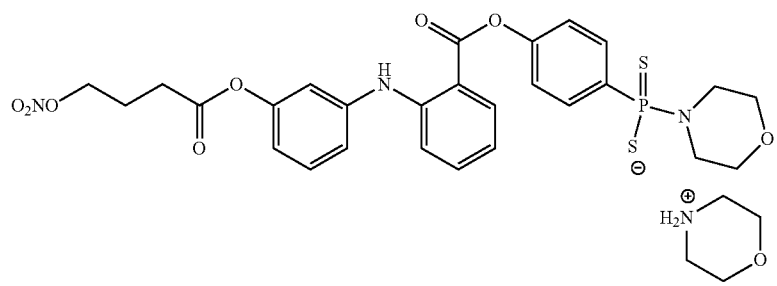

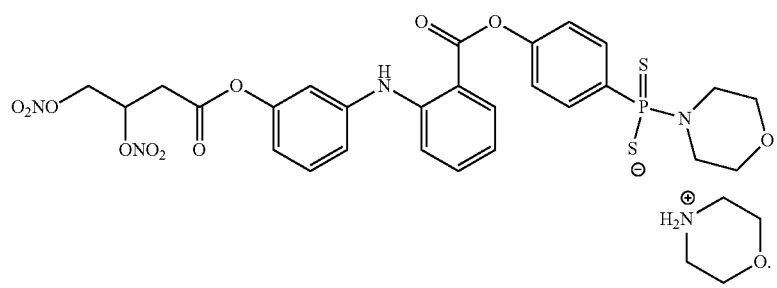

In some embodiments, the anti-inflammatory compounds disclosed herein can be of formula (VI):

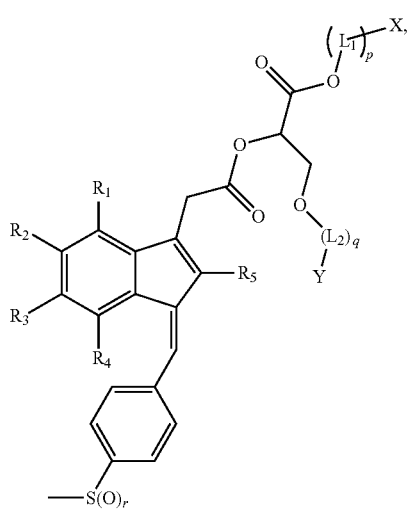

(VI)

in which each of p and q, independently, is 0 or 1; r is 1 or 2; each of $L_1$ and $L_2$, independently, is a linker, the linker being —C(O)—, —$(CH_2)_m$—, —$(CH_2)_m$—O—, —$(CH_2)_m$—C(O)—, —$(CH_2)_m$—C(O)O—, —$(CH_2)_m$—OC(O)O—, —C(O)—$(CH_2)_m$—O—, —C(O)—$(CH_2)_m$—C(O)—, —OC(O)—$(CH_2)_m$—O—, —OC(O)—$(CH_2)_m$—C(O)—, or —OC(O)—$(CH_2)_m$—C(O)O—, in which m is 1, 2, 3, 4, 5, 6, or 7; X is a $H_2S$-releasing moiety or a NO-releasing moiety; Y is a NO-releasing moiety or a $H_2S$-releasing moiety, provided that X and Y are not simultaneously $H_2S$-releasing moieties or NO-releasing moieties; and each of $R_1$, $R_2$, $R_3$, $R_4$, and $R_5$, independently, is H, halo, $NO_2$, $N_3$, $C_1$-$C_{10}$ alkyl, OR, OC(O)R, $N(R)_2$, NH—C(O)R, S(O)R, or N=N—R, in which each R, independently, is H, $C_1$-$C_{10}$ alkyl, or aryl. The $H_2S$-releasing moiety and NO-releasing moiety assigned to X and Y in formula (VI) can be those listed above.

Examples of the compounds of formula (VI) include:
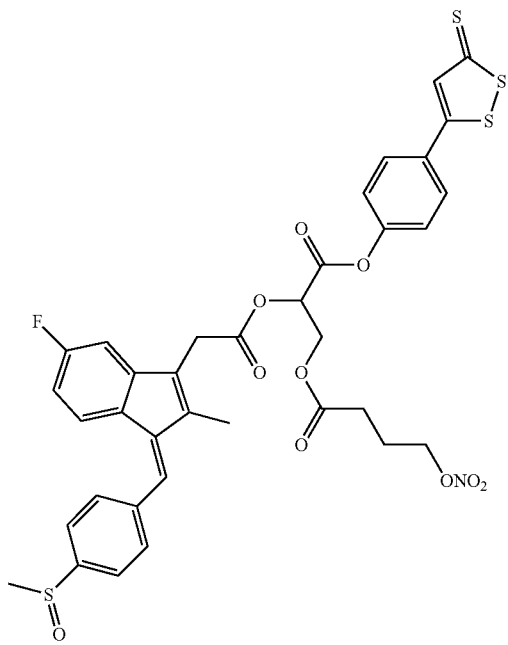
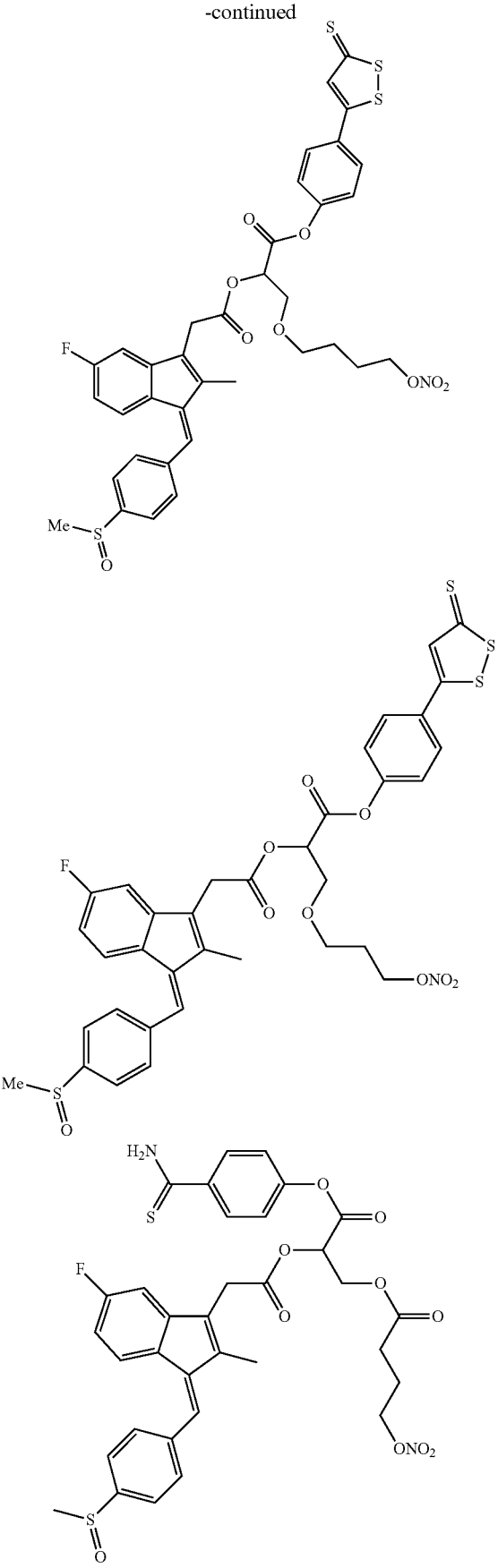

103
-continued
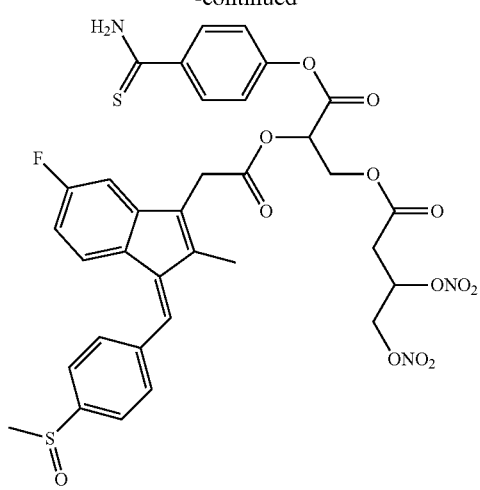
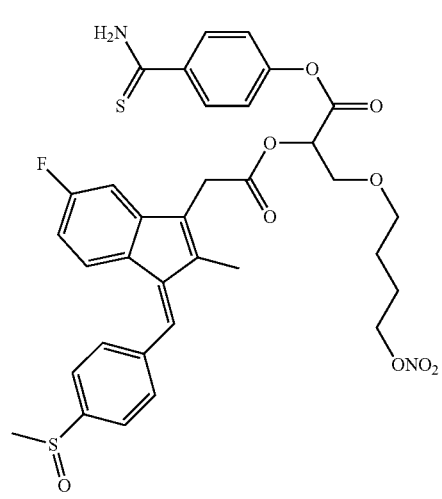
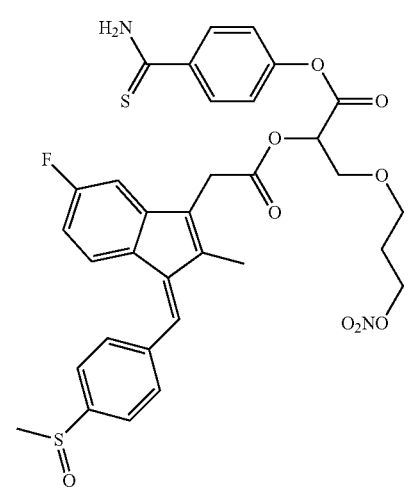
104
-continued
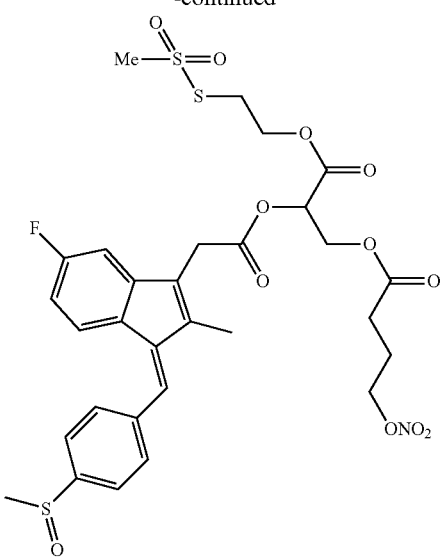
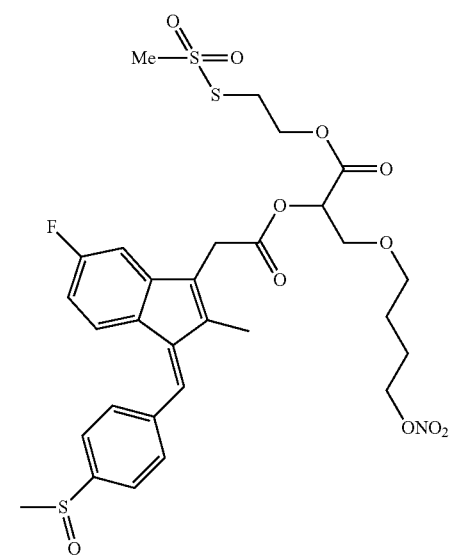

-continued
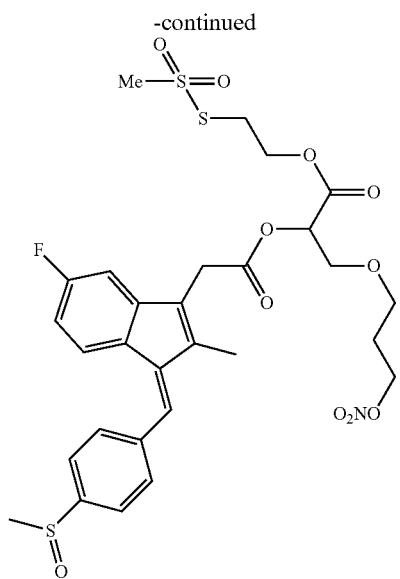
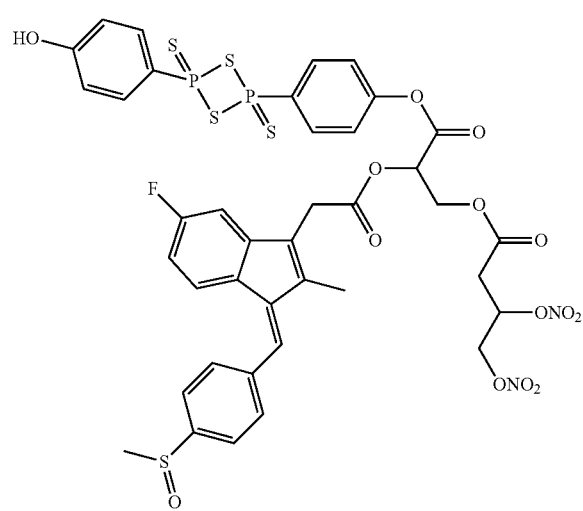
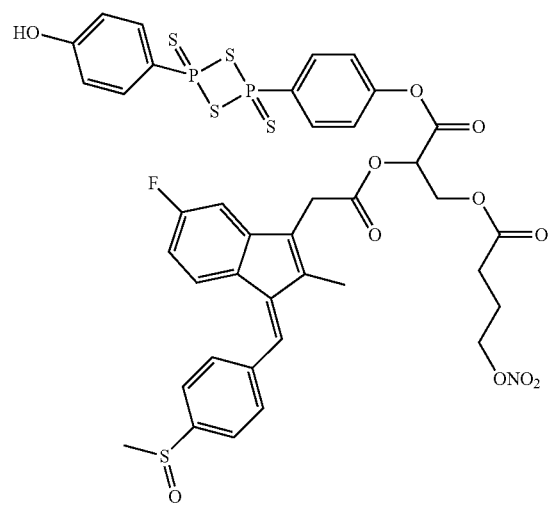
-continued
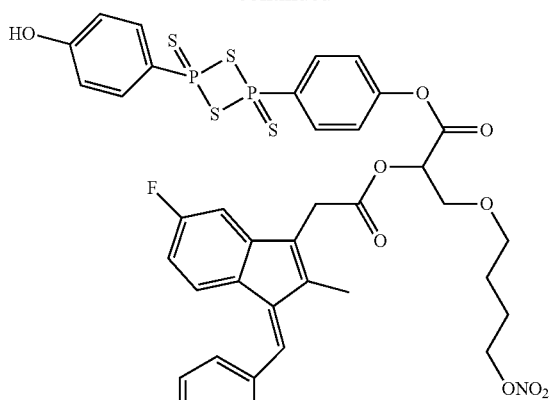
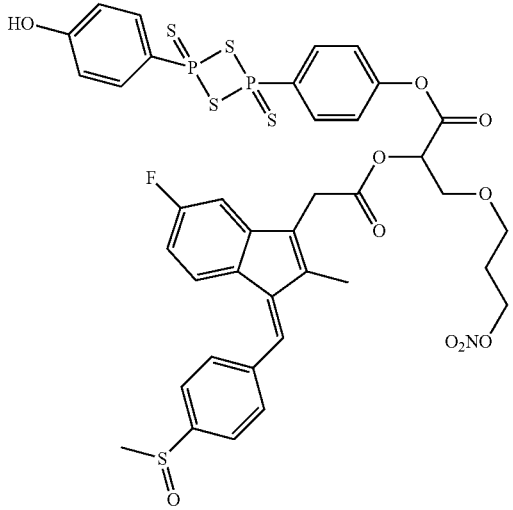
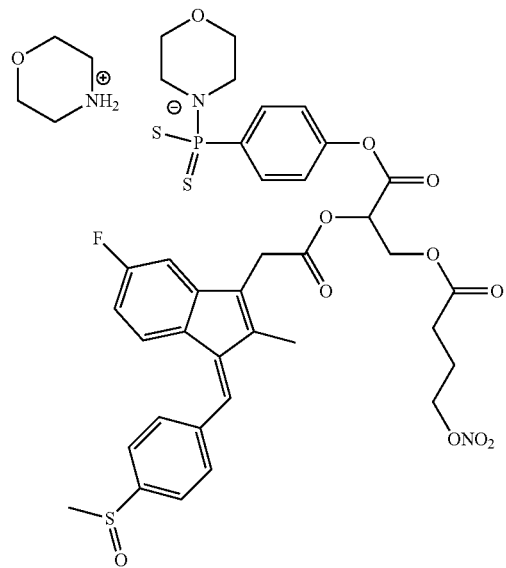

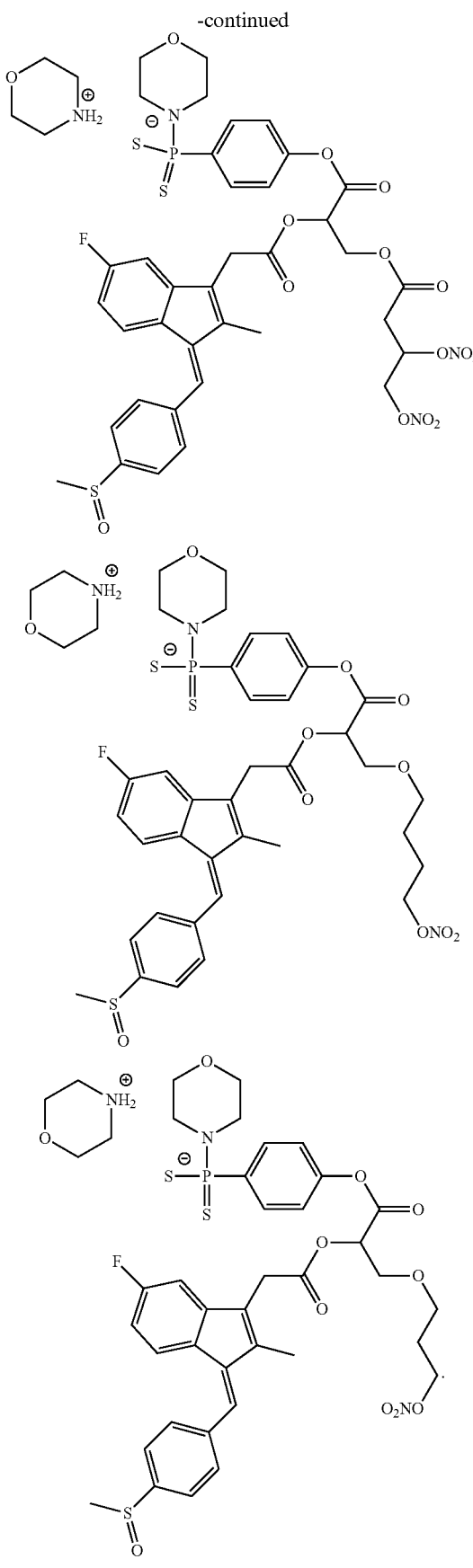

In some embodiments, the anti-inflammatory compounds disclosed herein can be of formula (VII):

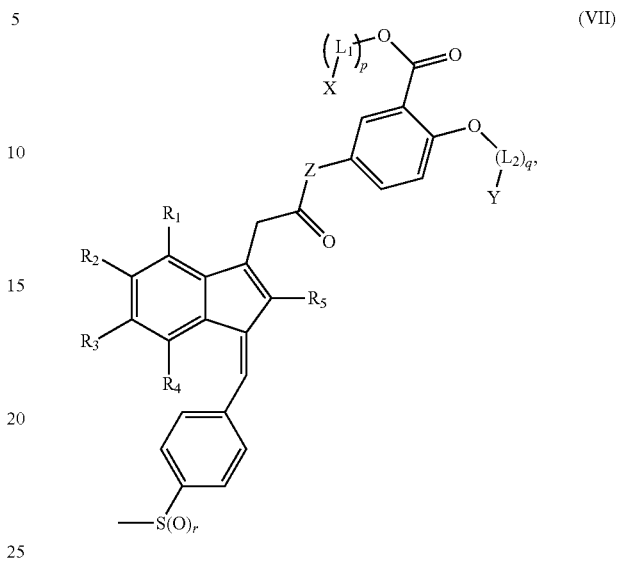

in which each of p and q, independently, is 0 or 1; r is 1 or 2; each of $L_1$ and $L_2$, independently, is a linker, the linker being —C(O)—, —(CH$_2$)$_m$—, —(CH$_2$)$_m$—O—, —(CH$_2$)$_m$—C(O)—, —(CH$_2$)$_m$—C(O)O—, —(CH$_2$)$_m$—OC(O)O—, —C(O)—(CH$_2$)$_m$—O—, —C(O)—(CH$_2$)$_m$—C(O)—, —OC(O)—(CH$_2$)$_m$—O—, —OC(O)—(CH$_2$)$_m$—C(O)—, or —OC(O)—(CH$_2$)$_m$—C(O)O—, in which m is 1, 2, 3, 4, 5, 6, or 7; X is a H$_2$S-releasing moiety or a NO-releasing moiety; Y is a NO-releasing moiety or a H$_2$S-releasing moiety, provided that X and Y are not simultaneously H$_2$S-releasing moieties or NO-releasing moieties; Z is O or NH; and each of $R_1$, $R_2$, $R_3$, $R_4$, $R_5$, independently, is H, halo, NO$_2$, N$_3$, C$_1$-C$_{10}$ alkyl, OR, OC(O)R, N(R), NH—C(O)R, S(O)R, or N=N—R, in which each R, independently, is H, C$_1$-C$_{10}$ alkyl, or aryl. The H$_2$S-releasing moiety and NO-releasing moiety assigned to X and Y in formula (VII) can be those listed above.

Examples of the compounds of formula (VII) include:

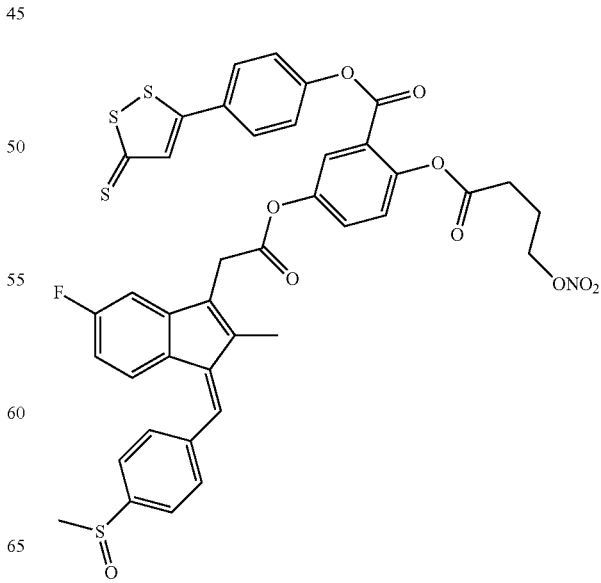

109 -continued
110 -continued
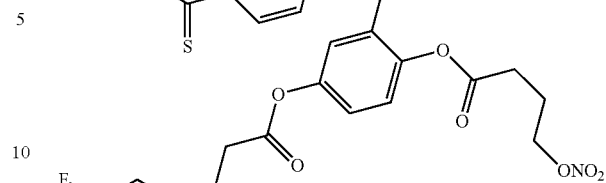
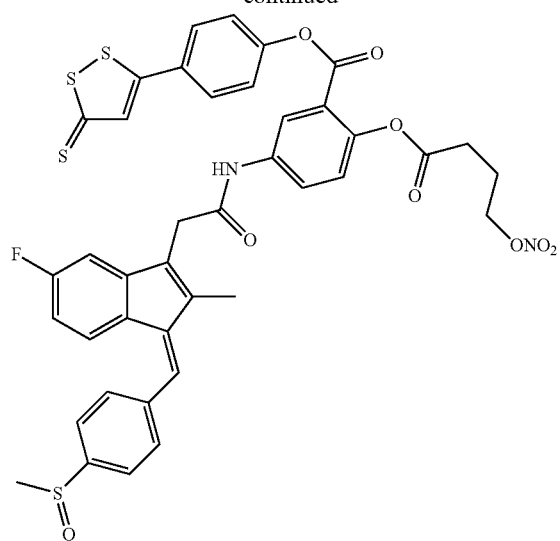
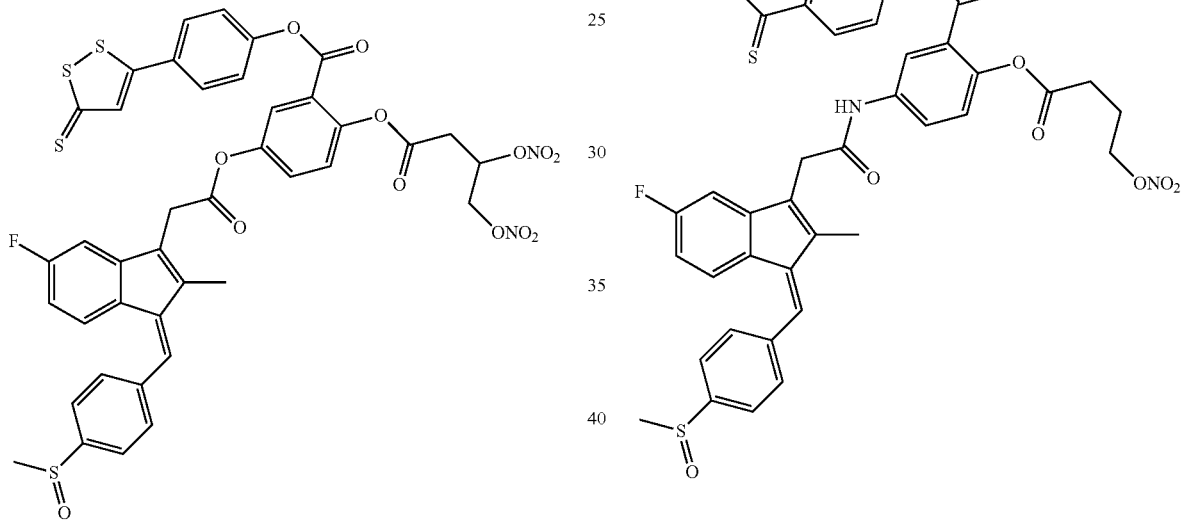
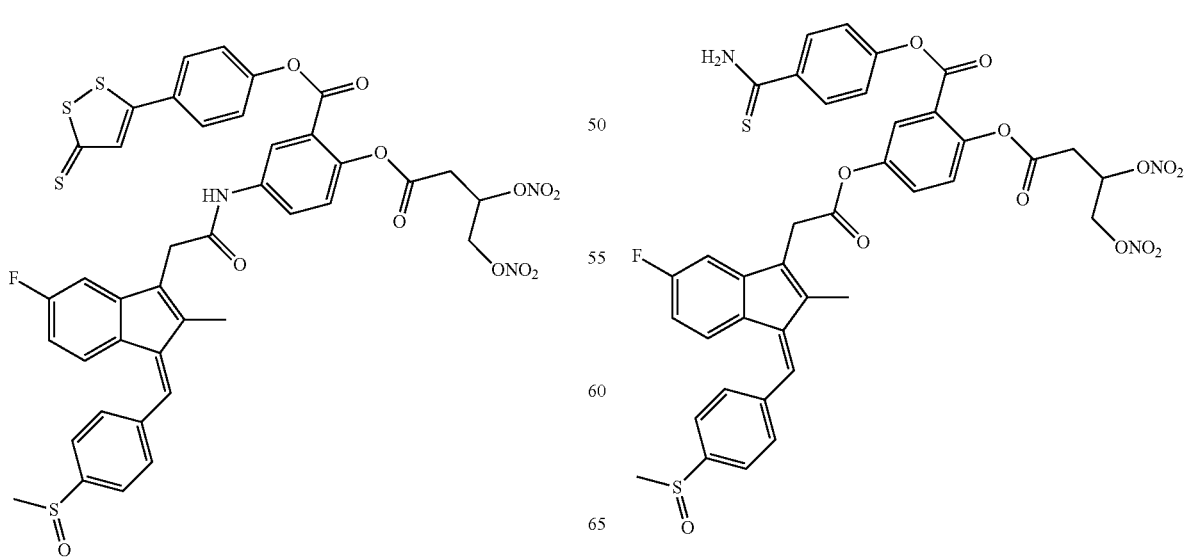

111
-continued
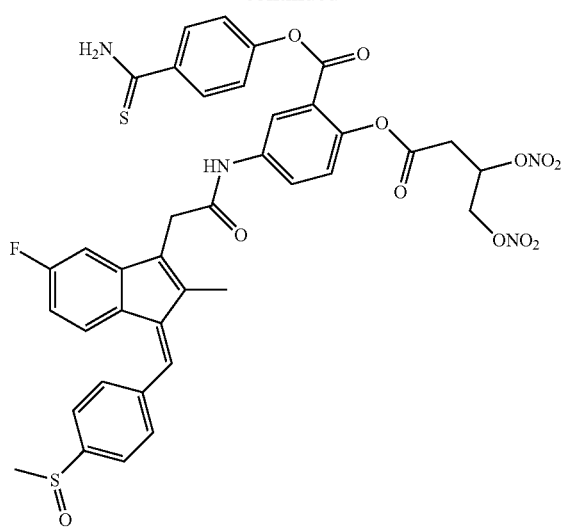
112
-continued
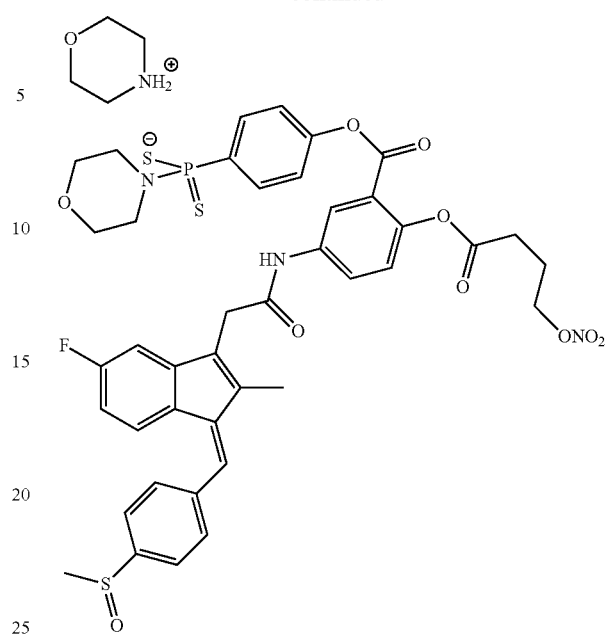
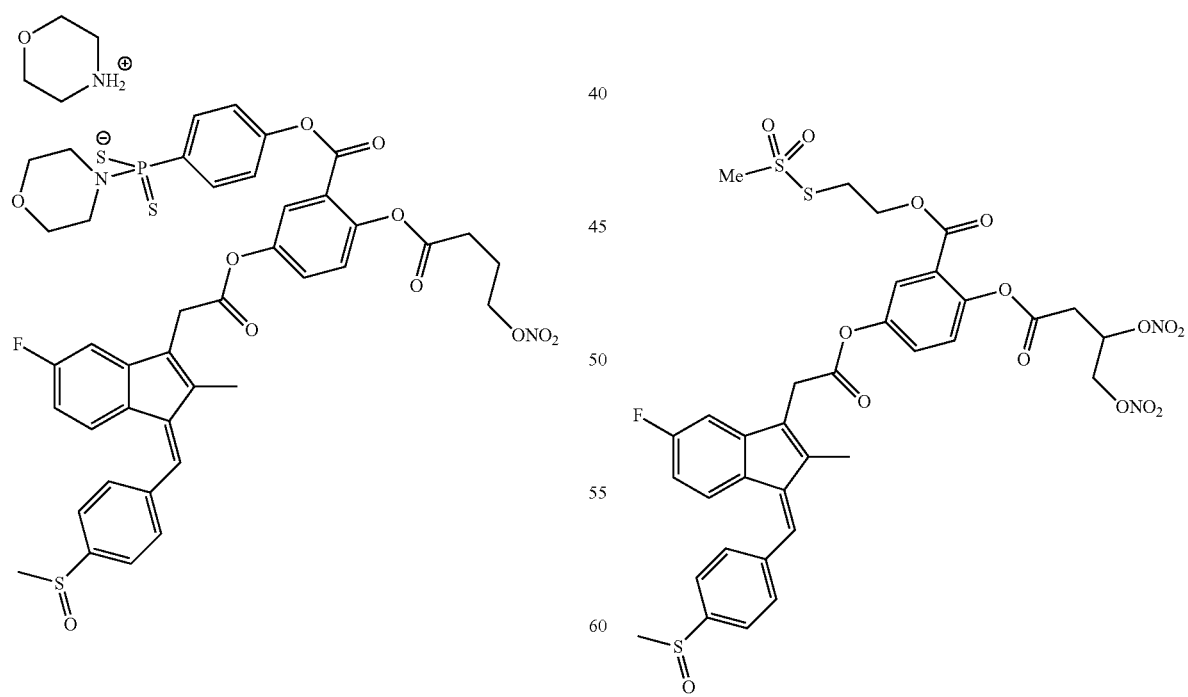

113

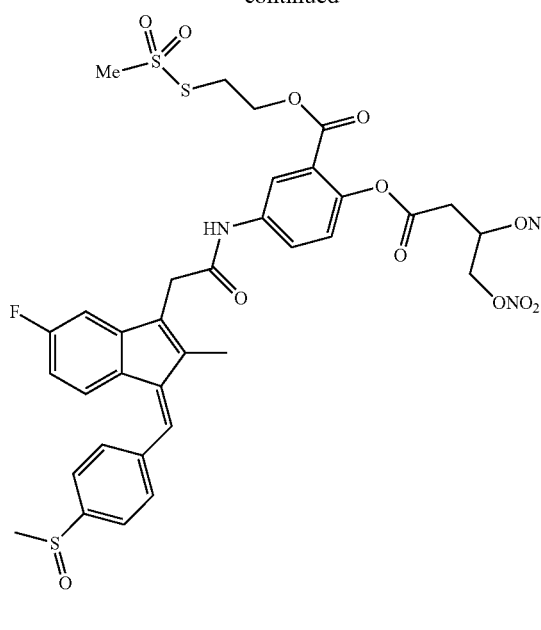

114

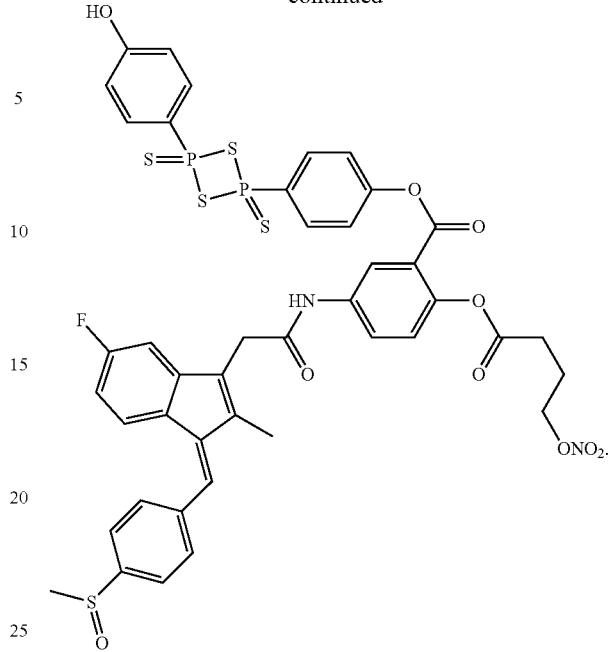

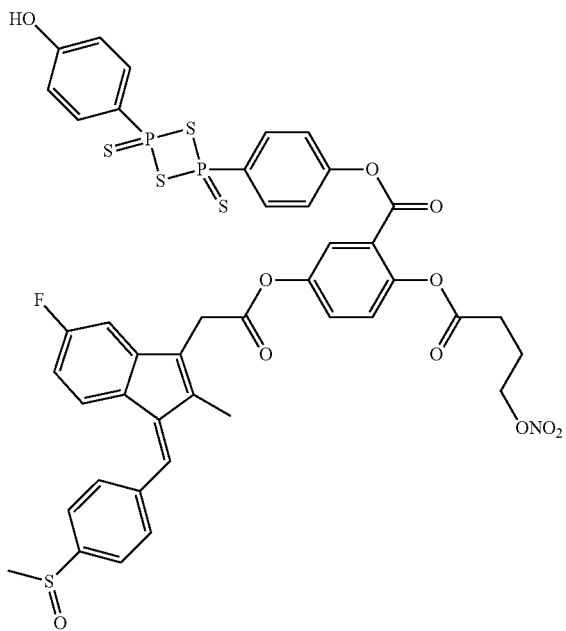

In some embodiments, the anti-inflammatory compounds disclosed herein can be of formula (VIII):

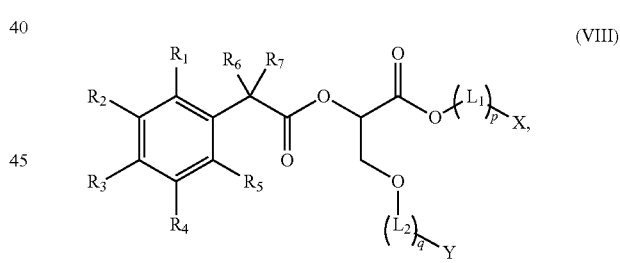

(VIII)

in which each of p and q, independently, is 0 or 1; each of $L_1$ and $L_2$, independently, is a linker, the linker being —C(O)—, —(CH$_2$)$_m$—, —(CH$_2$)$_m$—O—, —(CH$_2$)$_m$—C(O)—, —(CH$_2$)$_m$—C(O)O—, —(CH$_2$)$_m$—OC(O)O—, —C(O)—(CH$_2$)$_m$—O—, —C(O)—(CH$_2$)$_m$—C(O)—, —OC(O)—(CH$_2$)$_m$—O—, —OC(O)—(CH$_2$)$_m$—C(O)—, or —OC(O)—(CH$_2$)$_m$—C(O)O—, in which m is 1, 2, 3, 4, 5, 6, or 7; X is a H$_2$S-releasing moiety or a NO-releasing moiety; Y is a NO-releasing moiety or a H$_2$S-releasing moiety, provided that X and Y are not simultaneously H$_2$S-releasing moieties or NO-releasing moieties; and each of $R_1$, $R_2$, $R_3$, $R_4$, $R_5$, $R_6$, and $R_7$, independently, is H, halo, NO$_2$, N$_3$, C$_1$-C$_{10}$ alkyl, OR, OC(O)R, N(R)$_2$, NH—C(O)R, S(O)R, or N═N—R, in which each R, independently, is H, C$_1$-C$_{10}$ alkyl, or aryl. The H$_2$S-releasing moiety and NO-releasing moiety assigned to X and Y in formula (VIII) can be those listed above.

Examples of the compounds of formula (VIII) include:
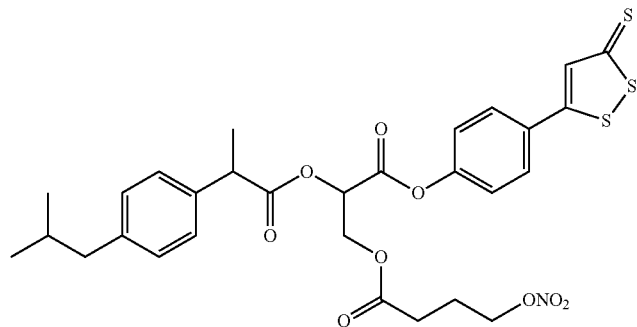
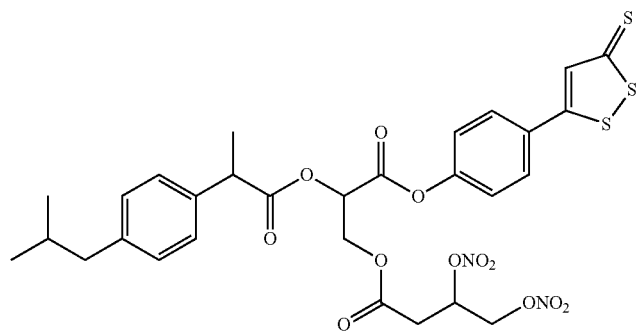
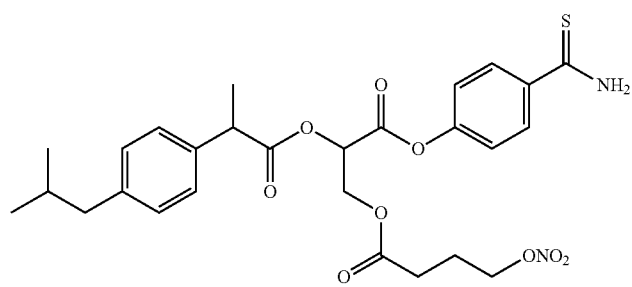
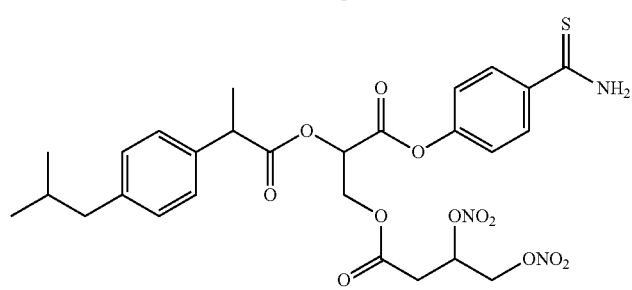
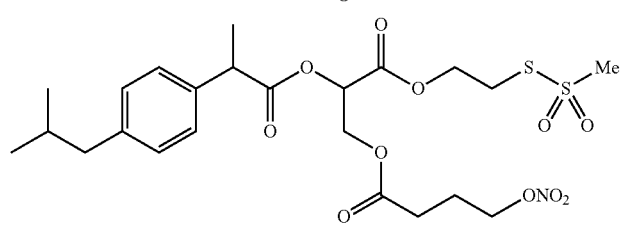
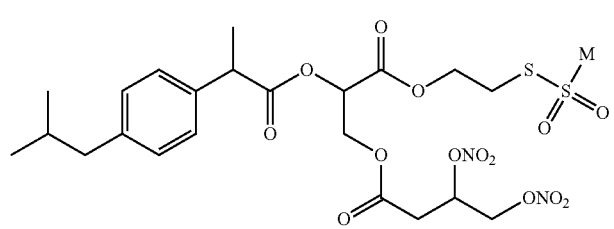

-continued

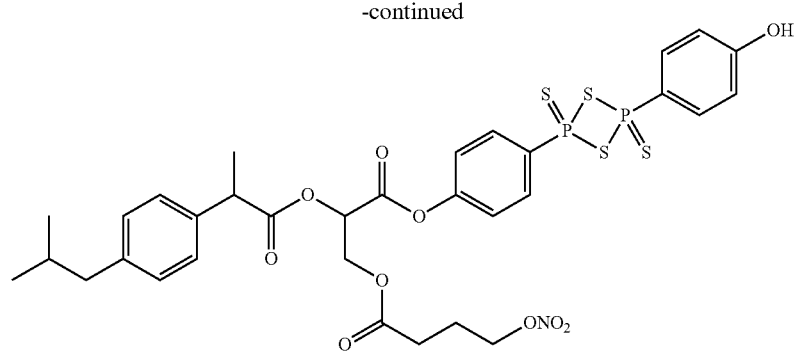

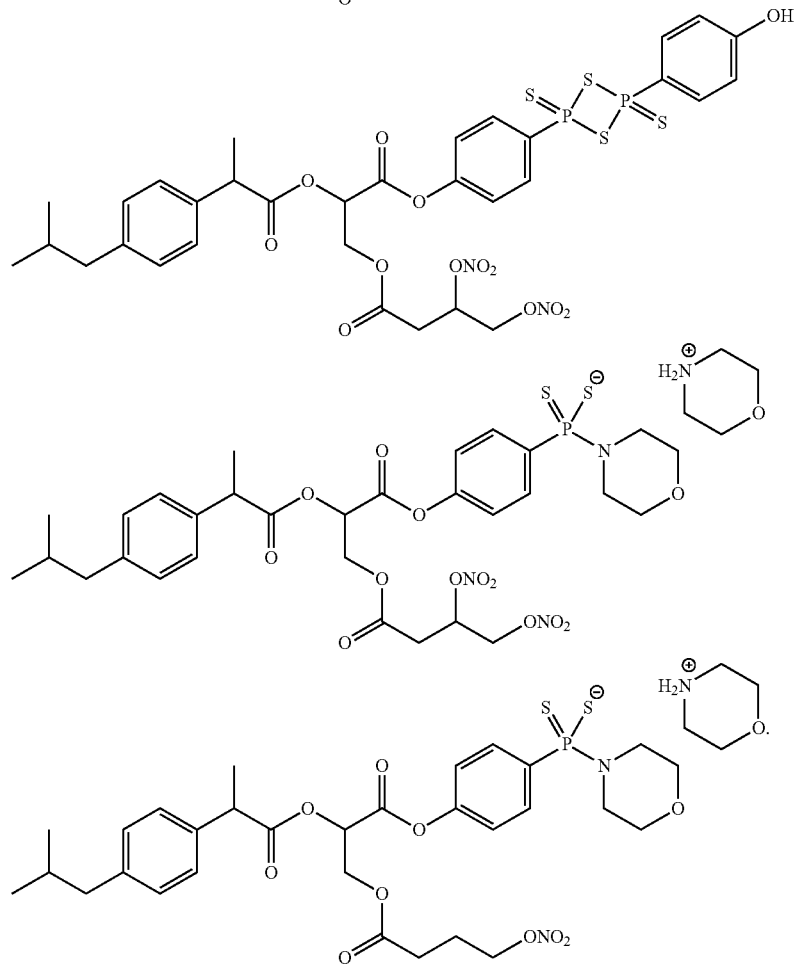

In some embodiments, the anti-inflammatory compounds disclosed herein can be of formula (IX):

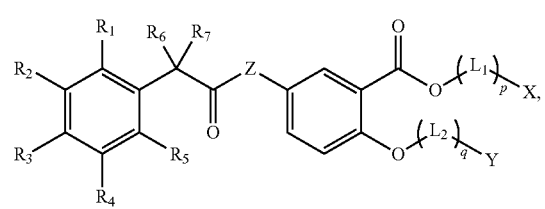

(IX)

in which each of p and q, independently, is 0 or 1; each of $L_1$ and $L_2$, independently, is a linker, the linker being —C(O)—, —(CH$_2$)$_m$—, —(CH$_2$)$_m$—O—, —(CH$_2$)$_m$—C(O)—, —(CH$_2$)$_m$—C(O)O—, —(CH$_2$)$_m$—OC(O)O—, —C(O)—(CH$_2$)$_m$—O—, —C(O)—(CH$_2$)$_m$—C(O)—, —OC(O)—(CH$_2$)$_m$—O—, —OC(O)—(CH$_2$)$_m$—C(O)—, or —OC(O)—(CH$_2$)$_m$—C(O)O—, in which m is 1, 2, 3, 4, 5, 6, or 7; X is a H$_2$S-releasing moiety or a NO-releasing moiety; Y is a NO-releasing moiety or a H$_2$S-releasing moiety, provided that X and Y are not simultaneously H$_2$S-releasing moieties or NO-releasing moieties; Z is O or NH; and each of $R_1$, $R_2$, $R_3$, $R_4$, $R_5$, $R_6$, and $R_7$, independently, is H, halo, NO$_2$, N$_3$, C$_1$-C$_{10}$ alkyl, OR, OC(O)R, N(R)$_2$, NH—C(O)R, S(O)R, or N=N—R, in which each R, independently, is H, C$_1$-C$_{10}$ alkyl, or aryl. The H$_2$S-releasing moiety and NO-releasing moiety assigned to X and Y in formula (IX) can be those listed above.

Examples of the compounds of formula (IX) include:
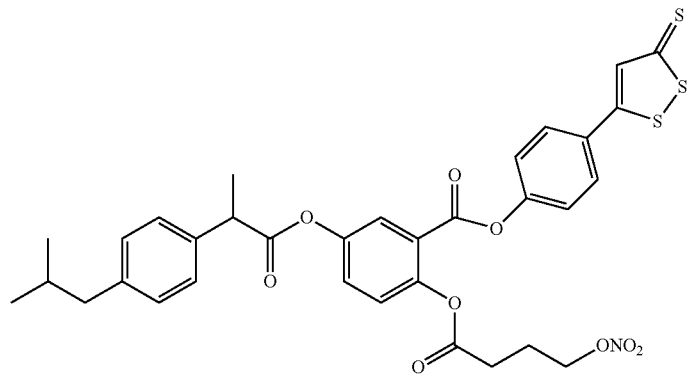
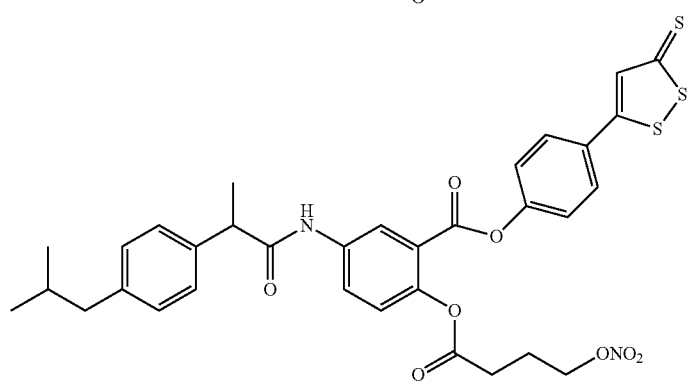
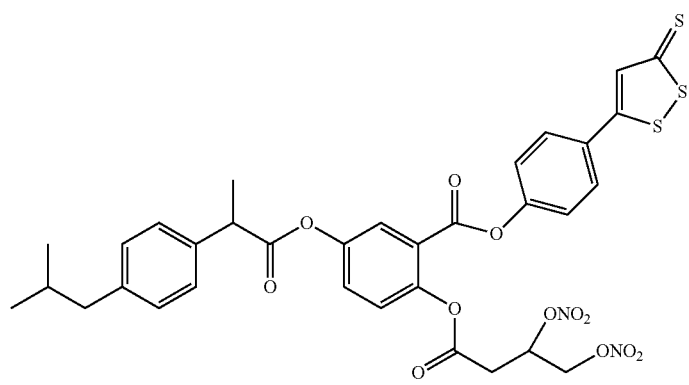
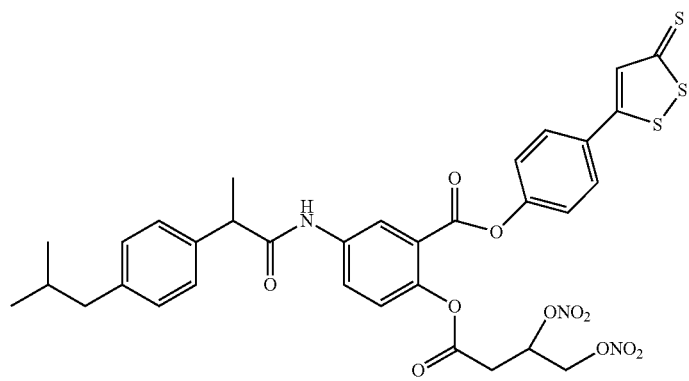

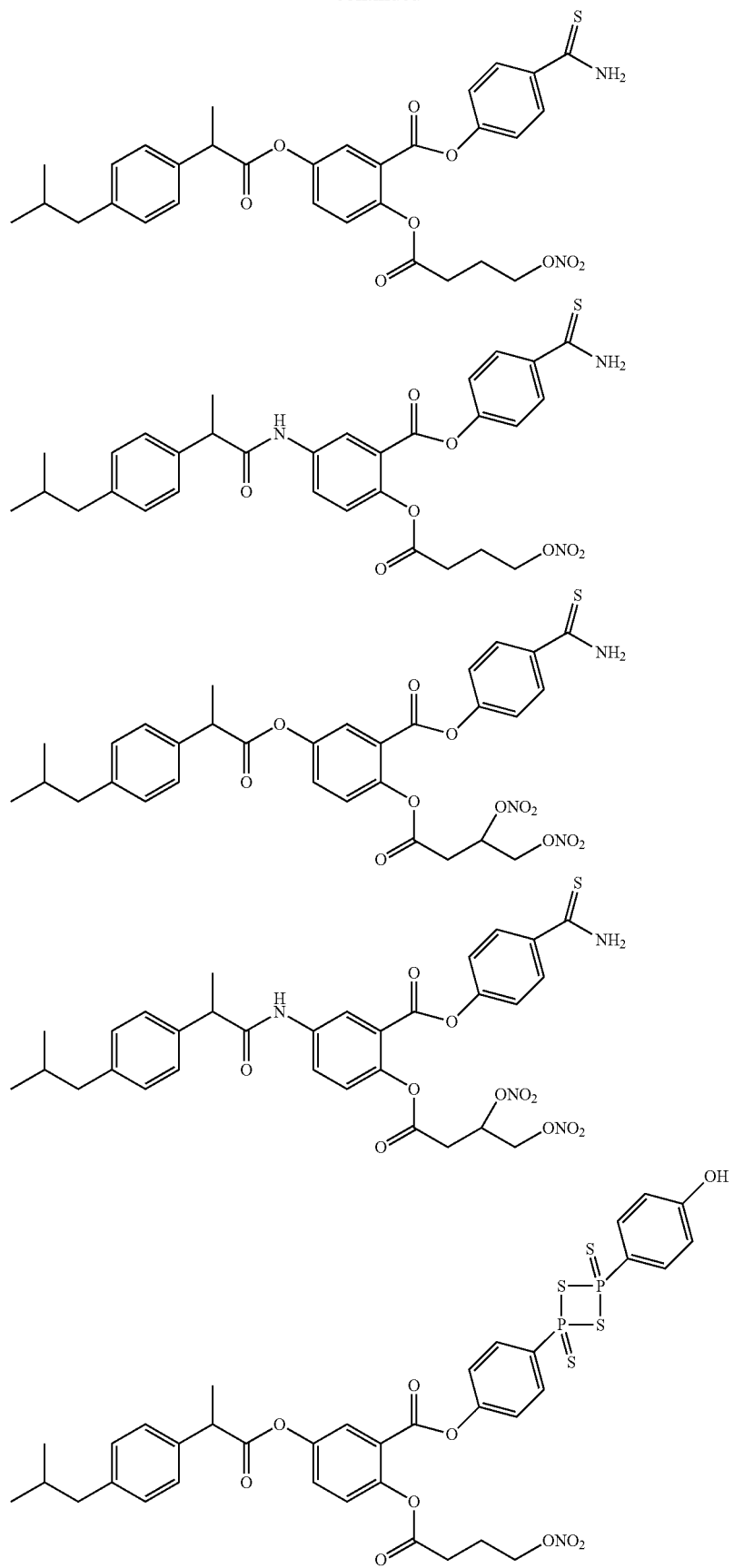

-continued
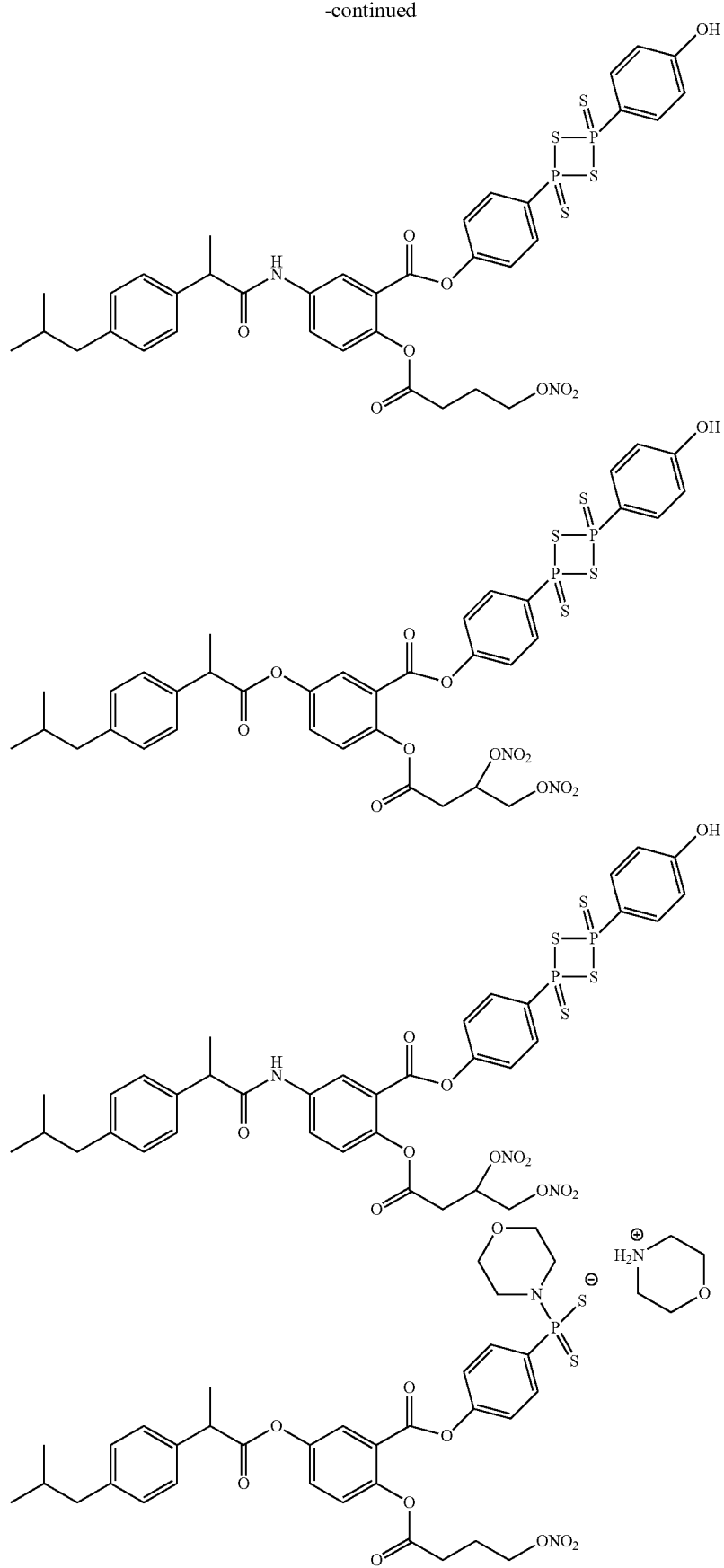

-continued
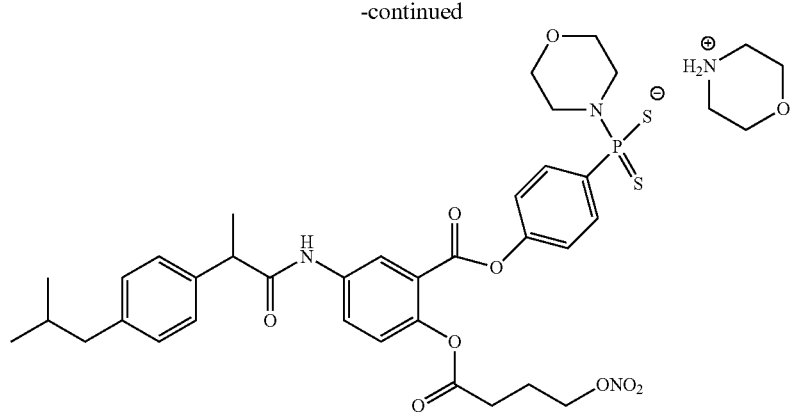
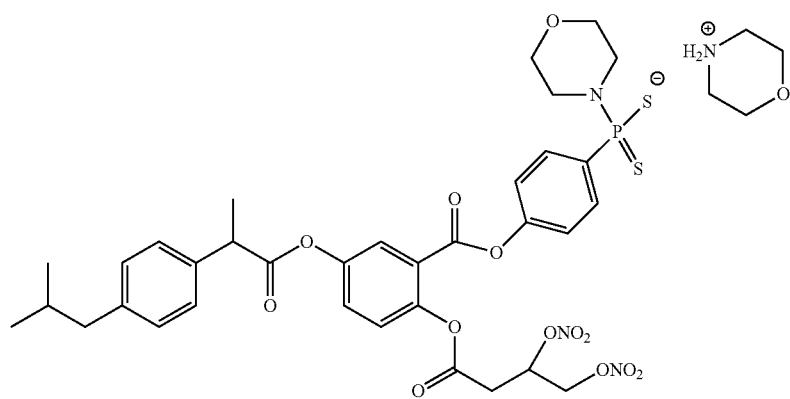
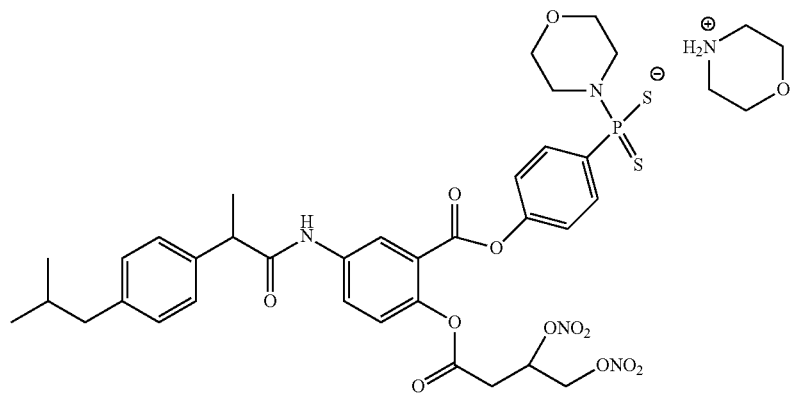
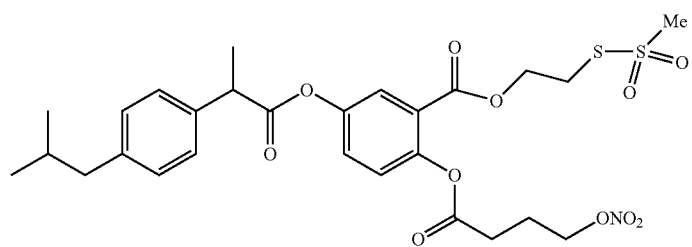

-continued

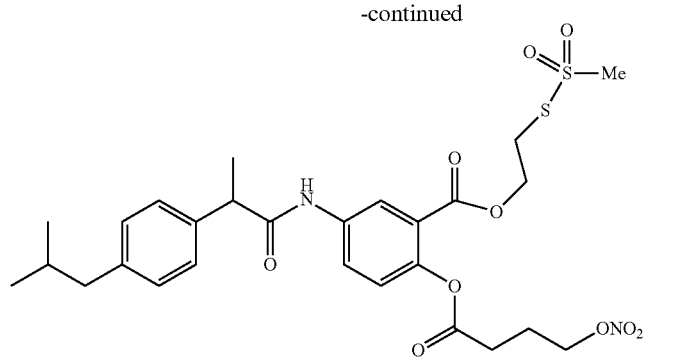

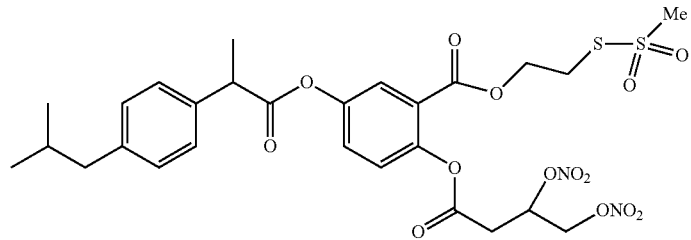

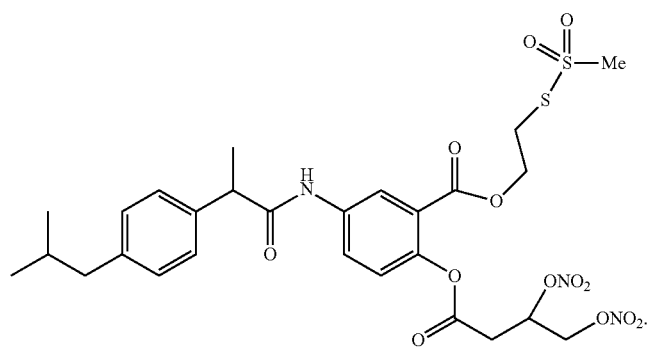

In some embodiments, the anti-inflammatory compounds disclosed herein can be of formula (X):

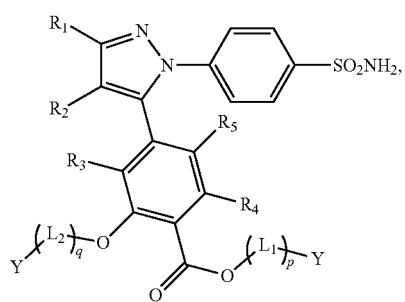

in which each of p and q, independently, is 0 or 1; each of $L_1$ and $L_2$, independently, is a linker, the linker being —C(O)—, —(CH$_2$)$_m$—, —(CH$_2$)$_m$—O—, —(CH$_2$)$_m$—C(O)—, —(CH$_2$)$_m$—C(O)O—, —(CH$_2$)$_m$—OC(O)O—, —C(O)—(CH$_2$)$_m$—O—, —C(O)—(CH$_2$)$_m$—C(O)—, —OC(O)—(CH$_2$)$_m$—O—, —OC(O)—(CH$_2$)$_m$—C(O)—, or —OC(O)—(CH$_2$)$_m$—C(O)O—, in which m is 1, 2, 3, 4, 5, 6, or 7; X is a H$_2$S-releasing moiety or a NO-releasing moiety; Y is a NO-releasing moiety or a H$_2$S-releasing moiety, provided that X and Y are not simultaneously H$_2$S-releasing moieties or NO-releasing moieties; and each of $R_1$, $R_2$, $R_3$, $R_4$, and $R_5$, independently, is H, halo, NO$_2$, N$_3$, C$_1$-C$_{10}$ alkyl (e.g., optionally substituted with halo such as F), OR, OC(O)R, N(R)$_2$, NH—C(O)R, S(O)R, or N=N—R, in which each R, independently, is H, C$_1$-C$_{10}$ alkyl, or aryl. The H$_2$S-releasing moiety and NO-releasing moiety assigned to X and Y in formula (X) can be those listed above.

Examples of the compounds of formula (X) include:

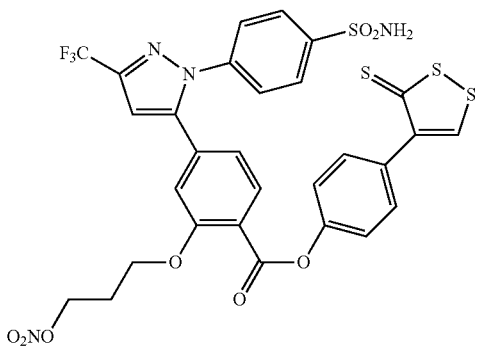

129
-continued
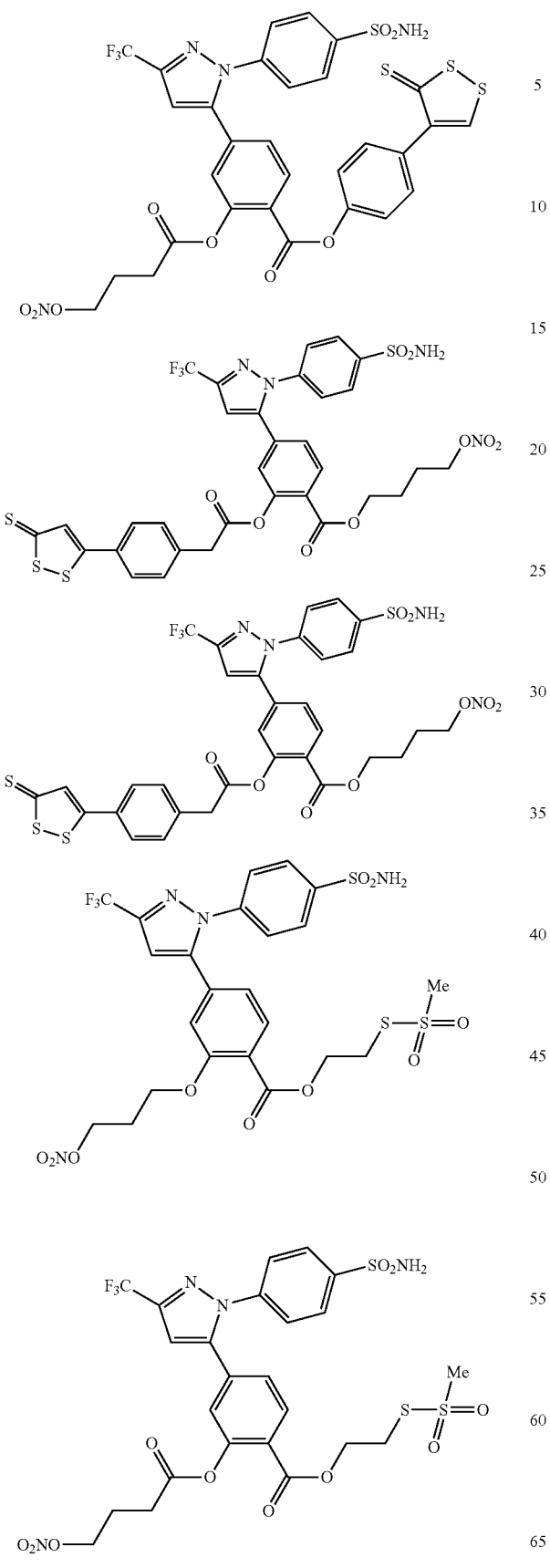
130
-continued
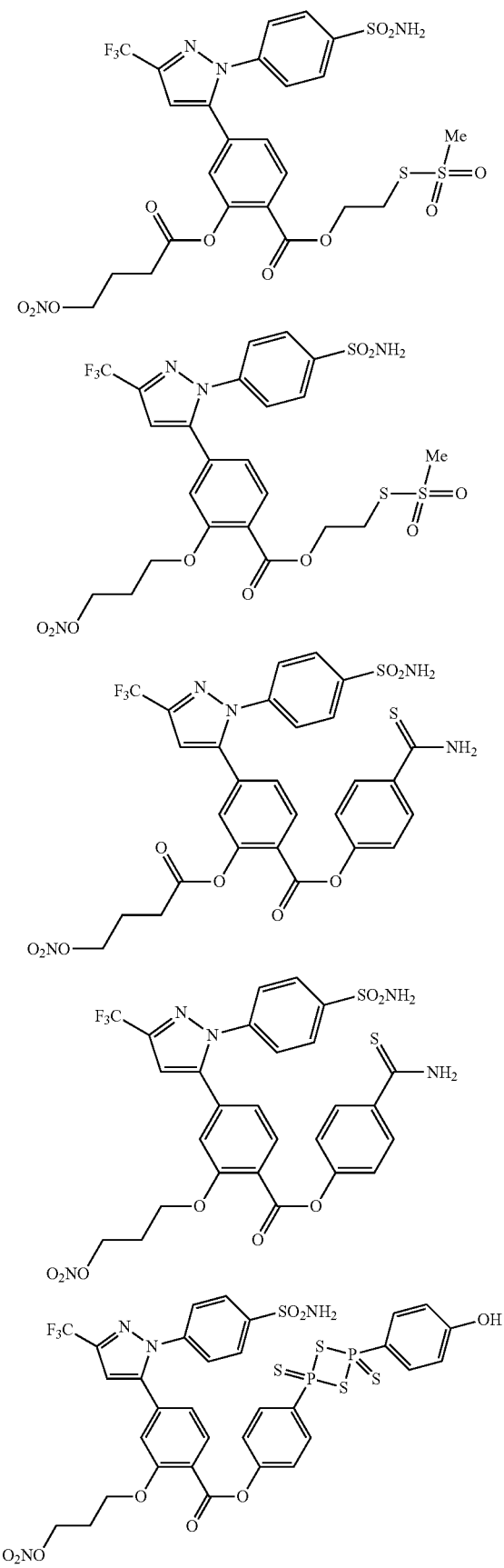

-continued

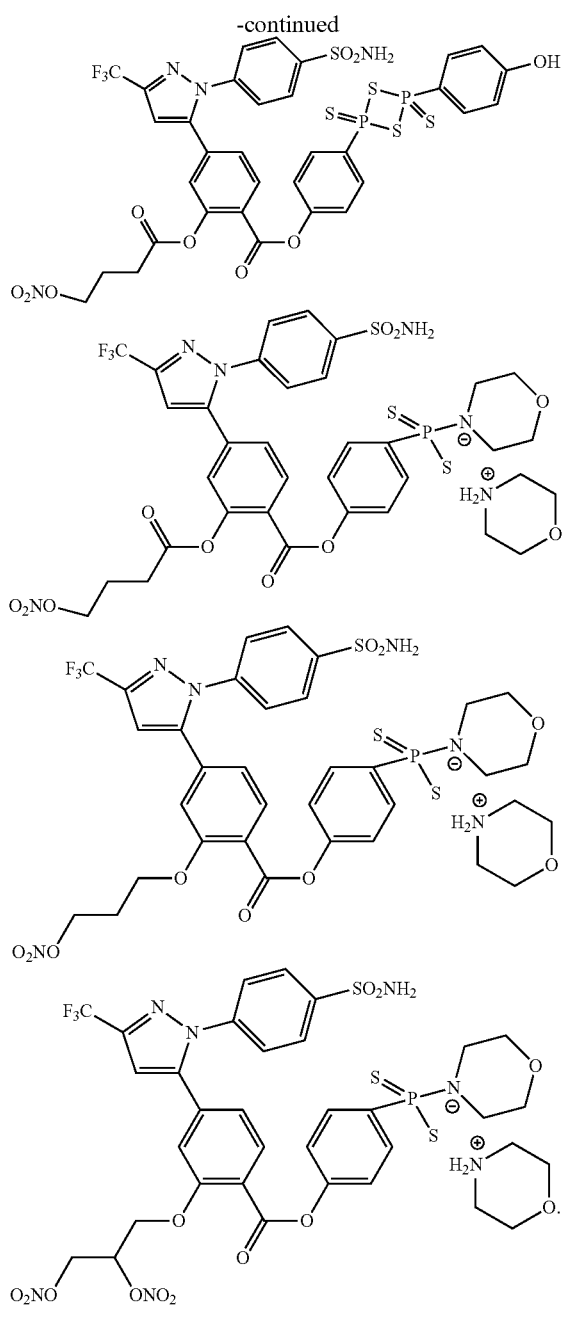

In some embodiments, the anti-inflammatory compounds disclosed herein can be of formula (XI):

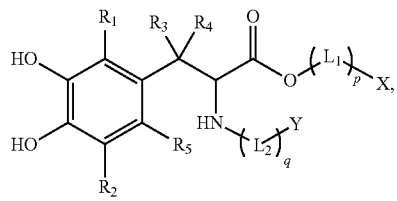

in which each of p and q, independently, is 0 or 1; each of $L_1$ and $L_2$, independently, is a linker, the linker being —C(O)—, —(CH$_2$)$_m$—, —(CH$_2$)$_m$—O—, —(CH$_2$)$_m$—C(O)—, —(CH$_2$)$_m$—C(O)O—, —(CH$_2$)$_m$—OC(O)O—, —C(O)—(CH$_2$)$_m$—O—, —C(O)—(CH$_2$)$_m$—C(O)—, —OC(O)—(CH$_2$)$_m$—O—, —OC(O)—(CH$_2$)$_m$—C(O)—, or —OC(O)—(CH$_2$)$_m$—C(O)O—, in which m is 1, 2, 3, 4, 5, 6, or 7; X is a H$_2$S-releasing moiety or a NO-releasing moiety; Y is a NO-releasing moiety or a H$_2$S-releasing moiety, provided that X and Y are not simultaneously H$_2$S-releasing moieties or NO-releasing moieties; and each of $R_1$, $R_2$, $R_3$, and $R_4$, independently, is H, halo, NO$_2$, N$_3$, C$_1$-C$_{10}$ alkyl, OR, OC(O)R, N(R)$_2$, NH—C(O)R, S(O)R, or N=N—R, in which each R, independently, is H, C$_1$-C$_{10}$ alkyl, or aryl. The H$_2$S-releasing moiety and NO-releasing moiety assigned to X and Y in formula (XI) can be those listed above.

Examples of the compounds of formula (XI) include:

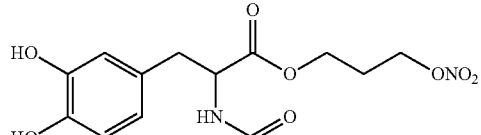

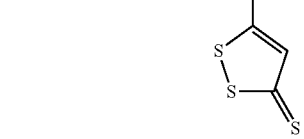

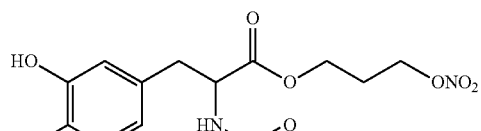

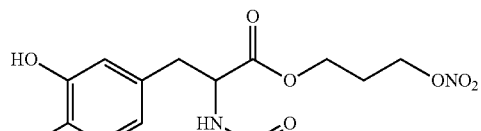

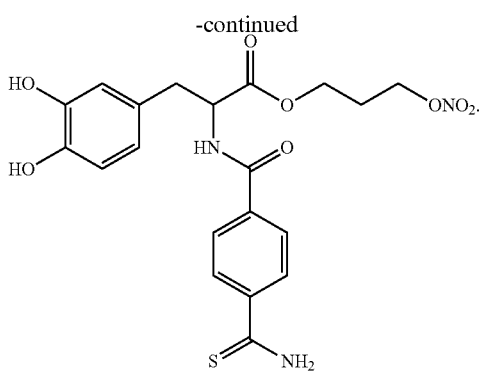

In some embodiments, the anti-inflammatory compounds disclosed herein can be of formula (XII):

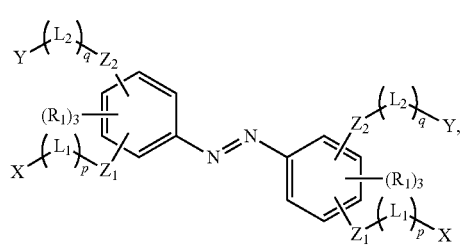

(XII)

in which each p, independently, is 0 or 1; each q, independently, is 0 or 1; each $Z_1$, independently, is —O—, —NH—, —N=N—, —C(O)O—, —C(O)—NH—, —NH—C(O)—, —NH—C(O)O—, or —OC(O)—NH—; each $Z_2$, independently, is —O—, —NH—, —N=N—, —C(O)O—, —C(O)—NH—, —NH—C(O)—, —NH—C(O)O—, or —OC(O)—NH—; each $L_1$, independently, is a linker, the linker being —C(O)—, —(CH$_2$)$_m$—, —(CH$_2$)$_m$—O—, —(CH$_2$)$_m$—C(O)—, —(CH$_2$)$_m$—C(O)O—, —(CH$_2$)$_m$—OC(O)O—, —C(O)—(CH$_2$)$_m$—O—, —C(O)—(CH$_2$)$_m$—C(O)—, —OC(O)—(CH$_2$)$_m$—O—, —OC(O)—(CH$_2$)$_m$—C(O)—, or —OC(O)—(CH$_2$)$_m$—C(O)O—, in which m is 1, 2, 3, 4, 5, 6, or 7; each $L_2$, independently, is a linker, the linker being —C(O)—, —(CH$_2$)$_m$—, —(CH$_2$)$_m$—O—, —(CH$_2$)$_m$—C(O)—, —(CH$_2$)$_m$—C(O)O—, —(CH$_2$)$_m$—OC(O)O—, —C(O)—(CH$_2$)—O—, —C(O)—(CH$_2$)$_m$—C(O)—, —OC(O)—(CH$_2$)$_m$—O—, —OC(O)—(CH$_2$)$_m$—C(O)—, or —OC(O)—(CH$_2$)$_m$—C(O)O—, in which m is 1, 2, 3, 4, 5, 6, or 7; each X, independently, is a H$_2$S-releasing moiety or a NO-releasing moiety; each Y, independently, is a NO-releasing moiety or a H$_2$S-releasing moiety, provided that not all of X and Y are simultaneously H$_2$S-releasing moieties or NO-releasing moieties; and each $R_1$, independently, is H, halo, NO$_2$, N$_3$, C$_1$-C$_{10}$ alkyl, OR, OC(O)R, N(R)$_2$, NH—C(O)R, S(O)R, or N=N—R, in which each R, independently, is H, C$_1$-C$_{10}$ alkyl, or aryl. The H$_2$S-releasing moiety and NO-releasing moiety assigned to X and Y in formula (XI) can be those listed above.

Examples of the compounds of formula (XII) include:

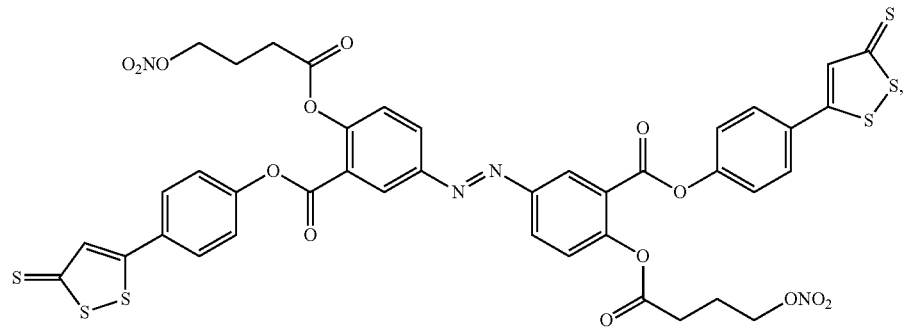

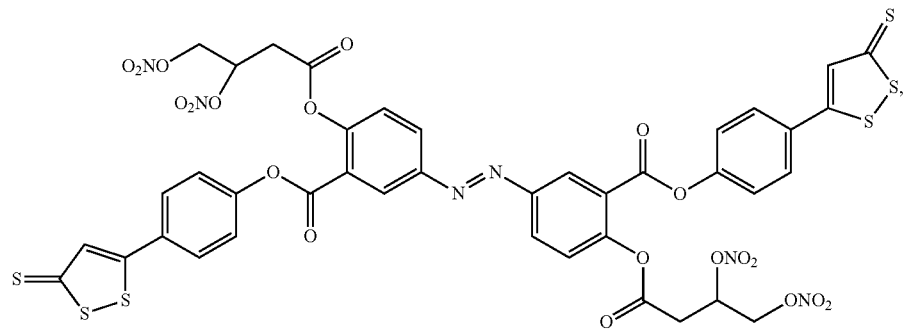

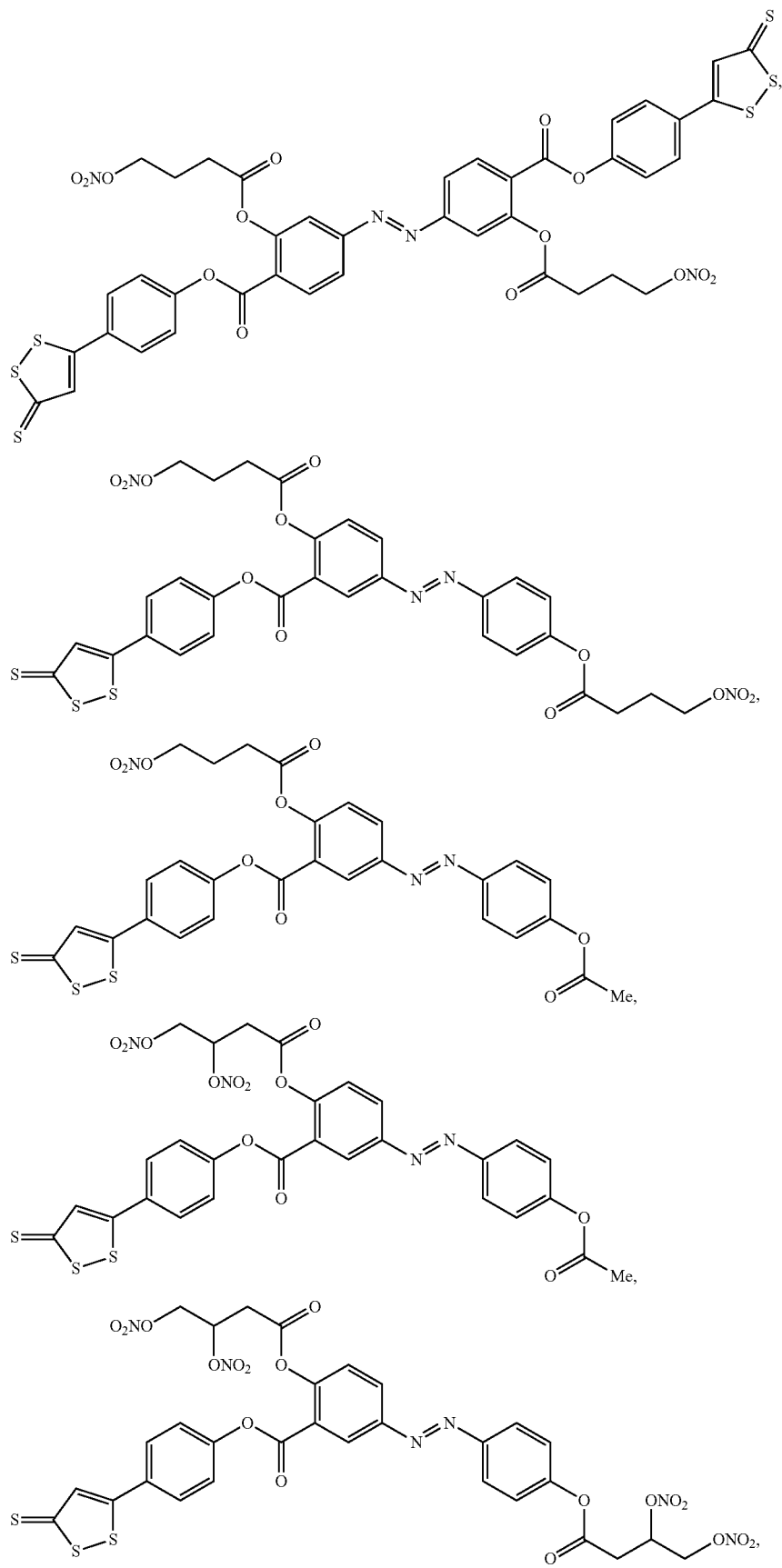

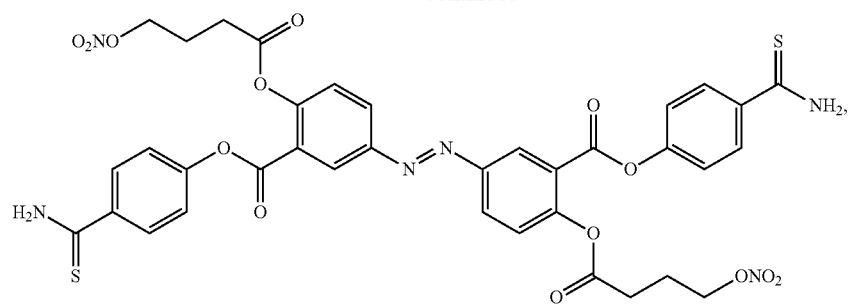
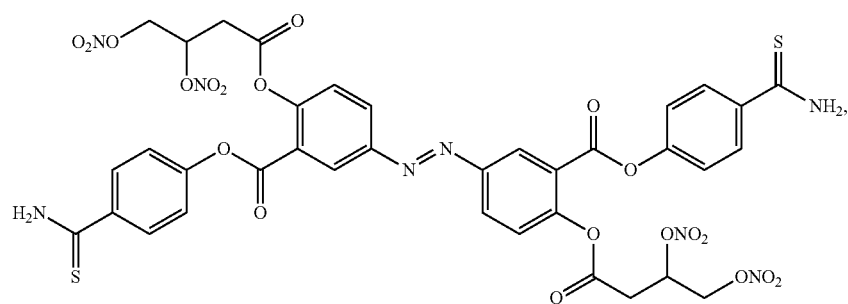
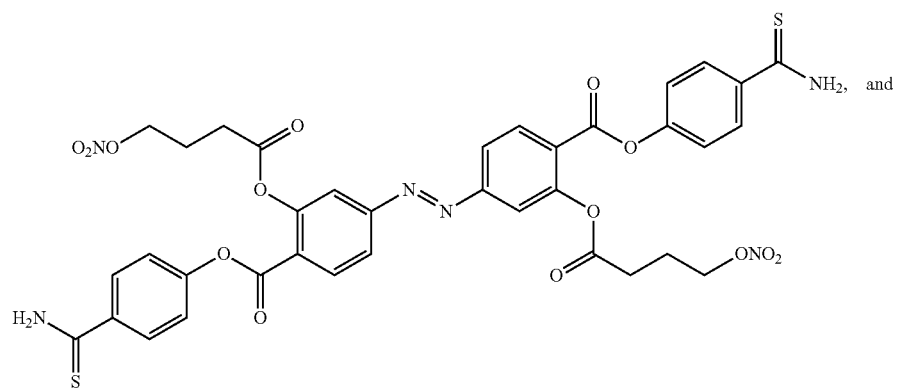
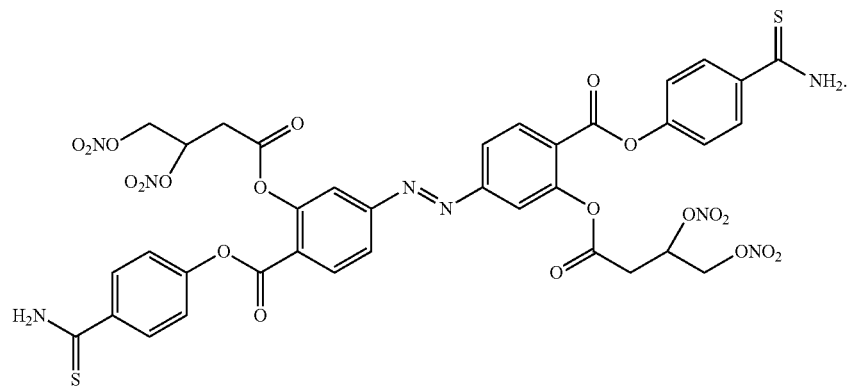

In some embodiments, the anti-inflammatory compounds disclosed herein can be of formula (XIII):

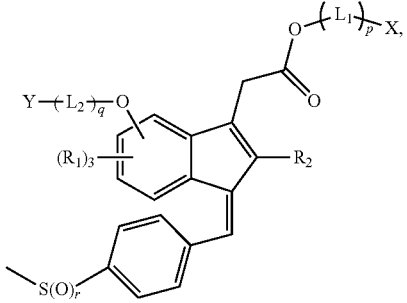

(XIII)

in which each of p and q, independently, is 0 or 1; r is 1 or 2; each of $L_1$ and $L_2$, independently, is a linker, the linker being —C(O)—, —(CH$_2$)$_m$—, —(CH$_2$)$_m$—O—, —(CH$_2$)$_m$—C(O)—, —(CH$_2$)$_m$—C(O)O—, —(CH$_2$)$_m$—OC(O)O—, —C(O)—(CH$_2$)$_m$—O—, —C(O)—(CH$_2$)$_m$—C(O)—, —OC(O)—(CH$_2$)$_m$—O—, —OC(O)—(CH$_2$)$_m$—C(O)—, or —OC(O)—(CH$_2$)$_m$—C(O)O—, in which m is 1, 2, 3, 4, 5, 6, or 7; X is a H$_2$S-releasing moiety or a NO-releasing moiety; Y is a NO-releasing moiety or a H$_2$S-releasing moiety, provided that X and Y are not simultaneously H$_2$S-releasing moieties or NO-releasing moieties; and each of $R_1$ and $R_2$ independently, is H, halo, NO$_2$, N$_3$, C$_1$-C$_{10}$ alkyl, OR, OC(O)R, N(R), NH—C(O)R, S(O)R, or N═N—R, in which each R, independently, is H, C$_1$-C$_{10}$ alkyl, or aryl. The H$_2$S-releasing moiety and NO-releasing moiety assigned to X and Y in formula (XIII) can be those listed above.

Examples of the compounds of formula (XIII) include:

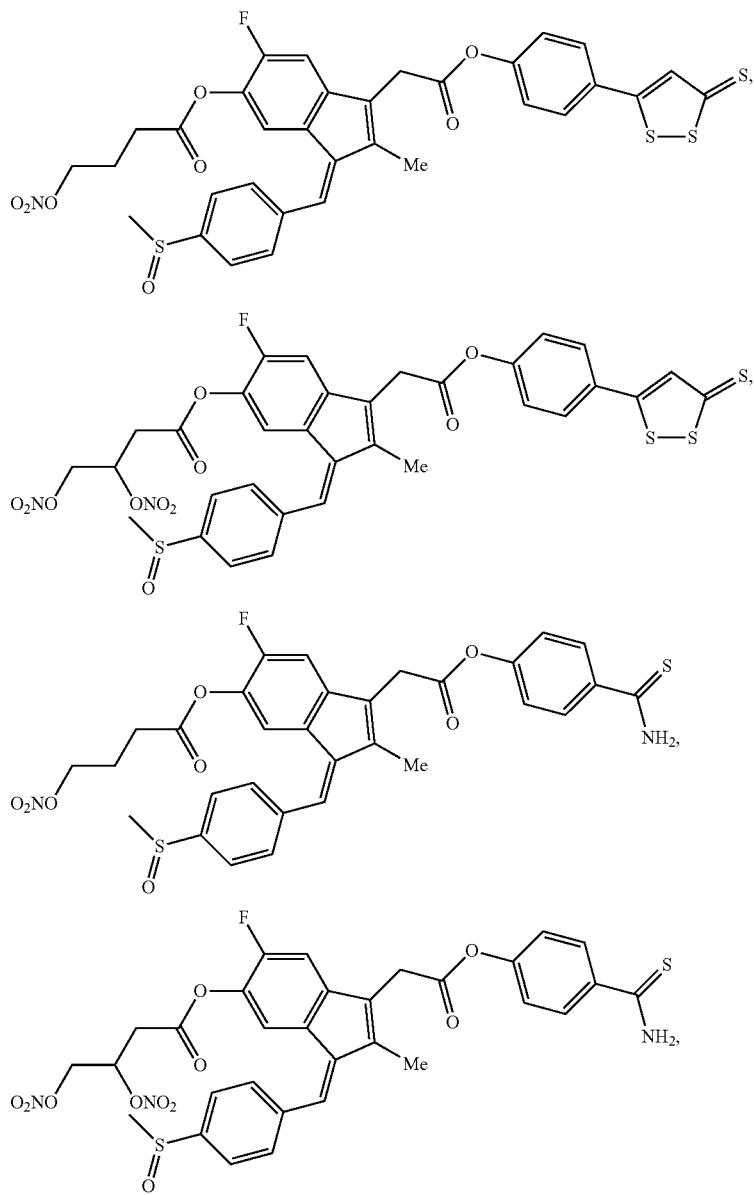

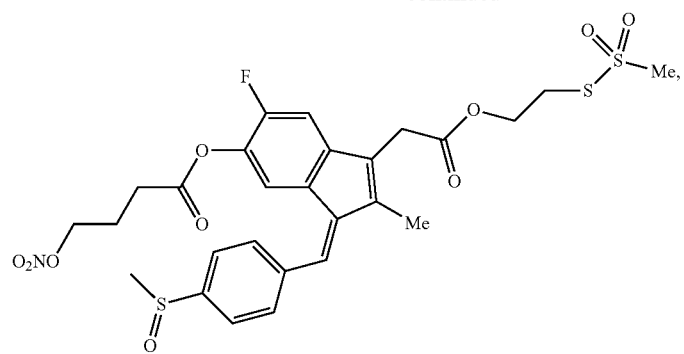
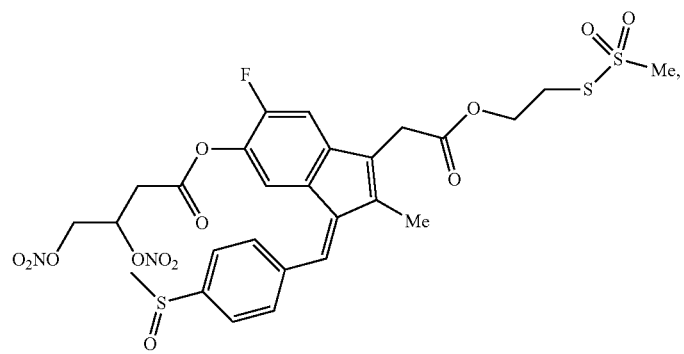
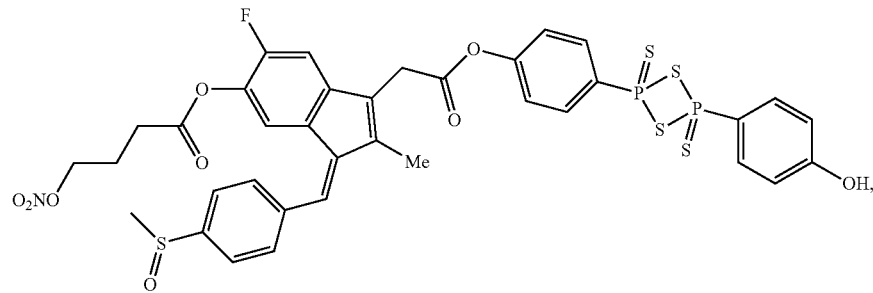
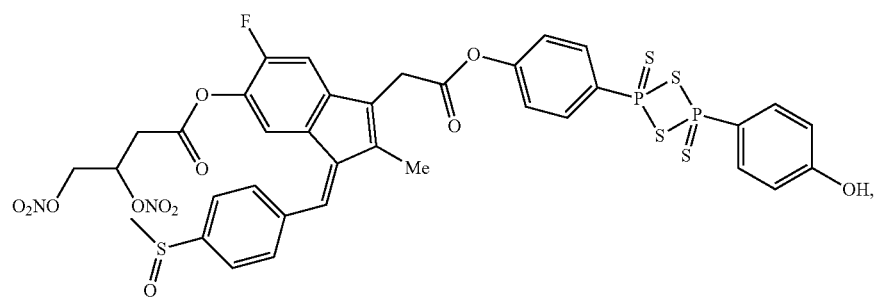
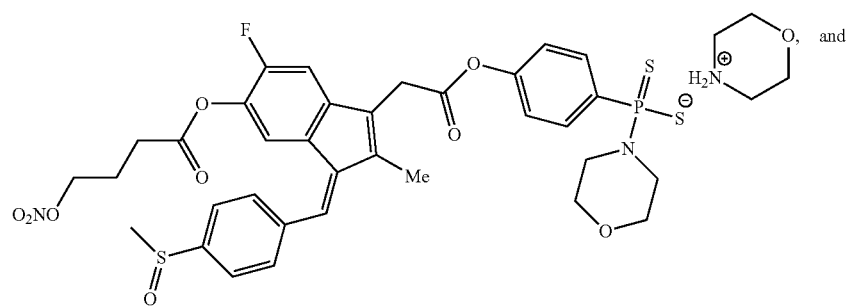

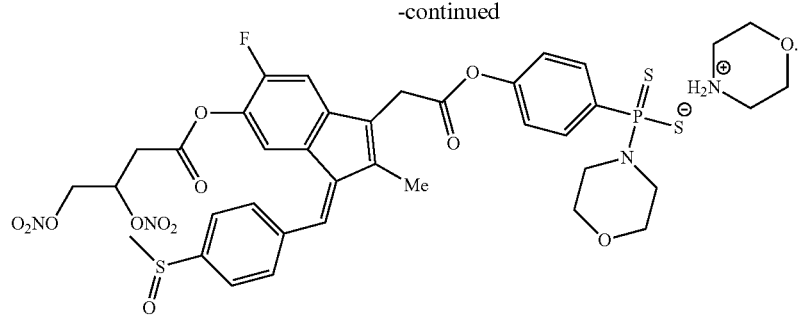

In some embodiments, the anti-inflammatory compounds disclosed herein can be of formula (XIV):

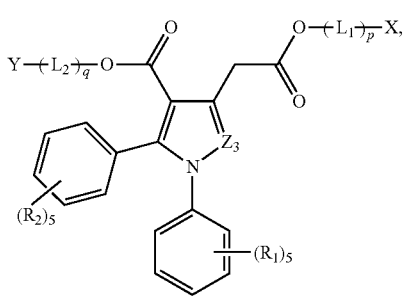

in which each of p and q, independently, is 0 or 1; $Z_3$ is N or C(R); each of $L_1$ and $L_2$, independently, is a linker, the linker being —C(O)—, —(CH$_2$)$_m$—, —(CH$_2$)$_m$O—, —(CH$_2$)$_m$—C(O)—, —(CH$_2$)$_m$—C(O)O—, —(CH$_2$)$_m$—OC(O)O—, —C(O)—(CH$_2$)$_m$—O—, —C(O)—(CH$_2$)$_m$—C(O)—, —OC(O)—(CH$_2$)$_m$—O—, —OC(O)—(CH$_2$)$_m$—C(O)—, or —OC(O)—(CH$_2$)$_m$—C(O)O—, in which m is 1, 2, 3, 4, 5, 6, or 7; X is a H$_2$S-releasing moiety or a NO-releasing moiety; Y is a NO-releasing moiety or a H$_2$S-releasing moiety, provided that X and Y are not simultaneously H$_2$S-releasing moieties or NO-releasing moieties; and each $R_1$ and each $R_2$, independently, is H, halo, NO$_2$, N$_3$, C$_1$-C$_{10}$ alkyl, OR, OC(O)R, N(R)$_2$, NH—C(O)R, S(O)R, or N=N—R, in which each R, independently, is H, C$_1$-C$_{10}$ alkyl, or aryl. The H$_2$S-releasing moiety and NO-releasing moiety assigned to X and Y in formula (XIV) can be those listed above.

Examples of the compounds of formula (XIV) include:

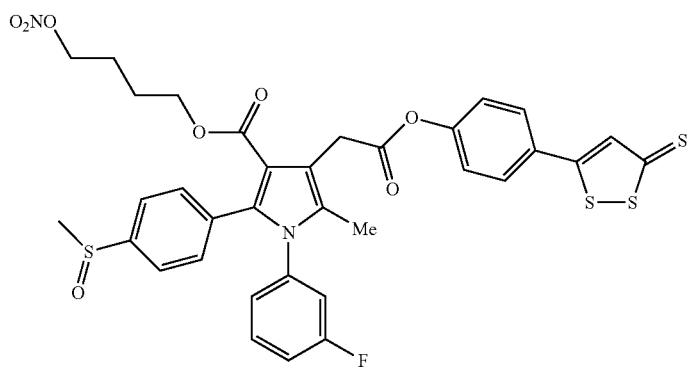

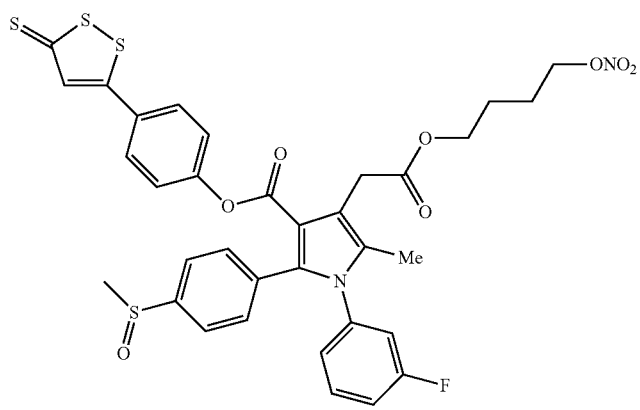

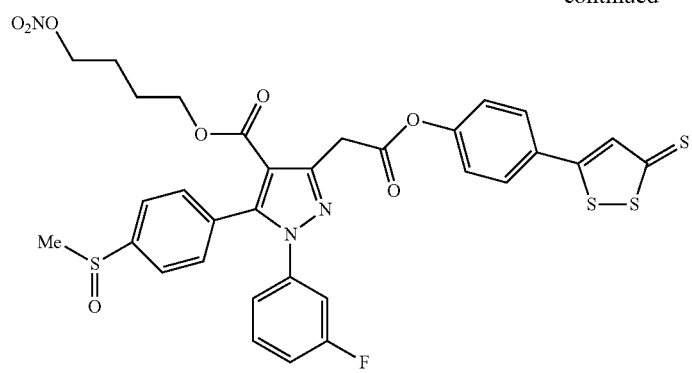
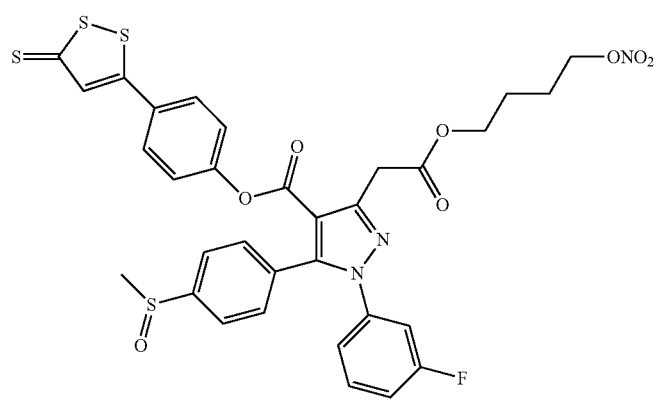
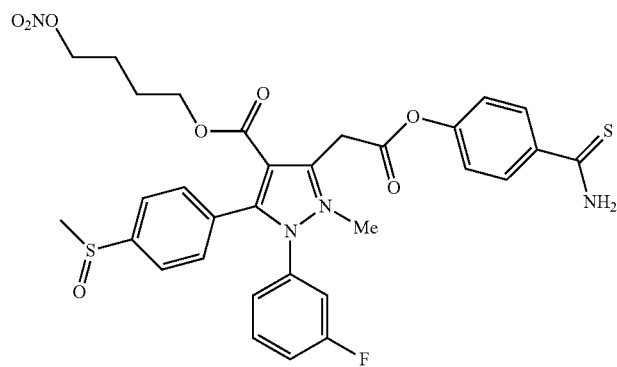
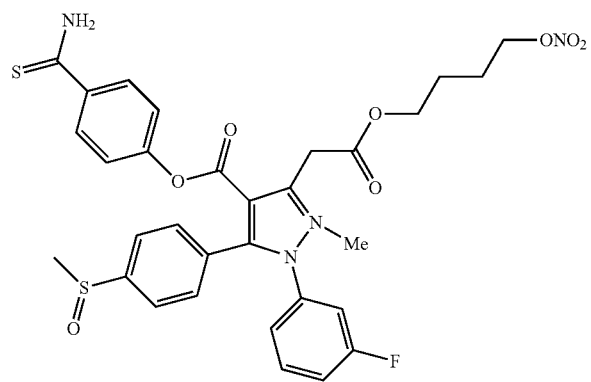

147
148
-continued
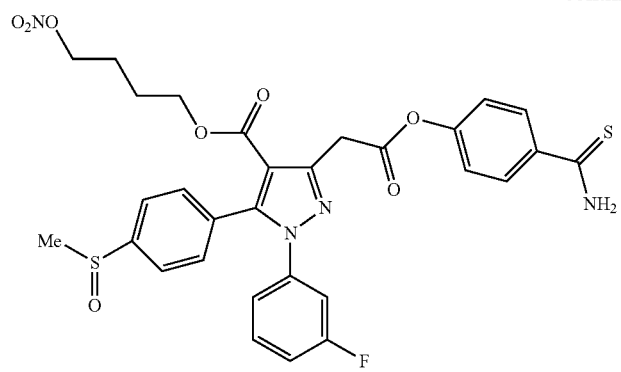
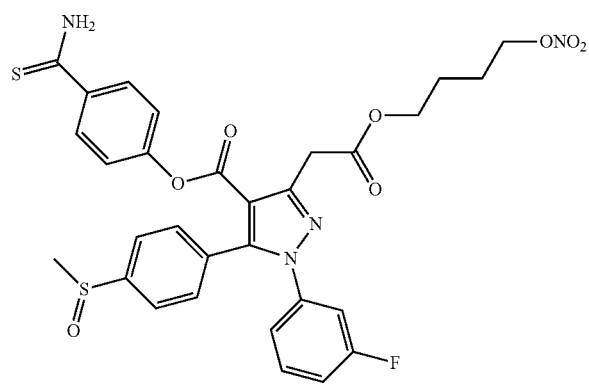
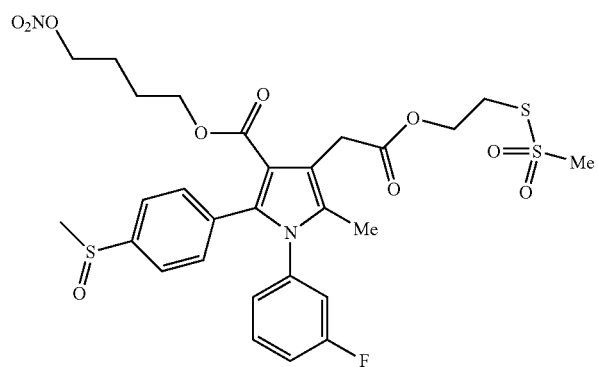
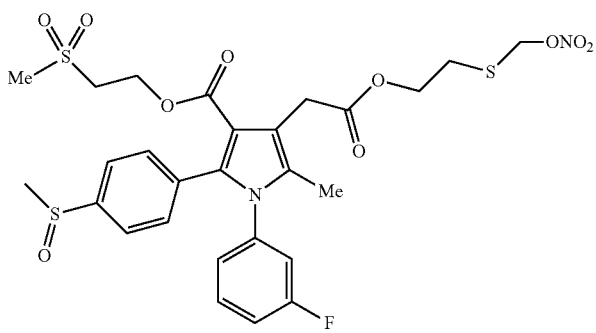
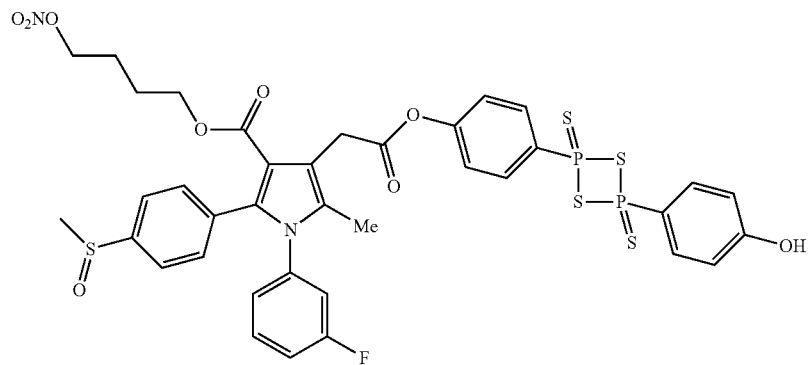

-continued

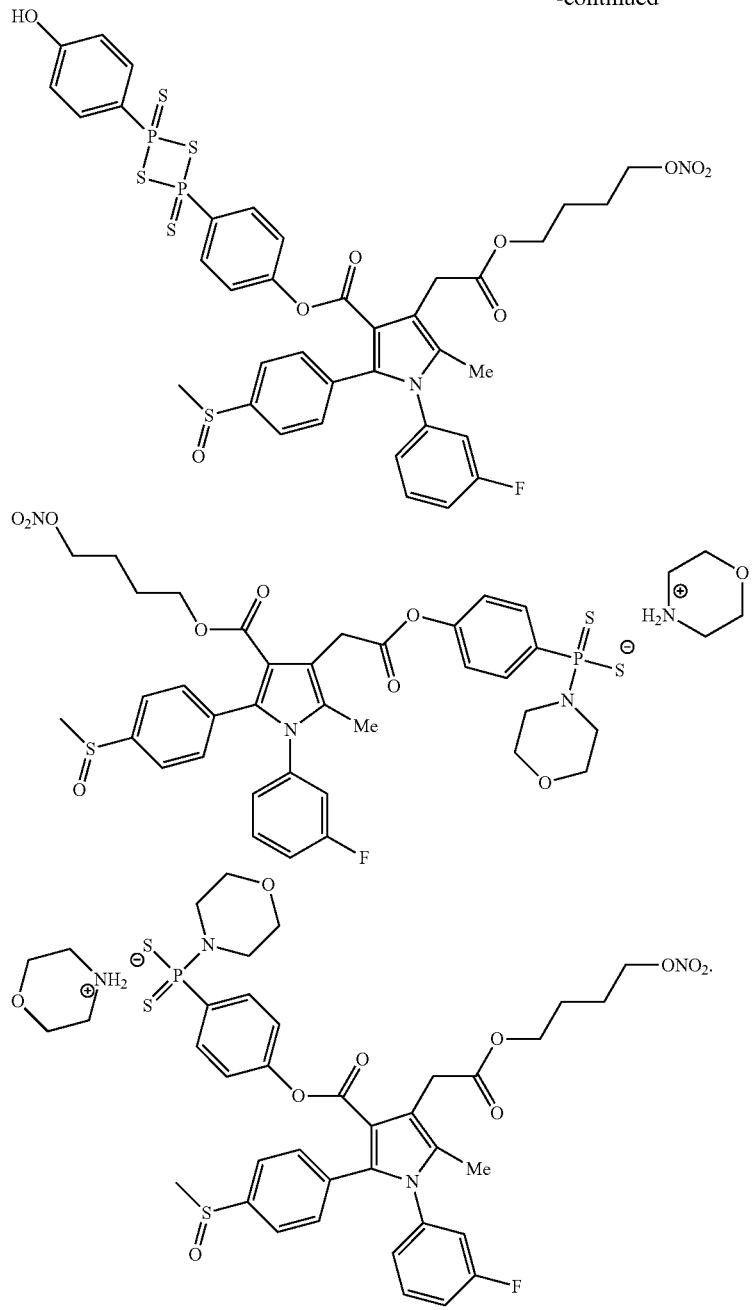

and

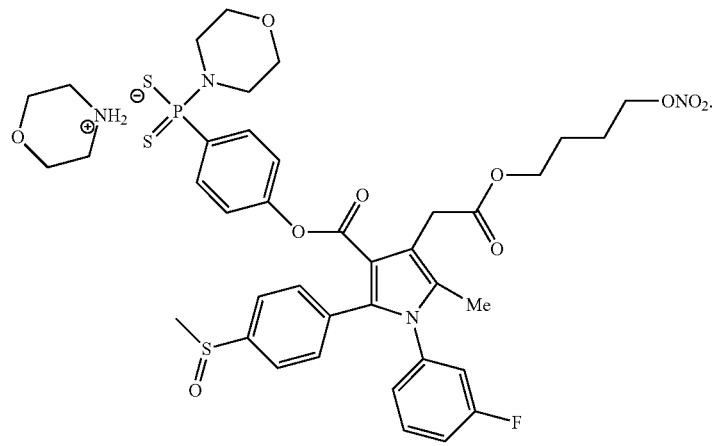

In some embodiments, the anti-inflammatory compounds disclosed herein can be of formula (XV):

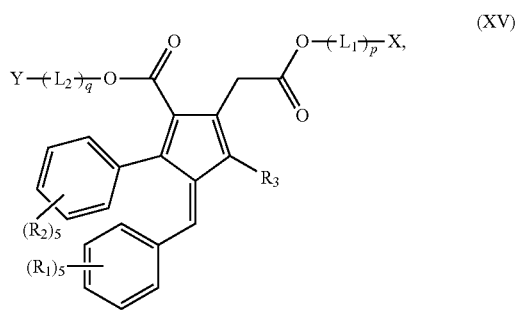

(XV)

in which each of p and q, independently, is 0 or 1; each of $L_1$ and $L_2$, independently, is a linker, the linker being —C(O)—, —(CH$_2$)$_m$—, —(CH$_2$)$_m$—O—, —(CH$_2$)$_m$—C(O)—, —(CH$_2$)$_m$—C(O)O—, —(CH$_2$)$_m$—OC(O)O—, —C(O)—(CH$_2$)$_m$—O—, —C(O)—(CH$_2$)$_m$—C(O)—, —OC(O)—(CH$_2$)$_m$—O—, —OC(O)—(CH$_2$)$_m$—C(O)—, or —OC(O)—(CH$_2$)$_m$—C(O)O—, in which m is 1, 2, 3, 4, 5, 6, or 7; X is a H$_2$S-releasing moiety or a NO-releasing moiety; Y is a NO-releasing moiety or a H$_2$S-releasing moiety, provided that X and Y are not simultaneously H$_2$S-releasing moieties or NO-releasing moieties; and each $R_1$, each $R_2$, and $R_3$, independently, is H, halo, NO$_2$, N$_3$, C$_1$-C$_{10}$ alkyl, OR, OC(O)R, N(R)$_2$, NH—C(O)R, S(O)R, or N═N—R, in which each R, independently, is H, C$_1$-C$_{10}$ alkyl, or aryl. The H₂S-releasing moiety and NO-releasing moiety assigned to X and Y in formula (XV) can be those listed above.

The compounds described above can be prepared by methods well known in the art. Examples 1-8 below provide detailed descriptions of how certain compounds described above were actually prepared.

Scheme I shown below illustrates an exemplary synthetic route for synthesizing certain compounds described herein.

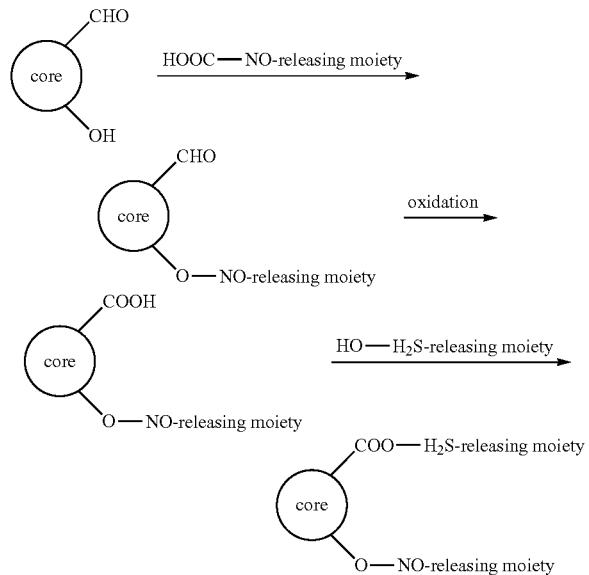

Scheme I

As shown in Scheme I, a compound containing a core covalently bonded to a hydroxyl group and an aldehyde group can first react with a compound containing a NO-releasing moiety (such as a NO-releasing moiety described herein) bonded to a carboxyl group via an esterification reaction to form a first intermediate containing a NO-releasing moiety. The aldehyde group in the intermediate thus formed can then be oxidized to form a second intermediate containing a NO-releasing moiety and a carboxyl group. The second intermediate can subsequently react with a compound containing a H₂S-releasing moiety (such as a H₂S-releasing moiety described herein) via an esterification to form an anti-inflammatory compound described herein.

Various linkers known in the art may be used to link NO and H₂S donor groups to a core compound. Preferred linkers for linking donor groups to a compound are aliphatic linkers, e.g., a butyl linker group. In certain embodiments, a butyl nitrate moiety is an NO donor moiety.

An anti-inflammatory compound synthesized above can be purified by a suitable method such as column chromatography, high-pressure liquid chromatography, or recrystallization.

Other anti-inflammatory compounds can be prepared using other suitable starting materials through the above synthetic routes and others known in the art. The methods described above may also additionally include steps, either before or after the steps described specifically herein, to add or remove suitable protecting groups in order to ultimately allow synthesis of the anti-inflammatory compounds. In addition, various synthetic steps may be performed in an alternate sequence or order to give the desired compounds.

Synthetic chemistry transformations and protecting group methodologies (protection and deprotection) useful in synthesizing applicable anti-inflammatory compounds are known in the art and include, for example, those described in R. Larock, *Comprehensive Organic Transformations*, VCH Publishers (1989); T. W. Greene and P. G. M. Wuts, *Protective Groups in Organic Synthesis*, 2$^{nd}$ Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995) and subsequent editions thereof.

The anti-inflammatory compounds mentioned herein may contain a non-aromatic double bond and one or more asymmetric centers. Thus, they can occur as racemates and racemic mixtures, single enantiomers, individual diastereomers, diastereomeric mixtures, and cis- or trans-isomeric forms. All such isomeric forms are contemplated.

The invention also encompasses pharmaceutically acceptable salts of the disclosed compounds. Pharmaceutically acceptable salts include pharmaceutically acceptable acid addition salts, pharmaceutically acceptable metal salts, ammonium and alkylated ammonium salts. Acid addition salts include salts of inorganic acids as well as organic acids. Examples of suitable inorganic acids include hydrochloric, hydrobromic, hydroiodic, phosphoric, sulfuric, sulfamic, nitric acids and the like. Examples of suitable organic acids include formic, acetic, trichloroacetic, trifluoroacetic, propionic, benzoic, cinnamic, citric, fumaric, glycolic, itaconic, lactic, methanesulfonic, maleic, malic, malonic, mandelic, oxalic, picric, pyruvic, salicylic, succinic, methane sulfonic, ethanesulfonic, tartaric, ascorbic, pamoic, bismethylene salicylic, ethanedisulfonic, gluconic, citraconic, aspartic, stearic, palmitic, EDTA, glycolic, p-aminobenzoic, glutamic, benzenesulfonic, p-toluenesulfonic acids, theophylline acetic acids, as well as the 8-halotheophyllines, for example 8-bromotheophylline and the like. Further examples of pharmaceutical acceptable inorganic or organic acid addition salts include the pharmaceutically acceptable salts listed in J. Pharm. Sci. 1977, 66, 2, which is incorporated herein by reference. Examples of metal salts include lithium, sodium, potassium, magnesium salts and the like. Examples of ammonium and alkylated ammonium salts include ammonium, methyl-, dimethyl-, trimethyl-, ethyl-, hydroxyethyl-, diethyl-, n-butyl-, sec-butyl-, tert-butyl-, tetramethylammonium salts and the like.

The invention also encompasses prodrugs of the present compounds, which on administration undergo chemical conversion by metabolic processes before becoming pharmacologically active substances. In general, such prodrugs will be functional derivatives of the compounds of the compounds described herein, which are readily convertible in vivo into the required compound. Conventional procedures for the selection and preparation of suitable prodrug derivatives are described, for example, in "Design of Prodrugs", ed. H. Bundgaard, Elsevier, 1985.

Also within the scope of this invention is a pharmaceutical composition containing an effective amount of at least one anti-inflammatory compound described herein and a pharmaceutical acceptable carrier. Further, this invention covers a method of treating an inflammatory disease described herein. The method includes administering to a subject (e.g., a patient) having the inflammatory disease an effective amount of one or more of the anti-inflammatory compounds. Examples of the inflammatory disease include cancer (e.g., colon, breast, lung, prostate, liver, ovarian, uterine, leukemia, or pancreatic cancer), rheumatoid arthritis, intestine inflammation (e.g., ulcerative colitis, duodenal ulcer, inflammatory bowel disease, or irritable bowel syndrome), stomach ulcer (e.g., stress ulcer), a cardiovascular disease (e.g., atherosclerosis), or a neurodegenerative disease (e.g., Alzheimer's disease, Parkinson's disease, or multiple sclerosis). The term "treating" or "treatment" mentioned herein refers to administering one or more of the anti-inflammatory compounds described herein to a subject, who has an inflammatory disease, a symptom of such a disease, or a predisposition toward such a disease, with the purpose to confer a therapeutic effect, e.g., to cure, relieve, alter, affect, ameliorate, or inhibit the development of an inflammatory disease, the symptom of it, or the predisposition toward it. Such a subject can be identified by a health care professional based on results from any suitable diagnostic method. "An effective amount" refers to the amount of an active anti-inflammatory compound that is required to confer a therapeutic effect on the treated subject. Effective doses will vary, as recognized by those skilled in the art, depending on the types of diseases treated, route of administration, excipient usage, and the possibility of co-usage with other therapeutic treatment.

In some embodiments, the amount of an anti-inflammatory compounds mentioned herein in a pharmaceutical composition can be about 0.1 to about 10 times the molar equivalent of the corresponding NSAID. As one example, the daily doses of an anti-inflammatory compound mentioned herein can be at least about 5 mg (e.g., at least about 10 mg, at least about 50 mg, or at least about 100 mg) and/or at most about 5 g (e.g., at most about 1 g, at most about 500 mg, or at most about 200 mg). As another example, the daily doses of an anti-inflammatory compound mentioned herein can be at least about 0.07 mg/kg (e.g., at least about 0.1 mg/kg, at least about 0.5 mg/kg, or at least about 1 mg/kg) and/or at most about 100 mg/kg (e.g., at most about 75 mg/kg, at most about 50 mg/kg, or at most about 25 mg/kg). The anti-inflammatory compounds mentioned herein can be administered on a regimen of up to 6 times per day (e.g., 1 to 4 times per day, or 1 to 2 times per day).

In certain embodiments, the compounds herein are used to treat an ulcer. In a preferred embodiment, a NOSH-misoprostol compound is used to treat an ulcer.

In certain embodiments, the compounds herein are used to treat colitis. In a preferred embodiment, a NOSH-mesalamine compound is used to treat colitis.

In certain embodiments, the compounds described herein are used to inhibit the activities of enzymes involved the inflammation process and/or to inhibit the production of or reduce the generation of agents that involved in the inflammation process. The compounds described herein may thus be used in methods of inhibiting an enzyme required for or involved in the production of prostaglandins, e.g., PGE2. The compounds described herein may also be used in methods of inhibiting a cyclooxygenase enzyme, e.g., COX-1 or COX-2. In certain embodiments, compounds inhibit both COX-1 and COX-2 activities with substantially equal potency, i.e., are non-specific COX inhibitors. In other embodiments, compounds are more potent COX-2 inhibitors, i.e., are COX-2 specific inhibitors. In other embodiments, compounds are more potent COX-1 inhibitors. The compounds described herein may also be used in methods of inhibiting a superoxide dismutase (SOD). The compounds described herein may also be used to reduce levels, e.g., plasma levels, of TNF-α in an individual. The compounds described herein may also be used to reduce levels of PGE2 in an individual, e.g., in the tissue of an individual.

In certain embodiments, the compounds described herein are administered to a subject and subsequently transported through the body, e.g., through normal circulation, thereby contacting tissue and effecting treatment. In certain embodiments, treatment of an inflammatory condition is therefore effected by contacting a tissue or tumor with a dual action compound that incorporates both NO and hydrogen sulfide donor, thereby exposing the tissue or tumor to such a compound.

The compounds disclosed herein exhibited enhanced antiproliferative activity in in vitro condition against eleven different human cancer cell lines of six different tissue origins. These included colon (HT-29: COX-1 and COX-2 positive, HCT 15: COX null, and SW480: COX-1 positive, low levels of endogenous COX-2), breast (MCF7: [ER(+)], MDA MB-231 and SKBR3: [ER(−)]); T-cell leukemia (Jurkat), pancreatic (BxPC3: both COX-1 and COX-2 positive, MIAPaCa-2: COX-null), prostate (LNCaP), and lung (A549).

To practice the method of the present invention, a composition having one or more anti-inflammatory compounds disclosed herein can be administered parenterally, orally, nasally, rectally, topically, or buccally. The term "parenteral" as used herein refers to subcutaneous, intracutaneous, intravenous, intramuscular, intraarticular, intraarterial, intrasynovial, intrasternal, intrathecal, intralesional, or intracranial injection, as well as any suitable infusion technique.

A sterile injectable composition can be a solution or suspension in a non-toxic parenterally acceptable diluent or solvent, such as a solution in 1,3-butanediol. Among the acceptable vehicles and solvents that can be employed are mannitol, water, Ringer's solution, and isotonic sodium chloride solution. In addition, fixed oils are conventionally employed as a solvent or suspending medium (e.g., synthetic mono- or diglycerides). Fatty acid, such as oleic acid and its glyceride derivatives are useful in the preparation of injectables, as are natural pharmaceutically acceptable oils, such as olive oil or castor oil, especially in their polyoxyethylated versions. These oil solutions or suspensions can also contain a long chain alcohol diluent or dispersant, carboxymethyl cellulose, or similar dispersing agents. Other commonly used surfactants such as Tweens or Spans or other similar emulsifying agents or bioavailability enhancers which are commonly used in the manufacture of pharmaceutically acceptable solid, liquid, or other dosage forms can also be used for the purpose of formulation.

A composition for oral administration can be any orally acceptable dosage form including capsules, tablets, emulsions and aqueous suspensions, dispersions, and solutions. In the case of tablets, commonly used carriers include lactose and corn starch. Lubricating agents, such as magnesium stearate, are also typically added. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added.

A nasal aerosol or inhalation composition can be prepared according to techniques well known in the art of pharmaceutical formulation. For example, such a composition can be prepared as a solution in saline, employing benzyl alcohol or other suitable preservatives, absorption promoters to enhance bioavailability, fluorocarbons, and/or other solubilizing or dispersing agents known in the art.

A composition having one or more active anti-inflammatory compounds disclosed herein can also be administered in the form of suppositories for rectal administration.

The carrier in the pharmaceutical composition must be "acceptable" in the sense that it is compatible with the active ingredient of the composition (and preferably, capable of stabilizing the active ingredient) and not deleterious to the subject to be treated. One or more solubilizing agents can be utilized as pharmaceutical excipients for delivery of an active anti-inflammatory compound disclosed herein. Examples of other carriers include colloidal silicon oxide, magnesium stearate, cellulose, sodium lauryl sulfate, and D&C Yellow #10.

The anti-inflammatory compounds disclosed herein can be preliminarily screened for their efficacy in treating above-described diseases by in vitro and in vivo assays (e.g., Examples 9-13 below) and then confirmed by animal experiments and clinic trials. Other methods will also be apparent to those of ordinary skill in the art.

The contents of all publications cited herein (e.g., patents, patent application publications, and articles) are hereby incorporated by reference in their entirety.

The following examples are illustrative and not intended to be limiting.

EXAMPLES

General Experimental Considerations

All moisture-sensitive reactions were performed under an argon atmosphere using oven-dried glassware and anhydrous solvents. Anhydrous solvents were freshly distilled from sodium benzophenone ketyl, for THF and DCM was distilled from calcium hydride. Extracts were dried over anhydrous $Na_2SO_4$ and filtered prior to removal of all volatiles under reduced pressure. Unless otherwise noted, commercially available materials were used without purification. Silica gel chromatography was performed using 100-200 mesh silica gel (Natland). Thin layer chromatography was performed using precoated 250µ plates (Analtech). Nuclear magnetic resonance (NMR) splitting patterns are described as singlet (s), doublet (d), triplet (t), quartet (q), and broad (b); the value of chemical shifts (δ) are given in ppm relative to residual solvent (chloroform δ=7.27 for $^1$HNMR or δ=77.23 for proton decoupled $^{13}$C NMR), and coupling constants (J) are given in hertz (Hz). The mass spectra were recorded on AB SCIEX 4000 QTRAP LC-MS/MS instrument (EI).

Example 1

Preparation of NOSH-1: 4-(3-thioxo-3H-1,2-dithiol-5-yl)phenyl 2-((4-(nitrooxy)butanoyl)oxy)benzoate As shown in the scheme below, NOSH-1 was synthesized starting with salicylaldehyde (i.e., Compound 1) and 4-bromobutyric acid (i.e., Compound 2), ADT-OH (i.e., Compound 6: 5-(4-hydroxyphenyl)-3H-1,2-dithiole-3-thione) in four steps.

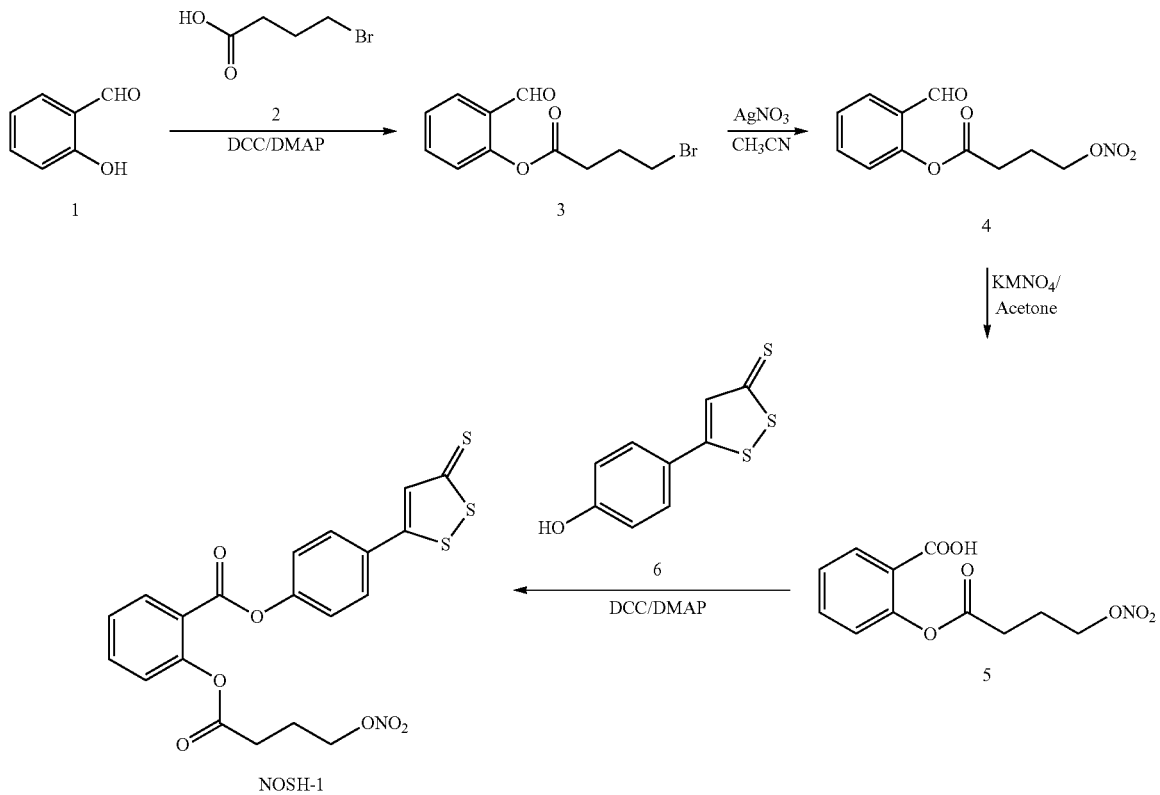

Step 1: Preparation of Compound 3: To the solution of 4-bromobutyric acid (6.83 gm, 40.94 mmol) in dichloromethane was added DCC (8.45 gm, 40.94 mmol), DMAP (500.0 mg, 4.09 mmol) at 0° C. under argon atmosphere.

After salicyladehyde (5.0 gm, 40.94 mmol) was, the whole reaction mixture was stirred at room temperature overnight. After completion of the reaction (as checked by TLC), the precipitate was filtered off. Water was added and the organic phase was extracted into dichloromethane (2×25 ml). The organic solvent was removed under reduced pressure to give the crude product, which was purified by column chromatography to afford 2-formylphenyl 4-bromobutanoate (Compound 3, 8.85 gm, 80% yield).

Step 2: Preparation of Compound 4: To the solution of Compound 3 (7.5 gm, 27.7 mmol) in acetonitrile was added silver nitrate ($AgNO_3$, 9.44 gm, 55.55 mmol) under dark and argon atmosphere. The whole reaction mixture was heated at 70° C. overnight. After completion of the reaction, the precipitate was filtered off. The solution was concentrated under reduced pressure to give the crude product, which was purified by column chromatography to obtain 2-formylphenyl 4-(nitrooxy)butanoate (Compound 4, 4.91 gm, 70% yield).

Step 3: Preparation of Compound 5: $KMnO_4$ was added to a stirred solution of Compound 4 (2.96 gm, 11.74 mmol) in acetone (50 ml) at 0° C. The reaction mixture was allowed to reach room temperature and was stirred for 3 hours. After completion of the reaction (as checked by TLC), oxalic acid was added and the precipitate was filtered off. The filtrate was diluted with dichloromethane and washed with water, dried, and concentrated under reduced pressure to give a crude product of compound 5 (i.e., 2-{[4-nitroxy)butanoyl]oxy}benzoic acid). The crude weight of the solid was 2.64 gm (83%).

Step 4: Preparation of NOSH-1: To the solution of Compound 5 (238.0 mg, 0.88 mmol) in dichloromethane was added DCC (201.0 mg, 0.97 mmol), DMAP (10.8 mg, 0.09 mmol) at 0° C. under argon atmosphere. After ADT-OH (5-(4-hydroxyphenyl)-3H-1,2-dithiole-3-thione) (200.0 mg, 0.88 mmol) was added, the reaction mixture was stirred at room temperature overnight. After completion of the reaction (as checked by TLC), the precipitate was filtered off. Water was added and the organic phase was extracted into dichloromethane (2×75 ml). The organic solvent was removed under reduced pressure to give a crude product, which was purified by column chromatography to afford orange solid (NOSH-1) (298.0 mg, 78% yield).

$^1$H-NMR ($CDCl_3$, 500 MHz): δ 2.18 (m, 2H), 2.78 (t, J=6.8 Hz, 2H), 4.56 (t, J=6.3 Hz, 2H), 7.22 (d, J=8.3 Hz, 1H), 7.32 (d, J=8.8 Hz, 2H), 7.44 (s, 1H), 7.45 (t, J=7.8 Hz, 1H), 7.72 (t, J=7.8 Hz, 1H), 7.75 (d, J=8.8 Hz, 2H), 8.27 (d, J=7.8 Hz, 1H). $^{13}$C-NMR ($CDCl_3$, 125 MHz): δ 22.08, 30.21, 71.91, 121.83, 123.23, 124.31, 126.68, 128.57, 129.76, 132.37, 135.43, 136.33, 151.48, 153.52, 162.34, 171.24, 171.75, 215.71. ESIMS: m/z 478 ($M^+$+1), 500 ($M^+$+Na).

Example 2

Preparation of NOSH-2: 4-(nitrooxy)butyl (2-((4-(3-thioxo-3H-1,2-dithiol-5-yl)phenoxy)carbonyl)phenyl) succinate Preparation of 2-formylphenyl (4-(nitrooxy)butyl)succinate

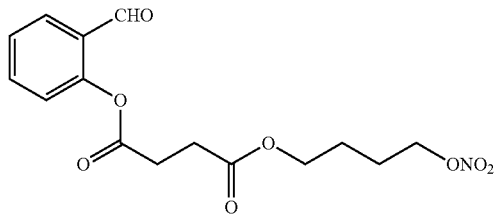

To the solution of salicyladehyde (1.0 g, 8.19 mmol) in methylene chloride were added succinic anhydride (0.819 g, 8.19 mmol) and catalytic amount of DMAP (0.1 g, 0.819 mmol). The solution was stirred for 24 hours at room temperature. Hydroxyl butyl nitrate (1.1 g, 8.19 mmol) and DCC (1.69 g, 8.196 mmol) were added sequentially at 0° C. under argon atmosphere. The reaction mixture was stirred at room temperature for 6 hours. After completion of the reaction (as checked by TLC), the precipitate was filtered off. Water was added and the organic phase was extracted into dichloromethane (2×75 ml). The organic solvent was removed under reduced pressure to give a crude product, which was purified by column chromatography to afford compound 2-formylphenyl (4-(nitrooxy)butyl)succinate (1.8 g, 65% yield).

$^1$H-NMR ($CDCl_3$, 500 MHz): δ 1.75-1.82 (m, 4H), 2.78 (t, J=6.8 Hz, 2H), 2.99 (t, J=6.8 Hz, 2H), 4.17 (t, J=6.35 Hz, 2H), 4.46 (t, J=6.35 Hz, 2H), 7.19 (d, J=7.8 Hz, 1H), 7.41 (t, J=7.32 Hz, 1H), 7.64 (dt, J=8.3, 1.95 Hz, 1H), 7.88 (dd, J=7.32, 1.45 Hz, 1H). 10.10 (s, 1H). $^{13}$C-NMR ($CDCl_3$, 125 MHz): δ 23.57, 24.98, 28.96, 29.14, 64.0, 72.72, 123.47, 126.62, 128.12, 131.19, 135.42, 151.47, 170.95, 172.10, 189.0. ESIMS: m/z 340 ($M^+$+1), 362 ($M^+$+Na).

Preparation of 2-((4-(4-(nitrooxy)butoxy)-4-oxobutanoyl)oxy)benzoic acid

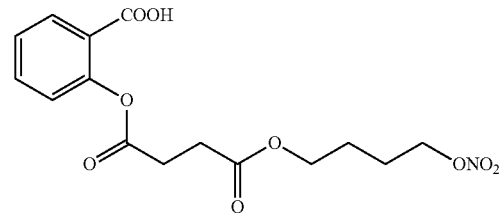

$KMnO_4$ (0.96 g, 6.084 mmol) was added to a stirred solution of 2-formylphenyl (4-(nitrooxy)butyl)succinate (1.375 g, 4.056 mmol) in acetone (50 ml) at 0° C. The reaction mixture was allowed to reach room temperature and was stirred for 3 hours. After completion of the reaction (as checked by TLC), oxalic acid was added and the precipitate was filtered off. The filtrate was diluted with dichloromethane and washed with water, dried, and concentrated under reduced pressure to give a crude product of 2-((4-(4-(nitrooxy)-butoxy)-4-oxobutanoyl)oxy)benzoic acid.

$^1$H-NMR ($CDCl_3$, 500 MHz): δ 1.76-1.83 (m, 4H), 2.77 (t, J=6.8 Hz, 2H), 2.99 (t, J=6.8 Hz, 2H), 4.18 (t, J=6.35 Hz, 2H), 4.47 (t, J=6.35 Hz, 2H), 7.17 (d, J=7.8 Hz, 1H), 7.37 (t, J=7.8 Hz, 1H), 7.65 (t, J=7.8 Hz, 1H), 8.13 (dd, J=7.81, 1H). $^{13}$C-NMR ($CDCl_3$, 125 MHz): δ 23.74, 25.15, 29.12, 29.48, 64.07, 72.79, 122.37, 124.16, 126.68, 132.68, 135.10, 151.25, 169.59, 171.29, 172.38. ESIMS: m/z 355 ($M^+$+1), 378 ($M^+$+Na).

Preparation of NOSH-2

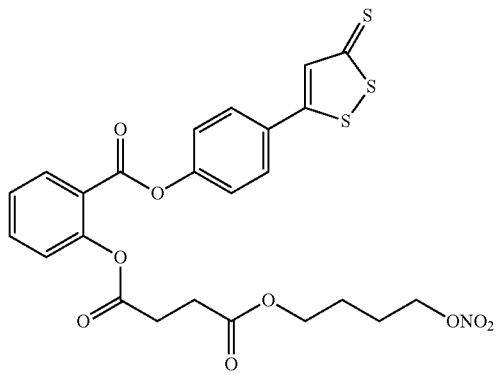

NOSH-2 was prepared following the procedures described in the last step in Example 1 using 2-((4-(4-(nitrooxy)-butoxy)-4-oxobutanoyl)oxy)benzoic acid and ADT-OH (i.e., Compound 6) as the starting materials. $^1$H-NMR (CDCl$_3$, 500 MHz): δ 1.73-1.80 (m, 4H), 2.71 (t, J=6.8 Hz, 2H), 2.94 (t, J=6.8 Hz, 2H), 4.13 (t, J=6.3 Hz, 2H), 4.45 (t, J=5.8 Hz, 2H), 7.22 (d, J=7.8 Hz, 1H), 7.33 (d, J=8.8 Hz, 2H), 7.41 (d, J=8.3 Hz, 1H), 7.42 (s, 1H), 7.68 (dt, J=7.8 Hz, 1.96 Hz, 1H), 7.73 (d, J=8.3 Hz, 2H), 8.22 (dd, J=7.8 Hz, 1.46 Hz, 1H). $^{13}$C-NMR (CDCl$_3$, 125 MHz): δ 23.78, 25.15, 29.10, 29.37, 64.03, 72.74, 121.94, 123.35, 124.41, 126.62, 128.55, 129.74, 132.34, 135.37, 136.32, 151.49, 153.63, 162.42, 171.23, 171.73, 172.18, 215.74. ESIMS: m/z 564 (M$^+$+1), 586 (M$^+$+Na).

Example 3

Preparation of NOSH-3: 4-carbamothioylphenyl 2-((4-(nitrooxy)butanoyl)-oxy)benzoate

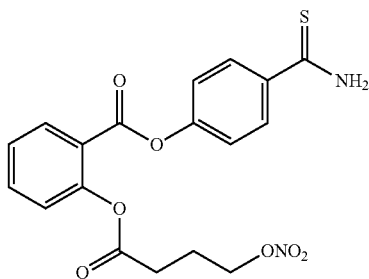

NOSH 3 was prepared following the procedures described in Example 1 by using suitable starting materials.
$^1$H-NMR (CDCl$_3$, 500 MHz): δ 2.11-2.16 (m, 2H), 2.75 (t, J=7.2 Hz, 2H), 4.53 (t, J=6.5 Hz, 2H), 7.19 (d, J=7.5 Hz, 1H), 7.20 (bs, 1H), 7.21 (d, J=8.0 Hz, 2H), 7.42 (t, J=8.0 Hz, 1H), 7.66 (bs, 1H), 7.68 (dt, J=8.5 Hz, 1.47 Hz, 1H), 7.94 (d, J=8.8 Hz, 2H), 8.24 (dd, J=8.5 Hz, 1.47 Hz, 1H). $^{13}$C-NMR (CDCl$_3$, 125 MHz): δ 22.08, 30.22, 72.0, 121.94, 122.02, 124.24, 126.68, 128.74, 132.43, 135.30, 135.37, 137.37, 151.40, 153.49, 162.54, 171.33, 201.81. ESIMS: m/z 405 (M$^+$+1), 427 (M$^+$+Na), 450 (M$^+$+2Na).

Example 4

Preparation of NOSH-4: (R)-4-(nitrooxy)butyl 2-((5-(1,2-dithiolan-3-yl)pentanoyl)oxy)benzoate

Preparation of 4-(nitrooxy)butyl 2-hydroxybenzoate

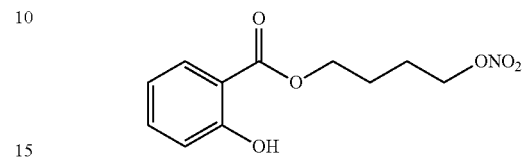

To the solution of compound 4-(nitrooxy)butyl 2-acetoxybenzoate (0.5 g, 1.68 mmol) in MeOH/THF (1:1) 20 mL was added K$_2$CO$_3$ (0.025 mmol) and stirred at room temperature for 15 minutes. After the solvent was removed, water was added and the organic phase extracted into ethyl acetate. The solvent was removed to give a crude product, which was purified by column chromatography to afford 4-(nitrooxy) butyl 2-hydroxybenzoate (0.3 g, 72%).
$^1$H-NMR (CDCl$_3$, 500 MHz): δ 1.94 (m, 4H), 4.41 (bt, 2H), 4.54 (bt, 2H), 6.90 (t, J=7.8 Hz, 1H), 7.0 (d, J=8.3 Hz, 1H), 7.48 (t, J=7.8 Hz, 1H), 7.83 (d, J=7.8, 1H), 10.75 (bs, 1H). $^{13}$C-NMR (CDCl$_3$, 125 MHz): δ 23.83, 25.19, 64.52, 72.69, 112.39, 117.86, 119.43, 129.90, 136.09, 161.88, 170.25. ESIMS: m/z 256 (M$^+$+1), 278 (M$^+$+Na).

Preparation of NOSH-4

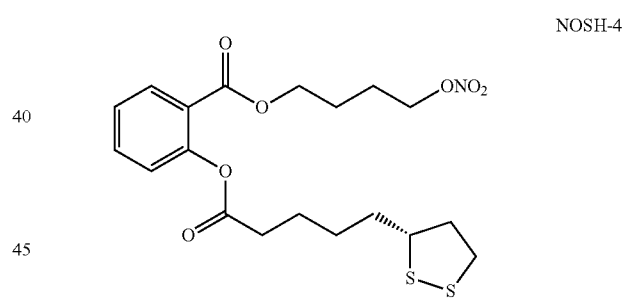

To the solution of compound 4-(nitrooxy)butyl 2-hydroxybenzoate (0.3 g, 1.176 mmol) in methylene chloride was added (R)-lipoic acid (0.24 g, 1.176 mmol) followed by addition of DCC (0.24 g, 1.176 mmol) and DMAP (0.024 g, 0.1176 mmol). The mixture was then stirred for 6 hours at room temperature. After completion of the reaction (as monitored by TLC), the precipitate was filtered off. The filtrate was concentrated under reduced pressure to obtain a crude product, which was purified by column chromatography to afford compound NOSH-4 (0.35 g, 68%).
$^1$H-NMR (CDCl$_3$, 500 MHz): δ 1.52-1.68 (m, 3H), 1.76-1.98 (m, 8H), 2.46-2.53 (m, 1H), 2.66 (t, J=7.8 Hz, 2H), 3.11-3.23 (m, 2H), 2.62 (q, J=6.3 Hz, 1H), 4.32 (t, J=5.3 Hz, 2H), 4.52 (t, J=5.3 Hz, 2H), 7.12 (d, J=8.3 Hz, 1H), 7.33 (t, J=6.8 Hz, 1H), 7.58 (t, J=6.8 Hz, 1H), 7.99 (d, J=7.3 Hz, 1H). $^{13}$C-NMR (CDCl$_3$, 125 MHz): δ 23.63, 24.31, 25.07, 28.71, 33.92, 34.61, 38.52, 40.25, 56.41, 64.07, 72.66, 123.24, 123.86, 125.97, 131.44, 133.95, 150.74, 164.24, 172.0. ESIMS: m/z 466 (M$^+$+Na).

Example 5

Preparation of NOSH-5: 4-(3-thioxo-3H-1,2-dithiol-5-yl)phenyl 5-(4-(nitrooxy)butanamido)-2-((4-(nitrooxy)butanoyl)oxy)benzoate NOSH-5 was synthesized by using mesalamine, 4-bromobutyric acid, ADT-OH ((5-(4-hydroxyphenyl)-3H-1,2-dithiole-3-thione) as starting materials in five steps as shown in the scheme below.

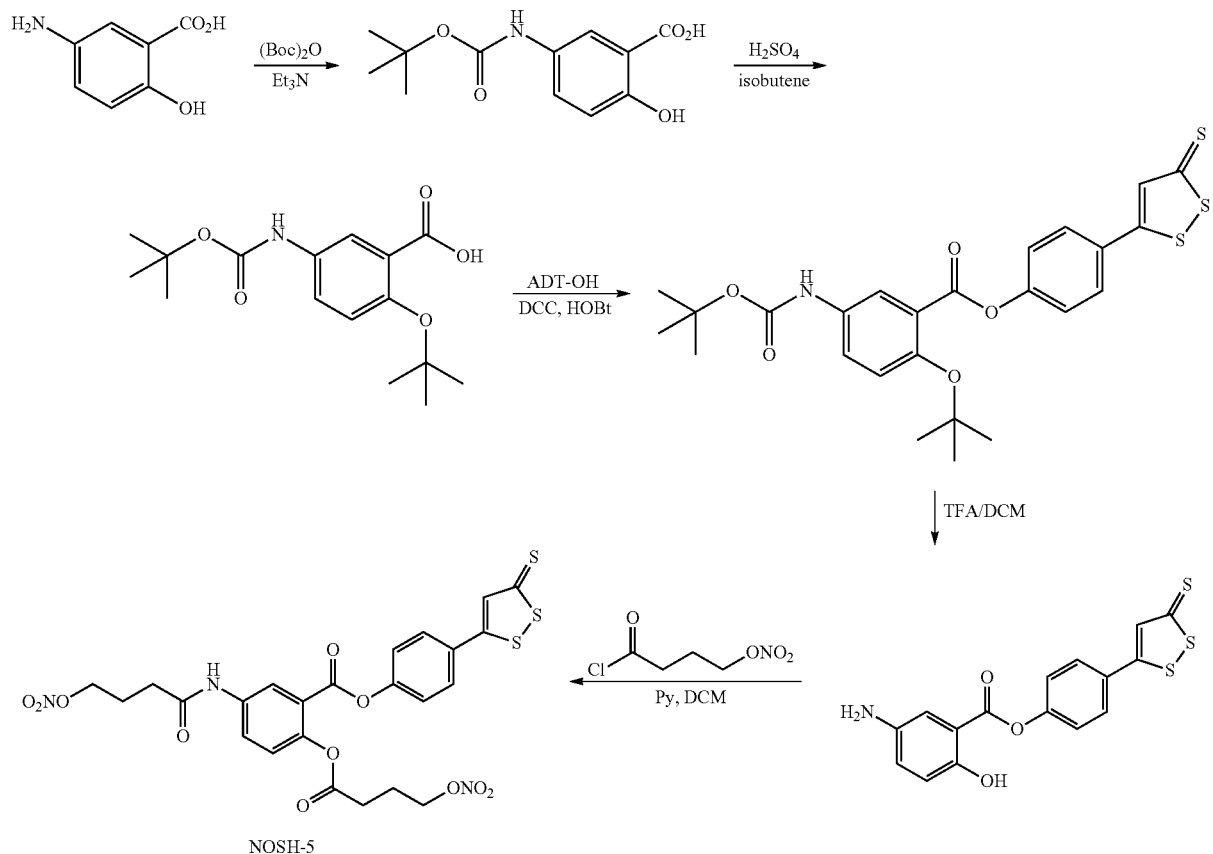

NOSH-5

Step 1: Preparation of 5-((tert-butoxycarbonyl)amino)-2-hydroxybenzoic acid: To the solution of mesalamine (1.0 g, 6.5 mmol) in 25 mL of dioxane and 12.5 mL of water, triethylamine (1.358 mL, 9.8 mmol) and (Boc)$_2$O (2.14 g, 9.8 mmol) were added with stirring at 0° C. for 30 minutes. After the addition was completed, the mixture was stirred at room temperature for 2 hours. After evaporation of the solvent, 3M HCl was added dropwise to the residue. The residue was loaded on a silica gel open column chromatography eluted with DCM/MeOH to afford the title compound.

Step 2: Preparation of 2-(tert-butoxy)-5-((tert-butoxycarbonyl)amino)-benzoic acid: A solution of 5-amino-2-hydroxybenzoic acid, concentrated H$_2$SO$_4$ and DCM (60 mL) was stirred under isobutene gas (5 psi) for 5 hours at room temperature. The solution was washed with 10% NaHCO$_3$ and brine solutions. The organic solution was dried (Na$_2$SO$_4$) and concentrated under reduced pressure. The residue was recrystallized by DCM/Hexane to give the title compound.

Step 3 & 4: Preparation of 4-(3-thioxo-3H-1,2-dithiol-5-yl)phenyl 5-amino-2-hydroxybenzoate: To a solution of 2-(tert-butoxy)-5-((tert-butoxycarbonyl)amino)-benzoic acid in dichloromethane was added DCC (201.0 mg, 0.97 mmol), DMAP (10.8 mg, 0.09 mmol) at 0° C. under argon atmosphere. After addition of ADT-OH ((5-(4-hydroxyphenyl)-3H-1,2-dithiole-3-thione) (200.0 mg, 0.88 mmol), the reaction mixture was stirred at room temperature overnight. After completion of the reaction as checked by TLC, the mixture was filtered, water was added, and the aqueous phase was extracted by dichloromethane (2×75 ml). The organic solvent was removed under reduced pressure to give the crude 4-(3-thioxo-3H-1,2-dithiol-5-yl)phenyl 2-(tert-butoxy)-5-((tert-butoxycarbonyl)amino)benzoate. This compound was treated with a solution of 40% TFA in DCM. After stirring for 2 hours, the solvent was removed to obtain the crude title compound, which was purified by column chromatography to afford the pure title compound.

Step 5: Preparation of NOSH-5: 4-Chloro-4-oxobutyl nitrate was synthesized from 4-bromo butyric acid. Specifically, 4-bromo butyric acid was treated with silver nitrate under dark condition at 70° C. The compound thus obtained was converted to its corresponding acid chloride (i.e., 4-chloro-4-oxobutyl nitrate) by refluxing with SOCl$_2$ under organ atmosphere.

The chloride was added dropwise into a solution of 4-(3-thioxo-3H-1,2-dithiol-5-yl)phenyl 5-amino-2-hydroxybenzoate in the presence of pyridine. After the reaction was complete, water was added and the aqueous phase was extracted by ethyl acetate to obtain crude NOSH-5, which was purified by column chromatography to obtain pure NOSH-5.

Example 6

Preparation of NOSH-6: 4-(3-thioxo-3H-1,2-dithiol-5-yl)phenyl 5-amino-2-((4-(nitrooxy)butanoyl)oxy)benzoate

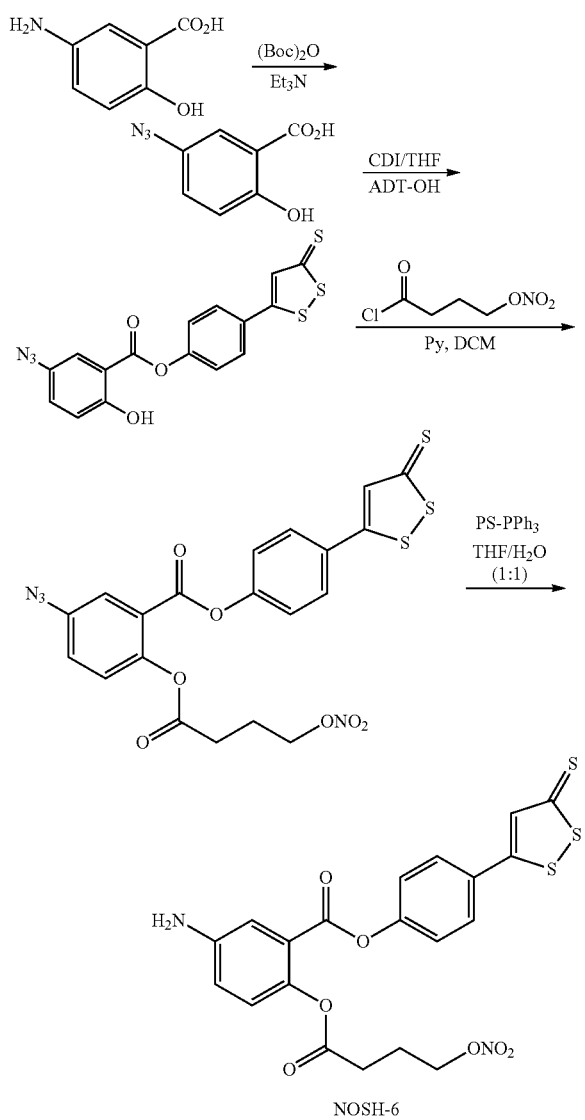

Step 1: Preparation of 5-azido-2-hydroxybenzoic acid: To a solution of mesalamine (1.0 g, 6.5 mmol) in 25 mL of dioxane and 12.5 mL of water, triethylamine (1.358 mL, 9.8 mmol) and $(Boc)_2O$ (2.14 g, 9.8 mmol) were added with stirring at 0° C. for 30 minutes. After the addition was complete, the mixture was stirred at room temperature for 2 hours. After evaporation of the solvent, 3M HCl was added dropwise to the residue. The residue thus obtained was loaded on a silica gel open column chromatography eluted with DCM/MeOH to afford the title compound.

Step 2: Preparation of 4-(3-thioxo-3H-1,2-dithiol-5-yl)phenyl 5-azido-2-hydroxybenzoate: 5-Azido-2-hydroxybenzoic acid and 1.1'-carbonyldiimidazole (CDI) were dissolved in anhydrous THF under argon atmosphere and heated at reflux for 3 hours. After ADT-OH ((5-(4-hydroxyphenyl)-3H-1,2-dithiole-3-thione) and triethylamine were added at room temperature, the reaction solution was brought to reflux. After 23 hours, the solution was cooled to room temperature. After saturated $NaHCO_3$ was added, the aqueous phase was extracted 3 times with $CH_2Cl_2$. The combined organic extracts were washed with water, dried over anhydrous $MgSO_4$, filtered, and concentrated. The residue was purified by column chromatography to afford the title compound.

Step 3: Preparation of 4-(3-thioxo-3H-1,2-dithiol-5-yl)phenyl 5-azido-2-((4-(nitrooxy)butanoyl)oxy)benzoate: To a solution of -(3-thioxo-3H-1,2-dithiol-5-yl)phenyl 5-azido-2-hydroxybenzoate in dichloromethane was added 4-chloro-4-oxobutyl nitrate prepared from Example 5 above dropwise at 0° C. under argon atmosphere. The reaction mixture was stirred at room temperature for 4 hours. After the reaction was completed (as checked by TLC), water was added and the aqueous phase was extracted by dichloromethane (2×75 ml). The organic solvent was removed under reduced pressure to give the crude title compound, which was purified by column chromatography to afford the pure title compound.

Step 4: Preparation of NOSH-6: To a solution of 4-(3-thioxo-3H-1,2-dithiol-5-yl)phenyl 5-azido-2-((4-(nitrooxy)butanoyl)oxy)benzoate was added $PS-PPh_3$ in THF/MeOH (1:1) and stirred overnight. After the reaction was completed (as checked by TLC), the mixture was filtered. After water was added to the filtrate, the aqueous phase was extracted by ethyl acetate. The organic extract was then dried and concentrated under reduced pressure to obtain the NOSH-6.

Example 7

Preparation of Compound NOSH-7: 6-(1-oxo-1-(4-(3-thioxo-3H-1,2-dithiol-5-yl)phenoxy)propan-2-yl)naphthalen-2-yl 4-(nitrooxy)butanoate

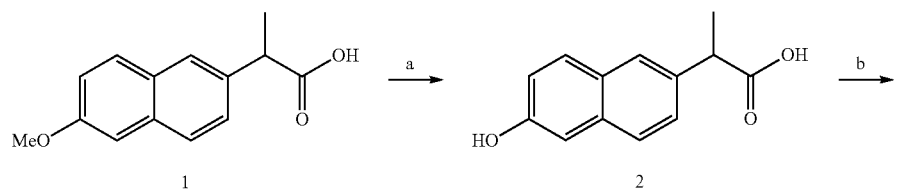

-continued

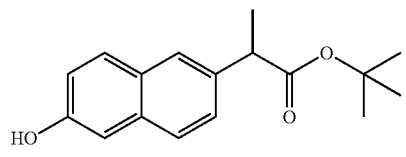
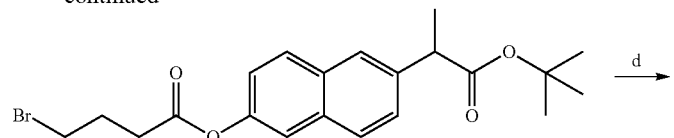

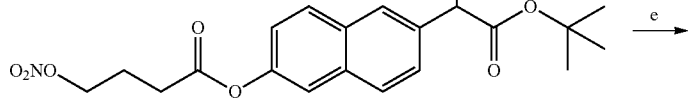

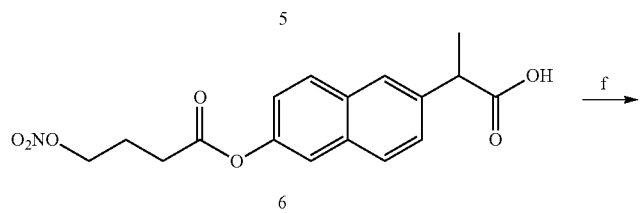

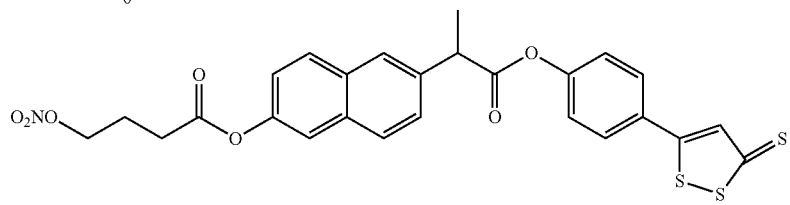

NOSH-7 a. HBr/AcOH, reflux, 4 h; b. Tf₂O, t-BuOH, NH₄OH; c. 4-bromobutyric acid, DCC/DMAP, DCM, rt, 6 h; d. AgNO₃/acetonitrile, 70° C., 6 h; e. TFA/DCM, 30 min; f. ADT-OH, DCC/DMAP, DCM, rt, 6 h.

Synthesis of Compound 2: To the solution of Naproxen (Compound 1, 5 g, 23 mmol) in AcOH (50 mL) was added HBr (47%, 25 mL). After the mixture was refluxed for 4 hours, the whole reaction mixture was condensed under reduced pressure then washed with water. The precipitate thus obtained was filtered, washed with petroleum ether, and recrystallized from toluene to give (7-hydroxynaphthalen-1-yl)acetic acid (Compound 2, 3.52 g, 75%).

$^1$H NMR (CDCl₃, 500 MHz): 7.64 (d, J=8.8 Hz, 2H), 7.62 (s, 1H), 7.58 (d, J=8.3 Hz, 2H), 7.35 (dd, J=8.8, 1.46 Hz, 1H), 7.09 (s, 1H), 7.08 (dd, J=8.8, 1.45 Hz, 1H), 3.77 (q, J=7.3 Hz, 1H), 1.52 (d, J=7.3 Hz, 3H). ESI-MS: m/z 217 (M⁺+1).

Synthesis of Compound 3: To the solution of Compound 2 (2.39 g, 11.05 mmol) in dry THF (100 mL) at 0° C. was added trifluoroacetic anhydride (13.92 ml, 66.32 mmol) dropwise. The mixture was then stirred for 4 hours at same temperature. After tert-butanol (30 mL) was added dropwise at 0° C., the mixture was stirred at room temperature overnight. At 0° C., NH₄OH (35% in water, 6 mL) was added dropwise, and the mixture was stirred at room temperature for 30 minutes. The volatiles were then evaporated under reduced pressure. After the crude product was titrated with boiling dichloromethane (DCM), the crystalline solid thus obtained was removed by filtration. The filtrate was washed with saturated aqueous NaHCO₃ and dried over Na₂SO₄. The organic layer was removed under reduced pressure to give tert-butyl 2-(6-hydroxynaphthalen-2-yl)propanoate (Compound 3,146 g, 82%) as a White solid.

$^1$H NMR (CDCl₃, 500 MHz): 7.67 (d, J=8.8 Hz, 2H), 7.62 (s, 1H), 7.59 (d, J=8.3 Hz, 2H), 7.37 (d, J=8.8, 1H), 7.09 (s, 1H), 7.04 (dd, J=8.8, 1.45 Hz, 1H), 3.72 (q, J=7.3 Hz, 1H), 1.50 (d, J=7.3 Hz, 3H). ESI-MS: m/z 273 (M⁺+1).

Synthesis of Compound 4: To the solution of 4-bromobutyric acid (614 mg, 3.67 mmol) in dry DCM were added DCC (757 mg, 3.67 mmol), a catalytic amount of DMAP, and Compound 3 (1.0 g, 3.67 mmol) sequentially. The reaction mixture was stirred overnight at room temperature. After completion of the reaction, dicyclohexyl urea (DCU) was filtered off and the solvent was removed under the reduced pressure to obtain the crude product. The crude product was purified by column chromatography to obtain 6-(1-(tert-butoxy)-1-oxopropan-2-yl)naphthalen-2-yl 4-bromobutanoate (Compound 4, 1.05 g, 65%).

$^1$H NMR (CDCl₃, 500 MHz): 7.83 (d, J=8.8 Hz, 1H), 7.77 (d, J=8.3 Hz, 1H), 7.74 (s, 1H), 7.54 (d, J=1.45, 1H), 7.47 (dd, J=8.8, 1.45 Hz, 1H), 7.22 (dd, J=8.8, 1.45 Hz, 1H), 3.79 (q, J=7.2 Hz, 1H), 3.58 (t, J=6.8 Hz, 2H), 2.84 (t, J=6.8 Hz, 2H), 2.34 (q, J=6.8 Hz, 2H), 1.54 (d, J=7.3 Hz, 3H). ESI-MS: m/z 421 (M⁺+1).

Synthesis of Compound 5: To the solution of Compound 4 (925 mg, 2.19 mmol) in acetonitrile was added AgNO₃ (747 mg, 4.39 mmol) under dark conditions (i.e., protected from light). The reaction mixture was heated at 70° C. for 6 hours. The mixture was then filtered through celite, concentrated, and purified by silica gel column chromatography to obtain 6-(1-(tert-butoxy)-1-oxopropan-2-yl)naphthalen-2-yl 4-(nitrooxy)butanoate (Compound 5, 575.5 mg, 65%).

$^1$H NMR (CDCl₃, 500 MHz): 7.81 (d, J=8.8 Hz, 1H), 7.77 (d, J=8.3 Hz, 1H), 7.76 (s, 1H), 7.53 (s, 1H), 7.46 (d, J=8.8 Hz, 1H), 7.20 (dd, J=8.8, 1.45 Hz, 1H), 4.62 (t, J=6.8 Hz, 2H), 3.76 (q, J=7.2 Hz, 1H), 2.78 (t, J=6.8 Hz, 2H), 2.22 (q, J=6.8 Hz, 2H), 1.53 (d, J=7.3 Hz, 3H). ESI-MS: m/z 426 (M⁺+Na).

Synthesis of Compound 6: To the solution of compound 5 (550 mg, 1.36 mmol) in dry DCM (5 mL) was added trifluoroacetic acid TFA (5 mL) at 0° C. The mixture was then stirred at room temperature for 30 minutes. After the volatiles were evaporated, the crude product was washed with water and extracted into DCM. The organic layers were combined, dried over $Na_2SO_4$, and concentrated under reduced pressure to give 2-(6-((4-(nitrooxy)butanoyl)oxy) naphthalen-2-yl)propanoic acid (Compound 6, 260.0 mg, 55%) as a solid, which was used for the subsequent reaction without further purification.

$^1$H NMR ($CDCl_3$, 500 MHz): 7.82 (d, J=8.8 Hz, 1H), 7.77 (d, J=8.3 Hz, 1H), 7.76 (s, 1H), 7.53 (s, 1H), 7.48 (d, J=8.8 Hz, 1H), 7.21 (dd, J=8.8, 1.45 Hz, 1H), 4.61 (t, J=6.8 Hz, 2H), 3.91 (q, J=7.2 Hz, 1H), 2.78 (t, J=6.8 Hz, 2H), 2.22 (q, J=6.8 Hz, 2H), 1.60 (d, J=7.3 Hz, 3H). ESI-MS: m/z 370 ($M^+$+Na).

Synthesis of NOSH-7: To the solution of Compound 6 (250.0 mg, 0.72 mmol) in dichloromethane were added DCC (148.0 mg, 0.72 mmol) and DMAP (12.4 mg, 0.07 mmol) at 0° C. under argon atmosphere. After addition of ADT-OH (5-(4-hydroxy-phenyl)-3H-1,2-dithiole-3-thione) (162.0 mg, 0.72 mmol), the reaction mixture was stirred at room temperature for 6 hours. After completion of the reaction (as checked by TLC), the precipitate was filtered off. Water was added and the organic phase was extracted into dichloromethane (2×25 ml). The organic solvent was removed under reduced pressure to get the crude product, which was purified by column chromatography to afford pure NOSH-7 (224.0 mg, 56% yield).

$^1$H NMR ($CDCl_3$, 500 MHz): 7.86 (d, J=8.8 Hz, 2H), 7.84 (s, 1H), 7.83 (d, J=8.8 Hz, 1H), 7.62 (d, J=8.8 Hz, 2H), 7.58 (d, J=1.5 Hz, 1H), 7.54 (dd, J=8.8, 1.5 Hz, 1H), 7.36 (s, 1H), 7.26 (dd, J=8.6, 1.4 Hz, 1H), 7.12 (d, J=8.8 Hz, 2H), 4.52 (t, J=7.2 Hz, 2H), 4.15 (q, J=7.3 Hz, 1H), 2.56 (t, J=7.2 Hz, 2H), 2.42 (m, 2H), 1.54 (d, J=7.3 Hz, 3H). ESI-MS: m/z 556 ($M^+$+1), 578 ($M^+$+Na).

Example 8

Preparation of Compound NOSH-8: (E)-4-(3-thioxo-3H-1,2-dithiol-5-yl)phenyl 5-(2-(5-fluoro-2-methyl-1-(4-(methylsulfinyl)benzylidene)-1H-inden-3-yl)acetoxy)-2-((4-(nitrooxy)butanoyl)oxy)benzoate

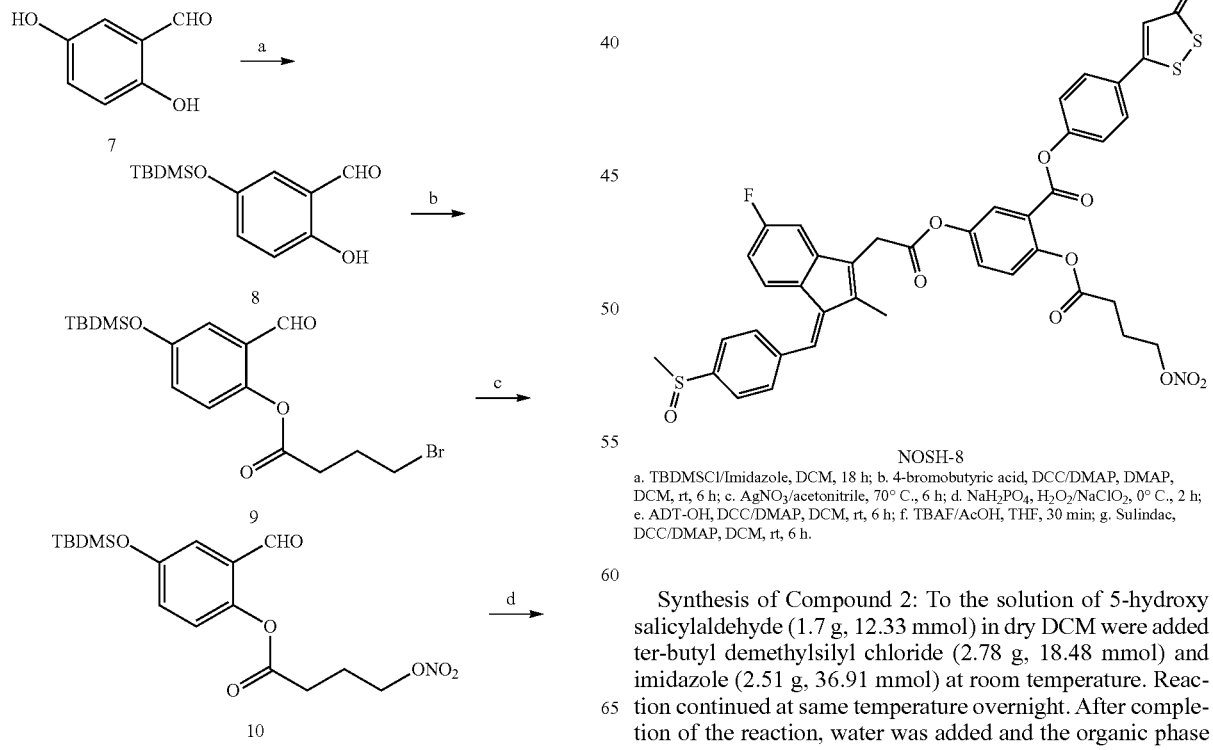

NOSH-8
a. TBDMSCl/Imidazole, DCM, 18 h; b. 4-bromobutyric acid, DCC/DMAP, DMAP, DCM, rt, 6 h; c. $AgNO_3$/acetonitrile, 70° C., 6 h; d. $NaH_2PO_4$, $H_2O_2$/$NaClO_2$, 0° C., 2 h; e. ADT-OH, DCC/DMAP, DCM, rt, 6 h; f. TBAF/AcOH, THF, 30 min; g. Sulindac, DCC/DMAP, DCM, rt, 6 h.

Synthesis of Compound 2: To the solution of 5-hydroxy salicylaldehyde (1.7 g, 12.33 mmol) in dry DCM were added ter-butyl demethylsilyl chloride (2.78 g, 18.48 mmol) and imidazole (2.51 g, 36.91 mmol) at room temperature. Reaction continued at same temperature overnight. After completion of the reaction, water was added and the organic phase was extracted into dichloromethane. The volatiles were removed under the reduced pressure to obtain the crude product, which was purified by column chromatography to obtain 5-((tert-butyldimethylsilyl)oxy)-2-hydroxybenzaldehyde (Compound 2, 2.5 g, 82%).

$^1$H NMR (CDCl$_3$, 500 MHz): 10.67 (s, 1H), 9.84 (s, 1H), 7.08 (dd, J=8.8, 2.9 Hz, 1H), 7.0 (d, J=2.6 Hz, 1H), 6.91 (d, J=8.8 Hz, 1H), 0.98 (s, 9H), 0.20 (s, 6H). ESIMS: m/z 253 (M$^+$+1).

Synthesis of Compound 3: To a solution of 4-bromobutyric acid (994 mg, 5.95 mmol) in dry DCM were added DCC (1.22 mg, 5.95 mmol), DMAP (102 mg, 0.595 mmol), and Compound 2 (1.5 g, 5.95 mmol). The reaction mixture was stirred overnight at room temperature. After completion of the reaction, DCU was filtered off and the solvent was removed under the reduced pressure to obtain the crude product. The crude product was purified by column chromatography to obtain 4-((tert-butyldimethylsilyl)oxy)-2-formylphenyl 4-bromobutanoate (Compound 3, 1.54 g, 65%).

$^1$H NMR (CDCl$_3$, 500 MHz): 9.99 (s, 1H), 7.26 (d, J=2.4 Hz, 1H), 7.07 (dd, J=8.2, 2.4 Hz, 1H), 7.05 (d, J=8.2 Hz, 1H), 3.52 (t, J=6.6 Hz, 2H), 2.84 (t, J=6.6 Hz, 2H), 2.31 (q, J=6.6 Hz, 2H), 0.98 (s, 9H), 0.21 (s, 6H). ESI-MS: m/z 401 (M$^+$+1).

Synthesis of Compound 4: To a solution of Compound 3 (1.5 g, 3.75 mmol) in acetonitrile was added AgNO$_3$ (1.27 g, 7.5 mmol) under dark conditions (i.e., protected from light). After the reaction mixture was heated at 70° C. for 6 hours, it was filtered through celite and concentrated to give a crude product, which was purified by silica gel column chromatography to obtain 4-((tert-butyldimethylsilyl)oxy)-2-formylphenyl 4-(nitrooxy)butanoate (Compound 4, 0.79 g, 55%).

$^1$H NMR (CDCl$_3$, 500 MHz): 9.97 (s, 1H), 7.27 (d, J=2.4 Hz, 1H), 7.07 (dd, J=8.8, 3.2 Hz, 1H), 7.05 (d, J=8.3 Hz, 1H), 4.62 (t, J=6.5 Hz, 2H), 2.80 (t, J=6.5 Hz, 2H), 2.22 (q, J=6.3 Hz, 2H), 1.00 (s, 9H), 0.23 (s, 6H). ESI-MS: m/z 484 (M$^+$+Na), 506 (M$^+$+Na).

Synthesis of Compound 5: To a solution of Compound 4 (0.75 g, 19.58 mmol) in CH$_3$CN (40 mL) kept 0° C. were added a solution of NaH$_2$PO$_4$ (2.0 g) in H$_2$O (15 mL) and 30% H$_2$O$_2$ (2.19 mL, 19.58 mmol). Subsequently, a solution of 80% NaClO$_2$ in H$_2$O (15 mL) was added to the above mixture dropwise. After the mixture was stirred for 2 hour at the same temperature, Na$_2$SO$_3$ was added to destroy the excess of H$_2$O$_2$. After the mixture was acidified by 6 M HCl, it was diluted with H$_2$O (100 mL) and extracted twice with DCM (100 mL). The organic layers were combined, dried, filtered, and concentrated under reduced pressure to obtain 5-((tert-butyldimethylsilyl)oxy)-2-((4-(nitrooxy)butanoyl)oxy)benzoic acid (Compound 5, 531.0 mg, 68%).

$^1$H NMR (CDCl$_3$, 500 MHz): 7.54 (d, J=2.9 Hz, 1H), 7.08 (dd, J=8.8, 2.9 Hz, 1H), 7.05 (d, J=8.8 Hz, 1H), 4.62 (t, J=6.5 Hz, 2H), 2.77 (t, J=6.5 Hz, 2H), 2.20 (q, J=6.3 Hz, 2H), 1.00 (s, 9H), 0.24 (s, 6H). ESI-MS: m/z 400 (M$^+$+Na), 422 (M$^+$+Na).

Synthesis of Compound 6: To a solution of compound 5 (500.0 mg, 1.25 mmol) in dichloromethane was added DCC (258.0 mg, 1.25 mmol) and DMAP (21.55 mg, 0.125 mmol) at 0° C. under argon atmosphere. After ADT-OH-(4 hydroxyphenyl)-3H-1,2-dithiole-3-thione) (283.0 mg, 1.25 mmol) was added, the reaction mixture was stirred at room temperature for 6 hours. After completion of the reaction (as checked by TLC), the precipitate was filtered off. Water was added and the organic phase was extracted into dichloromethane (2×25 ml). The organic solvent was removed under reduced pressure to obtain a crude product, which was purified by column chromatography to afford 4-(3-thioxo-3H-1,2-dithiol-5-yl)phenyl 5-((tert-butyldimethylsilyl)oxy)-2-((4-(nitrooxy)butanoyl)oxy)benzoate (Compound 6, 484.0 mg, 62% yield).

$^1$H NMR (CDCl$_3$, 500 MHz): 7.73 (d, J=8.8 Hz, 2H), 7.73 (d, J=2.93 Hz, 1H), 7.42 (s, 1 H), 7.31 (d, J=8.8 Hz, 1H), 7.12 (dd, J=8.8, 2.99 Hz, 1H), 7.05 (d, J=8.8 Hz, 1H), 4.52 (t, J=6.8 Hz, 2H), 2.72 (t, J=6.8 Hz, 2H), 2.14 (q, J=6.8 Hz, 2H), 1.00 (s, 9H), 0.24 (s, 6H). ESIMS: m/z 608 (M$^+$+1), 628 (M$^+$+Na).

Synthesis of Compound 7: A solution of tetrabutylammonium fluoride (1 mL, 1.0 mmol) and acetic acid (1 mL) in THF (5 mL) was added to Compound 6 (450.0 mg, 0.722 mmol). The mixture was stirred for 30 minutes. After completion of the reaction (as checked by TLC), volatiles were removed under reduced pressure to give a crude product, which was purified by column chromatography to obtain 4-(3-thioxo-3H-1,2-dithiol-5-yl)phenyl 5-hydroxy-2-((4-(nitrooxy)butanoyl)oxy)benzoate (Compound 7, 249.0 mg, 72%).

$^1$H NMR (CDCl$_3$, 500 MHz): 7.70 (d, J=8.8 Hz, 2H), 7.42 (s, 1 H), 7.27 (d, J=8.8 Hz, 2H), 7.19 (dd, J=8.8, 3.0 Hz, 1H), 7.01 (d, J=8.8 Hz, 1H), 4.54 (t, J=6.8 Hz, 2H), 2.73 (t, J=6.8 Hz, 2H), 2.15 (q, J=6.8 Hz, 2H). ESI-MS: m/z 494 (M$^+$+1), 514 (M$^+$+Na).

Synthesis of NOSH-8: To the solution of Sulindac (144.0 mg, 0.405 mmol) in dichloromethane were added DCC (83.0 mg, 0.405 mmol) and DMAP (12.4 mg, 0.07 mmol) at 0° C. under argon atmosphere. After Compound 13 (200.0 mg, 0.405 mmol) was added, the reaction mixture was stirred at room temperature for 6 hours. After completion of the reaction (as checked by TLC), the precipitate was filtered off. Water was added and the organic phase was extracted into dichloromethane (2×25 ml). The organic solvent was removed under reduced pressure to give a crude product, which was purified by column chromatography to afford NOSH-8. (216.0 mg, 63% yield).

$^1$H NMR (CDCl$_3$, 500 MHz): 7.95 (d, 1.8 Hz, 1H), 7.64-774 (m, 6H), 7.40 (s, 1H), 7.27 (d, J=8.8 Hz, 2H), 7.20 (m, 4H), 6.97 (dd, J=7.8 Hz, 1.5 Hz, 1H), 6.58 (t, J=7.8 Hz, 1H), 4.50 (t, J=8.8 Hz, 2H), 3.83 (s, 2H), 2.80 (s, 3H), 2.73 (t, J=8.8 Hz, 2H), 2.78 (s, 3H), 2.11 (m, 2H). ESI-MS: m/z 831 (M$^+$+1), 854 (M$^+$+Na).

Example 9

In Vitro Assays

Materials and Methods:

Cell Culture: HT-29, SW-480 and HCT-15 human colon adenocarcinoma, MIA PaCa-2 and BxPC-3 human pancreatic cancer, LNCAP human prostate cancer, A549 human lung cancer, MCF-7 (estrogen receptor positive), MDA-MB 231 and SK-BR-3 (estrogen receptor negative) human breast cancer, and Jurkats human leukemia cell lines were obtained from American Type Tissue Collection (Manassas, Va.). All cells lines were grown as monolayers except for the Jurkats which were grown in suspension. The pancreatic and breast cancer cells were grown in Dulbecco's modified Eagle's medium, the prostate, Jurkat, SW-480 and HCT-15 colon cells were grown in RPMI 1640 medium, the lung cells were grown in F-12 and the colon HT-29 cells were grown in McCoy 5A. All media were supplemented with 10% fetal calf serum (Invitrogen, Carlsbad, Calif.) penicillin (50 U/ml), and streptomycin (50 μg/ml) (Invitrogen, Carlsbad, Calif.). Cells were seeded on culture dishes at a density of 25×10$^3$ cells/cm$^2$ and incubated at 37° C. in 5% CO$_2$ and 90% relative humidity. Single cell suspensions were obtained by trypsinization (0.05% trypsin/EDTA), and cells were counted using a hemocytometer. Viability was determined by the trypan blue dye exclusion method.

MTT Assay: Cell growth inhibitory effect of NOSH compounds were measured using a colorimetric MTT assay kit (Roche, Indianapolis, Ind.). Cancer cells were plated in 96-well plates at a density of 50,000 cells/well. The cells were incubated for 24 h with different concentrations of NOSH compounds. After the indicated time, 10 µl of MTT dye (3-[4,5-dimethylthiazol-2-yl]-2,5-diphenyl tetrazolium bromide, 5 mg/ml in phosphate buffered saline), was added to each well, and the plates were incubated for 2 hours at 37° C. Then, the media was aspirated, and add 100 µl of the solubilization solution (10% SDS in 0.01 M HCl) was added to each well to solubilize the formant crystals. The absorbance of the plates was measured on an ELISA reader at a wavelength of 570 nm. Each sample was performed in triplicate, and the entire experiment was repeated three times.

LDH Release Assay: For determination of lactate dehydrogenase (LDH) activity, HT-29 cells ($1 \times 10^5$ cells/well) were incubated in 96-well plates with different concentrations of NOSH-1. After incubation for 2, 4, 8, 12 and 24 h, LDH activity in the supernatant was assessed using the LDH Cytotoxicity Assay Kit (Cayman Chemical Ann Arbor, Mich.), according to the manufacturer's instructions. Cytotoxicity was calculated as a percentage based on the LDH activity released from cells that had been treated with NOSH-1 compared with LDH activity from cultures incubated with Triton X-100. The % of LDH release was determined using the formula $(E-C)/(T-C) \times 100$, where E is the experimental absorbance of cell cultures, C is the control absorbance of cell-free culture medium, and T is the absorbance corresponding to the maximal (100%) LDH release of Triton-lysed cells.[1]

Determination of Plasma TNF-α: Fresh samples of blood from the animals were taken by cardiac puncture into heparin-containing vials. The determination of plasma TNF-α was carried out by an enzyme immunoassay kit from R&D systems (Minneapolis, Minn.). Briefly, each sample (50 µL) was incubated with antibodies specific for rat TNF-α and washed three times with assay buffer. An enzyme-linked polyclonal antibody specific for rat TNF-α conjugated to horseradish peroxidase was then added to the wells. Following washing of unbound antibody-enzyme reagent, a substrate solution (containing tetramethylbenzidine, TMB, plus hydrogen peroxide) was added to the wells. The enzyme reaction yielded a blue product (oxidized TMB) that turned yellow when the stop solution (dilute hydrochloride acid) was added. The intensity of the color was determined by measuring the OD of the yellow color in a standard ELISA plate reader at 450 nm. Sensitivity of this TNF-α assay was determined by adding two standard deviations to the mean optical density value of 20×zero standard replicates and calculating the corresponding concentration. The kit contains all reagents and standards needed for the TNF-α sensitivity assay. The results are expressed as pg/mL. Sensitivity for TNF-α is estimated to be around 1.6 pg/mL.

Inflammatory Edema Model: Carrageenan (1%, 100 µL, suspended in sterile saline solution, type IV lamda; Sigma-Aldrich) was subcutaneously injected into the plantar surface of the right hind paw in rat following the protocol described by Winter et al., *Proceedings of the Society for Experimental Biology and Medicine* 1962, 111:544-547. Paw volume was measured using a water displacement plethysmometer (model 520; IITC/Life Sciences Instruments, Woodland Hills, Calif.) before carrageenan injection and thereafter at 1-h intervals for 6 h. The paw volume measured just before carrageenan injection was used as the control volume. Data are expressed as the change in paw volume (milliliters) at each time point.

Determination of $PGE_2$ in Rat Paw Exudates: Rats were euthanized by asphyxiation in a $CO_2$ chamber. After cutting each hind paw at the level of the calcaneus bone, exudates (oedema fluid) and some tissue were collected, weighed and placed in a test tube containing 5 mL of 0.1 M phosphate buffer (pH7.4), 1 mM EDTA, and 10 µM indomethacin. The mixture was homogenized and centrifuged for 10 min at 12,000 r.p.m. at 4° C. $PGE_2$ content in supernatant was determined in duplicate by an enzyme immunoassay kit following the protocol described by the manufacturer (Cayman Chemical, Ann Arbor, Mich.). Briefly, standard (50 µL) or homogenate (50 µL), enzymatic tracer (50 µL) and specific antiserum (50 µL) were mixed. After incubation for 17 h (overnight) at 4° C., the plates were washed with wash buffer and Ellman's reagent (200 µL) was added into each well. The absorbance at 412 nm was measured after 1 h incubation at room temperature. Results are expressed as pg of $PGE_2$ per mg of protein. Proteins were determined by Biorad assay.

Western Blot Analysis: Exudates (oedema fluid) and some tissue were homogenized in lysis buffer (0.1% Triton X-100, 50 µM pepstatin, 0.2 mM leupeptin, 1 µg/mL aprotinin, 10 mg/ml phenylmethylsulfonyl flouride, 50 mM Tris, and 10 mM EDTA). Samples were then centrifuged, and the protein concentration of the supernatant was determined by colorimetric assay (Bio-Rad, Hercules, Calif.). Protein (30 µg) was separated on a 10% polyacrylamide gel and then transferred to a nitrocellulose membrane (Bio-Rad, Hercules, Calif.). Proteins were probed with monoclonal mouse antibody against COX-1 and COX-2 (1:500; Cayman Chemical, Ann Arbor, Mich.). The membrane was then incubated with a goat anti-mouse IgG secondary antibody conjugated to horseradish peroxidase (Santacruz Biotechnology, Santa Cruz, Calif.). A chemiluminescence reagent (Amersham Pittsburgh, Pa.) was added to visualize the labeling according to the manufacturer's instructions.

Determination of Plasma NO Content: Plasma concentration of NO was quantified indirectly as the concentration of nitrate ($NO_3^-$) and nitrite ($NO_2^-$) levels in plasma, by the Griess reaction using an assay kit and following the protocol described by the manufacturer. Rat plasma was filtered using a 10 KD molecular weight cut-off filter from Millipore (Bedford, Mass.) before each analysis, to reduced background absorbance due to the presence of haemoglobin. After centrifugation for 10 min at 3000 rpm, samples (40 µL/well) were mixed with 10 µL nitrate reductase mixture and incubated for 3 h after which Griess reagents 1 and 2 (50 µL each) were added. Absorbance was read after 10 min at 540 nm using a plate reader. The concentration of nitrate/nitrite was calculated graphically from a calibration curve prepared from $NaNO_2$ standard solution, and it is expressed as micromolar nitrate.

Measurement of $H_2S$ Levels: $H_2S$ levels were measured as previously described.[4,5] Aliquots (100 µL) of rat plasma from above were mixed with distilled water (100 µL), Zinc acetate (1% w/v, 250 µL), trichloroacetic acid (10% w/v, 250 µL), N,N-dimethyl-p-phenylenediamine sulfate (133 µl, 20 µM) in 7.2M HCl and $FeCl_3$ (133 µl, 30 µM) in 7.2M HCl. The absorbance of the resulting mixture (300 µL) was determined after 15 min using a 96-well microplate reader at 670 nm. All samples were assayed in duplicate and $H_2S$ levels were calculated against a calibration curve of NaHS (1-250 µM). This method overestimates $H_2S$ levels as it measures free $H_2S$, $HS^-$ (hydrosulfide anion), and $S^{2-}$ (sulfide).[6] Therefore, our results presented here indicate the sum total of these species.

Statistical Analysis: In vitro data are presented as mean±SEM for at least three different sets of plates done in triplicate. In vivo: treatment groups and number of animals in each group are indicated in the figure legends. Comparison between treatment groups was performed by one-factor analysis of variance (ANOVA) followed by Tukey's test for multiple comparisons. P<0.05 was regarded as statistically significant. The results are summarized in Table 1 and FIGS. 1-4. These results are also incorporated into Kodela et al., ACS Med. Chem. Lett., 2012, 3(3), 257-262.

Results:

As shown in Table 1, all four tested NOSH compounds (i.e., NOSH-1, NOSH-2, NOSH-3, and NOSH-4) exhibited efficacy in inhibiting cell growth of the tested cancer cell lines. NOSH-1 is the most potent compound among the four tested compounds. Note that colon HT-29 and pancreatic BxPC3 cells express both COX-1 and COX-2 whereas colon HCT15 and pancreatic MIA PaCa2 cells are COX null, suggesting that the effects observed are COX-independent.

Figure 2A:
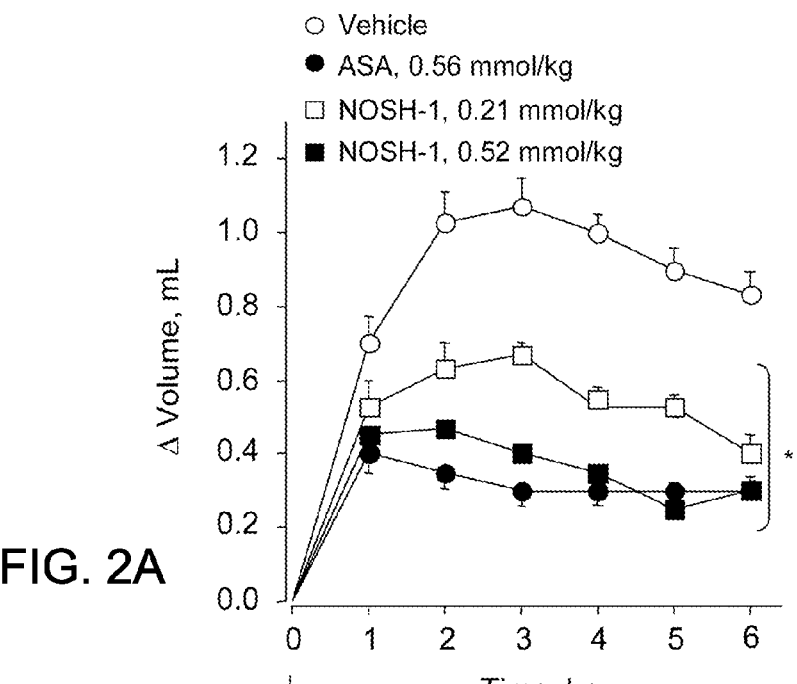
FIGS. 2A, 2B, and 2C are illustrations demonstrating anti-inflammatory properties of NOSH-1. Rat paw edema was induced by carrageenan injection.

NOSH-1 was dose-dependent. Rats treated with low dose NOSH-1 (0.21 mmol/kg) showed a change in paw volume $\Delta V=0.5$ ml, after 1 hour which increased to $\Delta V=0.6$ mL by 3 hours, and then came down to about $\Delta V=0.4$ mL over the next 3 hours. Rats treated with high dose NOSH-1 (0.52 mmol/kg), a dose which was slightly less than that of ASA (0.56 mmol/kg) showed a plateaued change in paw volume of $\Delta V=0.45$ mL after 1-2 hours, which then deceased steadily over the next 4 hours to $\Delta V=0.35$ mL, a change that was comparable to that of ASA (FIG. 2A).

Figure 2B:
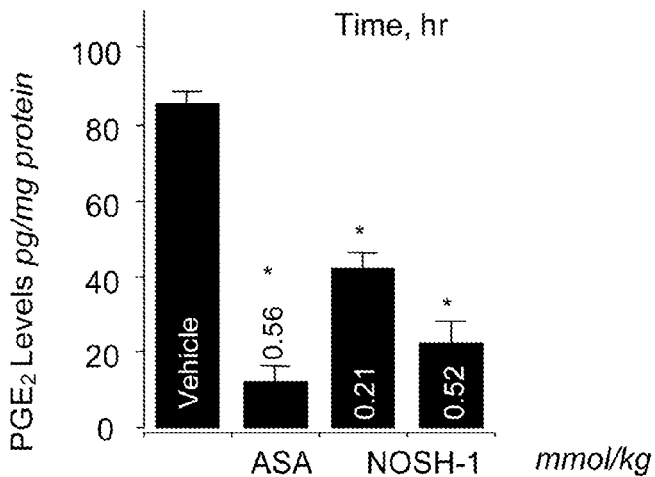
Figure 2C:
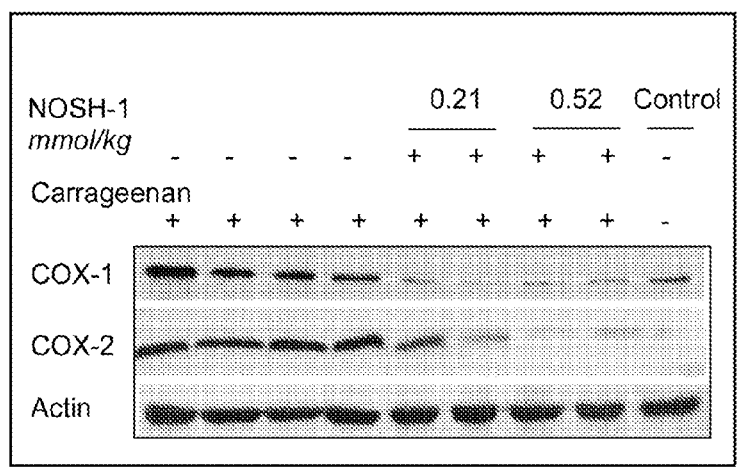
Figure 3:
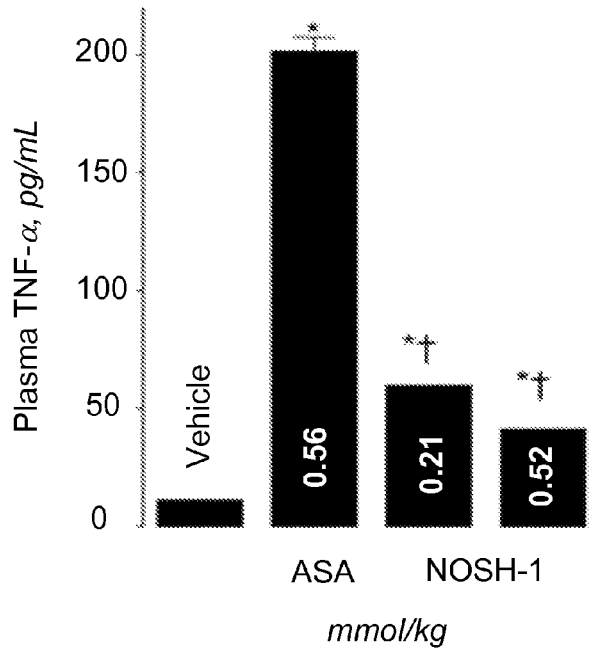
FIG. 3 is a graph showing the effect of ASA and NOSH-1 on plasma TNF-α. ASA caused a significant rise in plasma TNF-α. However, this rise was significantly less in the NOSH-1 treated rats. Results are mean±S.E.M. for 4 rats in each group, *P<0.01 vs vehicle, †P<0.01 vs ASA.

Prostaglandins ($PGE_2$) are the main product of cyclooxygenase-mediated arachidonic acid metabolism. Comparison of $PGE_2$ content of paw exudates from control, ASA-treated, and NOSH-1-treated animals showed a clear and significant COX inhibition by aspirin and NOSH-1. FIG. 2B shows that aspirin (0.21 mmol/kg) caused a considerable decrease in $PGE_2$ levels (12±3 pg/mg protein) compared with control group (82±2 pg/mg). Treatment with NOSH-1 reduced $PGE_2$ levels to 42±3 and 21±4 pg/mg at 0.21 and 0.52 mmol/kg, respectively. The effect of NOSH-1 on COX expression in paw exudates was further evaluated. FIG. 2C shows that COX-1 was constitutively expressed in the

TABLE 1

$IC_{50}$ nM for cell growth inhibition at 24 hours.

| | Colon | | | Breast | | | Pancreas | | Lung | Prostate | Leukemia |
|---|---|---|---|---|---|---|---|---|---|---|---|
| NOSH | HT-29 | HCT15 | SW480 | MB231 | SKBR3 | MCF7 | MIA PaCa2 | BxPC3 | A540 | LNCAP | Jurkat |
| 1 | 48 ± 3 | 50 ± 5 | 60 ± 4 | 100 ± 11 | 75 ± 5 | 280 ± 16 | 47 ± 5 | 57 ± 4 | 50 ± 7 | 88 ± 8 | 100 ± 8 |
| 2 | 80 ± 5 | 90 ± 6 | 97 ± 7 | 85 ± 8 | 88 ± 7 | 70 ± 5 | 102 ± 18 | 100 ± 9 | 120 ± 14 | 100 ± 12 | 90 ± 5 |
| 3 | 7500 ± 355 | 5900 ± 305 | 5300 ± 240 | 6000 ± 220 | 6500 ± 268 | 5700 ± 323 | 4800 ± 322 | 5500 ± 390 | 6500 ± 224 | 4300 ± 212 | 7000 ± 321 |
| 4 | 300 ± 35 | 520 ± 21 | 600 ± 25 | 800 ± 22 | 550 ± 28 | 280 ± 15 | 800 ± 39 | 700 ± 32 | 300 ± 12 | 500 ± 18 | 240 ± 11 |
| ASA | >5,000,000 nM at 24 hr in all cell lines | | | | | | | | | | |

Notes:
Colon, breast, pancreas, lung, prostate, and leukemia cancer cell lines were treated with various concentrations of NOSH-1, NOSH-2, NOSH-3, NOSH-4, and aspirin (ASA). Cell viability was determined at 24 h from which $IC_{50}$ values were calculated. Results are mean ± SEM of at least four different experiments performed in triplicates. P < 0.001 for all NOSH compounds compared to ASA in all cell lines.

Figure 1:
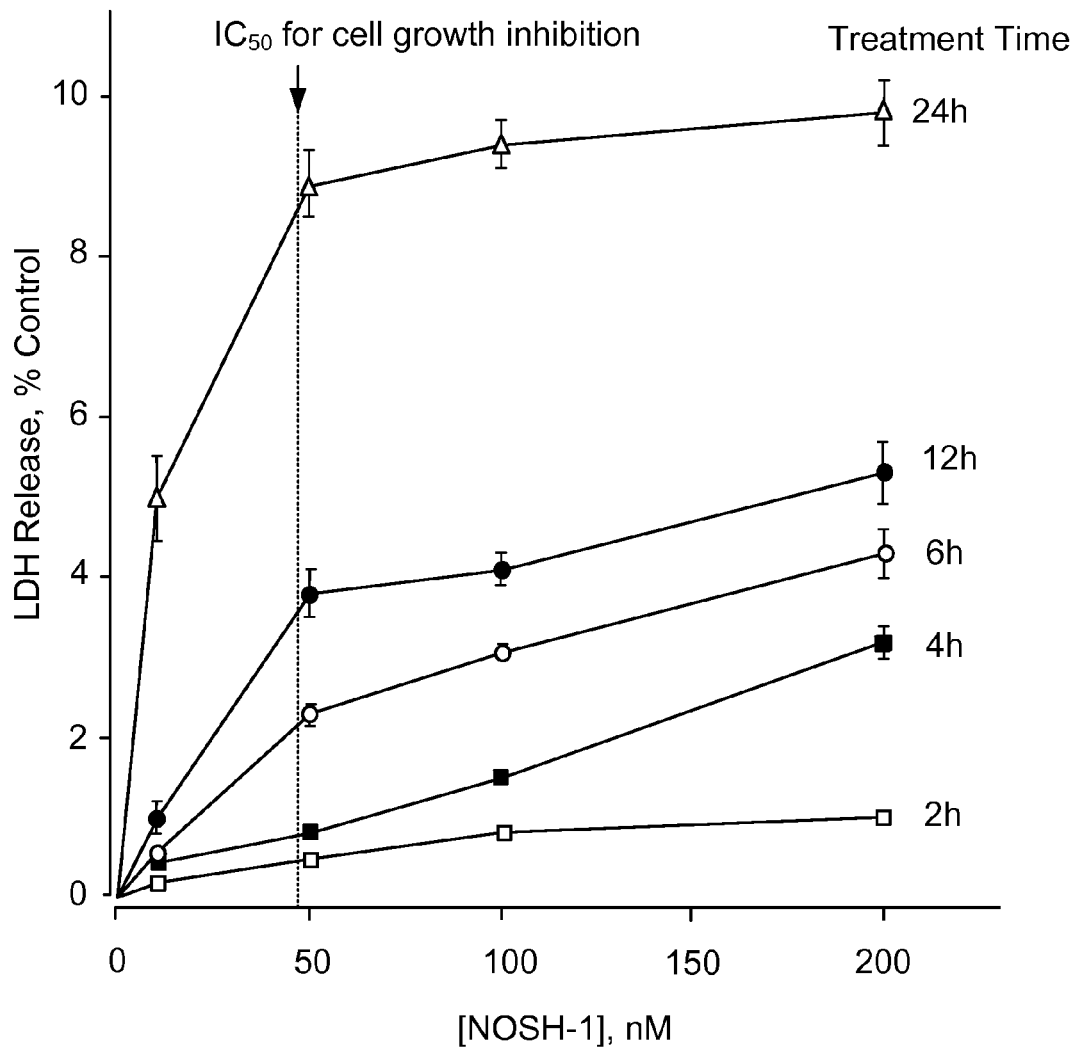
FIG. 1 is a graph showing the toxicity profile of NOSH-1 as measured by LDH release in HT-29 colon cancer cells.

As shown in FIG. 1, cells were treated with several concentrations of NOSH-1 for 2-24 hours and compared to untreated controls. Although the cytotoxicity caused by NOSH-1 was both dose- and time-dependent, this was minimal. At 4-times its $IC_{50}$, LDH release was less than 10% at 24 hours. LDH release for shorter durations of treatment (2 hours, 4 hours, 6 hours, and 8 hours) ranged between 0.5-4% at its $IC_{50}$ and between 1-5% at 4-times its $IC_{50}$. This demonstrates a remarkable degree of safety for a compound that is so potent.

The most common use for NSAIDs (including aspirin) is the treatment of inflammatory conditions. Therefore, the COX-dependent anti-inflammatory activity of ASA to that of NOSH-1 was compared. This was done by using the rat paw edema model as described above. After inducing inflammation in rat's paw with carrageenan, animals receiving vehicle showed a fast time-dependent increase in paw volume ($\Delta V=1.1$ mL) after 2-3 hours, which decreased gradually every hour thereafter until the end of the experiment (6 h) (FIG. 2A). In contrast, animals receiving ASA showed a weak inflammatory response ($\Delta V=0.4$ mL) at 1 hour, decreasing to about $\Delta V=0.35$ mL over the next 2 hours and then decreasing to about $\Delta V=0.35$ mL after 6 hours. The anti-inflammatory effect registered in animals treated with controls; this was induced by carrageenan and inhibited to the same extent by NOSH-1 regardless of the dose. On the other hand, COX-2, which produces inflammatory $PGE_2$ and was barely detectable in the controls, was significantly induced by carrageenan, and dose-dependently inhibited by NOSH-1.

The inhibitory effect of ASA and NOSH-1 on proinflammatory cytokine tumor necrosis factor-α (TNF-α) in plasma obtained from control and NOSH-1-treated animals was determined. Administration of ASA (0.56 mmol/kg) increased TNF-α concentration by about 20-fold (10±1 control and 200±10 pg/mL ASA); however, this rise was considerably lower in the NOSH-1 (55±2 pg/mL at 0.21 mmol/kg and 40±3 pg/mL at 0.52 mmol/kg) treated animals. See FIG. 3.

Figure 4A:
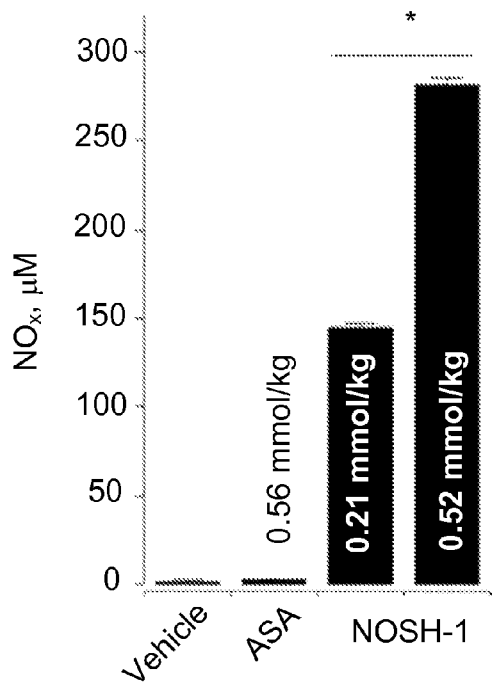
FIGS. 4A and 4B are graphs showing NO and H$_2$S levels in vivo after NOSH-1 administration. Results are mean±S.E.M. of four rats in each group. *P<0.001 versus vehicle and ASA-treated animals.
Figure 4B:
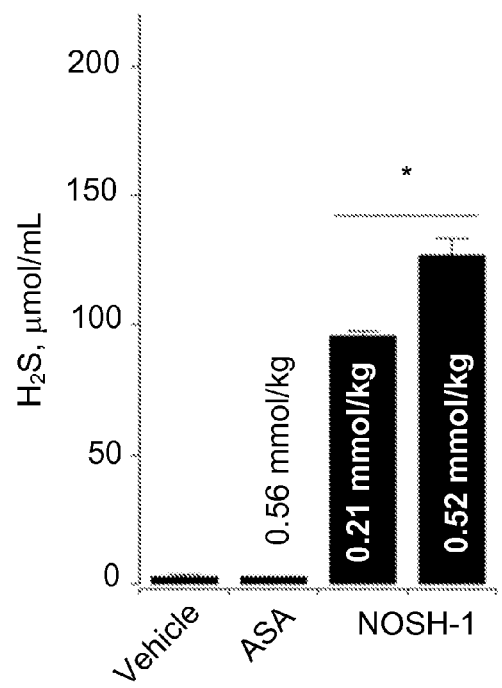

The NOSH compounds were designed to release both NO and $H_2S$. In order to show that indeed this was the case in vivo, blood was collected from vehicle-, ASA-, and NOSH-1-treated animals at the end of the carrageenan-induced edema studies. FIGS. 4A and 4B show that indeed both NO and $H_2S$ were dose-dependently significantly higher in NOSH-1-treated animals.

Example 10

In Vitro and In Vivo Assays for HT-29 Colon Cancer Cells

Materials and Methods:

Reagents: NOSH-1, (4-(3-thioxo-3H-1,2-dithiol-5-yl) phenyl 2-((4-(nitrooxy)butanoyl)oxy)benzoate), was synthesized and purified following the procedures described in Example 1. NO-ASA, para isomer, [2-(acetyloxy)benzoic acid 4-(nitrooxy methyl)phenyl ester]; ortho isomer, [2-(acetyloxy)benzoic acid 2-(nitrooxy methyl)phenyl ester]; meta isomer, [2-(acetyloxy)benzoic acid 3-(nitrooxy methyl)phenyl ester]; and NO-ASA with an aliphatic spacer, [3-(nitroperoxy)propyl 2-acetoxybenzoate] were synthesized following the procedures described in Penning et al., *J. Med. Chem.*, 40 (1997), 1347-1365. HS-aspirin (HS-ASA), [4-(5-thioxo-5H-1,2-dithiol-3-yl)-phenyl 2-acetoxybenzoate] was synthesized following the procedures described in Chattopadhyay et al., *Biochemical Pharmacology*, 2012, 83(6), 715-722. Stock solutions (100 mM) of test compounds were prepared in dimethyl sulfoxide (Fisher Scientific, Fair Lawn, N.J.). Traditional aspirin was purchased from Sigma-Aldrich (St. Louis Mo.).

Cell Culture: HT-29 human colon cancer cells were obtained from American Type Tissue Collection (Manassas, Va.) and grown as monolayer in McCoy 5A media that was supplemented with 10% fetal calf serum (Invitrogen, Carlsbad, Calif.), penicillin (50 U/ml), and streptomycin (50 μg/ml) (Invitrogen, Carlsbad, Calif.).

Cell Growth Inhibition, Cell Proliferation, Cell Cycle Analysis, and Apoptosis: Growth inhibition was measured using a colorimetric MTT assay kit (Roche, Indianapolis, Ind.). Proliferation (PCNA) was assessed using an ELISA kit from Calbiochem, (La Jolla, Calif.). Cell cycle phase distributions and apoptosis of control and treated cells were determined as previously described. All methods are described in Chattopadhyay et al., *Biochemical Pharmacology*, 2012, 83(6), 715-722.

Determination of NO and $H_2S$ Levels: Cells were treated with NOSH-1 at its $IC_{50}$ for cell growth inhibition (50 nM). At different time points (15 min-24 h), NO release was measured in the culture medium using a nitrate/nitrite colorimetric assay kit (Cayman Chemical Co., Ann Arbor, Mich.) as described in Kashfi et al., *J. Pharmacol. Exp. Ther.*, 312, (2005), 978-988.

Initially, $H_2S$ levels were determined using the standard methylene blue method as described in Bhatia et al., *Faseb. J.*, 19 (2005) 1196-1198 or Huang et al., *J. Mol. Biol.* 396, (2010), 708-718. However, because of the strong acid and prolonged incubation periods, this method overestimates $H_2S$ levels as it measures free $H_2S$, $HS^-$ (hydrosulfide anion), $S^{2-}$ (sulfide), acid-labile sulfide and other, as yet unidentified, sulfides and can only provide a rough estimate of $H_2S$ production (see Olson, *Biochim. Biophys. Acta*, 1787 (2009) 856-863). In order to illustrate that NOSH-1 and HS-ASA do liberate free $H_2S$, we used a polarographic (amperometric) $H_2S$ sensor that measures $H_2S$ gas in real-time and on unadulterated samples.

Measurement of COX Enzyme Activity: NOSH-1 was evaluated for its ability to inhibit COX-1 and COX-2 enzyme activities in vitro as described in Kulmacz et al., *Prostaglandins*, 25 (1983), 531-540 using a colorimetric COX (ovine, o-COX) inhibitor screening kit from Cayman Chemicals (Ann Arbor, Mich.).

In Vivo Efficacy of NOSH-1: Male athymic nude (NU/NU) mice (N=8), age 5 weeks, were purchased from Charles River Laboratories, Inc., (Wilmington, Mass.). HT-29 cells ($2 \times 10^6$) suspended in 50% v/v Matrigel (BD Biosciences, San Jose, Calif.) were inoculated subcutaneously in the right flanks of each mouse. When the tumors reached an average sizes of ~80 $mm^3$, the mice were randomly divided (N=4/group) and gavaged daily for 18 days with either vehicle (1% methylcelloluse) or NOSH-1 (100 mg/kg body weight). Tumor size (length and width) was measured at 3 day intervals with an electronic caliper from which tumor volume was calculated as length×width/2. The mice were weighed every 3 days and were closely monitored for signs of toxicity.

Statistical Analysis: In vitro: data are presented as mean±SEM for at least three different sets of plates done in triplicate. In vivo: treatment groups and number of animals in each group are indicated in the figure legend. Comparison among the groups was performed using a one-way analysis of variance followed by the least significant difference method. P<0.05 were considered significant.

Results:

NOSH-1 is a Potent Inhibitor of HT-29 Cell Growth

The results of the above assays are summarized in the Tables and Figures below. These results are also described in Chattopadhyay et al., *Biochemical and Biophysical Research Communications*, 2012, 419(3), 523-528.

TABLE 2

$IC_{50}$ values for NOSH-1 in HT-29 cells as a function of time.

| Compound | $IC_{50}$, nM | | |
|---|---|---|---|
| | 24 h | 48 h | 72 h |
| ASA | >5,000,000* | 2,500,000 ± 500,000 | 2,000,000 ± 300,000 |
| NOSH-1 | 45.5 ± 2.5† | 19.7 ± 3.3† | 7.7 ± 2.2† |
| Potency enhancement | >100,000 | ~125,000 | ~250,000 |

Cells were treated with various concentrations of aspirin and NOSH-1 as described above. Cell numbers were determined at 24, 48, and 72 h from which $IC_{50}$ values were calculated. Results are mean ± SEM of three to five different experiments done in triplicate.
*Exceeded the maximum concentrations used in these studies.
†P < 0.001 compared to aspirin.

As shown in Table 2, NOSH-1 at 24 hours strongly inhibited cell growth in a concentration dependent manner. The $IC_{50}$s for growth inhibition were reduced in a time-dependant manner. At 24, 48, and 72 hours, the $IC_{50}$s for NOSH-1 were 45.5±2.5 nM, 19.7±3.3 nM, and 7.7±2.2 nM, respectively. In contrast, the $IC_{50}$s for ASA were higher than 5,000,000 nM at 24 hours, 2,500,000±500,000 nM at 48 hours, and 2,000,000±300,000 nM at 72 hours. The enhanced potency calculated as the ratio of $IC_{50}$ values (traditional ASA/NOSH-1) indicated that NOSH-1 is >100,000-fold more potent than ASA at 24 hours, and ~125,000-fold and ~250,000-fold more potent than ASA at 48 hours and 72 hours, respectively.

TABLE 3

Comparison in $IC_{50}$ values for cell growth inhibition against HT-29 colon cancer cells between aspirin, NO-aspirin, HS-aspirin, and NOSH-1.

| Treatment | IC50 at 24 hours, μM | Fold-enhanced potency of NOSH-1 |
|---|---|---|
| ASA | >5000 | >100,000 |
| p-NO-ASA | 10 ± 2 | ~200 |
| o-NO-ASA | 8 ± 3 | ~160 |
| m-NO-ASA | 185 ± 15 | ~3,700 |

TABLE 3-continued

Comparison in $IC_{50}$ values for cell growth inhibition against HT-29 colon cancer cells between aspirin, NO-aspirin, HS-aspirin, and NOSH-1.

| Treatment | IC50 at 24 hours, μM | Fold-enhanced potency of NOSH-1 |
|---|---|---|
| HS-ASA | 4 ± 0.5 | ~80 |
| NOSH-1 | 0.05 ± 0.003 | — |

Cells were treated with various concentrations of test agents as described above. Cell numbers were determined at 24 hours from which $IC_{50}$ values were calculated. Results are mean ± SEM of four different experiments performed in triplicates.

Since NOSH-1 releases both NO and $H_2S$, we wanted to compare its cell growth inhibitory properties with that of nitric oxide-releasing aspirin (NO-ASA) and hydrogen sulfide-releasing aspirin (HS-ASA). NO-ASA is derived from ASA by covalently attaching to it —$ONO_2$ through an aromatic or an aliphatic spacer. With an aromatic spacer, there are 3 positional isomers of NO-ASA (p-, o-, and m-NO-ASA). HS-ASA is also derived from ASA to which 5-(4-hydroxyphenyl)-3H-1,2-dithiole-3-thione (ADT-OH) has been covalently attached to the carboxylic group of the ASA molecule. Using HT-29 colon cancer cells, the $IC_{50}$ values for cell growth inhibition at 24 hours were >5000 μM, 10±2 μM, 8±3 μM, 185±15 μM, 750±35 μM, 4±0.5 μM, and 0.05±0.003 μM for ASA, p-NO-ASA, o-NO-ASA, m-NO-ASA, aliphatic-NO-ASA, HS-ASA, and NOSH-1, respectively. See Table 3. This demonstrates an enhanced potency for NOSH-1 ranging from 80-fold to >100,000-fold over the other agents. The above data also illustrate the importance of $H_2S$ since the closest agent to NOSH-1 in terms of $IC_{50}$ for cell growth inhibition was HS-ASA.

NOSH-1 Alters HT-29 Colon Cancer Cell Kinetics

To evaluate the mechanism(s) involved in the reductions of cell growth, the effect of NOSH-1 on cell renewal and cell death, two determinants of cell growth was analyzed. Since the $IC_{50}$ for cell growth inhibition in this study ranged from 45.5±2.5 nM (Table 2) to 50±3 nM (Table 3), 50 nM was chosen as the standard $IC_{50}$ concentration and used multiples of this in all other studies presented below.

Cell Proliferation: At 24 hours, NOSH-1 reduced PCNA expression in a dose-dependant manner. At 0.5×$IC_{50}$ (25 nM), 1×$IC_{50}$ (50 nM), and 2×$IC_{50}$ (100 nM), the reduction was 18.2±1.5%, 50.3±3.2% and 77.4±2.2%, respectively (see FIG. 5A).

Cell Cycle: Cell cycle progression as measured by DNA content of treated cells using flow cytometry was also affected by NOSH-1. Cells treated with NOSH-1 at 0.5×, 1×, and 2×$IC_{50}$ accumulated progressively in $G_0/G_1$ phase of the cell cycle (see FIG. 5B). For example, at 1×$IC_{50}$ the cell populations in the different phases were altered in the following manner compared to control: $G_0/G_1$ increased from 42.9±2% to 62.0±2.3%; S phase was reduced from 30.2±2.3% to 22.6±1.3%, and $G_2/M$ reduced from 26.9±2.2 to 15.4±2.6%. At 2×$IC_{50}$, these changes were even more pronounced, $G_0/G_1$ phase increased to 74.2±1.2% while the population in S phase was reduced to 16.3±1.2 and $G_2/M$ was reduced to 9.5±1.8%.

Cell Death: Since cell apoptosis may be one of the consequences of cell-cycle arrest, we examined this in our NOSH-1-treated cells. The proportion of cells undergoing apoptosis increased in a dose dependent manner as determined by the Annexin V-FITC staining and flow cytometry. Treatment with 0.5×, 1× and 2×$IC_{50}$ NOSH-1 resulted in 24.7±1.4%, 32.8±2.1%, and 55.9±3.3% cells in early apoptotic phase, respectively, compared to untreated control (see FIG. 5C). Therefore, it is believed that NOSH-4 inhibited proliferation of HT-29 colon cancer cells by a combined induction of $G_0/G_1$ arrest and apoptosis.

NOSH-1 Releases Both Nitric Oxide and Hydrogen Sulfide

Figures 6A, 6B:
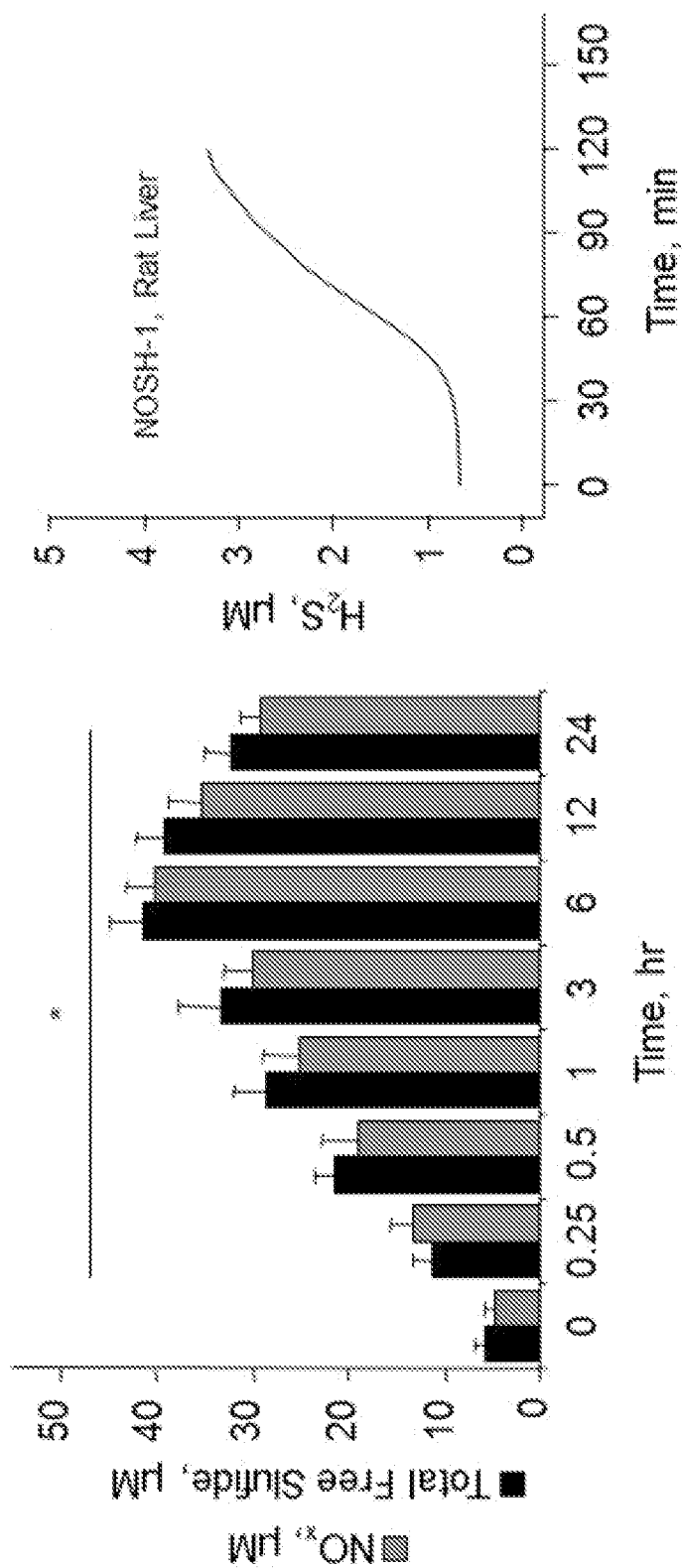
FIGS. 6A and 6B are graphs showing that NOSH-1 released both NO and H$_2$S.

NOSH-1 was designed to release both NO and $H_2S$. In order to show that indeed this was the case, HT-29 cells were treated with NOSH-1 at its $IC_{50}$ for cell growth inhibition (50 nM). NO and $H_2S$ levels were measured from the cell culture supernatants/homogenates as a function of time. As shown in FIG. 6A, NOSH-1 showed a time-dependent release of NO (as total $NO_3^-/NO_2^-$), more than doubling over the base line in the first 15 minutes (4.8 μM to 13.3 μM), thereafter increasing steadily to peak at 6 hours (40.1 μM) and then decreasing steadily to 29.1 μM by 24 hours. Even after 24 hours, the concentration of NO in the medium was 6-fold greater compared to the untreated cells.

TABLE 4

$H_2S$ release from NOSH-1 and HS-ASA.

| | Homogenized mouse liver (μmol/min/g wet weight) | Tissue culture media (μmol/min) |
|---|---|---|
| NOSH-1 | 57.3 ± 6.4[a,b] | 8.7 ± 4.4[b] |
| HS-ASA | 146 ± 15[a,c] | 3.5 ± 1.1[c] |

$H_2S$ from homogenized mouse liver or from tissue culture media was measured in real-time with a polarographic $H_2S$ sensor. $H_2S$ release by both donors was significantly greater in homogenized tissue than in media and in homogenized liver, the rate of $H_2S$ release from NOSH-1 was significantly less than that released by HS-ASA. Results are mean ± SEM (n = 3 animals or replicates). Significantly different from like symbol;
[a]P = 0.005;
[b]P = 0.001;
[c]P = 0.005.

Although the methylene blue method is associated with considerable artifact, as shown in FIG. 6A, there does appear to be an increase in some form of sulfide species that is a function of time and must be due to NOSH-1. The time course for this increase was similar to that for NO, it increased within 15 minutes, peaked at 6 hours, and then decreased steadily. Actual release of $H_2S$ gas from the $H_2S$-donating compounds was evident when homogenized mouse liver (1:10 W:V in oxygenated Krebs Henseit buffer) was incubated with 100 μM NOSH-1 or HS-ASA and examined in real time with the polarographic sensor (see FIG. 6B). The rate of $H_2S$ production under these conditions is shown in Table 4 above. It is evident that $H_2S$ production from either donor is significantly less in media than when incubated with tissue. This suggests that significantly more $H_2S$ is formed inside the cell, probably through enzymatic activity. This would not only provide considerably more $H_2S$ to an intracellular signaling cascade but it would also minimize $H_2S$ loss from the tissue culture wells due to volatilization. The latter is a common occurrence in these experiments and a considerable source of error in estimating potency of exogenous $H_2S$ (see, e.g., Deleon et al., Anal. Biochem. 421 (2012), 203-207). In addition, the slower rate of $H_2S$ production from NOSH-1 compared to that from HS-ASA would be expected to increase the duration of intracellular $H_2S$ exposure and could also contribute to the increased potency of NOSH-1.

Effects of NO- and $H_2S$-Releasing Groups on Cell Growth

TABLE 5

$IC_{50}$ values for HT-29 cell growth inhibition by various components of NOSH-1 or other agents that release NO or $H_2S$ alone or in combination.

| Compound | IC50 at 24 hours, μM |
|---|---|
| ASA | >1000 |
| SNAP | 530 ± 45 |

TABLE 5-continued

IC$_{50}$ values for HT-29 cell growth inhibition by
various components of NOSH-1 or other agents that release
NO or H$_2$S alone or in combination.

| Compound | IC$_{50}$ at 24 hours, µM |
|---|---|
| ADT-OH | 26 ± 3 |
| ASA + SNAP | 710 ± 35 |
| ASA + ADT-OH | 380 ± 45 |
| ASA + SNAP + ADT-OH | 450 ± 35 |
| NOSH-1 | 0.05 ± 0.005[†] |

Cells were treated with various concentrations of test agents shown above as described in Materials and Methods. Cell numbers were determined at 24 h from which IC$_{50}$ values were calculated. Results are mean ± SEM of four different experiments performed in triplicates.
[†] P < 0.001 compared to all other treatment groups. SNAP, S-nitroso-N-acetyl-penicillamine, releases NO. ADT-OH, 5-(4-hydroxyphenyl)-3H-1,2-dithiole-3-thione, releases H$_2$S, (used in NOSH-1).

A structure-activity and reconstitution study was performed in HT-29 cells using ASA, the exogenous NO donor SNAP, and ADT-OH which releases H$_2$S, in order to determine equivalency of NOSH-1 to the sum of its parts. We examined cell growth inhibitory function of intact NOSH-1 molecule, and the combinations of ASA plus SNAP, ASA plus ADT-OH, and ASA plus SNAP and ADT-OH. For the combination, various concentrations of ASA were combined with different fixed concentrations of SNAP, ADT-OH, or SNAP and ADT-OH. Such simulation of intact NOSH-1 using ASA plus SNAP and ADT-OH represents a fairly close approximation to the intact NOSH-1. The growth inhibition curves of HT-29 cells were analyzed with these combinations, the respective IC$_{50}$s of ASA in these were evaluated for a possible shift. Table 5 shows that various combinations had a synergistic effect in terms of cell growth inhibition, but the respective IC$_{50}$s of ASA in the combinations were far higher than those of NOSH-1. In particular, the combination of ASA plus SNAP and ADT-OH should have given an IC$_{50}$ for cell growth inhibition comparable to that of NOSH-1. Unexpectedly, the combination gave an IC$_{50}$ of 450±35 µM, whereas that for NOSH-1 was 0.05±0.005 µM. In other words, the intact NOSH-1 molecule was approximately 9000-fold more potent than the combination in different molecules (i.e., the sum of the parts does not equal the whole), which is clearly indicative of a strong synergistic effect in NOSH-1. These findings indicate that the combined molecular components cannot completely account for the biological activity of intact NOSH-1 and that these constituents may only, in part, contribute to its activity.

NOSH-1 Inhibits Cyclo-Oxygenase Enzyme Activity

TABLE 6

Effect of NOSH-1 on COX-1 and COX-2 enzyme activity.

| NOSH-1, nM | COX-1, % Inhibition* | COX-2 % Inhibition* |
|---|---|---|
| 25 | 8.3 ± 1 | 5.4 ± 0.7 |
| 50 | 45.2 ± 2 | 14.5 ± 1 |
| 100 | 69.4 ± 2.2 | 27.2 ± 0.7 |
| ASA, 1 mM | 53.2 ± 1.8 | 50.6 ± 1.1 |
| Indomethacin, 1 µM | 74.2 ± 1.8 | 63.5 ± 1.5 |

*Results are mean ± range of two independent studies performed in duplicate.

When metabolized, NOSH-1 should produce ASA, H$_2$S and NO. The above results have shown that NO and H$_2$S are released. In order to show the effects of the ASA component, the effects of NOSH-1 on COX-1 and COX-2 enzyme activity were evaluated. As shown in Table 6, NOSH-1 dose-dependently inhibited the enzymatic activity of both COX-1 and COX-2. However, it appears that NOSH-1 preferentially inhibits COX-1. At its IC$_{50}$ for cell growth inhibition (50 nM), COX-1 was inhibited by 45.2±2% and COX-2 was inhibited by 14.5±1%. The inhibition was higher at 2×IC$_{50}$ (100 nM), which were 69.4±2.2% and 27.2±0.7% for COX-1 and COX-2, respectively. Since we had used 1 mM ASA in our reconstitution studies, we also evaluated effects of ASA on COX-1 and COX-2 enzymatic activity at this concentration. As shown in Table 6, the results show that both enzymes were inhibited to the same extent at this concentration, i.e., 53.2±1.8% and 50.6±1.1% for COX-1 and COX-2, respectively. At lower concentrations, ASA is a 10- to 100-fold more potent inhibitor of COX-1 relative to COX-2 (see Meade et al., *J. Biol. Chem.*, 268 (1993) 6610-6614). To validate our assay system, we used the nonselective COX inhibitor indomethacin (1 µM) as a reference compound (see Riendeau et al., *Can. J. Physiol. Pharmacol.*, 75 (1997), 1088-1095). As shown in Table 6, the results show that inhibition of COX-1 by indomethacin was 74.2±1.8% and that of COX-2 was 63.5±1.5%.

Effect of NOSH-1 on Tumor Growth in a Xenograft Model

Figure 7A:
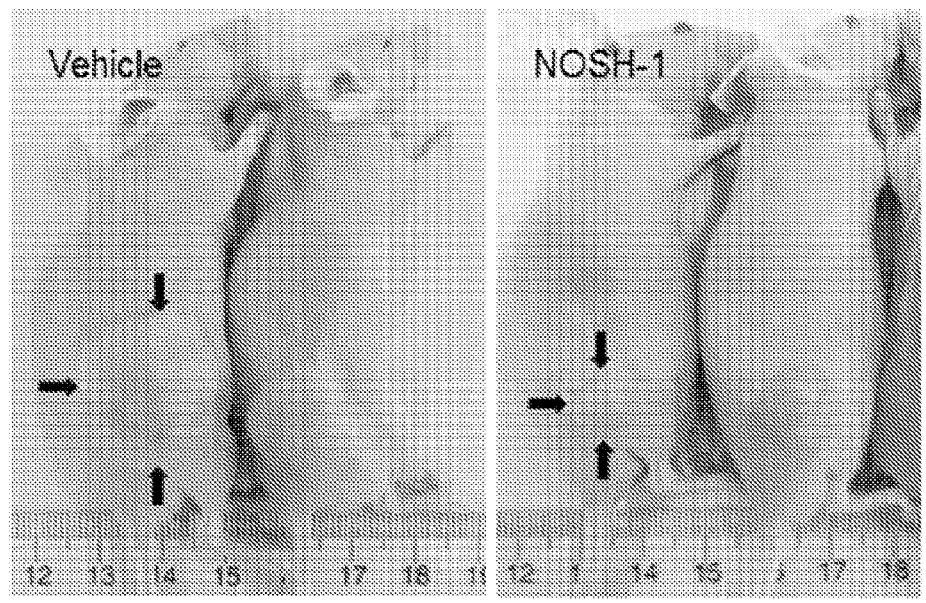
FIGS. 7A and 7B include graphs demonstrating that NOSH-1 inhibited tumor xenograft growth.
Figure 7B:
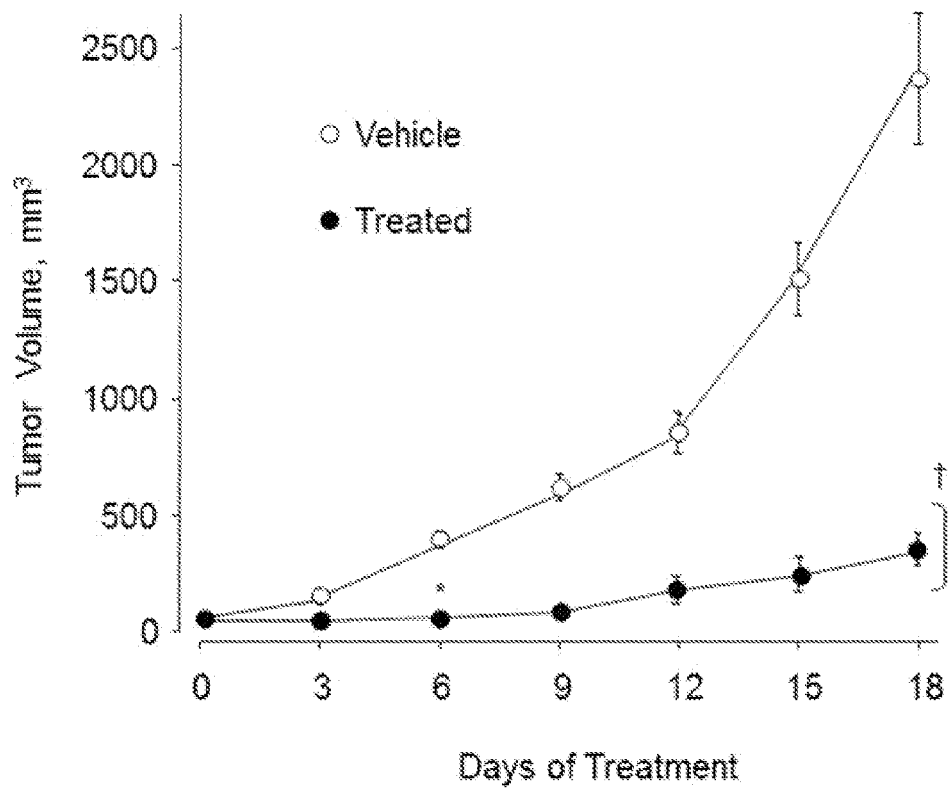

Male athymic nude (NU/NU) mice (n=8) were injected subcutaneously with HT-29 cells in the right flank, allowing for the development of subcutaneous tumors after 10 days. Following tumor formation, the mice were randomly divided into two groups of four each. One group was treated every day for 18 days with 100 mg/kg NOSH-1, whereas the other group received the vehicle for the same period of time. The mice were monitored closely, there were no overt signs of toxicity, the average weight of the mice in each group was comparable at the beginning and end of the study, 21.8±0.98 g to 28.8±1.9 g in the untreated mice and 21.7±0.82 g to 27.2±1.1 g in the treated mice. The NOSH-1-treated mice showed a considerable reduction in tumor volume compared with untreated mice. See FIGS. 7A and 7B. Compared with the control group with mean tumor volume of 2300±200 mm$^3$, NOSH-1 reduced the tumor volume to 350±35 mm$^3$, equivalent to a mean reduction of 85% (P<0.001).

Example 11

NOSH-Aspirin, NOSH-Naproxen, and
NOSH-Sulindac Inhibit the Growth of Various
Human Cancer Cells Lines In Vitro NOSH-1, NOSH-7, and NOSH-8 were tested for their efficacy in inhibiting the growth of various human cancer cells lines in vitro. NOSH-1 is also referred herein as NOSH-ASA or NOSH-aspirin. NOSH-7 is also referred herein as NOSH-naproxen. NOSH-8 is also referred herein as NOSH-sulindac.

Materials and Methods

Cell Culture: HT-29, SW-480 and HCT-15 human colon adenocarcinoma, MIA PaCa-2 and BxPC-3 human pancreatic cancer, LNCAP human prostate cancer, A549 and H383 human lung cancer, MCF-7, MDA-MB 231 and SK-BR-3 human breast cancer and Jurkat T cell human leukemia cell lines were obtained from American Type Tissue Collection (Manassas, Va.). All cells lines were grown as monolayers except for the Jurkat T cells which were grown as suspension culture. The pancreatic and breast cancer cells were grown in Dulbecco's modified Eagle's medium, the prostate, Jurkat, SW-480 and HCT-15 colon cells were grown in RPMI 1640 medium, the lung cells were grown in F-12 and the colon HT-29 cells were grown in McCoy 5A. All media were supplemented with 10% fetal calf serum (Invitrogen, Carlsbad, Calif.) penicillin (50 U/ml), and streptomycin (50 µg/ml) (Invitrogen, Carlsbad, Calif.). Cells were seeded on culture dishes at a density of $25 \times 10^3$ cells/cm$^2$ and incubated at 37° C. in 5% $CO_2$ and 90% relative humidity. Single cell suspensions were obtained by trypsinization (0.05% trypsin/ EDTA), and cells were counted using a hemacytometer. The final DMSO concentration was adjusted in all media to 1%. Viability was determined by the trypan blue dye exclusion method.

Growth Inhibition: Cell growth inhibitory effect of all NOSH-NSAIDs was measured using a colorimetric MTT assay kit (Roche, Indianapolis, Ind.). Cancer cells were plated in 96-well plates at a density of 30,000-50,000 cells/well depending on cell type. The cells were incubated for 24 hours with different concentrations of NOSH-NSAIDs. After the indicated time, 10 µL of MTT dye (3-[4,5-dimethylthiazol-2-yl]-2,5-diphenyl tetrazolium bromide, 5 mg/mL in phosphate buffered saline), was added to each well, and the plates were incubated for 2 hours at 37° C. Then, the media was aspirated, and 100 µL of the solubilization solution (10% SDS in 0.01 M HCl) was added to each well to solubilize the formant crystals. The absorbance of the plates was measured on a spectrophotometric plate reader at a wavelength of 570 nm. Each experiment was performed in triplicate, and the entire experiment was repeated three times.

Results:

The effects of NOSH-naproxen and NOSH-sulindac and their respective parent compounds on the growth properties of eleven different cancer cell lines of six different histological subtypes were investigated. The cell lines were that of colon (HT-29: COX-1 and COX-2 positive, HCT 15: COX null, and SW480: COX-1 positive, low levels of endogenous COX-2); breast (MCF7: [ER(+)], MDA MB-231 and SKBR3: [ER(–)]); T-cell leukemia (Jurkat); pancreatic (BxPC3: both COX-1 and COX-2 positive, MIAPaCa-2: COX-null); prostate (LNCaP); and lung (A549). Both NOSH-naproxen and NOSH-sulindac were effective in inhibiting the growth of these cell lines (Table 7). As shown in Table 7, the growth inhibition by NOSH-NSAIDs versus their traditional NSAID counterparts was very high in the cell lines studied. In a fold comparison study of the $IC_{50}$ values (Traditional/NOSH-NSAID), NOSH-naproxen was ~23,000 to ~34,000-fold more potent than naproxen across the cell lines examined. NOSH-sulindac was ~1,000 to ~9000-fold more potent than sulindac across the cell lines examined.

Example 12

In Vivo Properties and Safety of NOSH-Aspirin, NOSH-Naproxen, and NOSH-Sulindac in Rats Materials and Methods Animals: The institutional animal care and research committees approved all experimental procedures described herein. Male Wistar rats (4 per group) weighing 180-200 g were obtained from Charles River Laboratories International (Wilmington, Mass.). The rats were fed standard laboratory chow and water. Rats were fasted for 48 h with free access to drinking water. All agents were administered orally by gavage suspended in the vehicle 0.5% carboxymethylcellulose solution, at equimolar doses: ASA (180 mg/kg), NOSH-ASA (477 mg/kg); naproxen (80 mg/kg), NOSH-naproxen (188 mg/kg); sulindac (200 mg/kg), and NOSH-sulindac (467 mg/kg). Six hours post-administration, animals were euthanized by $CO_2$; blood samples were drawn by cardiac puncture into heparin-containing vials and used for determination of plasma TNF⟨, hydrogen sulfide and total nitrite/nitrate levels. Stomachs were then rapidly removed, cut along the greatest curvature, and rinsed with ice-cold distilled water. The ulcer index (UI) was determined as described by Best et al (Best R, et al. *Br J Pharmacol* 1984, 82:107-116). Tissues from stomachs were excised and processed for measurement of Prostaglandin $E_2$ ($PGE_2$), malondialdehyde (MDA) and Superoxide dismutase (SOD) activity.

Determination of $PGE_2$ Levels: Approximately 1 g of stomach tissue from each rat was placed in a test tube containing 5 mL of 0.1 M phosphate buffer (pH7.4), 1 mM EDTA, and 10 µM indomethacin. The tissue was homogenized and centrifuged for 10 min at 12,000 r.p.m. at 4° C. $PGE_2$ content in supernatant was determined in duplicate by an enzyme immunoassay kit following the protocol described by the manufacturer (Cayman Chemical, Ann Arbor, Mich.) and as previously reported (Chattopadhyay M, et al. *J Pharmacol Exp Ther.* 2010, 335, 443-50). Briefly, standard (50 µL) or homogenate (50 µL), enzymatic tracer (50 µL) and specific antiserum (50 µL) were mixed. After incubating overnight at 4° C., the plates were washed with wash buffer and Ellman's reagent (200 µL) was added into each well. After incubating for 1 h at room temperature, the absorbance at 412 nm was recorded. Results are expressed as pg of $PGE_2$ per mg of protein. Proteins were determined by Biorad assay. For determination of $PGE_2$ in the rat paw

TABLE 7

$IC_{50}$ values for cell growth inhibition by NOSH-naproxen and NOSH-sulindac in different cancer cell lines.

| | Colon | | | Breast | | | Pancreas | | Lung | Prostate | Leukemia |
|---|---|---|---|---|---|---|---|---|---|---|---|
| | | | | MDA | | | MIA- | | | | |
| Agent | HT-29 | HCT15 | SW480 | MB231 | SKBR3 | MCF7 | PaCa2 | BxPC3 | A549 | LNCAP | Jurkat |
| NAP | 2775 | 2850 | 3110 | 2900 | 2890 | 2350 | 3200 | 2450 | 2650 | 2990 | 2550 |
| NOSH-NAP | 0.08 | 0.10 | 0.098 | 0.11 | 0.10 | 0.11 | 0.095 | 0.08 | 0.10 | 0.13 | 0.10 |
| Ratio | 34,687 | 28,500 | 31,734 | 26,363 | 28,900 | 21,363 | 33,684 | 30,625 | 26,500 | 23,000 | 25,500 |
| SUL | 800 | 850 | 710 | 935 | 845 | 965 | 792 | 970 | 212 | 810 | 699 |
| NOSH-SUL | 0.089 | 0.11 | 0.11 | 0.098 | 0.12 | 0.11 | 0.098 | 0.11 | 0.18 | 0.09 | 0.27 |
| Ratio | 8,988 | 7,727 | 6,454 | 9,540 | 7,041 | 8,772 | 8,081 | 8,818 | 1,177 | 9,000 | 2,588 |

The indicated cancer cell lines and their traditional counterparts were treated with various concentrations of NOSH-naproxen ("NOSH-NAP") or NOSH-sulindac ("NOSH-SUL"), as described above. Cell numbers were determined after 24 hours from which $IC_{50}$ values were calculated. The ratios of NSAID/NOSH-NSAID represent fold-enhancement in potency of the NOSH-NSAID over the parent compound. Results are mean of two independent determinations.

exudates, the rats were euthanized by $CO_2$ after which each hind paw was cut at the level of the calcaneus bone, exudates (oedema fluid) were collected and processed for measurement of $PGE_2$, as described above.

Index of Lipid Peroxidation: This was determined using a colorimetric kit from Cayman Chemical (Ann Arbor, Mich.) following their prescribed protocol where the reaction of malondialdehyde (MDA) with thiobarbituric acid (TBA) at high temperature (90-100° C.) in acidic conditions produces an adduct with a chromophore which absorbs visible light at 530-540 nm. Stomach tissue (25 mg) was snap frozen and sonicated for 15 seconds at 40V over ice with 250 μL of radioimmunoprecipitation (RIPA) buffer (25 mM TrisHCl pH 7.6, 150 mM NaCl, 1% NP-40, 1% sodium deoxycholate, 0.1% SDS) with PMSF (phenylmethylsulphonyl fluoride) as protease inhibitor. Homogenates were centrifuged for 10 minutes at 1,600 r.p.m. at 4° C. Thiobarbituric acid reactant substances (TBARS) content was then measured in the supernatant. The results were expressed as picomoles of malondialdehyde per gram protein.

Antioxidant Enzymes: Superoxide dismutase (SOD) activity in the gastric mucosa was assayed using a colorimetric kit (Chattopadhyay M, et al. *J Pharmacol Exp Ther* 2010, 335, 443-50) following the protocol described by the manufacturer (Cayman Chemical, Ann Arbor, Mich.). Mucosal tissue (1 g) was homogenized with 5 mL of 20 mM HEPES buffer (pH 7.2) containing 1 mM EGTA and 300 mM of sucrose solution. Homogenates were centrifuged at 1,500 r.p.m. for 10 minutes at 4° C. The supernatant was then removed and stored at −80° C. until assayed. SOD activity was measured spectrophotometrically at 460 nm. As indicated in Cayman's SOD assay kit, "this procedure utilizes a tetazolium salt for detection of superoxide radicals generated by xanthine oxidase and hypoxanthine". SOD activity is expressed as the amount of the SOD standard showing activity equivalent to the determined activity. The results are expressed as units (U) of SOD activity/mg protein. One unit of SOD is defined as the amount of enzyme needed to exhibit 50% dismutation of the superoxide radical.

Determination of Plasma TNF-α: This was done by an enzyme immunoassay kit from R&D systems (Minneapolis, Minn.) following the protocol described by the manufacturer. Briefly, fresh blood (50 μL) was incubated with antibodies specific for rat TNF-α and washed three times with assay buffer. An enzyme-linked polyclonal antibody specific for rat TNF-α conjugated to horseradish peroxidase was then added to the wells. Following washing of unbound antibody-enzyme reagent, a substrate solution (containing tetramethylbenzidine, TMB, plus hydrogen peroxide) was added to the wells. The enzyme reaction yielded a blue product (oxidized TMB) that turned yellow when the stop solution (dilute hydrochloride acid) was added. The intensity of this was measured at 450 nm. Sensitivity of this TNF-α assay was determined by adding two standard deviations to the mean optical density value of 20×zero standard replicates and calculating the corresponding concentration. Sensitivity was estimated to be about 1.6 pg/mL.

Determination of Plasma NO Levels: The Griess method was used to estimate plasma NO levels indirectly as the concentration of nitrate ($NO_3^-$) and nitrite ($NO_2^-$) using an assay kit from Cayman Chemical (Ann Arbor, Mich.) and following the manufacturer's protocol. Plasma was filtered using a 10 KD molecular weight cut-off filter from Millipore (Bedford, Mass.) before each analysis, to reduce background absorbance due to the presence of hemoglobin. After centrifugation for 10 min at 3000 rpm, samples (40 μL/well) were mixed with 10 μL nitrate reductase mixture and incubated for 3 h after which Griess reagents 1 and 2 (50 μL each) were added. Absorbance was read after 10 min at 540 nm using a plate reader. The concentration of nitrate/nitrite was calculated graphically from a calibration curve prepared from $NaNO_2$ standard solution, and it is expressed as micromolar nitrate.

Measurement of $H_2S$ levels: $H_2S$ levels were measured as previously described (Li L, et al. *Free Radic Biol Med* 2007, 42, 706-19; Huang S, et al. *J Mol Biol* 2010, 396, 708-18). Aliquots (100 μL) of rat plasma were mixed with distilled water (100 μL), zinc acetate (1% w/v, 250 μL), trichloroacetic acid (10% w/v, 250 μL), N,N-dimethyl-p-phenylenediamine sulfate (133 μL, 20 μM) in 7.2M HCl and $FeCl_3$ (133 μl, 30 μM) in 7.2M HCl. The absorbance of the resulting mixture (300 μL) was determined after 15 min using a 96-well microplate reader at 670 nm. All samples were assayed in duplicate and $H_2S$ levels were calculated against a calibration curve of NaHS (1-250 μM). This method overestimates $H_2S$ levels as it measures free $H_2S$, $HS^-$ (hydrosulfide anion), and $S^{2-}$ (sulfide) (Lee Z W, et al. *PLoS One* 2011, 6, (6), e21077. Therefore, the results presented here indicate the sum total of these species.

Anti-Pyretic Activity: To induce fever, LPS (50 μg/kg, Sigma, St. Louis, Mo., USA) was administered intraperitoneally to the animals an hour before the administration of test drugs as described previously (Pinto L et al., *Pharm Pharmacol Communication* 1988: 4:502-505). Rectal temperature was measured by inserting a lubricated thermistor probe (external diameter: 3 mm) 2.8 cm into the rectum of the animal. The probe was linked to a digital reader, which displayed the temperature at the tip of the probe (±0.1° C.). The values displayed were manually recorded. Rectal temperatures were taken every hour for 5 hours.

Inflammatory Oedema Models: Carrageenan, type IV lambda (1%, 100 μL suspended in sterile saline solution), from Sigma Chemicals (St. Louis, Mo.) was subcutaneously injected into the plantar surface of the right hind paw in rat following the protocol described by Winter et al., *Proceedings of the Society for Experimental Biology and Medicine* 1962, 111:544-547. Paw volume was measured using a water displacement plethysmometer (Model 520, IITC/Life Sciences Instruments, Woodland Hills, Calif.) before carrageenan injection and thereafter at 1 hour intervals for 5 hours. The paw volume measured just prior to carrageenan injection was used as the control volume. Data are expressed as the change in paw volume (mL) at each time point.

Induction and Assessment of Carrageenan-Evoked Hyperalgesia: Hindpaw inflammation was produced by intraplantar injection of carrageenan (100 μL of 1% carrageenan in sterile saline solution) into either hindpaw chosen at random. Suspensions of aspirin (180 mg/kg), NOSH-aspirin (477 mg/kg); naproxen (80 mg/kg), NOSH-naproxen (188 mg/kg); sulindac (200 mg/kg), and NOSH-sulindac (467 mg/kg) or 0.5% w/v carboxymethylcellulose (vehicle) were administered orally 1 hour after carrageenan injection, and the mechanical nociceptive threshold determined 30 min after this and thereafter every hour for 5 hours. The paw hyperalgesia was measured with an electronic pressuremeter as reported earlier (Chattopadhyay M, et al. *J Pharmacol Exp Ther.* 2010, 335, 443-50). Each hindpaw was positioned in turn under a conical probe surface (tip radius approx. 1 mm) and gradually increasing pressure applied to the hindpaw surface until the animal vocalized at which point the measurement was terminated. Mechanical nociceptive threshold for both the injected and contralateral (i.e., non-injected) hindpaw were determined. The animals were tested before and after treatments, the results are expressed by the delta reaction force (g).

Inhibition of Human Platelet Aggregation In Vitro: Antiaggregatory effects of NOSH-aspirin, NOSH-naproxen, and their corresponding parent NSAID were studied on collagen-induced platelet aggregation of human platelet-rich plasma (PRP). It is known that collagen-induced aggregation occurs through a pathway dependent upon the arachidonic acid cascade. Venous blood samples were obtained from healthy volunteers who had not taken any drugs for at least 2 weeks. PRP was prepared by centrifugation of citrated blood at 200 g for 20 min. Aliquots (500/L) of PRP were added into aggregometer cuvettes, and aggregation was recorded as increased light transmission under continuous stirring (1000 rpm) at 37° C. for 10 min after the addition of the stimulus. Collagen at submaximal concentrations (1.0 µg/mL) was used as the platelet activator in PRP. Compounds under study were preincubated with PRP 10 min before the addition of collagen. Vehicle alone (0.5% DMSO) added to PRP did not affect platelet function in control samples. The anti-aggregatory activity of test compounds was evaluated as percent inhibition of platelet aggregation compared to control samples. $IC_{50}$ values were calculated by nonlinear regression analysis.

Measurement of COX Enzyme Activity: NOSH-naproxen and NOSH-sulindac were compared to naproxen and sulindac for their ability to inhibit COX-1 and COX-2 enzyme activities in vitro as described previously (Kulmacz R J, et al, *Prostaglandins* 1983, 25:531-540) using a colorimetric COX (ovine, o-COX) inhibitor screening kit from Cayman Chemicals (Ann Arbor, Mich.).

Statistical Analysis: All data are presented as the mean±SEM, with sample sizes of at least 5 rats/group (unless otherwise specified). Comparisons between groups were performed using a one-way analysis of variance followed by the Student-t test.

Figure 8:
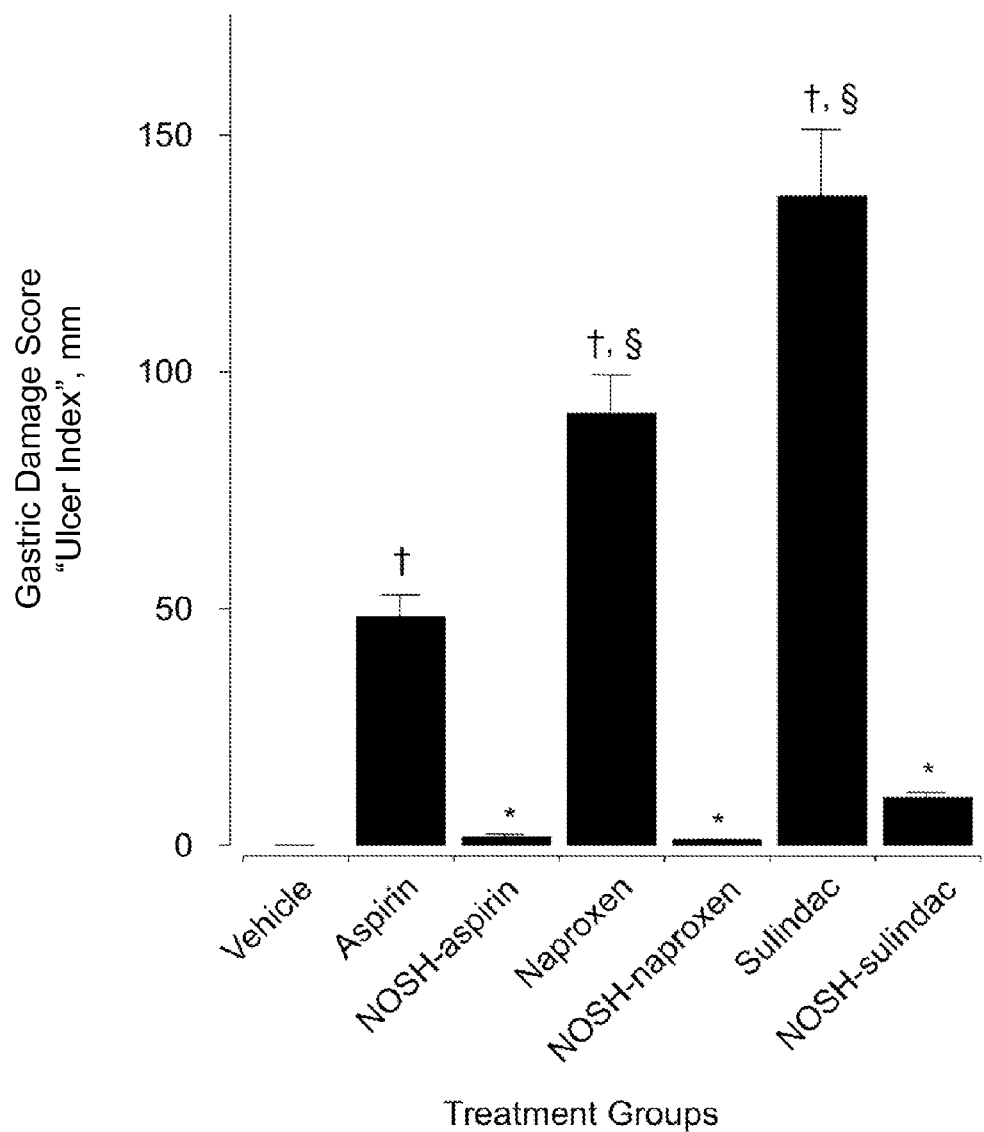
FIG. 8 is a bar graph quantifying the gastric damage (expressed as the score (ulcer index, mm) in rats treated with the indicated control, NSAID or NOSH-NSAID; †P<0.01 compared to vehicle, §P<0.05, compared to aspirin, *P<0.01 compared to corresponding NSAID.

Results:

Gastric Mucosal Lesions: The rats receiving the vehicle (0.5% CMC solution) had a normal glandular region on the surface of their stomach, and no ulcerative damage. For these rats, the gastric damage score (also described in the literature as "ulcer index", or UI), was zero (UI=0). However, administration of aspirin, naproxen, or sulindac resulted in extensive mucosal injury (UI=48, 80 and 130 for aspirin, naproxen, and sulindac, respectively) to the glandular portion of the gastric fundus. Unlike these NSAIDs, NOSH-aspirin, NOSH-naproxen, and NOSH-sulindac did not produce significant ulcerative damage (UI=2, 2, and 10, respectively) compared to the parent NSAID at equimolar doses, which represents a remarkable reduction (P<0.01) in gastrointestinal toxicity (FIG. 8).

Figures 9A, 9B, 9C:
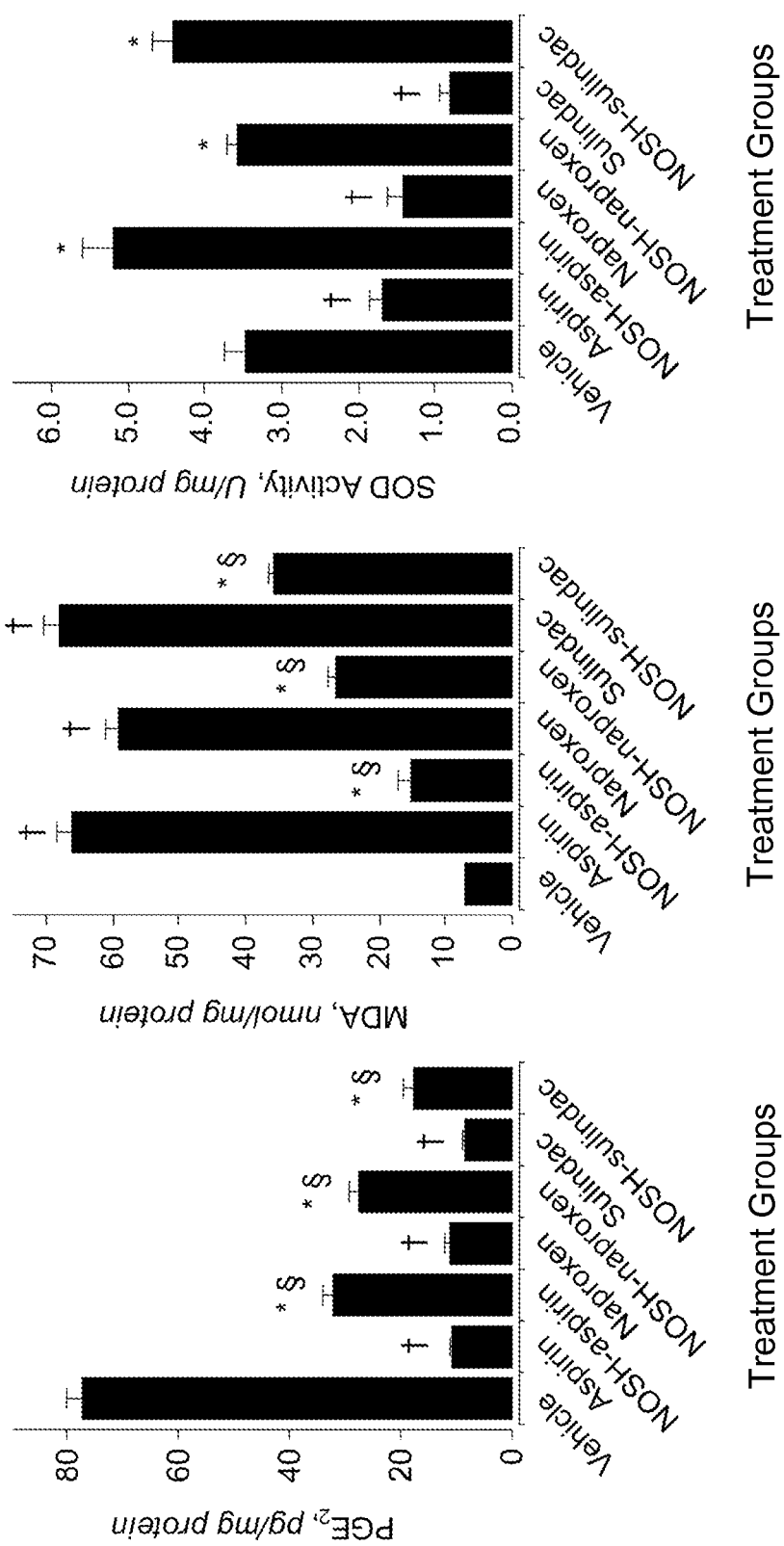
FIGS. 9A, 9B and 9C are bar graphs quantifying the levels of gastric PGE$_2$ (pg/mg protein), lipid peroxidation (MDA) (nmol/mg protein), and superoxide dismutase (SOD) activity (U/mg protein), respectively, in the indicated treatment groups.

Gastric Mucosal and Paw Exudate Prostaglandin $E_2$ Content: The effect of aspirin, naproxen, sulindac, NOSH-aspirin, NOSH-naproxen, and NOSH-sulindac on prostaglandin $E_2$ ($PGE_2$) content was investigated in gastric mucous (FIG. 9A) and paw exudates (FIG. 10D). Animals treated per os with aspirin (180 mg/kg), naproxen (80 mg/kg), and sulindac (200 mg/kg) produced about 80-85% less $PGE_2$ than rats in the control group. The NOSH-NSAIDs also reduced $PGE_2$ levels but not to the same extent as their parent NSAID (FIG. 9A). Prostaglandins are the main product of cyclooxygenase-mediated arachidonic acid metabolism in gastric mucosa. Therefore, comparison of $PGE_2$ content between control and drug-treated groups showed a clear and significant COX inhibition by the conventional NSAIDs and also the NOSH-NSAIDs. Subsequently, it was tested whether the NOSH-NSAIDs exerted a similar decrease in $PGE_2$ levels in the carrageenan-induced paw edema model in rats. In this assay, as for the gastric mucosa above, similar results were obtained (FIG. 10D).

Lipid Peroxidation: Oxidative stress in gastric tissue was assessed by measuring the concentration of MDA in intact mucosa 6 h post administration of drugs at the doses indicated above. MDA levels were 10±3 nmol/mg protein for vehicle (FIG. 9B), and this increased to 60-68 nmol/mg protein for the traditional NSAIDs, but was significantly less for the NOSH-NSAID treated animals (15-32 nmol/mg protein) (FIG. 9B).

SOD Activity: In intact gastric mucosal (control group) SOD activity was 3.4±0.3 U/mg protein. Following administration of the traditional NSAIDs, a significant decrease in SOD activity (0.9-1.8 U/mg protein) was observed (P<0.05). Treatment with the NOSH-NSAIDs had no effect on SOD activity, or increased it (3.8-5.2 U/mg protein) (FIG. 9C).

Carrageenan-Induced Paw Swelling: The most common use for NSAIDs (including aspirin, naproxen, and sulindac) is the treatment of inflammatory conditions. The COX-dependent anti-inflammatory activity of these NSAIDs was compared to that obtained with the NOSH-NSAIDs. After inducing inflammation, animals receiving vehicle showed a fast, time-dependent increase in paw volume ($\Delta V$=0.8 mL) after 2 h, and gradual increase to 13 mL over the course of the experiment (6 h) (FIG. 10A). In contrast, animals receiving the traditional NSAIDs showed a weak inflammatory response ($\Delta V$=0.3 mL by 2 h) which decreased over the next 3 h (FIGS. 10A, 10B, 10C). The anti-inflammatory effect registered in animals dosed with NOSH-aspirin was similar to that of aspirin or may be even better at times (FIG. 10A), NOSH-naproxen treated animals had even lower inflammatory response compared to naproxen (FIG. 10B); however, NOSH-sulindac treated animals had the same anti-inflammatory response as sulindac (FIG. 10C).

Plasma TNFα Levels: The inhibitory effect of aspirin, naproxen, sulindac, NOSH-aspirin, NOSH-naproxen, and NOSH-sulindac on proinflammatory cytokine tumor necrosis factor-α in plasma obtained from control and drug-treated animals was determined. Administration of ASA (1 mmol/kg) increased TNFα concentration by about 20-fold (11±0.3 control and 190±5 pg/mL ASA); and naproxen increased TNFα concentration to 150±2 pg/mL, whereas sulindac increased this to 230±5 pg/mL (FIG. 11). This rise was considerably lower in the NOSH-NSAID-treated animals, the values being 75±1 pg/mL for NOSH-aspirin, 48±2 pg/mL for NOSH-naproxen, and 50±3 pg/mL for NOSH-sulindac treated animals (FIG. 11).

Antipyretic Activity: It is well known that NSAIDs exerts a moderate antipyretic effect when administered orally. Thus, the decrease in body temperature induced by NOSH-NSAIDs was compared to that obtained with the parent NSAID. Experimental drugs at the doses indicated above were administered (per os) 30 minutes before injecting LPS (50 µg/kg intraperitoneally) in experimental animals. In this regard, control animals showed a time-dependent increase in body temperature ($\Delta T$=1.8° C.) up to 3 h and maintained it until the end of the screen (5 h). However, NSAID and NOSH-NSAID-treated animals showed only about half degree increase in body temperature 1 h after LPS injection and preserved it within this range throughout the experiment (FIGS. 12A, 12B, 12C). NOSH-aspirin and NOSH-naproxen appeared to be better in reducing LPS-induced fever 2-4 hours after LPS injection compared to aspirin and naproxen, respectively (FIGS. 12A, 12B).

Carrageenan-Induced Mechanical Hyperalgesia: This assay measures the ability of the test drugs to reverse hyperalgesia (decreased threshold to a painful stimuli) produced by injection of carrageenan reagent. The mechanical pain threshold was increased upon time by administering the traditional NSAIDs and the NOSH-NSAIDs (FIGS. 13A, 13B, 13C). Pain threshold was markedly reduced from 60-70 g to about 10 g in animals receiving vehicle (control group), indicating a higher sensitivity to mechanical stimuli (non-painful at normal conditions). Hyperalgesia was decreased in animals receiving the NSAIDs or NOSH-NSAIDs to the same extent, mechanical pain threshold reduced to about 30-35 g (~50% reduction compared to the initial response).

Nitric Oxide and Hydrogen Sulfide Release: The NOSH compounds were designed to release both NO and $H_2S$. In order to show that indeed this was the case in vivo, blood was collected from vehicle, NSAID and NOSH-NSAID-treated animals at the end of the carrageenan-induced edema studies. FIG. 14 shows that indeed both NO and $H_2S$ were significantly higher in the NOSH-NSAID-treated animals.

Platelet Anti-Aggregatory Activity: Anti-aggregatory effects of aspirin, naproxen, NOSH-aspirin, and NOSH-naproxen were studied on collagen-induced platelet aggregation of human platelet-rich plasma (PRP). The results expressed as $IC_{50}$ are shown in FIG. 15. Analysis of the data does not show any statistical differences between aspirin and NOSH-aspirin or between naproxen and NOSH-naproxen.

NOSH-NSAIDs Inhibit Cyclo-Oxygenase Enzyme Activity: When metabolized, NOSH-naproxen and NOSH-sulindac should produce naproxen, sulindac, $H_2S$ and NO. It has been presently demonstrated that NO and $H_2S$ are released (see Example 10). In order to show the effects of the naproxen and sulindac components, the effects of NOSH-naproxen and NOSH-sulindac on COX-1 and COX-2 enzyme activity were evaluated. As shown in Table 8 below, NOSH-naproxen and NOSH-sulindac dose-dependently inhibited the enzymatic activity of both COX-1 and COX-2. It appeared that they preferentially inhibited COX-1.

TABLE 8

NOSH-naproxen and NOSH-sulindac inhibit cyclooxygenase enzyme activity

| Groups | COX 1-% Inhibition | COX-2-% Inhibition |
|---|---|---|
| ASA 1 mM | 84.9, 85.9 | 68.4, 70.2 |
| ASA 3 mM | 86.5 | 74.6 |
| NOSH-ASA 50 nM | 52.6, 47.6 | 23.3, 20.9 |
| NOSH-ASA 100 nM | 67.93 | 29.05 |
| NAPROXEN 3 mM | 84.7, 80.1 | 68.6, 70.2 |
| NAPROXEN 6 mM | 91.9 | 74.64 |
| NOSH-NAPROXEN 80 nM | 42.5, 44.4 | 18.8, 15.8 |
| NOSH-NAPROXEN 160 nM | 52.3 | 11.02 |
| SULINDAC 800 µM | 84.0, 81.0 | 66.8, 68.5 |
| SULINDAC 1600 µM | 89.1 | 71.1 |
| NOSH-SULINDAC 89 nM | 43.4, 45.0 | 13.6, 12.3 |
| INDOMETHACIN 1 µM | 75.9, 72.6 | 69.9, 67.1 |

Pure ovine COX enzymes were treated with different concentrations of test agents for 15 min at 4° C., after which o-COX-1 and o-COX-2 enzyme activity was determined. Results from one or two independent studies performed in duplicate are shown.

Example 13

NOSH-Aspirin and NOSH-Naproxen Reduce Tumor Growth in Different Mouse xenograft models Materials and Methods Mouse Xenograft Model: Male athymic nude (NU/NU) mice, age 5 weeks, were purchased from Charles River Laboratories, Inc., (Wilmington, Mass.) and were housed according to institutional and NIH guidelines.

Human colon (SW480), Breast (MCF-7, MDA-MB-231), and pancreas (MIA PaCa2) cancer cells ($2 \times 10^6$) suspended in Matrigel (BD Biosciences, San Jose, Calif.) 50% v/v were inoculated subcutaneously in the right flanks of each mouse (10 mice per group) using a 1-mL syringe and 22-gauge needles. After 10 days the animals from each implanted cell line were randomly divided into 2 groups (N=5/group) and gavaged daily with either vehicle (1% methylcelloluse) or NOSH-naproxen (100 mg/kg) or NOSH (100 mg/kg), the ADT-OH-butyl nitrate compound that releases $H_2S$ and NO, in the case of colon cancer xenografts; or NOSH-aspirin (100 mg/kg body weight) in the breast and pancreatic cancers groups. The tumor size was measured every other day using electronic calipers, the tumor volumes were calculated using the following formula: length×width/2. The weights of the mice were also recorded every 3 days. Twenty-seven (27) to thirty (30) days post inoculation, the mice were sacrificed, the tumors collected, weighed, and photographed.

Results:

Athymic (NU/NU) male mice were injected subcutaneously with colon (SW480), Breast (MCF-7 (ER+), MDA-MB-231 (ER−), and pancreas (MIA PaCa2) cancer cells in the right flank, allowing for the development of subcutaneous tumors after 10 days. Following tumor formation, 5 mice were treated every day for 23 to 30 days with 100 mg/kg NOSH-ASA (breast and pancreas xenografts) or 100 mg/kg of NOSH-naproxen, or just NOSH (colon xenografts). NOSH is the $H_2S$-releasing component (ADT-OH) directly attached to the NO-releasing component (butyl nitrate). Five control mice in each group were left untreated for the same period of time. At the end of the study, the following observations were made:

i) ER(−) breast cancer: NOSH-ASA-treated mice showed a considerable reduction in tumor volume compared with untreated mice. Compared with the control group with mean tumor volume of 1886±200 mm³, NOSH-ASA reduced the tumor volume to 35±9 mm³, equivalent to a mean reduction of 98% (P=0.0008) (FIG. 16A). One mouse was totally tumor free starting on day 21 of treatment. Compared to the control group with average tumor mass 1.2±0.33 g, NOSH-ASA reduced the tumor mass to 0.11±0.058 g on day 27, i.e., when the experiment was terminated; equivalent to a reduction of 91% (P=0.006) which was consistent with continued regression of tumor volume over the same treatment period (FIG. 16B).

ii) ER(+) breast cancer: Compared with the control group with mean tumor volume of 935±93 mm³, NOSH-ASA reduced the tumor volume to 48±9 mm³, equivalent to a mean reduction of 98% (P=0.0007) (FIG. 17A). Compared to the control group with average tumor mass 0.46±0.056 g, NOSH-ASA reduced the tumor mass to 0.21±0.035 g on day 27, i.e., when the experiment was terminated; equivalent to a reduction of 55% (P=0.022) (FIG. 17B).

iii) Pancreatic cancer: Compared with the control group with mean tumor volume of 3265±476 mm³, NOSH-ASA reduced the tumor volume to 285±117 mm³, equivalent to a mean reduction of 91% (P=0.0089) (FIG. 18A). Compared to the control group with average tumor mass 2.45±2.7 g, NOSH-ASA reduced the tumor mass to 0.61±0.29 g on day 30, i.e., when the experiment was terminated; equivalent to a reduction of 75% (P=0.003) (FIG. 18B).

iv) Colon cancer: Compared with the control group with mean tumor volume of 2098±603 mm³, NOSH-naproxen reduced the tumor volume to 379±73 mm³, equivalent to a mean reduction of 82% (P=0.0475) (FIG. 19A). Compared to the control group with average tumor mass 1.42±0.48 g, NOSH-naproxen reduced the tumor mass to 0.63±0.11 g, equivalent to a reduction of 55% (P=0.042) (FIG. 19B) on day 30, i.e., when the experiment was terminated. However, when the xenografts were treated by NOSH only (the ADT-OH-butyl nitrate compound), the reductions in tumor volume and tumor mass were not significantly different to the controls (FIG. 19B).

Other embodiments are within the scope of the following claims.

What is claimed is:

1. A method of treating an inflammatory disease, comprising administering to a subject in need thereof an effective amount of a compound of formula (Ia):

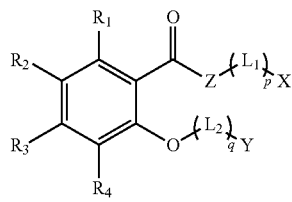

wherein
Z is O or NH;
$R_1$, $R_2$, $R_3$, and $R_4$, independently, is H, halo, $NO_2$, $N_3$, $C_1$-$C_{10}$ alkyl, OR, OC(O)R, N(R)$_2$, NH—C(O)R, S(O)R, or N=N—R, in which each R, independently, is H, $C_1$-$C_{10}$ alkyl, or aryl;
$L_1$ is a linker, the linker being —C(O)—, —(CH$_2$)$_m$—, —(CH$_2$)$_m$—O—, —(CH$_2$)$_m$—C(O)—, —(CH$_2$)$_m$—C(O)O—, —(CH$_2$)$_m$—OC(O)O—, —C(O)—(CH$_2$)$_m$—O—, —C(O)—(CH$_2$)$_m$—C(O)—, —OC(O)—(CH$_2$)$_m$—O—, —OC(O)—(CH$_2$)$_m$—C(O)—, or —OC(O)—(CH$_2$)$_m$—C(O)O—, in which m is 1, 2, 3, 4, 5, 6, or 7;
$L_2$ is a linker, the linker being —C(O)—, —(CH$_2$)$_m$—, —(CH$_2$)$_m$—O—, —(CH$_2$)$_m$—C(O)—, —(CH$_2$)$_m$—C(O)O—, —(CH$_2$)$_m$—OC(O)O—, —C(O)—(CH$_2$)$_m$—O—, —C(O)—(CH$_2$)$_m$—C(O)—, —OC(O)—(CH$_2$)$_m$—O—, —OC(O)—(CH$_2$)$_m$—C(O)—, or —OC(O)—(CH$_2$)$_m$—C(O)O—, in which m is 1, 2, 3, 4, 5, 6, or 7;
p and q, independently, is 0 or 1;
X is a $H_2$S-releasing moiety or a NO-releasing moiety;
Y is a NO-releasing moiety or a $H_2$S-releasing moiety, provided that not all of X and Y are simultaneously $H_2$S-releasing moieties or NO-releasing moieties;
the NO-releasing moiety is —C(O)—(CH$_2$)$_n$—ONO$_2$ or —(CH$_2$)$_n$—ONO$_2$, in which n is 1, 2, 3, 4, 5, 6, or 7; and
the $H_2$S-releasing moiety is

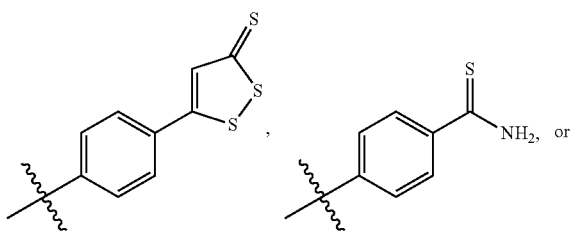

2. The method of claim 1, wherein the inflammatory disease is cancer, rheumatoid arthritis, intestine inflammation, stomach ulcer, a cardiovascular disease, or a neurodegenerative disease.

3. A pharmaceutical composition comprising a compound according to formula (Ia) and a pharmaceutically acceptable excipient, wherein formula (Ia) is represented by the following:

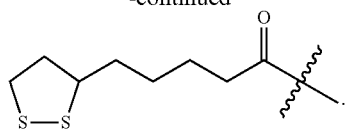

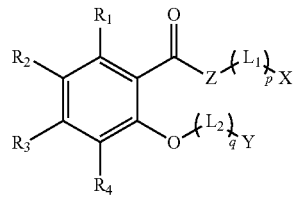

wherein
Z is O or NH;
$R_1$, $R_2$, $R_3$, and $R_4$, independently, is H, halo, $NO_2$, $N_3$, $C_1$-$C_{10}$ alkyl, OR, OC(O)R, N(R)$_2$, NH—C(O)R, S(O)R, or N=N—R, in which each R, independently, is H, $C_1$-$C_{10}$ alkyl, or aryl;
$L_1$ is a linker, the linker being —C(O)—, —(CH$_2$)$_m$—, —(CH$_2$)$_m$—O—, —(CH$_2$)$_m$—C(O)—, —(CH$_2$)$_m$—C(O)O—, —(CH$_2$)$_m$—OC(O)O—, —C(O)—(CH$_2$)$_m$—O—, —C(O)—(CH$_2$)$_m$—C(O)—, —OC(O)—(CH$_2$)$_m$—O—, —OC(O)—(CH$_2$)$_m$—C(O)—, or —OC(O)—(CH$_2$)$_m$—C(O)O—, in which m is 1, 2, 3, 4, 5, 6, or 7;
$L_2$ is a linker, the linker being —C(O)—, —(CH$_2$)$_m$—, —(CH$_2$)$_m$—(O)—, —(CH$_2$)$_m$—C(O)—, —(CH$_2$)$_m$—C(O)O—, —(CH$_2$)$_m$—OC(O)O—, —C(O)—(CH$_2$)$_m$—O—, —C(O)—(CH$_2$)$_m$—C(O)—, —OC(O)—(CH$_2$)$_m$—O—, —OC(O)—(CH$_2$)$_m$—C(O)—, or —OC(O)—(CH$_2$)$_m$—C(O)O—, in which m is 1, 2, 3, 4, 5, 6, or 7;
p and q, independently, is 0 or 1;
X is a $H_2$S-releasing moiety or a NO-releasing moiety;
Y is a NO-releasing moiety or a $H_2$S-releasing moiety, provided that not all of X and Y are simultaneously $H_2$S-releasing moieties or NO-releasing moieties;
the NO-releasing moiety is —C(O)—(CH$_2$)$_n$—ONO$_2$ or —(CH$_2$)$_n$—ONO$_2$, in which n is 1, 2, 3, 4, 5, 6, or 7; and
the $H_2$S-releasing moiety is

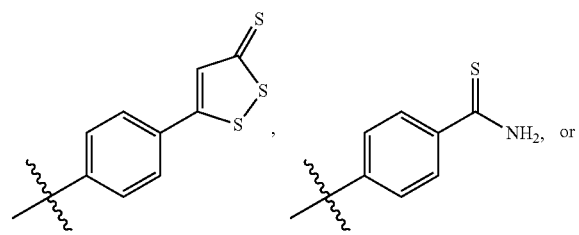

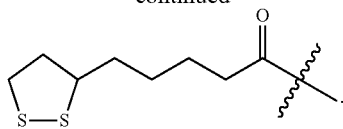

4. A compound of formula (Ia):

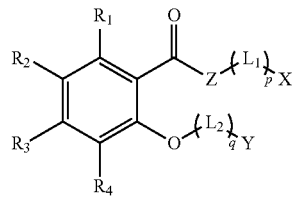

wherein
Z is O or NH;
R₁, R₂, R₃, and R₄, independently, is H, halo, NO₂, N₃, C₁-C₁₀ alkyl, OR, OC(O)R, N(R)₂, NH—C(O)R, S(O) R, or N=N—R, in which each R, independently, is H, C₁-C₁₀ alkyl, or aryl;
L₁ is a linker, the linker being —C(O)—, —(CH₂)ₘ—, —(CH₂)ₘ—O—, —(CH₂)ₘ—C(O)—, —(CH₂)ₘ—C(O)O—, —(CH₂)ₘ—OC(O)O—, —C(O)—(CH₂)ₘ—O—, —C(O)—(CH₂)ₘ—C(O)—, —OC(O)—(CH₂)ₘ—O—, —OC(O)—(CH₂)ₘ—C(O)—, or —OC(O)—(CH₂)ₘ—C(O)O—, in which m is 1, 2, 3, 4, 5, 6, or 7;
L₂ is a linker, the linker being —C(O)—, —(CH₂)ₘ—, —(CH₂)ₘ—O—, —(CH₂)ₘ—C(O)—, —(CH₂)ₘ—C(O)—, —(CH₂)ₘ—C(O)O—, —(CH₂)ₘ—OC(O)O—, —C(O)—(CH₂)ₘ—O—, —C(O)—(CH₂)ₘ—C(O)—, —OC(O)—(CH₂)ₘ—O—, —OC(O)—(CH₂)ₘ—C(O)—, or —OC(O)—(CH₂)ₘ—C(O)O—, in which m is 1, 2, 3, 4, 5, 6, or 7;
p and q, independently, is 0 or 1;
X is a H₂S-releasing moiety or a NO-releasing moiety;
Y is a NO-releasing moiety or a H₂S-releasing moiety, provided that not all of X and Y are simultaneously H₂S-releasing moieties or NO-releasing moieties;
the NO-releasing moiety is —C(O)—(CH₂)ₙ—ONO₂ or —(CH₂)ₙ—ONO₂, in which n is 1, 2, 3, 4, 5, 6, or 7; and
the H₂S-releasing moiety is

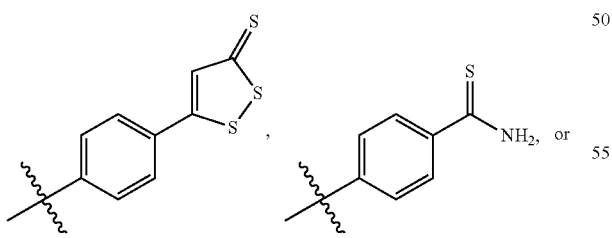

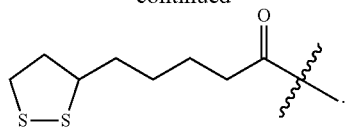

5. A compound having the formula:

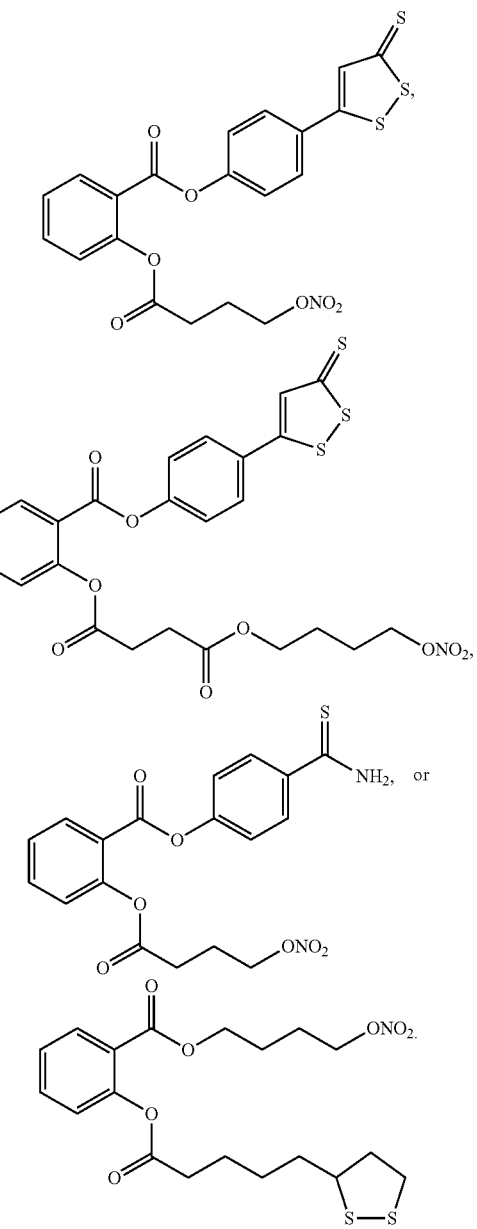

* * * * *

UNITED STATES PATENT AND TRADEMARK OFFICE
CERTIFICATE OF CORRECTION

PATENT NO. : 9,688,607 B2
APPLICATION NO. : 13/981378
DATED : June 27, 2017
INVENTOR(S) : Kashfi et al.

Page 1 of 1

It is certified that error appears in the above-identified patent and that said Letters Patent is hereby corrected as shown below:

In the Specification

Column 114, Line 62:
Now reads: "$R_1, R_2, R_3, R_4, R_5, R_6, R_2$…"
Should read: --$R_1, R_2, R_3, R_4, R_5, R_6, R_7$…--

Column 118, Line 63:
Now reads: "$R_1, R_2, R_3, R_4, R_5, R_6, R_2$…"
Should read: --$R_1, R_2, R_3, R_4, R_5, R_6, R_7$…--

Column 156, Lines 65 and 66:
Now reads: "…8.45gm …5.0gm…"
Should read: --…8.45mg …5.0mg…--

Column 157, Line 1:
Now reads: "…8.45gm …5.0gm…"
Should read: --…8.45mg …5.0mg…--

Column 174, Line 8:
Now reads: "…then deceased…"
Should read: --…then decreased…--

Signed and Sealed this
Nineteenth Day of September, 2017

Joseph Matal
*Performing the Functions and Duties of the*
*Under Secretary of Commerce for Intellectual Property and*
*Director of the United States Patent and Trademark Office*